US008409834B2

(12) United States Patent
Burlew et al.

(10) Patent No.: US 8,409,834 B2

(45) Date of Patent: Apr. 2, 2013

(54) EXTRACTION SOLVENTS DERIVED FROM OIL FOR ALCOHOL REMOVAL IN EXTRACTIVE FERMENTATION

(75) Inventors: Keith H. Burlew, Middleton, DE (US); Robert DiCosimo, Chadds Ford, PA (US); Michael Charles Grady, Oaklyn, NJ (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/162,643

(22) Filed: Jun. 17, 2011

(65) Prior Publication Data

US 2011/0312043 A1 Dec. 22, 2011

Related U.S. Application Data

(60) Provisional application No. 61/440,034, filed on Feb. 7, 2011, provisional application No. 61/379,546, filed on Sep. 2, 2010, provisional application No. 61/368,429, filed on Jul. 28, 2010, provisional application No. 61/368,444, filed on Jul. 28, 2010, provisional application No. 61/368,436, filed on Jul. 28, 2010, provisional application No. 61/368,451, filed on Jul. 28, 2010, provisional application No. 61/356,290, filed on Jun. 18, 2010.

(51) Int. Cl.

*C12P 7/02* (2006.01)

*C12P 7/16* (2006.01)

(52) U.S. Cl. ........................................ 435/155; 435/160

(58) Field of Classification Search ........................ None

See application file for complete search history.

(56) References Cited

U.S. PATENT DOCUMENTS

| | | | |
|---|---|---|---|
| 6,646,146 | B1 | 11/2003 | Sinnema et al. |
| 7,851,188 | B2 | 12/2010 | Donaldson et al. |
| 7,932,063 | B2 | 4/2011 | Dunson et al. |
| 2007/0077635 | A1 | 4/2007 | Brunner et al. |
| 2008/0182308 | A1 | 7/2008 | Donaldson et al. |
| 2009/0163376 | A1 | 6/2009 | Li et al. |
| 2009/0171129 | A1 | 7/2009 | Evanko et al. |
| 2009/0269823 | A1 | 10/2009 | Bramucci et al. |
| 2009/0305363 | A1 | 12/2009 | Anthony |
| 2009/0305370 | A1 | 12/2009 | Grady et al. |
| 2010/0081154 | A1 | 4/2010 | Flint et al. |
| 2010/0124773 | A1 | 5/2010 | Yang |
| 2011/0124060 | A1 | 5/2011 | Anthony et al. |
| 2011/0244536 | A1 | 10/2011 | Nagarajan et al. |

FOREIGN PATENT DOCUMENTS

| | | | |
|---|---|---|---|
| GB | 2146638 | A | 4/1985 |
| JP | 1986192291 | | 8/1986 |
| WO | 2009149270 | A2 | 12/2009 |
| WO | 2010049491 | A1 | 5/2010 |
| WO | 2011063402 | A2 | 5/2011 |

OTHER PUBLICATIONS

Barros et al., Integration of Enzyme Catalysis in an Extraction Fermentation Process, Studies in Organic Chemistry 29, 1986.

Kim et al., Extractive Recovery of Products from Fermentation Broths, Biotechnology and Bioprocess Engineering, 1999, 4:1-11.

Oliveira et al., Production and Extractive Biocatalysis of Ethanol Using Microencapsulated Yeast Cells and Lipase System, Journal of Chemical Technology and Biotechnology, 1991, 52:219-225.

Oliveira et al., Immobilization of *Saccharomyces cerevisiae* Cells and *Rhizomucor miehi* Lipase for the Production and Extractive Biocatalysis of Ethanol, Bioprocess Engineering, 1997, 16:349-353.

Oliveira et al., Improvement of Alcoholic Fermentations by Simultaneous Extraction and Enzymatic Esterification of Ethanol, Journal of Molecular Catalysis B: Enzymatic, 1998, 5:29-33.

Oliveira et al., Effect of extraction and Enzymatic Esterification of Ethanol on Glucose Consumption by Two *Saccharomyces cerevisiae* Strains: A comparative study, Journal of Chemical Technology and Biotechnology, 2001, 76:285-290.

Ban et al., Whole cell biocatalyst for biodiesel fuel production utilizing *Rhizopus oryzae* cells immobilized within biomass support particles, Biochemical Engineering Journal, 2001, pp. 39-43, vol. 8.

Bellion et al., Microb. Growth C1 Compd., [Int. Symp.], 7th (1993), 415 32, Editor(s): Murrell, J. Collin; Kelly, Don P. Publisher: Intercept, Andover, UK.

Bligh et al., A Rapid Method of Total Lipid Extraction and Purification, Canadian Journal of Biochemistry and Physiology, Aug. 1959, pp. 911-917, vol. 37, No. 8.

Gupta et al., Bacterial lipases: an overview of production, purification and biochemical properties, Applied Microbiology and Biotechnology, 2004, pp. 763-781, vol. 64.

Horton et al., Engineering hybrid genes without the use of restriction enzymes: gene splicing by overlap extension, Gene, 1989, pp. 61-68, vol. 77.

Kohlhase et al., Catalytic Effects in the Ammonolysis of Vegetable Oils, The Journal of the American Oil Chemists' Society, 1971, pp. 265-270, vol. 48.

Lynd et al., Microbial Cellulose Utilization: Fundamentals of Biotechnology, Microbiology and Molecular Biology Reviews, Sep. 2002, pp. 506-577, vol. 66, No. 3.

(Continued)

*Primary Examiner* — Nashaat Nashed

(57) ABSTRACT

In an alcohol fermentation process, oil derived from biomass is hydrolyzed into an extractant available for in situ removal of a product alcohol such as butanol from a fermentation broth. The glycerides in the oil can be catalytically (e.g., enzymatically) hydrolyzed into free fatty acids, which form a fermentation product extractant having a partition coefficient for a product alcohol greater than a partition coefficient of the oil of the biomass for the product alcohol. Oil derived from a feedstock of an alcohol fermentation process can be hydrolyzed by contacting the feedstock including the oil with one or more enzymes whereby at least a portion of the oil is hydrolyzed into free fatty acids forming a fermentation product extractant, or the oil can be separated from the feedstock prior to the feedstock being fed to a fermentation vessel, and the separated oil can be contacted with the enzymes to form the fermentation product extractant. The fermentation product extractant can be contacted with a fermentation broth for in situ removal of a product alcohol.

12 Claims, 9 Drawing Sheets

OTHER PUBLICATIONS

Ma et al., Plasmid construction by homologous recombination in yeast, Gene, 1987, pp. 201-216, vol. 58.

Malinowski, Two-phase partitioning bioreactors in fermentation technology, Biotechnology Advances, 2001, pp. 525-538, vol. 19.

Methods in Yeast Genetics, 2005, Cold Spring Harbor Laboratory Press, Cold Spring Harbor, NY, pp. 201-202.

Oudshoorn et al., Assessment of Options for Selective 1-Butanol Recovery from Aqueous Solution, Industrial and Engineering Chemistry Research, 2009, pp. 7325-7336, vol. 48.

Roe et al., Fatty Acid Amides. IV. Reaction of Fats With Ammonia and Amines, The Journal of the American Oil Chemists' Society, Jan. 1952, pp. 18-22, vol. 29.

Roffler, Steve Ronald: Extractive fermentation—lactic acid and acetone/butanol production, 1986, pp. 1-289, PhD. Dissertation in Chemical Engineering, University of California, Berkeley.

Sulter et al., Proliferation and metabolic significance of peroxisomes in *Candida boidinii* during growth on D-alanine or oleic acid as the sole carbon source, Archives of Microbiology,1990, pp. 485-489, vol. 153, No. 9.

Yoo et al., Enzymatic Synthesis of Sugar Fatty Acid Esters, Journal of Industrial Engineering Chemistry, 2007, pp. 1-5, vol. 13, No. 1.

U.S. Appl. No. 12/980,607, filed Dec. 29, 2010.

U.S. Appl. No. 13/162,631, filed Jun. 17, 2011.

U.S. Appl. No. 13/163,243, filed Jun. 17, 2011.

U.S. Appl. No. 13/162,868, filed Jun. 17, 2011.

U.S. Appl. No. 13/193,147, filed Jul. 28, 2011.

U.S. Appl. No. 13/162,828, filed Jun. 17, 2011.

U.S. Appl. No. 61/440,034, filed Feb. 7, 2011.

International Search Report and Written Opinion dated Oct. 14, 2011, International Application No. PCT/US2011/040806.

EXTRACTION SOLVENTS DERIVED FROM OIL FOR ALCOHOL REMOVAL IN EXTRACTIVE FERMENTATION

This application claims the benefit of U.S. Provisional Application No. 61/356,290, filed on Jun. 18, 2010; U.S. Provisional Application No. 61/368,451, filed on Jul. 28, 2010; U.S. Provisional Application No. 61/368,436, filed on Jul. 28, 2010; U.S. Provisional Application No. 61/368,444, filed on Jul. 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; U.S. patent application Ser. No. 13/160,766, filed on Jun. 15, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates the production of fermentative alcohols such as butanol, and in particular to extraction solvents for extractive fermentation and processes for converting oil derived from biomass into the extraction solvents.

BACKGROUND OF THE INVENTION

Alcohols have a variety of applications in industry and science such as a beverage (i.e., ethanol), fuel, reagents, solvents, and antiseptics. For example, butanol is an alcohol that is an important industrial chemical with a variety of applications including use as a fuel additive, as a feedstock chemical in the plastics industry, and as a food-grade extractant in the food and flavor industry. Accordingly, there is a high demand for alcohols such as butanol, as well as for efficient and environmentally-friendly production methods.

Production of alcohol utilizing fermentation by microorganisms is one such environmentally-friendly production method. In the production of butanol, in particular, some microorganisms that produce butanol in high yields also have low butanol toxicity thresholds. Removal of butanol from the fermentation vessel as it is being produced is a means to manage these low butanol toxicity thresholds.

In situ product removal (ISPR) (also referred to as extractive fermentation) can be used to remove butanol (or other fermentative alcohol) from the fermentation vessel as it is produced, thereby allowing the microorganism to produce butanol at high yields. One ISPR method for removing fermentative alcohol that has been described in the art is liquid-liquid extraction (U.S. Patent Application Publication No. 2009/0305370). In order to be technically and economically viable, liquid-liquid extraction calls for good contact between the extractant and the fermentation broth for efficient mass transfer of the product alcohol into the extractant; good phase separation of the extractant from the fermentation broth (during and/or after fermentation); efficient recovery and recycle of the extractant; minimal degradation of the ability of the extractant to extract the product alcohol (e.g., by preventing the lowering of the partition coefficient for the product alcohol into the extractant); and minimal contamination of the extractant by lipids that lower the partition coefficient over a long-term operation.

The partition coefficient of the extractant can be degraded over time with each recycle, for example, by the build-up of lipids present in the biomass that is fed to the fermentation vessel as feedstock of hydrolysable starch. As an example, a liquefied corn mash loaded to a fermentation vessel at 30 wt % dry corn solids can result in a fermentation broth that contains about 1.2 wt % corn oil during conversion of glucose to butanol by simultaneous saccharification and fermentation (SSF) (with saccharification of the liquefied mash occurring during fermentation by the addition of glucoamylase to produce glucose). The dissolution of the corn oil lipids in oleyl alcohol (OA) serving as an extractant during ISPR can result in build-up of lipid concentration with each OA recycle, decreasing the partition coefficient for the product alcohol in OA as the lipid concentration in OA increases with each recycle of OA.

In addition, the presence of the undissolved solids during extractive fermentation can negatively affect the efficiency of alcohol production. For example, the presence of the undissolved solids may lower the mass transfer coefficient inside the fermentation vessel, impede phase separation in the fermentation vessel, result in the accumulation of corn oil from the undissolved solids in the extractant leading to reduced extraction efficiency over time, increase the loss of solvent because it becomes trapped in solids and ultimately removed as Dried Distillers' Grains with Solubles (DDGS), slow the disengagement of extractant drops from the fermentation broth, and/or result in a lower fermentation vessel volume efficiency.

Several approaches for reducing the degradation of the extractant used in extractive fermentation with lipid have included biomass wet milling, fractionation, and removal of solids. Wet milling is an expensive, multi-step process that separates a biomass (e.g., corn) into its key components (germ, pericarp fiber, starch, and gluten) in order to capture value from each co-product separately. This process gives a purified starch stream; however, it is costly and includes the separation of the biomass into its non-starch components which is unnecessary for fermentative alcohol production. Fractionation removes fiber and germ which contains a majority of the lipids present in ground whole grain such as corn, resulting in corn that has a higher starch (endosperm) content. Dry fractionation does not separate the germ and fiber and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn. Removal of solids including germ containing lipids, from liquefied mash prior to use in fermentation can substantially eliminate undissolved solids as described, for example, in co-pending, commonly owned U.S. Provisional Application Ser. No. 61/356,290, filed Jun. 18, 2010. However, it would be advantageous if the degradation of the partition coefficient of the extractant can be reduced even without fractionation or removal of undissolved solids. Thus, there is a continuing need to develop more efficient methods and systems for producing product alcohols, such as butanol, through extractive fermentation in which the degradation of the partition coefficient of the extractant is reduced.

Moreover, the extractant (e.g., oleyl alcohol) is typically added to the fermentation process, rather than produced at a step in the process and therefore, the extractant is a raw material expense. Since extractant can be lost by adsorption on non-fermentable solids and/or diluted by lipids introduced into the fermentation process, the economics of an alcohol production process can be affected by the efficiency of the extractant recovery and recycle. Thus, there exists a continuing need for alternative extractants for ISPR that can result in a more economical process by reducing capital and/or operating costs.

BRIEF SUMMARY OF THE INVENTION

The present invention satisfies the above needs by providing methods for producing product alcohols such as butanol, in which the lipids in a biomass are converted into an extractant that can be used in ISPR, and in which the amount of lipids that are fed to the fermentation vessel with the feedstock and/or upon extractant recycle, are decreased. The present invention offers a solution to the degradation of the ability of the extractant to extract a product alcohol (e.g., butanol) by preventing the lowering of the partition coefficient for the product alcohol into the extractant. The application offers a solution to the contamination of the extractant by triglycerides that lower the partition coefficient of the extractant for a product alcohol. The present invention provides further related advantages as will be made apparent by the description of the embodiments that follow.

Catalytic (e.g., enzymatic) hydrolysis of lipids derived from biomass into fatty acids can decrease the rate of undesirable build-up of lipids in the ISPR extractant. The fatty acids can be obtained from hydrolysis of lipids found in the biomass which supplies the fermentable carbon for fermentation. Fatty acids would not be expected to decrease the partition coefficient of the product alcohol such as a butanol into the extractant phase as much as the lipids, as the partition coefficient for butanol from water to fatty acids has been determined to be significantly greater than the partition coefficient for butanol from water to fatty acid esters or triglycerides. Moreover, the fatty acids can be used as an ISPR extractant which can be produced at a step in the alcohol production process and can be used in place of, or in addition to, a supplied, exogenous ISPR extractant that is not produced in the process (such as, but not limited to, oleyl alcohol or oleic acid), thereby reducing the raw material expense for the ISPR extractant.

In one embodiment, the present invention is directed to a method comprising contacting biomass comprising water, fermentable carbon source, and oil with one or more catalyst whereby at least a portion of the oil is hydrolyzed by one or more catalyst to form an extractant, wherein the fermentable carbon source and the oil are both derived from the biomass. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase.

In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids and fatty amides. In a further embodiment, a partition coefficient of the extractant for the product alcohol may be greater than a partition coefficient of the oil of the biomass for the product alcohol.

The method of the present invention may further comprise the step of inactivating the catalyst after at least a portion of the oil is hydrolyzed. In another embodiment, the method may further comprise the step of separating the oil from the biomass prior to hydrolysis by one or more catalyst. The claimed method may also further comprise the steps of contacting the biomass with a fermentation broth in a fermentation vessel; fermenting the carbon source of the biomass to produce a product alcohol; and removing in situ the product alcohol from the fermentation broth by contacting the broth with the extractant. The product alcohol may be butanol.

In another embodiment, the present invention is directed to a method for producing an alcohol comprising (a) providing biomass comprising water, fermentable carbon source, and oil; (b) liquefying the biomass to produce a liquefied biomass; (c) contacting the liquefied biomass with one or more catalysts whereby at least a portion of the oil is hydrolyzed to form an extractant; (d) contacting the liquefied biomass with a saccharification enzyme capable of converting oligosaccharides into fermentable sugar; (e) contacting the liquefied biomass with a fermentation broth in a fermentation vessel; (f) fermenting the carbon source of the liquefied biomass to produce a product alcohol; (g) removing in situ the product alcohol from the fermentation broth by contacting the broth with the extractant; and optionally steps (c) and (d) occur concurrently. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase. In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids or fatty amides. In a further embodiment, a partition coefficient of the extractant for the product alcohol may be greater than a partition coefficient of the oil of the biomass for the product alcohol. The method of the present invention may further comprise the step of inactivating the catalyst after at least a portion of the oil is hydrolyzed. The product alcohol may be butanol.

The present invention is also directed to a composition comprising a recombinant microorganism capable of producing an alcohol; fermentable carbon source; one or more catalysts capable of hydrolyzing glycerides into fatty acids; oil comprising glycerides; and fatty acids. The one or more catalysts may be selected from esterase, lipase, phospholipase, and lysophospholipase, and the oil may be corn, tallow, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha and vegetable oil blends. In a further embodiment, the fermentable carbon source and the oil are derived from biomass. The biomass may comprise corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. The composition may further comprise a saccharification enzyme and/or undissolved solids. The composition may also comprise at least one or more of monoglycerides, diglycerides, triglycerides, glycerol, monosaccharides, oligosaccharides, or alcohol. In addition, the alcohol may be butanol.

In some embodiments, a method of removing oil derived from biomass from a fermentation process includes contacting an aqueous biomass feedstream with a catalyst. The feedstream includes water, fermentable carbon and an amount of oil, and the fermentable carbon and the oil are both derived from the biomass. At least a portion of the oil is hydrolyzed according to methods described in the present invention into fatty acids to form a catalyst-treated biomass feedstream including the fatty acids.

In some embodiments, a method of producing an extractant for in situ removal of a product alcohol includes providing biomass which includes sugar and oil, the oil having an amount of triglycerides, and contacting the oil with a composition including one or more enzymes capable of hydrolyzing the triglycerides into fatty acids. The triglycerides in the oil are hydrolyzed to form a fermentation product extractant having a partition coefficient for the product alcohol greater than a partition coefficient of the oil of the biomass for the product alcohol.

In some embodiments, a method for producing butanol includes (a) providing biomass having starch and oil, the oil including an amount of glycerides; (b) liquefying the biomass to produce a liquefied biomass, the liquefied biomass including oligosaccharides hydrolyzed from the starch; (c) contacting the biomass of step (a) or the liquefied biomass of step (b) with a composition having one or more enzymes capable of converting the glycerides into free fatty acids whereby the free fatty acids form a fermentation product extractant; (d) contacting the liquefied biomass with a saccharification enzyme capable of converting oligosaccharides into fermentable sugar including monomeric glucose; (e) contacting the liquefied biomass with a biocatalyst capable of converting the fermentable sugar to butanol whereby a fermentation product comprising butanol is produced; and (f) contacting the fermentation product with the fermentation product extractant whereby the butanol is separated from the fermentation product, the fermentation product extractant having a partition coefficient for the butanol greater than a partition coefficient of the oil of the biomass for the butanol.

In some embodiments, a method includes, at a step during a process to produce a product alcohol from a feedstock, contacting the product alcohol with an extractant comprising free fatty acids obtained from enzymatic hydrolysis of a native oil wherein the oil comprises glycerides. The extractant has a partition coefficient for the product alcohol greater than a partition coefficient of the native oil for the product alcohol.

In some embodiments, the process to produce a product alcohol from a feedstock includes (a) liquefying the feedstock to create a feedstock slurry; (b) centrifuging the feedstock slurry of (a) to produce a centrifuge product including (i) an aqueous layer comprising sugar, (ii) a plant-derived oil layer, and (iii) a solids layer; (c) feeding the aqueous layer of (b) to a fermentation vessel; and (d) fermenting the sugar of the aqueous layer to produce the product alcohol.

In some embodiments, the process to produce a product alcohol from a feedstock further includes adding the extractant to the fermentation vessel to form a two-phase mixture comprising an aqueous phase and a product alcohol-containing organic phase.

In some embodiments, the native oil is a plant-derived oil, and in some embodiments, the process to produce a product alcohol from a feedstock further includes obtaining the plant-derived oil from the plant-derived oil layer; and converting the plant-derived oil into the extractant by contacting the oil with one or more enzymes that hydrolyze the glycerides into free fatty acids.

In some embodiments, the process to produce a product alcohol from a feedstock further includes inactivating the one or more enzymes after at least a portion of the glycerides have been hydrolyzed into free fatty acids.

In some embodiments, the process to produce a product alcohol from a feedstock further includes feeding the plant-derived oil to the fermentation vessel prior to the step of converting the plant-derived oil into the extractant.

In some embodiments, the process to produce a product alcohol from a feedstock further includes adding a second extractant to the fermentation vessel to form a two-phase mixture comprising an aqueous phase and a product alcohol-containing organic phase.

In some embodiments, the plant-derived oil is converted to the extractant after the step of adding a second extractant.

In some embodiments, a method of removing oil derived from biomass from a fermentation process, includes (a) providing a fermentation broth comprising a product alcohol and oil derived from biomass, the oil including glycerides; (b) contacting the fermentation broth with a first extractant to form a two-phase mixture comprising an aqueous phase and an organic phase, wherein the product alcohol and the oil partition into the organic phase to form a product alcohol-containing organic phase; (c) separating the product alcohol-containing organic phase from the aqueous phase; (d) separating the product alcohol from the organic phase to produce a lean organic phase; and (e) contacting the lean organic phase with a composition comprising one or more catalysts capable of hydrolyzing the glycerides into free fatty acids to produce a second extractant comprising at least a portion of the first extractant and free fatty acids.

In some embodiments, the method further includes repeating step (b) by contacting the fermentation broth with the second extractant of step (e).

In some embodiments, an in situ fermentation extractant-forming composition includes (a) mash formed from biomass and including water, starch and oil, (b) a catalyst capable of hydrolyzing at least a portion of the triglycerides into free fatty acids, and (c) free fatty acids. The starch and the oil are both derived from the biomass, and the oil includes an amount of triglycerides.

In some embodiments, a fermentation broth includes (a) a recombinant microorganism capable of producing butanol, (b) oligosaccharides, (c) a catalyst for hydrolyzing glycerides into free fatty acids, (d) glycerides, and (e) free fatty acids.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which a liquefied biomass is contacted with a catalyst for lipid hydrolysis before fermentation.

FIG. 2 schematically illustrates an exemplary method and system of the present invention, in which a liquefied and saccharified biomass is contacted with a catalyst for lipid hydrolysis before fermentation.

FIG. 3 schematically illustrates an exemplary method and system of the present invention, in which lipids in a biomass feedstream are contacted with a catalyst for lipid hydrolysis before or during liquefaction.

FIG. 4 schematically illustrates an exemplary method and system of the present invention, in which undissolved solids and lipids are removed from a liquefied biomass before fermentation, and in which the removed lipids are hydrolyzed into free fatty acids using a catalyst, and the free fatty acids are supplied to the fermentation vessel.

FIG. 5 schematically illustrates an exemplary method and system of the present invention, in which lipids derived from native oil are hydrolyzed into free fatty acids using a catalyst, and the free fatty acids are supplied to the fermentation vessel.

FIG. 6 schematically illustrates an exemplary method and system of the present invention, in which biomass lipids present in a first extractant exiting a fermentation vessel are converted into free fatty acids that are supplied to a fermentation vessel as a second extractant.

DETAILED DESCRIPTION OF THE INVENTION

Figure 1:
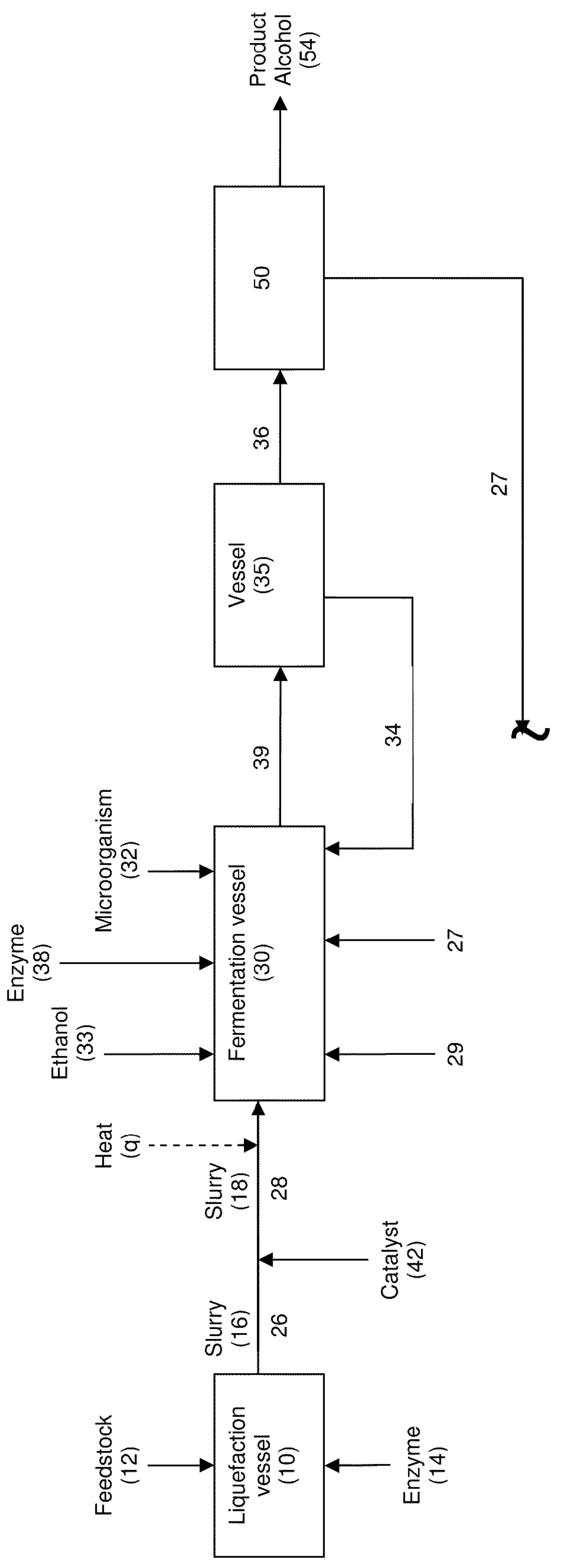

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Mash, juice, molasses, or hydrolysate may include feedstock 12 and feedstock slurry 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, cane, barley, cellulosic material, lignocellulosic material, or mixtures thereof.

"Fermentation broth" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation medium" and "fermented mixture" can be used synonymously with "fermentation broth."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Fermentation vessel" as used herein means the vessel in which the fermentation reaction is carried out whereby product alcohol such as butanol is made from sugars.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessel may be one in the same vessel.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten.

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), tert-butanol, and/or isobutanol (iBuOH or i-BuOH or I-BUOH, also known as 2-methyl-1-propanol), either individually or as mixtures thereof. From time to time, when referring to esters of butanol, the terms "butyl esters" and "butanol esters" may be used interchangeably.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "alcohol equivalent" as used herein refers to the weight of alcohol that would be obtained by a perfect hydrolysis of an alcohol ester and the subsequent recovery of the alcohol from an amount of alcohol ester.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium. For example, the effective titer of butanol in a unit volume of a fermentation includes: (i) the amount of butanol in the fermentation medium; (ii) the amount of butanol recovered from the organic extractant; (iii) the amount of butanol recovered from the gas phase, if gas stripping is used; and (iv) the alcohol equivalent of the butanol ester in either the organic or aqueous phase.

"In Situ Product Removal (ISPR)" as used herein means the selective removal of a specific fermentation product from a biological process such as fermentation, to control the product concentration in the biological process as the product is produced.

"Extractant" or "ISPR extractant" as used herein means an organic solvent used to extract any product alcohol such as butanol or used to extract any product alcohol ester produced by a catalyst from a product alcohol and a carboxylic acid or lipid. From time to time, as used herein the term "solvent" may be used synonymously with "extractant." For the processes described herein, extractants are water-immiscible.

The terms "water-immiscible" or "insoluble" refer to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The term "carboxylic acid" as used herein refers to any organic compound with the general chemical formula —COOH in which a carbon atom is bonded to an oxygen atom by a double bond to make a carbonyl group (—C═O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein refers to an alcohol having an aliphatic chain of $C_4$ to $C_{22}$ carbon atoms, which is either saturated or unsaturated.

The term "fatty aldehyde" as used herein refers to an aldehyde having an aliphatic chain of $C_4$ to $C_{22}$ carbon atoms, which is either saturated or unsaturated.

The term "fatty amide" as used herein refers to an amide having a long, aliphatic chain of $C_4$ to $C_{22}$ carbon atoms, which is either saturated or unsaturated The term "fatty ester" as used herein refers to an ester having a long aliphatic chain of $C_4$ to $C_{22}$ carbon atoms, which is either saturated or unsaturated.

"Native oil" as used herein refers to lipids obtained from plants (e.g., biomass) or animals. "Plant-derived oil" as used herein refers to lipids obtain from plants in particular. From time to time, "lipids" may be used synonymously with "oil" and "acyl glycerides." Native oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

The term "separation" as used herein is synonymous with "recovery" and refers to removing a chemical compound from an initial mixture to obtain the compound in greater purity or at a higher concentration than the purity or concentration of the compound in the initial mixture.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

The present invention provides extractants obtained by catalytic hydrolysis of oil glycerides derived from biomass and methods of producing the extractants. In particular, the glycerides in biomass oil can be catalytically hydrolyzed into fatty acids using a catalyst such as an enzyme. The fatty acids can serve as extractants for in situ removal of a product alcohol such as butanol from a fermentation broth. Thus, the present invention also provides methods for producing a product alcohol such as butanol through extractive fermentation using the extractants that were produced from the biomass oil. The present invention also provides methods for catalytically hydrolyzing the oil present in a feedstock slurry into fatty acids prior to fermentation, whereby the oil is converted to fatty acids and the degradation of the partition coefficient of the ISPR extractant over time that is attributable to the presence of the oil in the fermentation vessel can be reduced. Moreover, the fatty acids obtained by hydrolysis of the feedstock oil can serve as an ISPR extractant having a partition coefficient for a fermentative alcohol greater than a partition coefficient of the feedstock oil for the fermentative alcohol. The feedstock oil can be separated from the feedstock slurry prior to hydrolysis and used as an ISPR extractant, or the oil can be hydrolyzed into fatty acids while in the feedstock slurry. Further, fatty acids as ISPR extractant can be used in place of or in addition to a conventional exogenous extractant, such as oleyl alcohol or oleic acid, thereby reducing the raw material expense associated with the exogenous extractant.

The present invention will be described with reference to the Figures. FIG. 1 illustrates an exemplary process flow diagram for production of fermentative alcohol according to an embodiment of the present invention. As shown, a feedstock 12 can be introduced to an inlet in a liquefaction vessel 10 and liquefied to produce a feedstock slurry 16. Feedstock 12 contains hydrolysable starch that supplies a fermentable carbon source (e.g., fermentable sugar such as glucose), and can be a biomass such as, but not limited to, rye, wheat, corn, cane, barley, cellulosic material, lignocellulosic material, or mixtures thereof, or can otherwise be derived from a biomass. In some embodiments, feedstock 12 can be one or more components of a fractionated biomass and in other embodiments, feedstock 12 can be a milled, unfractionated biomass. In some embodiments, feedstock 12 can be corn such as dry milled, unfractionated corn kernels, and the undissolved solids can include germ, fiber, and gluten. The undissolved solids are non-fermentable portions of feedstock 12. For purposes of the discussion herein with reference to the embodiments shown in the Figures, feedstock 12 will often be described as constituting milled, unfractionated corn in which the undissolved solids have not been separated therefrom. However, it should be understood that the exemplary methods and systems described herein can be modified for different feedstocks whether fractionated or not, as apparent to one of skill in the art. In some embodiments, feedstock 12 can be high-oleic corn, such that corn oil derived therefrom is a high-oleic corn oil having an oleic acid content of at least about 55 wt % oleic acid. In some embodiments, the oleic acid content in high-oleic corn oil can be up to about 65 wt %, as compared with the oleic acid content in normal corn oil which is about 24 wt %. High-oleic oil can provide some advantages for use in the methods of the present invention, as hydrolysis of the oil provides fatty acids having a high oleic acid content for contacting with a fermentation broth. In some embodiments, the fatty acids or mixtures thereof comprise unsaturated fatty acids. The presence of unsaturated fatty acids decreases the melting point, providing advantages for handling. Of the unsaturated fatty acids, those which are monounsaturated, that is, possessing a single carbon-carbon double bond, may provide advantages with respect to melting point without sacrificing suitable thermal and oxidative stability for process considerations.

The process of liquefying feedstock 12 involves hydrolysis of starch in feedstock 12 into sugars including, for example, dextrins and oligosaccharides, and is a conventional process. Any known liquefying processes, as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to liquefaction vessel 10. In some embodiments, a saccharification enzyme, for example, glucoamylase, may also be introduced to liquefaction vessel 10. In additional embodiments, a lipase may also be introduced to liquefaction vessel 10 to catalyze the conversion of one or more components of the oil to fatty acids.

Feedstock slurry 16 produced from liquefying feedstock 12 includes sugar, oil 26, and undissolved solids derived from the biomass from which feedstock 12 was formed. In some embodiments, the oil is in an amount of about 0 wt % to at least about 2 wt % of the fermentation broth composition. In some embodiments, the oil is in an amount of at least about 0.5 wt % of the feedstock. Feedstock slurry 16 can be discharged from an outlet of liquefaction vessel 10. In some embodiments, feedstock 12 is corn or corn kernels and therefore, feedstock slurry 16 is a corn mash slurry.

A catalyst 42 can be added to feedstock slurry 16. Catalyst 42 is capable of hydrolyzing glycerides in oil 26 to free fatty acids (FFA) 28. For example, when feedstock 12 is corn, then oil 26 is the feedstock's constituent corn oil, and the free fatty acids 28 are corn oil fatty acids (COFA). Thus, after introduction of catalyst 42 to feedstock slurry 16, at least a portion of the glycerides in oil 26 are hydrolyzed to FFA 28, resulting in a feedstock slurry 18 having FFA 28 and catalyst 42. The resulting acid/oil composition from hydrolyzing oil 26 is typically at least about 17 wt % FFA. In some embodiments, the resulting acid/oil composition from hydrolyzing oil 26 is at least about 20 wt % FFA, at least about 25 wt % FFA, at least about 30 wt % FFA, at least about 35 wt % FFA, at least about 40 wt % FFA, at least about 45 wt % FFA, at least about 50 wt % FFA, at least about 55 wt % FFA, at least about 60 wt % FFA, at least about 65 wt % FFA, at least about 70 wt % FFA, at least about 75 wt % FFA, at least about 80 wt % FFA, at least about 85 wt % FFA, at least about 90 wt % FFA, at least about 95 wt % FFA, or at least about 99 wt % FFA. In some embodiments, the concentration of the fatty acid (such as carboxylic acid) in the fermentation vessel exceeds the solubility limit in the aqueous phase and results in the production a two-phase fermentation mixture comprising an organic phase and an aqueous phase. In some embodiments, the concentration of carboxylic acid (or fatty acid) in the fermentation broth is typically not greater than about 0.8 g/L and is limited by the solubility of the carboxylic acid (or fatty acid) in the broth.

In some embodiments, catalyst 42 can be one or more enzymes, for example, hydrolase enzymes such as lipase enzymes. Lipase enzymes used may be derived from any source including, for example, *Absidia, Achromobacter, Aeromonas, Alcaligenes, Alternaria, Aspergillus, Achromobacter, Aureobasidium, Bacillus, Beauveria, Brochothrix, Candida, Chromobacter, Coprinus, Fusarium, Geotricum, Hansenula, Humicola, Hyphozyma, Lactobacillus, Metarhizium, Mucor, Nectria, Neurospora, Paecilomyces, Penicillium, Pseudomonas, Rhizoctonia, Rhizomucor, Rhizopus, Rhodosporidium, Rhodotorula, Saccharomyces, Sus, Sporobolomyces, Thermomyces, Thiarosporella, Trichoderma, Verticillium*, and/or a strain of *Yarrowia*. In a preferred aspect, the source of the lipase is selected from the group consisting of *Absidia blakesleena, Absidia corymbifera, Achromobacter iophagus, Alcaligenes* sp., *Alternaria brassiciola, Aspergillus flavus, Aspergillus niger, Aspergillus tubingensis, Aureobasidium pullulans, Bacillus pumilus, Bacillus strearothermophilus, Bacillus subtilis, Brochothrix thermosohata, Candida cylindracea* (*Candida rugosa*), *Candida paralipolytica, Candida Antarctica* lipase A, *Candida antartica* lipase B, *Candida ernobii, Candida deformans, Chromobacter viscosum, Coprinus cinerius, Fusarium oxysporum, Fusarium solani, Fusarium solani pisi, Fusarium roseum culmorum, Geotricum penicillatum, Hansenula anomala, Humicola brevispora, Humicola brevis* var. *thermoidea, Humicola insolens, Lactobacillus curvatus, Rhizopus oryzae, Penicillium cyclopium, Penicillium crustosum, Penicillium expansum, Penicillium* sp. I, *Penicillium* sp. II, *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri*, and *Pseudomonas wisconsinensis, Rhizoctonia solani, Rhizomucor miehei, Rhizopus japonicus, Rhizopus microsporus, Rhizopus nodosus, Rhodosporidium toruloides, Rhodotorula glutinis, Saccharomyces cerevisiae, Sporobolomyces shibatanus, Sus scrofa, Thermomyces lanuginosus* (formerly *Humicola lanuginose*), *Thiarosporella phaseolina, Trichoderma harzianum, Trichoderma reesei*, and *Yarrowia lipolytica*. In a further preferred aspect, the lipase is selected from the group consisting of *Thermomcyces lanuginosus* lipase, *Aspergillus* sp. lipase, *Aspergillus niger lipase, Aspergillus tubingensis lipase, Candida antartica* lipase B, *Pseudomonas* sp. lipase, *Penicillium roqueforti* lipase, *Penicillium camembertii* lipase, *Mucor javanicus lipase, Burkholderia cepacia lipase, Alcaligenes* sp. *lipase, Candida rugosa lipase, Candida parapsilosis lipase, Candida deformans* lipase, lipases A and B from *Geotrichum candidum, Neurospora crassa lipase, Nectria haematococca lipase, Fusarium heterosporum* lipase *Rhizopus delemar lipase, Rhizomucor miehei* lipase, *Rhizopus arrhizus* lipase, and *Rhizopus oryzae* lipase. Suitable commercial lipase preparations suitable as enzyme catalyst 42 include, but are not limited to Lipolase® 100 L, Lipex® 100L, Lipoclean® 2000T, Lipozyme® CALB L, Novozyme® CALA L, and Palatase 20000L, available from Novozymes, or from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* available from SigmaAldrich.

Phospholipases are enzymes that hydrolyze the ester bonds of phospholipids, but many phospholipases also can hydrolyze triglycerides, diglycerides, and monoglycerides (lipid acyl hydrolase (LAH) activity). As used herein, the term "phospholipase" encompasses enzymes having any phospholipase activity, for example, cleaving a glycerolphosphate ester linkage (catalyzing hydrolysis of a glycerolphosphate ester linkage), for example, in an oil, such as a crude oil or a vegetable oil. The phospholipase activity of the invention can generate a water extractable phosphorylated base and a diglyceride. The phospholipase activity can comprise a phospholipase C (PLC) activity; a PI-PLC activity, a phospholipase A (PLA) activity such as a phospholipase A1 or phospholipase A2 activity; a phospholipase B (PLB) activity such as a phospholipase B1 or phospholipase B2 activity, including lysophospholipase (LPL) activity and/or lysophospholipase-transacylase (LPT A) activity; a phospholipase D (PLD) activity such as a phospholipase DI or a phospholipase D2 activity; and/or a patatin activity or any combination thereof. The term "phospholipase" also encompasses enzymes having lysophospholipase activity, where the two substrates of this enzyme are 2-lysophosphatidylcholine and $H_2O$, and where its two products are glycerophosphocholine and carboxylate. Phospholipase AI (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and l-acyl-2-lysophospholipid. PLA1 and PLA2 enzymes can be intra- or extra-cellular, membrane-bound or soluble. Phospholipase C (PLC) enzymes remove the phosphate moiety to produce 1,2 diacylglycerol and a phosphate ester. Phospholipase D (PLD) enzymes produce 1,2-diacylglycerophosphate and base group. A phospholipase useful in the present invention may be obtained from a variety of biological sources, for example, but not limited to, filamentous fungal species within the genus *Fusarium*, such as a strain of *F. culmorum, F. heterosporum, F. solani*, or *F. oxysporum*; or a filamentous fungal species within the genus *Aspergillus*, such as a strain of *Aspergillus awamori, Aspergillus foetidus, Aspergillus japonicus, Aspergillus niger* or *Aspergillus oryzae*. Also useful in the present invention are *Thermomyces lanuginosus* phospholipase variants such as the commercial product Lecitase® Ultra (Novozymes A'S, Denmark). One or more phospholipases may be applied as lyophilized powder, immobilized or in aqueous solution.

After at least a portion of the glycerides are hydrolyzed, in some embodiments, catalyst 42 can be inactivated. Any method known in the art can be used to render catalyst 42 inactive. For example, in some embodiments, catalyst 42 can be inactivated by the application of heat, by adjusting the pH of the reaction mass to a pH where catalyst 42 is irreversibly inactivated, and/or by adding a chemical or biochemical species capable of selectively inactivating the catalyst activity. As shown, for example, in the embodiment of FIG. 1, heat q is applied to feedstock slurry 18, whereby catalyst 42 becomes inactive. The application of heat q can be applied to feedstock slurry 18 before feedstock slurry 18 is fed to a fermentation vessel 30. Heat-treated feedstock slurry 18 (with inactive catalyst 42) is then introduced into a fermentation vessel 30 along with a microorganism 32 to be included in a fermentation broth held in fermentation vessel 30. Alternatively, feedstock slurry 18 can be fed to fermentation vessel 30 and subjected to heat q while in the fermentation vessel, before fermentation vessel inoculation of microorganism 32. For example, in some embodiments, catalyst inactivation treatment can be achieved by heating feedstock slurry 18 with heat q to temperature of at least about 75° C. for at least about 5 minutes, at least about 75° C. for at least about 10 minutes, at least about 75° C. for at least about 15 minutes, at least about 80° C. for at least about 5 minutes, at least about 80° C. for at least about 10 minutes, at least about 80° C. for at least about 15 minutes, at least about 85° C. for at least about 5 minutes, at least about 85° C. for at least about 10 minutes, or at least about 85° C. for at least about 15 minutes. In some embodiments, after being subject to heat q, feedstock slurry 18 is cooled to an appropriate temperature for fermentation prior to introduction to fermentation vessel 30 (or prior to fermentation vessel inoculation in the case that the application of heat q is conducted in the fermentation vessel). For example, in some embodiments, the temperature of feedstock slurry 18 is about 30° C. prior to contacting with a fermentation broth.

Inactivation of catalyst 42 is preferred when it is desirable to prevent catalyst 42 from esterifying alcohol with fatty acids 28 in the fermentation vessel. In some embodiments, production of an alcohol ester by esterification of product alcohol in a fermentation medium with an organic acid (e.g., fatty acid) and a catalyst (e.g., lipase) is desirable, as further described in co-pending, commonly owned U.S. Provisional Application Ser. No. 61/368,429, filed on Jul. 28, 2010; U.S. Provisional Application Ser. No. 61/379,546, filed on Sep. 2, 2010; and U.S. Provisional Application Ser. No. 61/440,034, filed on Feb. 7, 2011, all incorporated herein in its entirety by reference thereto. For example, for butanol production, active catalyst 42 in fermentation vessel (introduced via slurry 18) can catalyze the esterification of the butanol with fatty acids 28 (introduced via slurry 18) to form fatty acid butyl esters (FABE) in situ.

Fermentation vessel 30 is configured to ferment slurry 18 to produce a product alcohol such as butanol. In particular, microorganism 32 metabolizes the fermentable sugar in slurry 18 and excretes a product alcohol. Microorganism 32 is selected from the group of bacteria, cyanobacteria, filamentous fungi, and yeasts. In some embodiments, microorganism 32 can be a bacteria such as *E. coli*. In some embodiments, microorganism 32 can be a fermentative recombinant microorganism. The slurry can include sugar, for example, in the form of oligosaccharides, and water, and can comprise less than about 20 g/L of monomeric glucose, more preferably less than about 10 g/L or less than about 5 g/L of monomeric glucose. Suitable methodology to determine the amount of monomeric glucose is well known in the art. Such suitable methods known in the art include HPLC.

In some embodiments, slurry 18 is subjected to a saccharification process in order to break the complex sugars (e.g., oligosaccharides) in slurry 18 into monosaccharides that can be readily metabolized by microorganism 32. Any known saccharification process that is routinely utilized by the industry can be used including, but not limited to, the acid process, the acid-enzyme process, or the enzyme process. In some embodiments, simultaneous saccharification and fermentation (SSF) can occur inside fermentation vessel 30, as shown in FIG. 1. In some embodiments, an enzyme 38, such as glucoamylase, can be introduced to an inlet in fermentation vessel 30 in order to breakdown the starch or oligosaccharides to glucose capable of being metabolized by microorganism 32.

Optionally, ethanol 33 may be supplied to fermentation vessel 30 to be included in the fermentation broth. In some embodiments, when a recombinant microorganism having a butanol biosynthetic pathway is used as microorganism 32 for butanol production, microorganism 32 may require supplementation of a 2-carbon substrate (e.g., ethanol) to survive and grow. Thus, in some embodiments, ethanol 33 may be supplied to fermentation vessel 30.

However, it has been surprisingly found that methods of the present invention, in which free fatty acid (e.g., FFA 28) is present in the fermentation vessel, can allow reduction of the amount of ethanol 33 typically supplied for a given recombinant microorganism without detriment to the vitality of the recombinant microorganism. Further, in some embodiments, the methods of the present invention provide that the alcohol (e.g., butanol) production rate without ethanol supplementation to be comparable with the production rate that can be realized when ethanol 33 is supplemented. As further demonstrated by the comparative examples presented in Examples 1-14 below, the butanol production rate when fatty acid but not ethanol is in the fermentation vessel can be greater than the butanol production rate when neither fatty acid nor ethanol is in the fermentation vessel. Thus, in some embodiments, the amount of ethanol 33 supplementation is reduced compared to conventional processes. For example, a typical amount of ethanol added to a fermentation vessel for microorganisms requiring supplementation of a 2-carbon substrate is about 5 g/L anhydrous ethanol (i.e., 5 g anhydrous ethanol per liter of fermentation medium). In some embodiments, the butanol fermentation is not supplemented with any ethanol 33. In the latter case, the stream of ethanol 33 is entirely omitted from the fermentation vessel. Thus, in some embodiments of the present invention, it is possible to reduce or eliminate the cost associated with supplemental ethanol 33, as well as the inconvenience associated with storing vats of ethanol 33 and supplying it to the fermentation vessel during butanol fermentation.

Moreover, regardless of ethanol supplementation, in some embodiments, the methods of the present invention can provide a higher rate of glucose uptake by microorganism 32 by virtue of the presence of fatty acids during the fermentation. The fatty acids can be introduced into fermentation vessel 30 as carboxylic acid 28, hydrolyzed from supplied oil 26, and/or derived from hydrolysis of constituent biomass oil of slurry 16. Methods for producing a product alcohol from a fermentation process in which fatty acids are produced at a step in the process and are contacted with microorganism cultures in a fermentation vessel for improving microorganism growth rate and glucose consumption are described in co-pending, commonly owned U.S. Provisional Application Ser. No. 61/368,451, filed on Jul. 28, 2010, which is incorporated herein in its entirety by reference thereto.

In fermentation vessel 30, alcohol is produced by microorganism 32. In situ product removal (ISPR) can be utilized to remove the product alcohol from the fermentation broth. In some embodiments, ISPR includes liquid-liquid extraction. Liquid-liquid extraction can be performed according to the processes described in U.S. Patent Application Publication No. 2009/0305370, the disclosure of which is hereby incorporated in its entirety. U.S. Patent Application Publication No. 2009/0305370 describes methods for producing and recovering butanol from a fermentation broth using liquid-liquid extraction, the methods comprising the step of contacting the fermentation broth with a water-immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, triglycerides, and mixtures thereof, which contacts a fermentation broth and to form a two-phase mixture comprising an aqueous phase and an organic phase. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, $C_4$ to $C_{22}$ fatty amides, and mixtures thereof, which contacts a fermentation broth and to form a two-phase mixture comprising an aqueous phase and an organic phase. Free fatty acids 28 from slurry 18 can also serve as an ISPR extractant 28. For example, when free fatty acids 28 are corn oil fatty acids (COFA), ISPR extractant 28 is COFA. ISPR extractant (FFA) 28 contacts the fermentation broth and forms a two-phase mixture comprising an aqueous phase 34 and an organic phase. The product alcohol present in the fermentation broth preferentially partitions into the organic phase to form an alcohol-containing organic phase 36. In some embodiments, fermentation vessel 30 has one or more inlets for receiving one or more additional ISPR extractants 29 which form a two-phase mixture comprising an aqueous phase and an organic phase, with the product alcohol partitioning into the organic phase.

The biphasic mixture can be removed from fermentation vessel 30 as stream 39 and introduced into a vessel 35, in which the alcohol-containing organic phase 36 is separated from the aqueous phase 34. The alcohol-containing organic phase 36 is separated from the aqueous phase 34 of the biphasic mixture stream 39 using methods known in the art including, but not limited to, siphoning, aspiration, decantation, centrifugation, using a gravity settler, membrane-assisted phase splitting, and the like. All or part of the aqueous phase 34 can be recycled into fermentation vessel 30 as fermentation medium (as shown), or otherwise discarded and replaced with fresh medium, or treated for the removal of any remaining product alcohol and then recycled to fermentation vessel 30. Then, the alcohol-containing organic phase 36 is treated in a separator 50 to recover product alcohol 54, and the resulting alcohol-lean extractant 27 can then be recycled back into fermentation vessel 30, usually in combination with fresh FFA 28 from slurry 18 and/or with fresh extractant 29 for further extraction of the product alcohol. Alternatively, fresh FFA 28 (from slurry 18) and/or extractant 29 can be continuously added to the fermentation vessel to replace the ISPR extractant(s) removed in biphasic mixture stream 39.

In some embodiments, any additional ISPR extractant 29 can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. In some embodiments, ISPR extractant 29 can be a carboxylic acid and in some embodiments, ISPR extractant 29 can be a fatty acid. In some embodiments, the carboxylic acid or fatty acid can have 4 to 28 carbons, 4 to 22 carbons in other embodiments, 8 to 22 carbons in other embodiments, 10 to 28 carbons in other embodiments, 7 to 22 carbons in other embodiments, 12 to 22 carbons in other embodiments, 4 to 18 carbons in other embodiments, 12 to 22 carbons in other embodiments, and 12 to 18 carbons in still other embodiments. In some embodiments, ISPR extractant 29 is one or more of the following fatty acids: azaleic, capric, caprylic, castor, coconut (i.e., as a naturally-occurring combination of fatty acids, including lauric, myrisitic, palmitic, caprylic, capric, stearic, caproic, arachidic, oleic, and linoleic, for example), dimer, isostearic, lauric, linseed, myristic, oleic, olive, palm oil, palmitic, palm kernel, peanut, pelargonic, ricinoleic, sebacic, soya, stearic acid, tall oil, tallow, #12 hydroxy stearic, or any seed oil. In some embodiments, ISPR extractant 29 is one or more of diacids, azelaic, dimer and sebacic acid. Thus, in some embodiments, ISPR extractant 29 can be a mixture of two or more different fatty acids. In some embodiments, ISPR extractant 29 can be a fatty acid derived from chemical or enzymatic hydrolysis of glycerides derived from native oil. For example, in some embodiments, ISPR extractant 29 can be free fatty acids 28' obtained by enzymatic hydrolysis of native oil such as biomass lipids as later described with reference to the embodiment of FIG. 5. In some embodiments, ISPR extractant 29 can be a fatty acid extractant selected from the group consisting of fatty acids, fatty alcohols, fatty amides, fatty acid methyl esters, lower alcohol esters of fatty acids, fatty acid glycol esters, hydroxylated triglycerides, and mixtures thereof, obtained from chemical conversion of native oil such as biomass lipids as described for example in co-pending, commonly owned U.S. Provisional Application Ser. No. 61/368,436, filed on Jul. 28, 2010. In such embodiments, the biomass lipids for producing extractant 29 can be from a same or different biomass source from which feedstock 12 is obtained. For example, in some embodiments, the biomass lipids for producing extractant 29 can be derived from soya, whereas the biomass source of feedstock 12 is corn. Any possible combination of different biomass sources for extractant 29 versus feedstock 12 can be used, as should be apparent to one of skill in the art. In some embodiments, additional ISPR extractant 29 includes COFA.

In situ extractive fermentation can be carried out in a batch mode or a continuous mode in fermentation vessel 30. For in situ extractive fermentation, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production, for example, the ISPR extractant can contact the fermentation medium at a time before the butanol concentration reaches a level which would be toxic to the microorganism. After contacting the fermentation medium with the ISPR extractant, the butanol product partitions into the extractant, decreasing the concentration in the aqueous phase containing the microorganism, thereby limiting the exposure of the production microorganism to the inhibitory butanol product.

The volume of the ISPR extractant to be used depends on a number of factors including the volume of the fermentation medium, the size of the fermentation vessel, the partition coefficient of the extractant for the butanol product, and the fermentation mode chosen, as described below. The volume of the extractant can be about 3% to about 60% of the fermentation vessel working volume. Depending on the efficiency of the extraction, the aqueous phase titer of butanol in the fermentation medium can be, for example, from about 1 g/L to about 85 g/L, from about 10 g/L to about 40 g/L, from about 10 g/L to about 20 g/L, from about 15 g/L to about 50 g/L or from about 20 g/L to about 60 g/L. In some embodiments, the resulting fermentation broth after alcohol esterification can comprise free (i.e., unesterified) alcohol and in some embodiments, the concentration of free alcohol in the fermentation broth after alcohol esterification is not greater than 1, 3, 6, 10, 15, 20, 25, 30 25, 40, 45, 50, 55, or 60 g/L when the product alcohol is butanol, or when the product alcohol is ethanol, the concentration of free alcohol in the fermentation broth after alcohol esterification is not greater than 15, 20, 25, 30 25, 40, 45, 50, 55, 60, 65, 70, 75, 80, 85, 90, 95, or 100 g/L. Without being held to theory, it is believed that higher butanol titer may obtained with the extractive fermentation method, in part, from the removal of the toxic butanol product from the fermentation medium, thereby keeping the level below that which is toxic to the microorganism.

In a batchwise mode of in situ extractive fermentation, a volume of organic extractant is added to the fermentation vessel and the extractant is not removed during the process. This mode requires a larger volume of organic extractant to minimize the concentration of the inhibitory butanol product in the fermentation medium. Consequently, the volume of the fermentation medium is less and the amount of product produced is less than that obtained using the continuous mode. For example, the volume of the extractant in the batchwise mode can be 20% to about 60% of the fermentation vessel working volume in one embodiment, and about 30% to about 60% in another embodiment.

Gas stripping (not shown) can be used concurrently with the ISPR extractant to remove the product alcohol from the fermentation medium.

In the embodiment of FIG. 1, the product alcohol is extracted from the fermentation broth in situ, with the separation of the biphasic mixture 39 occurring in a separate vessel 35. In some embodiments, separation of the biphasic mixture 39 can occur in the fermentation vessel, as shown in the embodiments of later described FIGS. 2 and 3 in which the alcohol-containing organic phase stream 36 exits directly from fermentation vessel 30. Aqueous phase stream 34 can also exit directly from fermentation vessel 30, be treated for the removal of any remaining product alcohol and recycled, or discarded and replaced with fresh fermentation medium. The extraction of the product alcohol by the organic extractant(s) can be done with or without the removal of the microorganism from the fermentation broth. The microorganism can be removed from the fermentation broth by means known in the art including, but not limited to, filtration or centrifugation. For example, aqueous phase stream 34 can include microorganism 32 such as yeast. Microorganism 32 can be easily separated from the aqueous phase stream, for example, in a centrifuge (not shown). Microorganism 32 can then be recycled to fermentation vessel 30 which over time can increase the production rate of alcohol production, thereby resulting in an increase in the efficiency of the alcohol production.

In a continuous mode of in situ extractive fermentation, the volume of the extractant can be about 3% to about 50% of the fermentation vessel working volume in one embodiment, about 3% to about 30% in another embodiment, 3% to about 20% in another embodiment; and 3% to about 10% in another embodiment. Because the product is continually removed from the reactor, a smaller volume of extractant is required enabling a larger volume of the fermentation medium to be used.

As an alternative to in situ extractive fermentation, the product alcohol can be extracted from the fermentation broth downstream of fermentation vessel 30. In such an instance, the fermentation broth can be removed from fermentation vessel 30 and introduced into vessel 35. Extractant 28 can then be introduced into vessel 35 and contacted with the fermentation broth to obtain biphasic mixture 39 in vessel 35, which is then separated into the organic and aqueous phases 36 and 34. Alternatively, extractant 28 can be added to the fermentation broth in a separate vessel (not shown) prior to introduction to vessel 35.

As a non-limiting prophetic example, with reference to the embodiment of FIG. 1, an aqueous suspension of ground whole corn (as feedstock 12), which can nominally contain about 4 wt % corn oil, can be treated with amylase (as liquefaction enzyme 14) at about 85° C. to 120° C. for 30 minutes to 2 hours, and the resulting liquefied mash 16 cooled to between 65° C. and 30° C. and treated with 0.1 ppm to 10 ppm (in some embodiments, 0.5 ppm to 1.0 ppm) of lipase (as catalyst 42) at pH 4.5 to 7.5 (in some embodiments, between pH 5.5 and 6.5) for sufficient time to produce from at least 30% to as high as at least 99% conversion of the available fatty acid content in lipids to free fatty acids. Optionally, the liquefied and lipase-treated mash 18 can be heated to inactivate lipase 42 prior to fermentation. Mash 18 can be cooled to about 30° C. (e.g., using a heat-exchanger) and loaded to fermentation vessel 30 at about 25% to 30 wt % dry corn solids. Saccharification of the liquefied mash 18 during fermentation by the addition of glucoamylase (as saccharification enzyme 38) can result in the production of glucose. The resulting fermentation broth can contain significantly less than the amount of corn oil (e.g., about 1.2 wt % corn oil) that can be present in a fermentation broth using a liquefied mash that has not been treated with lipase 42. In particular, the lipase 42 treatment can result in the conversion of corn oil lipids 26 (triglycerides (TG)) into COFA as FFA 28 (and some diglycerides (DG) or monoglycerides (MG)), decreasing the rate of build-up of lipids 26 in any ISPR extractant 29 (e.g., oleyl alcohol), and dissolution of COFA 28 into organic phase 36 during ISPR should not decrease the partition coefficient of butanol in organic phase 36 as much as would the dissolution of lipids (TG) into the organic phase 36.

In some embodiments, the system and processes of FIG. 1 can be modified such that feedstock slurry 16 (having oil 26) and catalyst 42 are introduced and contacted in fermentation vessel 30 so as to produce slurry 18 (having FFA 28). The fermentation vessel temperature can then be raised to heat inactivate catalyst 42. The fermentation vessel temperature can then be reduced, and the fermentation vessel can be inoculated with microorganism 32, whereby the sugars of slurry 18 can be fermented to produce a product alcohol.

In some embodiments, the system and processes of FIG. 1 can be modified such that simultaneous saccharification and fermentation (SSF) in fermentation vessel 30 is replaced with a separate saccharification vessel 60 (see FIG. 2) prior to fermentation vessel 30, as should be apparent to one of skill in the art. Thus, slurry 18 can be saccharified either before fermentation or during fermentation in an SSF process. It should also be apparent that catalyst 42 for hydrolysis of feedstock oil 26 can be introduced before, after, or contemporaneously with saccharification enzyme 38. Thus, in some embodiments, addition of enzyme 38 and catalyst 42 can be stepwise (e.g., catalyst 42, then enzyme 38, or vice versa), or substantially simultaneous (i.e., at exactly the same time as in the time it takes for a person or a machine to perform the addition in one stroke, or one enzyme/catalyst immediately following the other catalyst/enzyme as in the time it takes for a person or a machine to perform the addition in two strokes).

Figure 2:
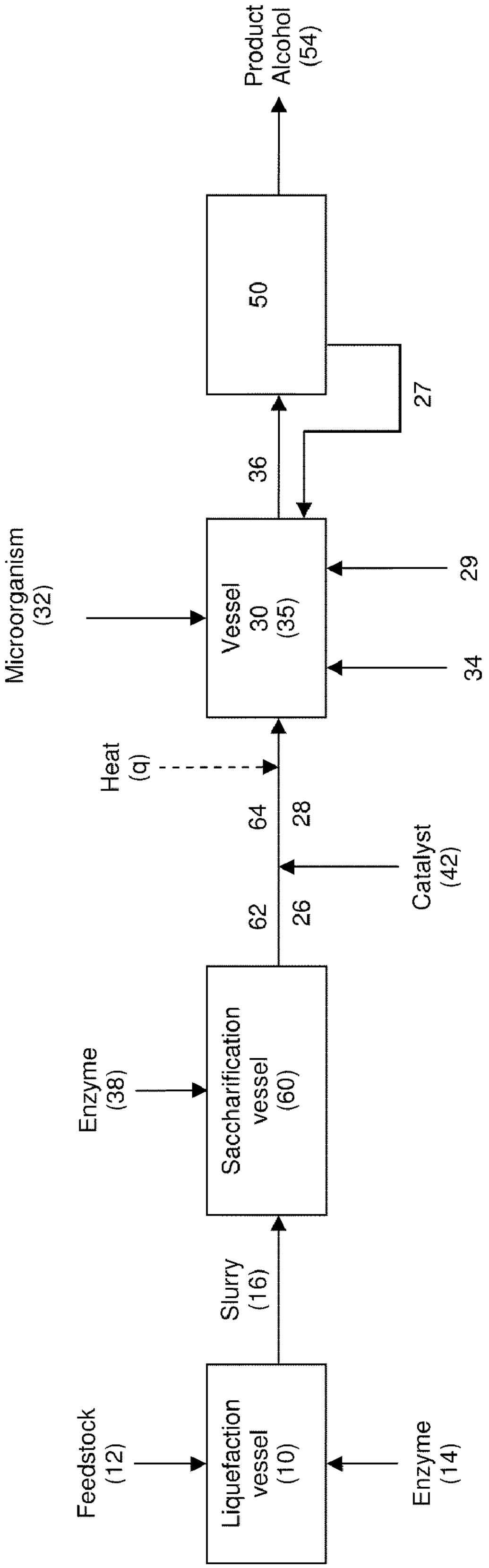

For example, as shown in the embodiment of FIG. 2, the system and processes of FIG. 1 can be modified such that simultaneous saccharification and fermentation (SSF) in fermentation vessel 30 is replaced with a separate saccharification vessel 60 prior to fermentation vessel 30. FIG. 2 is substantially identical to FIG. 1 except for the inclusion of a separate saccharification vessel 60 receiving enzyme 38, with catalyst 42 being introduced to a liquefied, saccharified feedstock stream 62. Feedstock slurry 16 is introduced into saccharification vessel 60 along with enzyme 38 such as glucoamylase, whereby sugars in the form of oligosaccharides in slurry 16 can be broken down into monosaccharides. A liquefied, saccharified feedstock stream 62 exits saccharification vessel 60 to which catalyst 42 is introduced. Feedstock stream 62 includes monosaccharides, oil 26, and undissolved solids derived from the feedstock. Oil 26 is hydrolyzed by the introduction of catalyst 42 resulting in a liquefied, saccharified feedstock slurry 64 having free fatty acids 28 and catalyst 42.

Alternatively, in some embodiments, catalyst 42 can be added with saccharification enzyme 38 to simultaneously produce glucose and hydrolyze oil lipids 26 to free fatty acids 28. The addition of enzyme 38 and catalyst 42 can be stepwise (e.g., catalyst 42, then enzyme 38, or vice versa) or simultaneous. Alternatively, in some embodiments, slurry 62 can be introduced to fermentation vessel with catalyst 42 being added directly to the fermentation vessel 30.

In the embodiment of FIG. 2, heat q is applied to feedstock slurry 64, whereby catalyst 42 becomes inactive, and heat-treated slurry 64 is then introduced to fermentation vessel 30 along with alcohol-producing microorganism 32, which metabolizes the monosaccharides to produce a product alcohol (e.g., butanol). Alternatively, slurry 64 can be fed to fermentation vessel 30 and subjected to heat q while in the fermentation vessel, before inoculation of microorganism 32.

As described above with reference to FIG. 1, free fatty acids 28 can also serve as an ISPR extractant for preferentially partitioning the product alcohol from the aqueous phase. In some embodiments, one or more additional ISPR extractants 29 can also be introduced into fermentation vessel 30. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. The remaining process operations of the embodiment of FIG. 2 are identical to FIG. 1 and therefore, will not be described in detail again.

In still other embodiments of the present invention, oil 26 derived from feedstock 12 can be catalytically hydrolyzed into FFA 28 either prior to or during liquefaction. For example, in the embodiment of FIG. 3, feedstock 12 having oil 26 is fed to liquefaction vessel 10, along with catalyst 42 for hydrolysis of at least a portion of the glycerides in oil 26 into FFA 28. Enzyme 14 (e.g., alpha-amylase) for hydrolyzing the starch in feedstock 12 can also be introduced to vessel 10 to produce a liquefied feedstock. The addition of enzyme 14 and catalyst 42 can be stepwise or simultaneous. For example, catalyst 42 can be introduced, and then enzyme 14 can be introduced after at least a portion of oil 26 has been hydrolyzed. Alternatively, enzyme 14 can be introduced, and then catalyst 42 can be introduced. The liquefaction process can involve the application of heat q. In such embodiments, it is preferred that catalyst 42 is introduced prior to or during liquefaction when the process temperature is below that which inactivates catalyst 42, so that oil 26 can be hydrolyzed. Thereafter, application of heat q can provide a two-fold purpose of liquefaction and inactivation of catalyst 42.

In any case, oil 26 in feedstock 12 is converted to FFA 28 in liquefaction vessel 10, such that biphasic feedstock slurry 18 exits liquefaction vessel 10. Biphasic slurry 18 includes both an organic phase of FFA 28 as well as sugar, water, and undissolved solids of an aqueous phase. In some embodiments, the aqueous phase can include glycerol (glycerin) from converting the glycerides in the oil to fatty acids. In some embodiments, such glycerol, if present, can be removed from the stream 18 prior to introduction into fermentation vessel 30.

Figure 3:
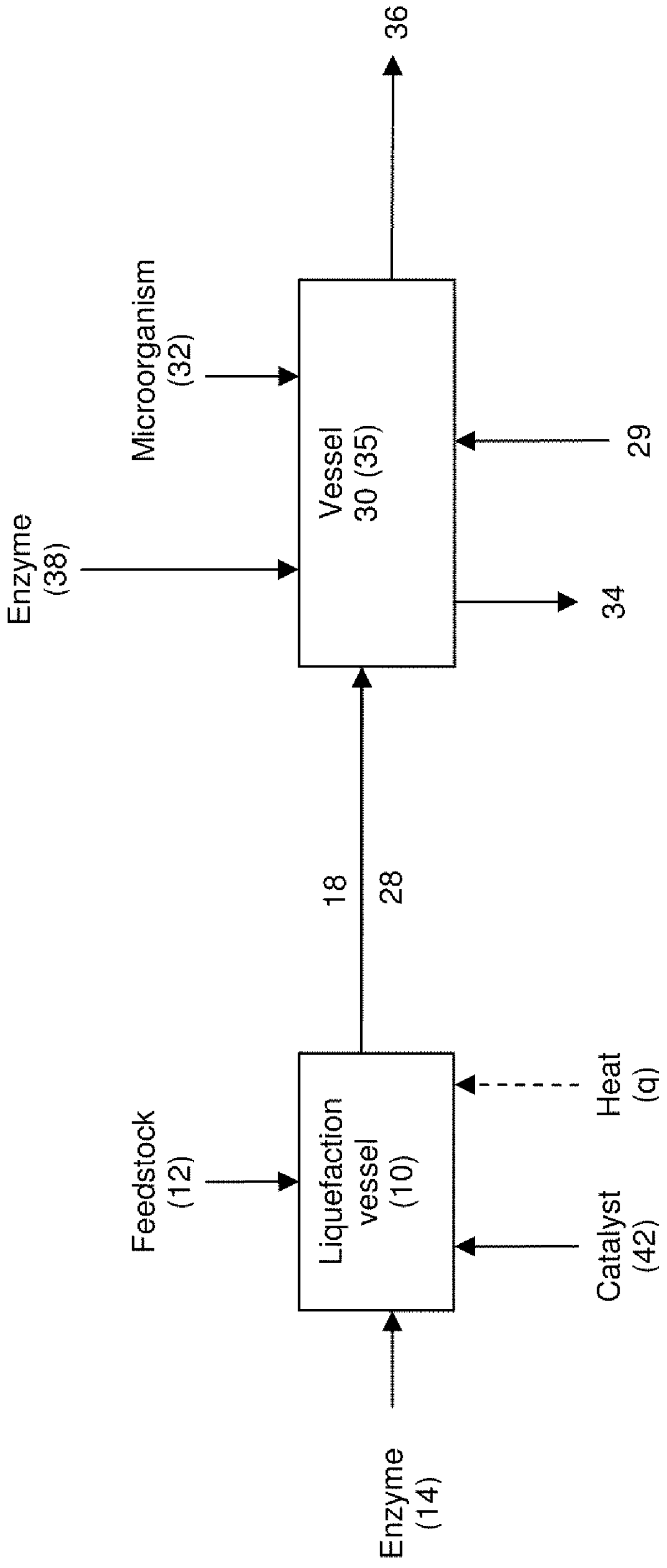

With reference to FIG. 3, biphasic stream 18 is contacted with the fermentation broth in fermentation vessel 30 to form a biphasic mixture. In fermentation vessel 30, product alcohol produced by SSF partitions into the organic phase including FFA 28. Alternatively, in some embodiments, the process can be modified to include a separate saccharification vessel as discussed in connection with FIG. 2. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Optionally, one or more additional extractants 29 can be introduced into fermentation vessel 30 to form an organic phase that preferentially partitions the product alcohol from the aqueous phase. Alcohol-containing organic phase 36 can be introduced to separator 50 for recovery of product alcohol 54 and optional recycle of recovered extractant 27 as shown in FIG. 1. The remaining process operations of the embodiment of FIG. 3 can be identical to the previously described figures and therefore, will not be described in detail again.

Figure 4:
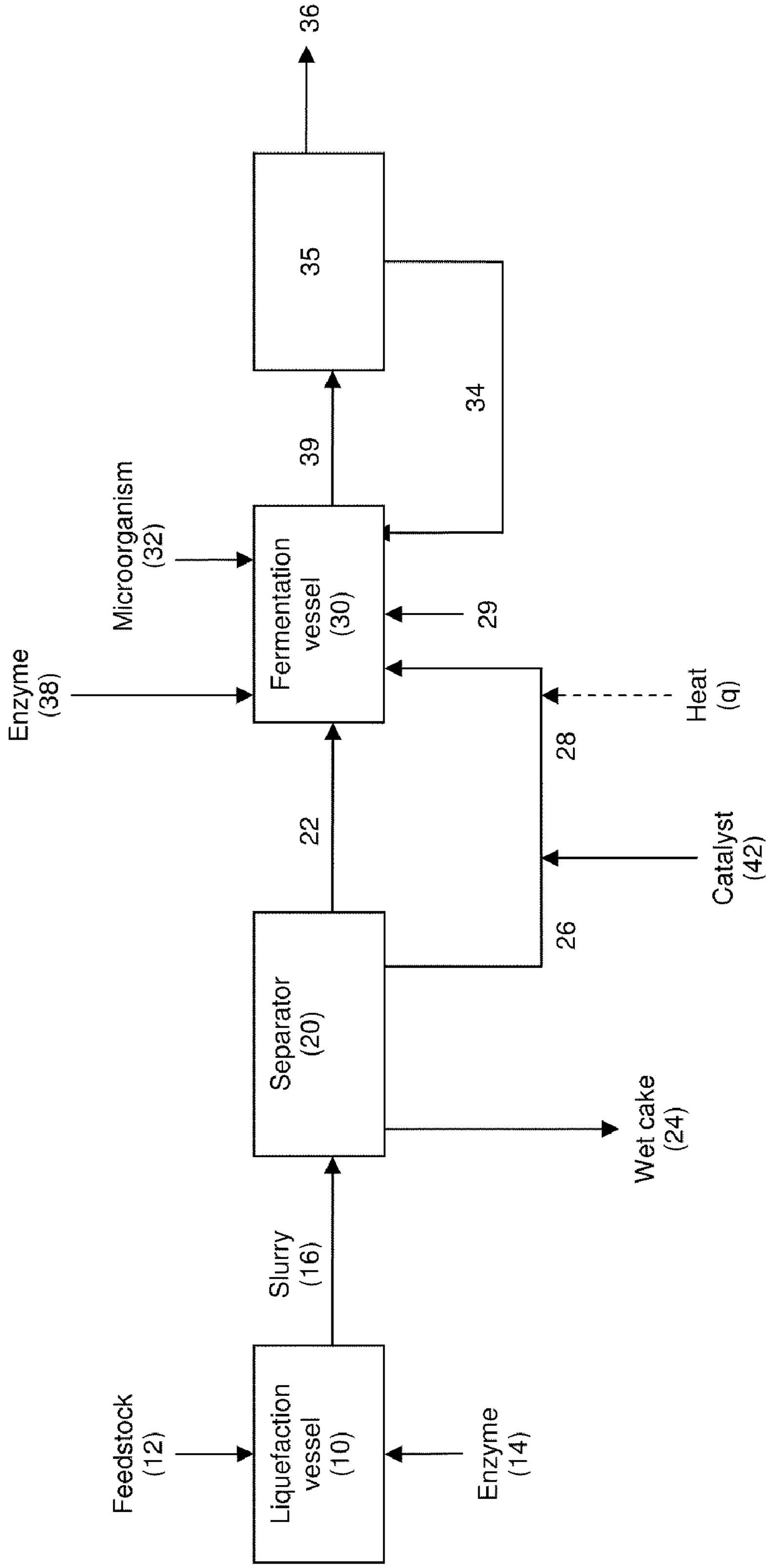

In some embodiments, including any of the earlier described embodiments with respect to FIGS. 1-3, undissolved solids can be removed from the feedstock slurry prior to introduction into fermentation vessel 30. For example, as shown in the embodiment of FIG. 4, feedstock slurry 16 is introduced into an inlet of a separator 20 which is configured to discharge the undissolved solids as a solid phase or wet cake 24. For example, in some embodiments, separator 20 may include a filter press, vacuum filtration, or a centrifuge for separating the undissolved solids from feedstock slurry 16. Optionally, in some embodiments, separator 20 can also be configured to remove some, or substantially all, of oil 26 present in feedstock slurry 16. In such embodiments, separator 20 can be any suitable separator known in the art for removing oil from an aqueous feedstream including, but not limited to, siphoning, decantation, aspiration, centrifugation, using a gravity settler, membrane-assisted phase splitting, and the like. The remaining feedstock including the sugar and water is discharged as an aqueous stream 22 to fermentation vessel 30.

In some embodiments, separator 20 removes oil 26 but not undissolved solids. Thus, aqueous stream 22 fed to fermentation vessel 30 includes undissolved solids. For example, in some embodiments, separator 20 includes a tricanter centrifuge 20 that agitates or spins feedstock slurry 16 to produces a centrifuge product comprising an aqueous layer containing the sugar and water (i.e., stream 22), a solids layer containing the undissolved solids (i.e., wet cake 24), and an oil layer (i.e., oil stream 26). In such a case, catalyst 42 can be contacted with the removed oil 26 to produce a stream of FFA 28 including catalyst 42, as shown in FIG. 4. Heat q can then be applied to the stream of FFA 28, whereby catalyst 42 becomes inactive. The stream of FFA 28 and inactive catalyst 42 can then be introduced into fermentation vessel 30, along with stream 22 and microorganism 32. Alternatively, FFA 28 and active catalyst 42 can be fed to fermentation vessel 30 from vessel 40, and active catalyst 42 can thereafter be subjected to heat q and inactivated while in the fermentation vessel, before inoculation of microorganism 32.

FFA 28 can serve as ISPR extractant 28 and forms a biphasic mixture in fermentation vessel 30. Product alcohol produced by SSF partitions into organic phase 36 constituted by FFA 28. In some embodiments, one or more additional ISPR extractants 29 can also be introduced into fermentation vessel 30. Thus, oil 26 (e.g., from feedstock) can be catalytically hydrolyzed to FFA 28, thereby decreasing the rate of build-up of lipids in an ISPR extractant while also producing an ISPR extractant. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced to separator 50 for recovery of product alcohol 54 and optional recycle of recovered extractant 27 as shown in FIG. 1. The remaining process operations of the embodiment of FIG. 4 are identical to FIG. 1 and therefore, will not be described in detail again.

When wet cake 24 is removed via centrifuge 20, in some embodiments, a portion of the oil from feedstock 12, such as corn oil when the feedstock is corn, remains in wet cake 24. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 20 can be dried to form Dried Distillers' Grains with Solubles (DDGS) through any suitable known process. The formation of the DDGS from wet cake 24 formed in centrifuge 20 has several benefits. Since the undissolved solids do not go to the fermentation vessel, DDGS does not have trapped extractant and/or product alcohol such as butanol, it is not subjected to the conditions of the fermentation vessel, and it does not contact the microorganisms present in the fermentation vessel. All these benefits make it easier to process and sell DDGS, for example, as animal feed. In some embodiments, oil 26 is not discharged separately from wet cake 24, but rather oil 26 is included as part of wet cake 24 and is ultimately present in the DDGS. In such instances, the oil can be separated from the DDGS and converted to an ISPR extractant 29 for subsequent use in the same or different alcohol fermentation process. Methods and systems for removing undissolved solids from feedstock 16 via centrifugation are described in detail in co-pending, commonly owned U.S. Patent Application No. 61/356,290, filed Jun. 18, 2010, which is incorporated herein in its entirety by reference thereto.

In still other embodiments (not shown), saccharification can occur in a separate saccharification vessel 60 (see FIG. 2) which is located between separator 20 and liquefaction vessel 10, as should be apparent to one of skill in the art.

Figure 5:
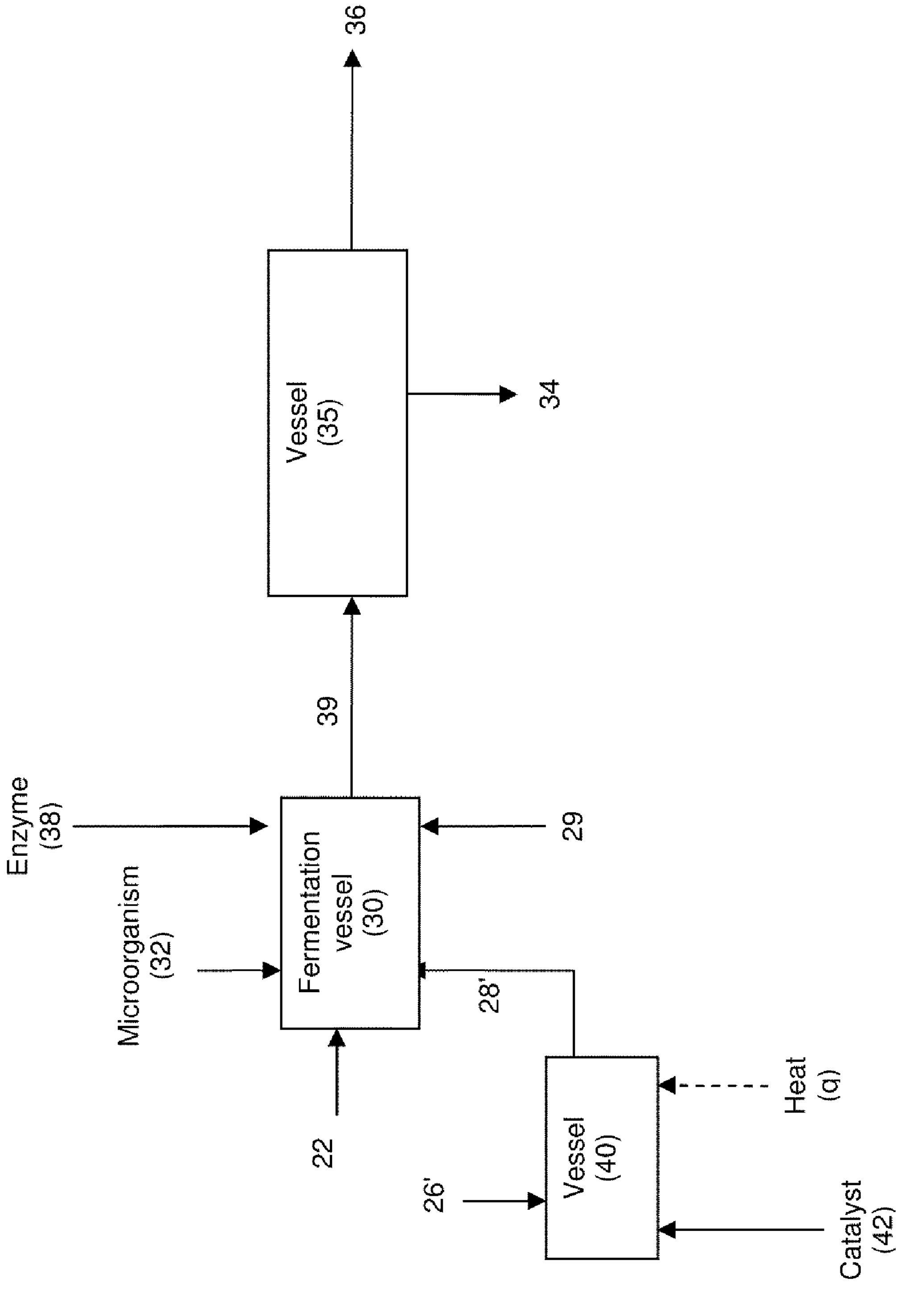

In still other embodiments, as shown, for example, in the embodiment of FIG. 5, a native oil 26' is supplied to a vessel 40 to which catalyst 42 is also supplied, whereby at least a portion of glycerides in oil 26' are hydrolyzed to form FFA 28'. Catalyst 42 can be subsequently inactivated, such as by the application of heat q. A product stream from vessel 40 containing FFA 28' and inactive catalyst 42 are then introduced into fermentation vessel 30, along with aqueous feedstock stream 22 in which feedstock oil 26, and in some embodiments, the undissolved solids have been previously removed by means of separator 20 (see, e.g., the embodiment of FIG. 4). Saccharification enzyme 38 and microorganism 32 are also introduced into fermentation vessel 30, whereby a product alcohol is produced by SSF.

Alternatively, oil 26' and catalyst 42 can be fed directly to fermentation vessel 30 in which oil 26' is hydrolyzed to FFA 28' rather than using vessel 40. Thereafter, active catalyst 42 can be subjected to heat q and inactivated while in the fermentation vessel before inoculation of microorganism 32. Alternatively, FFA 28' and active catalyst 42 can be fed to fermentation vessel 30 from vessel 40, and active catalyst 42 can thereafter be subjected to heat q and inactivated while in the fermentation vessel before inoculation of microorganism 32. In such embodiments, feedstock slurry 16 including oil 26, rather than stream 22 in which oil 26 was removed, can be fed to fermentation vessel 30 and contacted with active catalyst 42. Active catalyst 42 can therefore be used to hydrolyze oil 26 into FFA 28, thereby reducing the loss and/or degradation of the partition coefficient of the extractant over time that is attributable to the presence of the oil in the fermentation vessel.

In some embodiments, the system and processes of FIG. 5 can be modified such that simultaneous saccharification and fermentation in fermentation vessel 30 is replaced with a separate saccharification vessel 60 prior to fermentation vessel 30, as should be apparent to one of skill in the art (see, e.g., the embodiment of FIG. 2).

In some embodiments, native oil 26' can be tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, vegetable oil blends, and mixtures thereof. In some embodiments, native oil 26' is a mixture of two or more native oils, for example, a mixture of palm and soybean oils. In some embodiments, native oil 26' is a plant-derived oil. In some embodiments, the plant-derived oil can be, though not necessarily, derived from biomass that can be used in a fermentation process. The biomass can be the same or different source from which feedstock 12 (shown in FIG. 5 as stream 22) is obtained. Thus, for example, in some embodiments, oil 26' can be derived from corn, whereas feedstock 12 can be cane. For example, in some embodiments, oil 26' can be derived from corn, and the biomass source of feedstock 12 is also corn. Any possible combination of different biomass sources for oil 26' versus feedstock 12 can be used, as should be apparent to one of skill in the art.

FFA 28' can serve as an ISPR extractant 28' to form a two-phase mixture including an aqueous phase and an organic phase, with the product alcohol produced in the fermentation medium preferentially partitioning into the organic phase constituted by ISPR extractant 28'. In some embodiments, one or more additional ISPR extractants 29 can be introduced into fermentation vessel 30 as described above with reference to FIG. 1. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced in separator 50 for recovery of product alcohol 54 and optional recycle of recovered extractant 27 as shown in FIG. 1. The remaining process operations of the embodiment of FIG. 5 are identical to FIG. 1 and therefore, will not be described in detail again.

Figure 6:
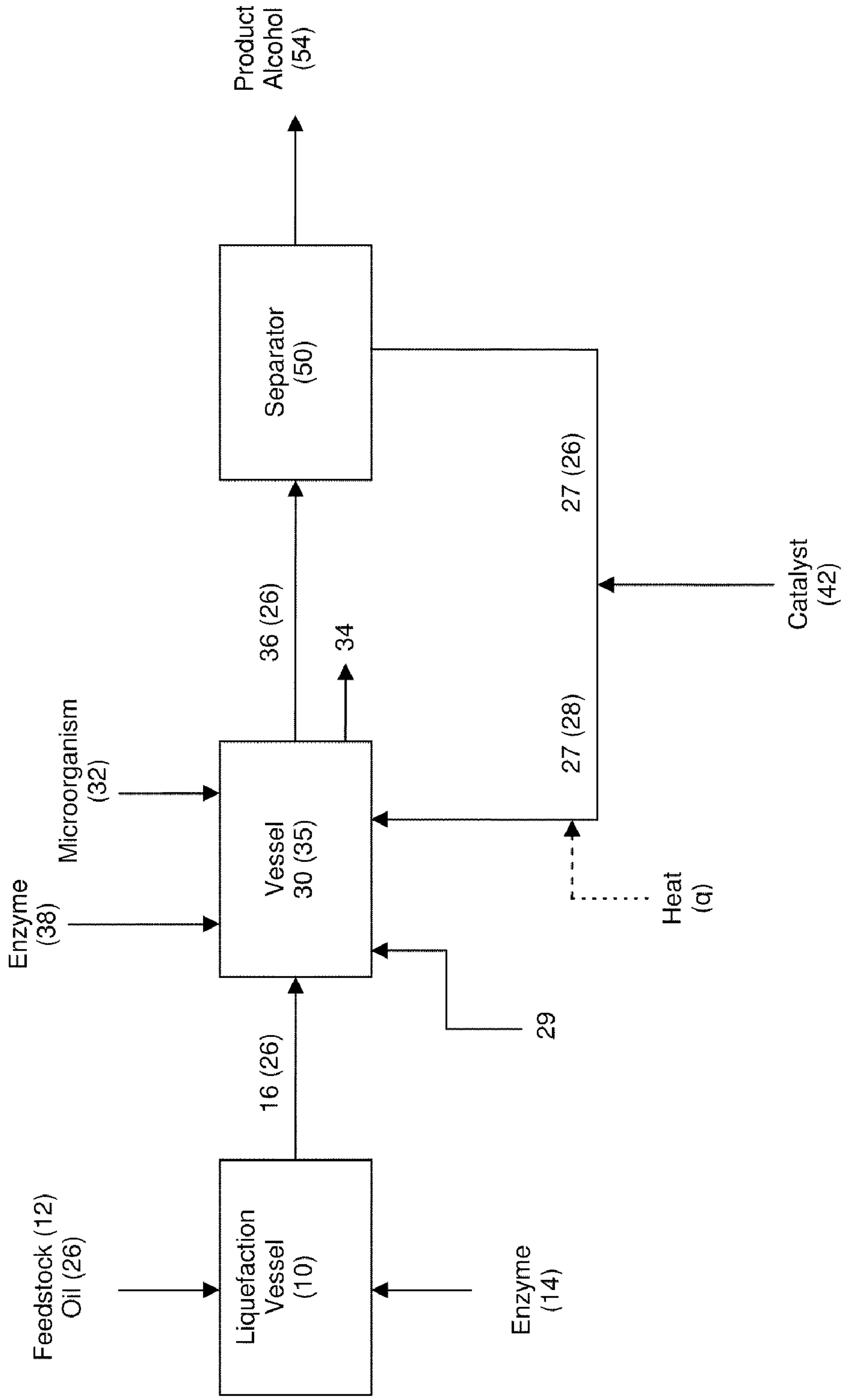

In some embodiments of the present invention, biomass oil present in feedstock 12 can be converted to FFA 28 at a step following alcoholic fermentation. FFA 28 can then be introduced as ISPR extractant 28 in the fermentation vessel. For example, in the embodiment of FIG. 6, feedstock 12 is liquefied to produced feedstock slurry 16 which includes oil 26 derived from the feedstock. Feedstock slurry 16 can also include undissolved solids from the feedstock. Alternatively, the undissolved solids can be separated from slurry 16 via a separator, such as a centrifuge (not shown). Feedstock slurry 16 containing oil 26 is introduced directly to fermentation vessel 30 containing a fermentation broth including saccharification enzyme 38 and microorganism 32. A product alcohol is produced by SSF in fermentation vessel 30. Alternatively, in some embodiments, the process can be modified to include a separate saccharification vessel as discussed in connection with FIG. 2.

ISPR extractant 29 is introduced to fermentation vessel 30 to form a biphasic mixture, and the product alcohol is removed by partitioning into the organic phase of the ISPR extractant 29. Oil 26 also partitions into the organic phase. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Organic phase stream 36 including oil 26 is introduced into separator 50 to recover product alcohol 54 from extractant 29. The resulting alcohol-lean extractant 27 includes recovered extractant 29 and oil 26. Extractant 27 is contacted with catalyst 42, whereby at least a portion of glycerides in oil 26 are hydrolyzed to form FFA 28. Heat q can then be applied to extractant 27 including FFA 28 so as to inactivate catalyst 42 before being recycled back into fermentation vessel 30. Such recycled extractant stream 27 can be a separate stream or a combined stream with fresh, make-up extractant stream 29. The subsequent withdrawal of alcohol-containing organic phase 36 from fermentation vessel 30 can then include FFA 28 and ISPR extractant 29 (as fresh extractant 29 and recycled extractant 27), in addition to the product alcohol and additional oil 26 from newly introduced feedstock slurry 16. Organic phase 36 can then be treated to recover the product alcohol, and recycled back into fermentation vessel 30 after contacting with catalyst 42 for hydrolysis of additional oil 26, in the same manner as just described. In some embodiments, use of make-up ISPR extractant 29 can be phased out as the fermentation process is operated over time because the process itself can produce FFA 28 as a make-up ISPR extractant for extracting the product alcohol. Thus, the ISPR extractant can be the stream of recycled extractant 27 with FFA 28.

Thus, FIGS. 1-5 provide various non-limiting embodiments of methods and systems involving fermentation processes and FFAs 28 produced from catalytic hydrolysis of biomass derived oil 26, and FFAs 28' produced from catalytic hydrolysis of native oil 26' such as plant-derived oil that can be used as ISPR extractants 28 and 28' to remove product alcohol in extractive fermentation.

In some embodiments, including any of the aforementioned embodiments described with reference to FIGS. 1-6, the fermentation broth in fermentation vessel 30 includes at least one recombinant microorganism 32 which is genetically modified (that is, genetically engineered) to produce butanol via a biosynthetic pathway from at least one fermentable carbon source. In particular, recombinant microorganisms can be grown in a fermentation broth which contains suitable carbon substrates. Additional carbon substrates may include, but are not limited to, monosaccharides such as fructose; oligosaccharides such as lactose, maltose, or sucrose; polysaccharides such as starch or cellulose; or mixtures thereof, and unpurified mixtures from renewable feedstocks such as cheese whey permeate, cornsteep liquor, sugar beet molasses, and barley malt. Other carbon substrates may include ethanol, lactate, succinate, or glycerol.

Additionally the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C1 Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter, et al., Arch. Microbiol. 153:485-489, 1990). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassaya, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described in, for example, in U.S. Patent Application Publication No. 2007/0031918 A1, which is herein incorporated by reference. In addition to an appropriate carbon source (from aqueous stream 22), fermentation broth must contain suitable minerals, salts, cofactors, buffers and other components, known to those skilled in the art, suitable for the growth of the cultures and promotion of an enzymatic pathway comprising a dihydroxyacid dehydratase (DHAD).

Recombinant microorganisms that produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula*, or *Saccharomyces*. In one embodiment, recombinant microorganisms can be selected from the group consisting of *Escherichia coli, Lactobacillus plantarum*, and *Saccharomyces cerevisiae*. In one embodiment, the recombinant microorganism is a crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*. For example, the production of butanol utilizing fermentation with a microorganism, as well as which microorganisms produce butanol, is known and is disclosed, for example, in U.S. Patent Application Publication No. 2009/0305370, herein incorporated by reference. In some embodiments, microorganisms comprise a butanol biosynthetic pathway. Suitable isobutanol biosynthetic pathways are known in the art (see, e.g., U.S. Patent Application Publication No. 2007/0092957, herein incorporated by reference). In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in U.S. Patent Application Publication No. 2009/0305363, herein incorporated by reference.

Construction of certain strains, including those used in the Examples, is provided herein.

Construction of *Saccharomyces cerevisiae* Strain BP1083 ("NGCI-070")

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, described in U.S. Provisional Application Ser. No. 61/246,844) and pLH468 (SEQ ID NO: 2) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

URA3 Deletion

To delete the endogenous URA3 coding region, a ura3::loxP-kanMX-IoxP cassette was PCR-amplified from pLA54 template DNA (SEQ ID NO: 3). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-IoxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 μg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from

*Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 (described herein and in U.S. Provisional Application No. 61/246,709) genomic DNA as template, prepared with a Gentra® Puregene® Yeast/Bact. kit (Qiagen, Valencia, Calif.). PDC1 Fragment A-ilvDSm (SEQ ID NO: 141) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 142) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccaromyces* cerevisiae situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccaromyces* cerevisiae CEN.PK 113-7D genomic DNA was amplified with primers oBP438 (SEQ ID NO: 12) containing BamHI, Ascl, Pmel, and FseI restriction sites, and oBP439 (SEQ ID NO: 13) containing XbaI, PacI, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 (SEQ ID NO: 143) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 144) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 145) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3::loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Construction of Strains NYLA74, NYLA83, and NYLA84

Insertion-inactivation of endogenous PDC1 and PDC6 genes of *S. cerevisiae*. PDC1, PDC5, and PDC6 genes encode the three major isozymes of pyruvate decarboxylase is described as follows:

Construction of pRS425::GPM-sadB

A DNA fragment encoding a butanol dehydrogenase (SEQ ID NO: 70) from *Achromobacter xylosoxidans* (disclosed in U.S. Patent Application Publication No. 2009/0269823) was cloned. The coding region of this gene called sadB for secondary alcohol dehydrogenase (SEQ ID NO: 69) was amplified using standard conditions from *A. xylosoxidans* genomic DNA, prepared using a Gentra® Puregene® kit (Qiagen, Valencia, Calif.) following the recommended protocol for gram negative organisms using forward and reverse primers N473 and N469 (SEQ ID NOs: 74 and 75), respectively. The PCR product was TOPO®-Blunt cloned into pCR®4 BLUNT (Invitrogen™, Carlsbad, Calif.) to produce pCR4Blunt::sadB, which was transformed into *E. coli* Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs: 76 and 77). The PCR product was then cloned using "gap repair" methodology in *Saccharomyces cerevisiae* (Ma, et al., Gene 58:201-216, 1987) as follows. The yeast-*E. coli* shuttle vector pRS425::GPM::kivD::ADH which contains the GPM1 promoter (SEQ ID NO: 72), kivD coding region from *Lactococcus lactis* (SEQ ID NO: 71), and ADH1 terminator (SEQ ID NO: 73) (described in U.S. Patent Application Publication No. 2007/0092957 A1, Example 17) was digested with BbvCl and PacI restriction enzymes to release the kivD coding region. Approximately 1 μg of the remaining vector fragment was transformed into *S. cerevisiae* strain BY4741 along with 1 μg of sadB PCR product. Transformants were selected on synthetic complete medium lacking leucine. The proper recombination event, generating pRS425::GPM-sadB, was confirmed by PCR using primers N142 and N459 (SEQ ID NOs: 108 and 109).

Construction of pdc6:: PGPM1-sadB Integration Cassette and PDC6 Deletion:

A pdc6::PGPM1-sadB-ADH1t-URA3r integration cassette was made by joining the GPM-sadB-ADHt segment (SEQ ID NO: 79) from pRS425::GPM-sadB (SEQ ID NO: 78) to the URA3r gene from pUC19-URA3r. pUC19-URA3r (SEQ ID NO:80) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England BioLabs Inc., Ipswich, Mass.) and primers 114117-11A through 114117-11D (SEQ ID NOs: 81, 82, 83, and 84), and 114117-13A and 114117-13B (SEQ ID NOs: 85 and 86).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-34G and 112590-34H (SEQ ID NOs: 87 and 88), and 112590-34F and 112590-49E (SEQ ID NOs: 89 and 90) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::PGPM1-sadB-ADH1t.

Construction of pdc1:: PPDC1-ilvD Integration Cassette and PDC1 Deletion:

A pdc1:: PPDC1-ilvD-FBA1t-URA3r integration cassette was made by joining the ilvD-FBA1t segment (SEQ ID NO: 91) from pLH468 (SEQ ID NO: 2) to the URA3r gene from pUC19-URA3r by SOE PCR (as described by Horton, et al., Gene 77:61-68, 1989) using as template pLH468 and pUC19-URA3r plasmid DNAs, with Phusion® DNA polymerase (New England BioLabs Inc., Ipswich, Mass.) and primers 114117-27A through 114117-27D (SEQ ID NOs: 111, 112, 113, and 114).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::PGPM1-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs: 92 and 93), and primers 112590-49E and 112590-30F (SEQ ID NOs: 90 and 94) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6:: PGPM1-sadB-ADH1t pdc1:: PPDC1-ilvD-FBA1t.

HIS3 Deletion

To delete the endogenous HIS3 coding region, a his3::URA3r2 cassette was PCR-amplified from URA3r2 template DNA (SEQ ID NO: 95). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England BioLabs Inc., Ipswich, Mass.) and primers 114117-45A and 114117-45B (SEQ ID NOs: 96 and 97) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6:: PGPM1-sadB-ADH1t pdc1:: PPDC1-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion® DNA polymerase (New England BioLabs Inc., Ipswich, Mass.) and primers PDC5::KanMXF and PDC5::KanMXR (SEQ ID NOs: 98 and 99) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 μg/mL) at 30° C. Transformants were screened by PCR to verify correct integration at the PDC locus with replacement of the PDC5 coding region using primers PDC5kofor and N175 (SEQ ID NOs: 100 and 101). The identified correct transformants have the genotype: BY4700 pdc6:: PGPM1-sadB-ADH1t pdc1:: PPDC1-ilvD-FBA1t Δhis3 pdc5::kanMX4. The strain was named NYLA74.

Plasmid vectors pRS423::CUP1-alsS+FBA-budA and pRS426::FBA-budC+GPM-sadB were transformed into NYLA74 to create a butanediol producing strain (NGCI-047).

Plasmid vectors pLH475-Z4B8 (SEQ ID NO: 140) and pLH468 were transformed into NYLA74 to create an isobutanol producing strain (NGCI-049).

Deletion of HXK2 (Hexokinase II):

A hxk2::URA3r cassette was PCR-amplified from URA3r2 template (described above) using Phusion® DNA polymerase (New England BioLabs Inc., Ipswich, Mass.) and primers 384 and 385 (SEQ ID NOs: 102 and 103) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 104 and 105). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 106 and 107). The resulting identified strain named NYLA83 has the genotype: BY4700 pdc6:: PGPM1-sadB-ADH1t pdc1:: PPDC1-ilvD-FBA1t Δhis3 Δhxk2.

Construction of pdc5::kanMX Integration Cassette and PDC5 Deletion:

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6:: PGPM1-sadB-ADH1t pdc1:: PPDC1-ilvD-FBA1t Δhis3 Δhxk2 pdc5::kanMX4.

Plasmid vectors pLH468 and pLH532 were simultaneously transformed into strain NYLA84 (BY4700 pdc6:: PGPM1-sadB-ADH1t pdc1::PPDC1-ilvD-FBA1t Δhis3 Δhxk2 pdc5::kanMX4) using standard genetic techniques (Methods in Yeast Genetics, 2005, Cold Spring Harbor Laboratory Press, Cold Spring Harbor, N.Y.) and the resulting "butanologen NYLA84" was maintained on synthetic complete media lacking histidine and uracil, and supplemented with 1% ethanol at 30° C.

Expression Vector pLH468

The pLH468 plasmid (SEQ ID NO: 2) was constructed for expression of DHAD, KivD, and HADH in yeast and is described in U.S. Patent Application Publication No. 2009/0305363, herein incorporated by reference. pLH486 was constructed to contain: a chimeric gene having the coding region of the ilvD gene from *Streptococcus mutans* (nt position 3313-4849) expressed from the *S. cerevisiae* FBA1 promoter (nt 2109-3105) followed by the FBA1 terminator (nt 4858-5857) for expression of DHAD; a chimeric gene having the coding region of codon optimized horse liver alcohol dehydrogenase (nt 6286-7413) expressed from the *S. cerevisiae* GPM1 promoter (nt 7425-8181) followed by the ADH1 terminator (nt 5962-6277) for expression of ADH; and a chimeric gene having the coding region of the codon-optimized kivD gene from *Lactococcus* lactis (nt 9249-10895) expressed from the TDH3 promoter (nt 10896-11918) followed by the TDH3 terminator (nt 8237-9235) for expression of KivD.

Coding regions for *Lactococcus lactis* ketoisovalerate decarboxylase (KivD) and horse liver alcohol dehydrogenase (HADH) were synthesized by DNA2.0, Inc. (Menlo Park, Calif.) based on codons that were optimized for expression in *Saccharomyces cerevisiae* (SEQ ID NO: 71 and 118, respectively) and provided in plasmids pKivDy-DNA2.0 and pHadhy-DNA2.0. The encoded proteins are SEQ ID NOs: 117 and 119, respectively. Individual expression vectors for KivD and HADH were constructed. To assemble pLH467 (pRS426::PTDH3-kivDy-TDH3t), vector pNY8 (SEQ ID NO: 121; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 122) from pNY8 was PCR amplified to add an AscI site at the 5' end and an SpeI site at the 3' end, using 5' primer OT1068 and 3' primer OT1067 (SEQ ID NOs: 123 and 124). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::PTDH3-kivDy-TDH3t). pLH467 was verified by restriction mapping and sequencing.

pLH435 (pRS425::PGPM1-Hadhy-ADH1t) was derived from vector pRS425::GPM-sadB (SEQ ID NO: 78) which is described in U.S. Provisional Application Ser. No. 61/058,970, Example 3, which is herein incorporated by reference. pRS425::GPM-sadB is the pRS425 vector (ATCC No. 77106) with a chimeric gene containing the GPM1 promoter (SEQ ID NO:72), coding region from a butanol dehydrogenase of *Achromobacter xylosoxidans* (sadB; DNA SEQ ID NO: 69; protein SEQ ID NO:70: disclosed in U.S. Patent Application Publication No. 2009/0269823), and ADH1 terminator (SEQ ID NO: 73). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NOs: 126 and 127) to generate vector pRS425-GPMp-sadB-NheI, which was verified by sequencing. pRS425::PGPM1-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the PTDH3-kivDy-TDH3t cassette together with the SalI-NotI fragment from pLH435 that contains the PGPM1-Hadhy-ADH1t cassette in a triple ligation reaction. This yielded the vector pRS411::PTDH3-kivDy-PGPM1-Hadhy (pLH441) which was verified by restriction mapping.

In order to generate a co-expression vector for all three genes in the lower isobutanol pathway: ilvD, kivDy, and Hadhy, pRS423 FBA ilvD(Strep) (SEQ ID NO: 128) which is described in U.S. Patent Application Publication No. 2010/0081154 as the source of the ilvD gene, was used. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO: 120) and FBA terminator (nt 4861 to 5860; SEQ ID NO: 129). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 115; protein SEQ ID NO: 116) from *Streptococcus mutans* UA159 (ATCC No. 700610) is between the FBA promoter and FBA terminator forming a chimeric gene for expression. In addition, there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-ilvD (*Streptococcus mutans*)-Lumio. This generated vector pLH468 (pRS423::PFBA1-ilvD(Strep) Lumio-FBA1t-PTDH3-kivDy-TDH3t-PGPM1-hadhy-ADH1t) which was confirmed by restriction mapping and sequencing.

pLH532 Construction

The pLH532 plasmid (SEQ ID NO: 130) was constructed for expression of ALS and KARI in yeast. pLH532 is a pHR81 vector (ATCC No. 87541) containing the following chimeric genes: 1) the CUP1 promoter (SEQ ID NO: 139), acetolactate synthase coding region from *Bacillus subtilis*

(AlsS; SEQ ID NO: 137; protein SEQ ID NO: 138) and CYC1 terminator2 (SEQ ID NO: 133); 2) an ILV5 promoter (SEQ ID NO: 134), Pf5.1IvC coding region (SEQ ID NO: 132) and ILV5 terminator (SEQ ID NO: 135); and 3) the FBA1 promoter (SEQ ID NO: 136), S. cerevisiae KARI coding region (ILV5; SEQ ID NO: 131); and CYC1 terminator.

The Pf5.IlvC coding region is a sequence encoding KARI derived from Pseudomonas fluorescens that was described in U.S. Patent Application Publication No. 2009/0163376, which is herein incorporated by reference.

The Pf5.IlvC coding region was synthesized by DNA2.0, Inc. (Menlo Park, Calif.; SEQ ID NO: 132) based on codons that were optimized for expression in Saccharomyces cerevisiae.

pYZ090 Construction pYZ090 (SEQ ID NO: 1) is based on the pHR81 (ATCC No. 87541) backbone and was constructed to contain a chimeric gene having the coding region of the alsS gene from Bacillus subtilis (nt position 457-2172) expressed from the yeast CUP1 promoter (nt 2-449) and followed by the CYC1 terminator (nt 2181-2430) for expression of ALS, and a chimeric gene having the coding region of the ilvC gene from Lactococcus lactis (nt 3634-4656) expressed from the yeast ILV5 promoter (2433-3626) and followed by the ILV5 terminator (nt 4682-5304) for expression of KARI.

pYZ067 Construction pYZ067 was constructed to contain the following chimeric genes: 1) the coding region of the ilvD gene from S. mutans UA159 (nt position 2260-3971) expressed from the yeast FBA1 promoter (nt 1161-2250) followed by the FBA terminator (nt 4005-4317) for expression of dihydroxy acid dehydratase (DHAD), 2) the coding region for horse liver ADH (nt 4680-5807) expressed from the yeast GPM promoter (nt 5819-6575) followed by the ADH1 terminator (nt 4356-4671) for expression of alcohol dehydrogenase, and 3) the coding region of the KivD gene from Lacrococcus lactis (nt 7175-8821) expressed from the yeast TDH3 promoter (nt 8830-9493) followed by the TDH3 terminator (nt 5682-7161) for expression of ketoisovalerate decarboxylase.

pRS423::CUP1-alsS+FBA-budA and pRS426::FBA-budC+GPM-sadB and pLH475-Z4B8 Construction Construction of pRS423::CUP1-alsS+FBA-budA and pRS426::FBA-budC+GPM-sadB and pLH475-Z4B8 is described in U.S. Patent Application Publication No. 2009/0305363, incorporated herein by reference.

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock and COFA as carboxylic acid, other biomass sources can be used for feedstock and acids other than COFA can serve as carboxylic acid, without departing from the present invention. Moreover, while the following examples involve butanol and butyl ester production, other alcohols including ethanol, and alcohol esters can be produced without departing from the present invention.

As used herein, the meaning of abbreviations used was as follows: "g" means gram(s), "kg" means kilogram(s), "L" means liter(s), "mL" means milliliter(s), "μL" means microliter(s), "mL/L" means milliliter(s) per liter, "mL/min" means milliliter(s) per min, "DI" means deionized, "uM" means micrometer(s), "nm" means nanometer(s), "w/v" means weight/volume, "OD" means optical density, "$OD_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

General Methods
Seed Flask Growth

A Saccharomyces cerevisiae strain that was engineered to produce isobutanol from a carbohydrate source, with pdc1 deleted, pdc5 deleted, and pdc6 deleted, was grown to 0.55-1.1 g/L dcw ($OD_{600}$ 1.3-2.6—Thermo Helios α Thermo Fisher Scientific Inc., Waltham, Mass.) in seed flasks from a frozen culture. The culture was grown at 26° C. in an incubator rotating at 300 rpm. The frozen culture was previously stored at −80° C. The composition of the first seed flask medium was:
- 3.0 g/L dextrose
- 3.0 g/L ethanol, anhydrous
- 3.7 g/L ForMedium™ Synthetic Complete Amino Acid (Kaiser) prop-Out: without HIS, without URA (Reference No. DSCK162CK)
- 6.7 g/L Difco Yeast Nitrogen Base without amino acids (No. 291920)

Twelve milliliters from the first seed flask culture was transferred to a 2 L flask and grown at 30° C. in an incubator rotating at 300 rpm. The second seed flask has 220 mL of the following medium:
- 30.0 g/L dextrose
- 5.0 g/L ethanol, anhydrous
- 3.7 g/L ForMedium™ Synthetic Complete Amino Acid (Kaiser) prop-Out: without HIS, without URA (Reference No. DSCK162CK)
- 6.7 g/L Difco Yeast Nitrogen Base without amino acids (No. 291920)
- 0.2 M MES Buffer titrated to pH 5.5-6.0

The culture was grown to 0.55-1.1 g/L dcw ($OD_{600}$ 1.3-2.6). An addition of 30 mL of a solution containing 200 g/L peptone and 100 g/L yeast extract was added at this cell concentration. Then, an addition of 300 mL of 0.2 uM filter sterilized Cognis, 90-95% oleyl alcohol was added to the flask. The culture continues to grow to >4 g/L dcw ($OD_{600}$>10) before being harvested and added to the fermentation.

Fermentation Preparation
Initial Fermentation Vessel Preparation

A glass jacked, 2 L fermentation vessel (Sartorius AG, Goettingen, Germany) was charged with house water to 66% of the liquefaction weight. A pH probe (Hamilton Easyferm Plus K8, part number: 238627, Hamilton Bonaduz AG, Bonaduz, Switzerland) was calibrated through the Sartorius DCU-3 Control Tower Calibration menu. The zero was calibrated at pH=7. The span was calibrated at pH=4. The probe was then placed into the fermentation vessel through the stainless steel head plate. A dissolved oxygen probe ($pO_2$ probe) was also placed into the fermentation vessel through the head plate. Tubing used for delivering nutrients, seed culture, extracting solvent, and base were attached to the head plate and the ends were foiled. The entire fermentation vessel was placed into a Steris (Steris Corporation, Mentor, Ohio) autoclave and sterilized in a liquid cycle for 30 minutes.

The fermentation vessel was removed from the autoclave and placed on a load cell. The jacket water supply and return line was connected to the house water and clean drain, respectively. The condenser cooling water in and water out lines were connected to a 6-L recirculating temperature bath running at 7° C. The vent line that transfers the gas from the fermentation vessel was connected to a transfer line that was connected to a Thermo mass spectrometer (Prima dB, Thermo Fisher Scientific Inc., Waltham, Mass.). The sparger line was connected to the gas supply line. The tubing for adding nutrients, extract solvent, seed culture, and base was plumbed through pumps or clamped closed.

The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 29-30% (dry corn solids weight) of the liquefaction reaction mass.

Lipase Treatment Pre-Liquefaction

A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the lipase treatment was complete, liquefaction was performed as described below (Liquefaction).

Liquefaction

An alpha-amylase was added to the fermentation vessel per its specification sheet while the fermentation vessel was mixing at 300-1200 rpm, with sterile, house $N_2$ being added at 0.3 slpm through the sparger. The temperature set-point was changed from 55° C. to 85° C. When the temperature was >80° C., the liquefaction cook time was started and the liquefaction cycle was held at >80° C. for 90-120 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

Lipase Treatment Post-Liquefaction

The fermentation vessel temperature was set to 55° C. instead of 30° C. after the liquefaction cycle was complete (Liquefaction). The pH was manually controlled at pH=5.8 by making bolus additions of acid or base when needed. A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the Lipase Treatment was complete, the fermentation vessel temperature was set to 30° C.

Lipase Heat Inactivation Treatment (Heat Kill Treatment Method)

The fermentation vessel temperature was held at >80° C. for >15 minutes to inactivate the lipase. After the Heat Inactivation Treatment was complete, the fermentation vessel temperature was set to 30° C.

Nutrient Addition Prior to Inoculation

Ethanol (6.36 mL/L, post-inoculation volume, 200 proof, anhydrous) was added to the fermentation vessel just prior to inoculation. Thiamine was added to a final concentration of 20 mg/L and 100 mg/L nicotinic acid was also added just prior to inoculation.

Oleyl Alcohol or Corn Oil Fatty Acids Addition Prior to Inoculation

Added 1 L/L (post-inoculation volume) of oleyl alcohol or corn oil fatty acids immediately after inoculation.

Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated after the second seed flask with >4 g/L dcw. The shake flask was removed from the incubator/shaker for 5 minutes allowing a phase separation of the oleyl alcohol phase and the aqueous phase. The aqueous phase (110 mL) was transferred to a sterile, inoculation bottle. The inoculum was pumped into the fermentation vessel through a peristaltic pump.

Fermentation Vessel Operating Conditions

The fermentation vessel was operated at 30° C. for the entire growth and production stages. The pH was allowed to drop from a pH between 5.7-5.9 to a control set-point of 5.2 without adding any acid. The pH was controlled for the remainder of the growth and production stage at a pH=5.2 with ammonium hydroxide. Sterile air was added to the fermentation vessel, through the sparger, at 0.3 slpm for the remainder of the growth and production stages. The $pO_2$ was set to be controlled at 3.0% by the Sartorius DCU-3 Control Box PID control loop, using stir control only, with the stirrer minimum being set to 300 rpm and the maximum being set to 2000 rpm. The glucose was supplied through simultaneous saccharification and fermentation of the liquified corn mash by adding a α-amylase (glucoamylase). The glucose was kept excess (1-50 g/L) for as long as starch was available for saccharification.

Analytical

Gas Analysis

Process air was analyzed on a Thermo Prima (Thermo Fisher Scientific Inc., Waltham, Mass.) mass spectrometer. This was the same process air that was sterilized and then added to each fermentation vessel. Each fermentation vessel's off-gas was analyzed on the same mass spectrometer. This Thermo Prima dB has a calibration check run every Monday morning at 6:00 am. The calibration check was scheduled through the Gas Works v1.0 (Thermo Fisher Scientific Inc., Waltham, Mass.) software associated with the mass spectrometer. The gas calibrated for were:

| GAS | Calibration Concentration mole % | Cal Frequency |
|---|---|---|
| Nitrogen | 78% | weekly |
| Oxygen | 21% | weekly |
| Isobutanol | 0.2% | yearly |
| Argon | 1% | weekly |
| Carbon Dioxide | 0.03% | weekly |

Carbon dioxide was checked at 5% and 15% during calibration cycle with other known bottled gases. Oxygen was checked at 15% with other known bottled gases. Based on the analysis of the off-gas of each fermentation vessel, the amount of isobutanol stripped, oxygen consumed, and carbon dioxide respired into the off-gas was measured by using the mass spectrometer's mole fraction analysis and gas flow rates (mass flow controller) into the fermentation vessel. Calculate the gassing rate per hour and then integrating that rate over the course of the fermentation.

Biomass Measurement

A 0.08% Trypan Blue solution was prepared from a 1:5 dilution of 0.4% Trypan Blue in NaCl (VWR BDH8721-0) with 1×PBS. A 1.0 mL sample was pulled from a fermentation vessel and placed in a 1.5 mL Eppendorf centrifuge tube and centrifuged in an Eppendorf, 5415C at 14,000 rpm for 5 minutes. After centrifugation, the top solvent layer was removed with an m200 Variable Channel BioHit pipette with 20-200 μL BioHit pipette tips. Care was made not to remove the layer between the solvent and aqueous layers. Once the solvent layer was removed, the sample was re-suspended using a Vortex-Genie® set at 2700 rpm.

A series of dilutions was required to prepare the ideal concentration for hemacytometer counts. If the OD was 10, a 1:20 dilution would be performed to achieve 0.5 OD which would give the ideal amount of cells to be counted per square, 20-30. In order to reduce inaccuracy in the dilution due to corn solids, multiple dilutions with cut 100-1000 μL BioHit pipette tips were required. Approximately, 1 cm was cut off the tips to increase the opening which prevented the tip from clogging. For a 1:20 final dilution, an initial 1:1 dilution of fermentation sample and 0.9% NaCl solution was prepared. Then, a 1:1 dilution of the previous solution (i.e., the initial 1:1 dilution) and 0.9% NaCl solution (the second dilution) was generated followed by a 1:5 dilution of the second dilution and Trypan Blue Solution. Samples were vortexed between each dilution and cut tips were rinsed into the 0.9% NaCl and Trypan Blue solutions.

The cover slip was carefully placed on top of the hemacytometer (Hausser Scientific Bright-Line 1492). An aliquot (10 μL) was drawn of the final Trypan Blue dilution with an m20 Variable Channel BioHit pipette with 2-20 μL BioHit pipette tips and injected into the hemacytometer. The hemacytometer was placed on the Zeis Axioskop 40 microscope at 40× magnification. The center quadrant was broken into 25 squares and the four corner and center squares in both chambers were then counted and recorded. After both chambers were counted, the average was taken and multiplied by the dilution factor (20), then by 25 for the number for squares in the quadrant in the hemacytometer, and then divided by 0.0001 mL which is the volume of the quadrant that was counted. The sum of this calculation is the number cells per mL.

LC Analysis of Fermentation Products in the Aqueous Phase

Samples were refrigerated until ready for processing. Samples were removed from refrigeration and allowed to reach room temperature (about one hour). Approximately 300 μL of sample was transferred with a m1000 Variable Channel BioHit pipette with 100-1000 μL BioHit pipette tips into a 0.2 um centrifuge filter (Nanosep® MF modified nylon centrifuge filter), then centrifuged using a Eppendorf, 5415C for five minutes at 14,000 rpm. Approximately 200 μL of filtered sample was transferred into a 1.8 auto sampler vial with a 250 μL glass vial insert with polymer feet. A screw cap with PTFE septa was used to cap the vial before vortexing the sample with a Vortex-Genie® set at 2700 rpm.

Sample was then run on Agilent 1200 series LC equipped with binary, isocratic pumps, vacuum degasser, heated column compartment, sampler cooling system, UV DAD detector and RI detector. The column used was an Aminex HPX-87H, 300×7.8 with a Bio-Rad Cation H refill, 30×4.6 guard column. Column temperature was 40° C., with a mobile phase of 0.01 N sulfuric acid, at a flow rate of 0.6 mL/min for 40 minutes. Results are shown in Table 1.

TABLE 1

Retention times of fermentation products in aqueous phase

| HPLC 302/310 Normalized to 10 μL injections | FW | RID Retention Time, min | Range of Standards, g/L | UV Retention Time, min |
|---|---|---|---|---|
| citric acid | 192.12 | 8.025 | 0.3-17 | 7.616 |
| glucose | 180.16 | 8.83 | 0.5-71 | |
| pyruvic acid (Na) | 110.04 | 9.388 | 0.1-5.2 | 8.5 |
| A-Kiv (Na) | 138.1 | 9.91 | 0.07-5.0 | 8.55 |
| 2,3-dihydroxyisovaleric acid (Na) | 156.1 | 10.972 | 0.2-8.8 | 10.529 |
| succinic acid | 118.09 | 11.561 | 0.3-16 | 11.216 |
| lactic acid (Li) | 96.01 | 12.343 | 0.3-17 | 11.948 |
| glycerol | 92.09 | 12.974 | 0.8-39 | |
| formic acid | 46.03 | 13.686 | 0.2-13 | 13.232 |
| acetate (Na) | 82.03 | 14.914 | 0.5-16 | 14.563 |
| meso-butanediol | 90.12 | 17.583 | 0.1-19 | |
| (+/−)-2,3-butanediol | 90.12 | 18.4 | 0.2-19 | |
| isobutyric acid | 88.11 | 19.685 | 0.1-8.0 | 19.277 |
| ethanol | 46.07 | 21.401 | 0.5-34 | |
| isobutyraldehyde | 72.11 | 27.64 | 0.01-0.11 | |
| isobutanol | 74.12 | 32.276 | 0.2-15 | |
| 3-OH-2-butanone (acetoin) | 88.11 | | 0.1-11 | 17.151 |

GC Analysis of Fermentation Products in the Solvent Phase

Samples were refrigerated until ready for processing. Samples were removed from refrigeration and allowed to reach room temperature (about one hour). Approximately 150 μL of sample was transferred using a m1000 Variable Channel BioHit pipette with 100-1000 μL BioHit pipette tips into a 1.8 auto sampler vial with a 250 μL glass vial insert with polymer feet. A screw cap with PTFE septa was used to cap the vial.

Sample was then run on Agilent 7890A GC with a 7683B injector and a G2614A auto sampler. The column was a HP-InnoWax column (30 m×0.32 mm ID, 0.25 μm film). The carrier gas was helium at a flow rate of 1.5 mL/min measured at 45° C. with constant head pressure; injector split was 1:50 at 225° C.; oven temperature was 45° C. for 1.5 minutes, 45° C. to 160° C. at 10° C./min for 0 minutes, then 230° C. at 35° C./min for 14 minutes for a run time of 29 minutes. Flame ionization detection was used at 260° C. with 40 mL/min helium makeup gas. Results are shown in Table 2.

TABLE 2

Retention times of fermentation products in solvent phase.

| GC 302/310 Normalized to 10 μL injections | FW | Solvent Retention Time, min | Range of Standards, g/L |
|---|---|---|---|
| isobutyraldehyde | 72.11 | 2.75 | 0.7-10.4 |
| ethanol | 46.07 | 3.62 | 0.5-34 |
| isobutanol | 74.12 | 5.53 | 0.2-16 |
| 3-OH-2-butanone (acetoin) | 88.11 | 8.29 | 0.1-11 |
| (+/−)-2,3-butanediol | 90.12 | 10.94 | 0.1-19 |
| isobutyric acid | 88.11 | 11.907 | 0.1-7.9 |
| meso-butanediol | 90.12 | 11.26 | 0.1-6.5 |
| glycerol | 92.09 | 16.99 | 0.8-9 |

Samples analyzed for fatty acid butyl esters were run on Agilent 6890 GC with a 7683B injector and a G2614A auto sampler. The column was a HP-DB-FFAP column (15 meters×0.53 mm ID (Megabore), 1-micron film thickness column (30 m×0.32 mm ID, 0.25 μm film). The carrier gas was helium at a flow rate of 3.7 mL/min measured at 45° C. with constant head pressure; injector split was 1:50 at 225° C.; oven temperature was 100° C. for 2.0 minutes, 100° C. to 250° C. at 10° C./min, then 250° C. for 9 minutes for a run time of 26 minutes. Flame ionization detection was used at 300° C. with 40 mL/min helium makeup gas. The following GC standards (Nu-Chek Prep; Elysian, Minn.) were used to confirm the identity of fatty acid isobutyl ester products: iso-butyl palmitate, iso-butyl stearate, iso-butyl oleate, iso-butyl linoleate, iso-butyl linolenate, iso-butyl arachidate.

Examples 1-14 describe various fermentation conditions that may be used for the claimed methods. As an example, some fermentations were subjected to Lipase Treatment pre-liquefaction and others were subjected to Lipase Treatment post-liquefaction. In other examples, the fermentation was subjected to Heat inactivation Treatment. Following fermentation, the effective isobutanol titer (Eff Iso Titer) was measured, that is, the total grams of isobutanol produced per liter aqueous volume. Results are shown in Table 3.

Example 1

Control

Experiment identifier 2010Y014 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 2

Experiment identifier 2010Y015 included: Seed Flask Growth method, Initial Fermentation Vessel Preparation method, Liquefaction method, Lipase Treatment Post-Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 3

Experiment identifier 2010Y016 included: Seed Flask Growth method, Initial Fermentation Vessel Preparation method, Liquefaction method, Lipase Treatment Post-Liquefaction method, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 4

Experiment identifier 2010Y017 included: Seed Flask Growth method, Initial Fermentation Vessel Preparation method, Liquefaction method, Heat Kill Treatment method Post-Liquefaction, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 5

Experiment identifier 2010Y018 included: Seed Flask Growth method, Initial Fermentation Vessel Preparation method, Liquefaction method, Lipase Treatment Post-Liquefaction method with the exception of only adding 7.2 ppm lipase after liquefaction, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 6

Control

Experiment identifier 2010Y019 included: Seed Flask Growth method, Initial Fermentation Vessel Preparation method, Liquefaction method, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 7

Control

Experiment identifier 2010Y021 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 8

Experiment identifier 2010Y022 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 9

Experiment identifier 2010Y023 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 10

Experiment identifier 2010Y024 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 11

Experiment identifier 2010Y029 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 12

Experiment identifier 2010Y030 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 13

Control

Experiment identifier 2010Y031 included: Seed Flask Growth method, Initial Fermentation Vessel Preparation method, Liquefaction method, Lipase Treatment Post Liquefaction method, no Heat Kill Treatment, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 14

Experiment identifier 2010Y032 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

TABLE 3

Fermentation conditions for Examples 1-14.

| Example # | Experimental Identifier | Lipase | Max cell Count × $10^7$ | Ethanol g/L | Solvent | Heat Kill Lipase | Eff Iso Titer g/L* | max Eff Iso rate g/L/h |
|---|---|---|---|---|---|---|---|---|
| 1 | 2010Y014 | none | 27.2 | 5 | Oleyl alcohol | none | 56.0 | 0.79 |
| 2 | 2010Y015 | 10 ppm | 31.5 | 5 | Oleyl alcohol | none | 52.4 | 0.74 |
| 3 | 2010Y016 | 10 ppm | 6.7 | 0 | Oleyl alcohol | none | 25.9 | 0.36 |
| 4 | 2010Y017 | none | 7.9 | 0 | Oleyl alcohol | post-liquefaction | 17.2 | 0.25 |
| 5 | 2010Y018 | 7.2 ppm | 16.2 | 5 | Oleyl alcohol | post-liquefaction | 45.8 | 0.66 |
| 6 | 2010Y019 | none | 17.5 | 5 | Oleyl alcohol | post-liquefaction | 48.1 | 0.69 |
| 7 | 2010Y021 | 10 ppm | 21.2 | 5 | Oleyl alcohol | during liquefaction | 46.8 | 0.82 |
| 8 | 2010Y022 | none | 9 | 5 | Oleyl alcohol | during liquefaction | 56.2 | 0.87 |
| 9 | 2010Y023 | 10 ppm | 12.8 | 5 | Corn Oil Fatty Acids | none | 60.3 | 1.3 |
| 10 | 2010Y024 | 10 ppm | 25.3 | 0 | Oleyl alcohol | during liquefaction | 19.8 | 0.33 |
| 11 | 2010Y029 | 10 ppm | 21.2 | 5 | Corn Oil Fatty Acids | during liquefaction | 28.36 | 0.52 |
| 12 | 2010Y030 | 10 ppm | 9 | 0 | Corn Oil Fatty Acids | during liquefaction | 12.71 | 0.24 |
| 13 | 2010Y031 | 10 ppm | 12.8 | 0 | Corn Oil Fatty Acids | none | 18.86 | 0.35 |
| 14 | 2010Y032 | 10 ppm | 25.3 | 5 | Corn Oil Fatty Acids | none | 53.36 | 0.92 |

*The "Eff Iso Titer g/L" = total grams of isobutanol produced per liter aqueous volume Example 15

The experimental identifier was GLNOR432A. NYLA74 (a butanediol producer—NGCI-047) was grown in 25 mL of medium in a 250 mL flask from a frozen vial to ~10D. The pre-seed culture was transferred to a 2 L flask and grown to 1.7-1.8 OD. The medium for both flasks was:

3.0 g/L dextrose
3.0 g/L ethanol, anhydrous
6.7 g/L Difco Yeast Nitrogen Base without amino acids (No. 291920)
1.4 g/L Yeast propout Mix (Sigma Y2001)
10 mL/L1% w/v L-Leucine stock solution
2 mL/L1% w/v L-Tryptophan stock solution A 1 L, Applikon fermentation vessel was inoculated with 60 mL of the seed flask. The fermentation vessel contained 700 mL of the following sterile medium:

20.0 g/L dextrose
8.0 mL/L ethanol, anhydrous
6.7 g/L Difco Yeast Nitrogen Base without amino acids (No. 291920)
2.8 g/L Yeast propout Mix (Sigma Y2001)
20 mL/L 1% w/v L-Leucine stock solution
4 mL/L 1% w/v L-Tryptophan stock solution
0.5 mL Sigma 204 Antifoam
0.8 mL/L 1% w/v Ergesterol solution in 1:1::Tween 80:Ethanol The residual glucose was kept excess with a 50% w/w glucose solution. The dissolved oxygen concentration of the fermentation vessel was controlled at 30% with stir control. The pH was controlled at pH=5.5. The fermentation vessel was sparged with 0.3 slpm of sterile, house air. The temperature was controlled at 30° C.

Example 16

The experimental identifier was GLNOR434A. This example is the same as example 15 with the exception of the addition of 3 g of oleic acid and the addition of 3 g of palmitic acid prior to inoculation. NYLA74 (a butanediol producer—NGCI-047) was the biocatalyst.

Figure 7:
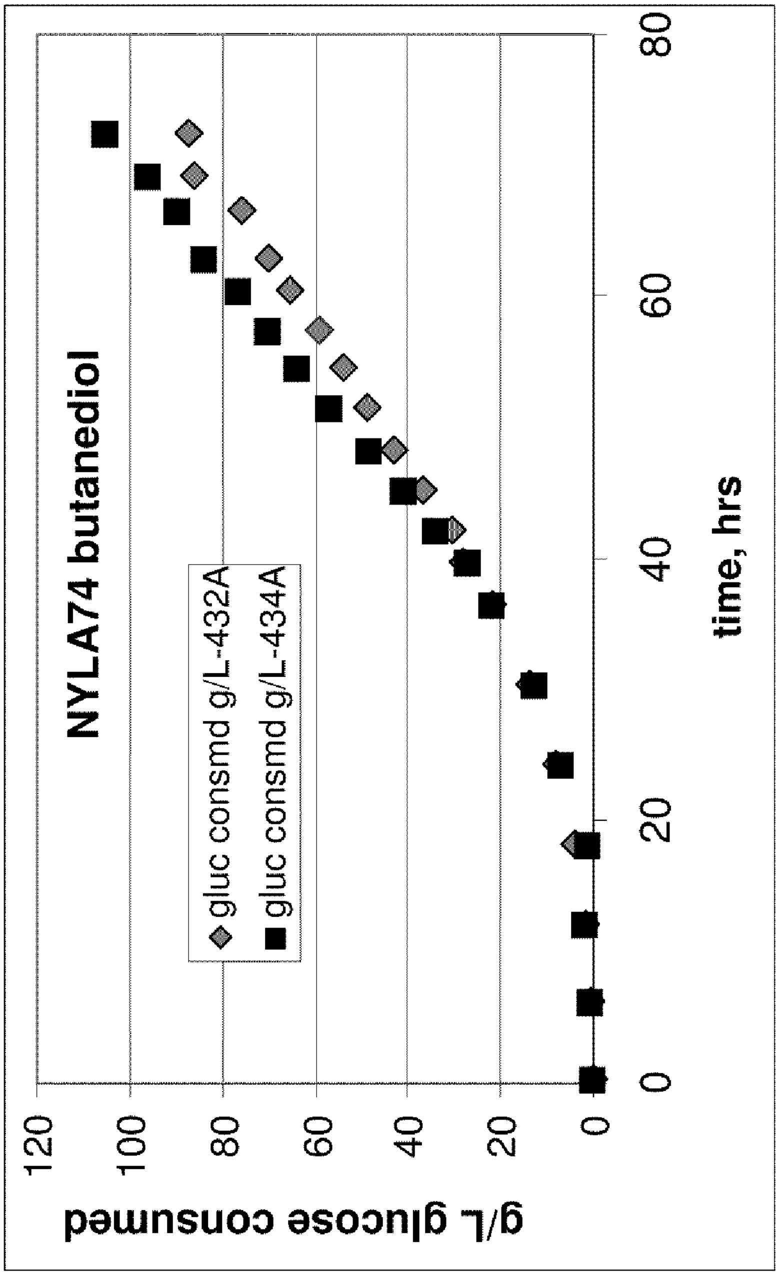
FIG. 7 is a chart illustrating the effect that the presence of fatty acids in a fermentation vessel has on glucose consumption for butanologen strain NGCI-047.

FIG. 7 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 17

The experimental identifier was GLNOR435A. This example was the same as example 15 except it was inoculated with NYLA74 (an isobutanol producer—NGCI-049).

Example 18

The experimental identifier was GLNOR437A. This example was the same as Example 16 except it was inoculated with NYLA74 (an isobutanol producer) (NGCI-049).

Figure 8:
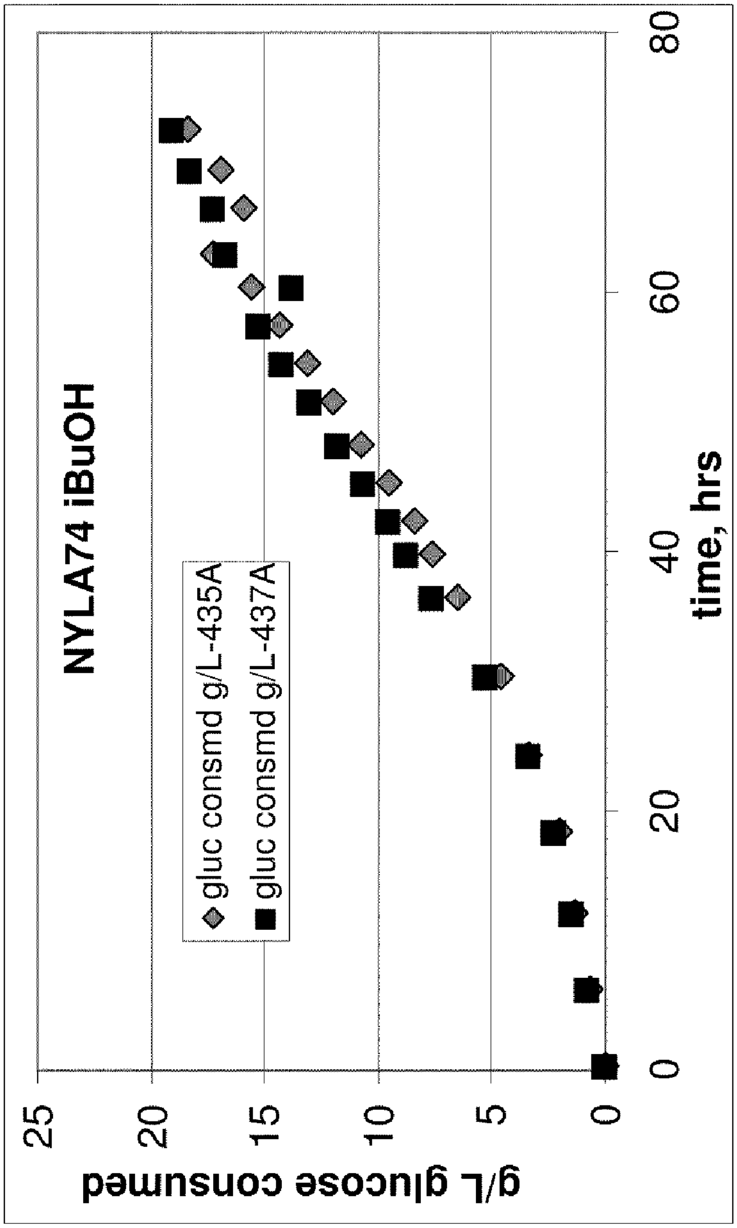
FIG. 8 is a chart illustrating the effect that the presence of fatty acids in a fermentation vessel has on glucose consumption for butanologen strain NGCI-049.

FIG. 8 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 19

The experimental identifier was 090420_3212. This example was run similarly to Example 15 except it was inoculated with butanologen NYLA84 (an isobutanol producer). This fermentation was run in a 1 L Sartorius fermentation vessel.

Example 20

The experimental identifier was 2009Y047. This example was run similarly to Example 16 except it was inoculated with butanologen NYLA84 (an isobutanol producer). This fermentation was run in a 1 L Sartorius fermentation.

Figure 9:
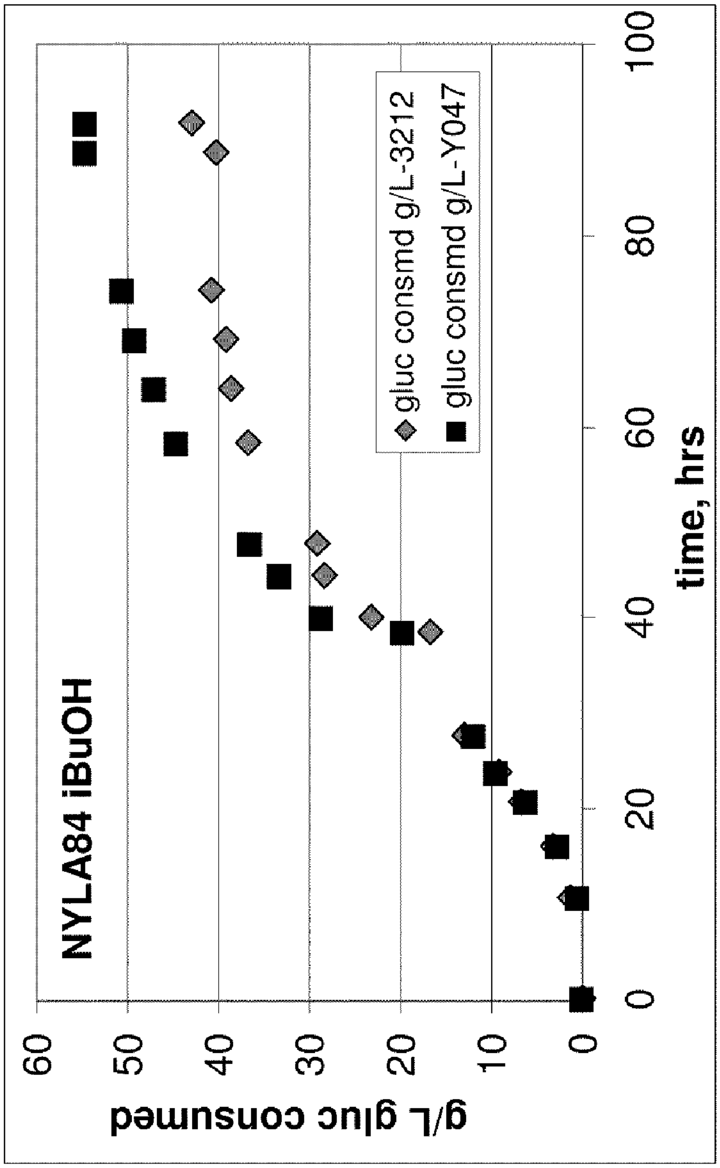
FIG. 9 is a chart illustrating the effect that the presence of fatty acids in a fermentation vessel has on glucose consumption for butanologen strain NYLA84.

FIG. 9 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Table 4 shows +/− fatty acid addition, maximum optical density, and g/L glucose consumed.

TABLE 4

| Example # | Experimental Identifier | Strain | Fatty Acids Added | Product | 69 hours $OD_{600}$ | 69 hours g/L glucose consumed |
|---|---|---|---|---|---|---|
| 15 | GLNOR432A | NYLA74 | − | butanediol | 12.8 | 86.0 |
| 16 | GLNOR434A | NYLA74 | + | butanediol | 23.1 | 95.9 |
| 17 | GLNOR435A | NYLA74 | − | isobutanol | 2.4 | 16.9 |
| 18 | GLNOR437A | NYLA74 | + | isobutanol | 4.5 | 18.3 |
| 19 | 090420_3212 | NYLA84 | − | isobutanol | 9.6 | 39.3 |
| 20 | 2009Y047 | NYLA84 | + | isobutanol | 20.2 | 49.1 |

Example 21

Lipase Treatment of Liquefied Corn Mash for Simultaneous Saccharification and Fermentation with In-Situ Product Removal Using Oleyl Alcohol Samples of broth and oleyl alcohol taken from fermentations run as described above in Examples 1, 2, and 3 were analyzed for wt % lipid (derivatized as fatty acid methyl esters, FAME) and for wt % free fatty acid (FFA, derivatized as fatty acid methyl esters, FAME) according to the method described by E. G. Bligh and W. J. Dyer (Canadian Journal of Biochemistry and Physiology, 37:911-17, 1959, hereafter Reference 1). The liquefied corn mash that was prepared for each of the three fermentations was also analyzed for wt % lipid and for wt % FFA after treatment with Lipolase® 100 L (Novozymes) (10 ppm of Lipolase® total soluble protein (BCA protein analysis, Sigma Aldrich)) per kg of liquefaction reaction mass containing 30 wt % ground corn kernels). No lipase was added to the liquefied corn mash in Example 1 (control), and the fermentations described in Examples 2 and 3 containing liquefied corn mash treated with lipase (no heat inactivation of lipase) were identical except that no ethanol was added to the fermentation described in Example 3.

The % FFA in lipase-treated liquefied corn mash prepared for fermentations run as described in Examples 2 and 3 was 88% and 89%, respectively, compared to 31% without lipase treatment (Example 1). At 70 h (end of run (EOR)), the concentration of FFA in the OA phase of fermentations run as described in Examples 2 and 3 (containing active lipase) was 14% and 20%, respectively, and the corresponding increase in lipids (measured as corn oil fatty acid methyl ester derivatives) was determined by GC/MS to be due to the lipase-catalyzed esterification of COFA by OA, where COFA was first produced by lipase-catalyzed hydrolysis of corn oil in the liquefied corn mash. Results are shown in Table 5.

TABLE 5

Lipid and free fatty acid content of fermentations containing oleyl alcohol as ISPR solvent and active lipase

| fermentation | lipase | time (h), sample | lipids (wt %) | FFA (wt %) | lipids (g) | FFA (g) | lipids + FFA (g) | % FFA |
|---|---|---|---|---|---|---|---|---|
| Example 1 | none | liq. mash | 0.61 | 0.28 | 5.3 | 2.4 | 7.7 | 31 |
| Example 1 | none | 0.8 h, broth | 0.49 | 0.22 | 5.5 | 2.5 | 8.0 | 31 |
| Example 1 | none | 31 h, broth | 0.19 | 0.03 | 2.1 | 0.3 | 2.4 | 13 |
| Example 1 | none | 31 h, OA | 0.36 | 0.21 | 3.4 | 2.0 | 5.3 | 37 |
| Example 1 | none | 70 h, broth | 0.15 | 0.03 | 1.7 | 0.3 | 2.0 | 15 |
| Example 1 | none | 70 h, OA | 0.57 | 0.25 | 5.3 | 2.3 | 7.7 | 31 |
| Example 2 | 10 ppm | liq. mash | 0.13 | 0.97 | 1.1 | 8.5 | 9.6 | 88 |
| Example 2 | 10 ppm | 0.8 h, broth | 0.15 | 0.62 | 1.7 | 7.0 | 8.7 | 81 |
| Example 2 | 10 ppm | 31 h, broth | 0.16 | 0.05 | 1.8 | 0.5 | 2.3 | 23 |
| Example 2 | 10 ppm | 31 h, OA | 0.37 | 0.23 | 3.5 | 2.2 | 5.7 | 38 |
| Example 2 | 10 ppm | 70 h, broth | 0.17 | 0.02 | 1.9 | 0.3 | 2.2 | 13 |
| Example 2 | 10 ppm | 70 h, OA | 0.60 | 0.10 | 5.7 | 1.0 | 6.7 | 14 |
| Example 3 | 10 ppm | liq. mash | 0.12 | 0.97 | 1.0 | 8.5 | 9.5 | 89 |
| Example 3 | 10 ppm | 0.8 h, broth | 0.32 | 0.40 | 3.6 | 4.5 | 8.1 | 56 |
| Example 3 | 10 ppm | 31 h, broth | 0.17 | 0.05 | 1.9 | 0.6 | 2.5 | 24 |
| Example 3 | 10 ppm | 31 h, OA | 0.38 | 0.22 | 3.6 | 2.1 | 5.7 | 37 |
| Example 3 | 10 ppm | 70 h, broth | 0.15 | 0.02 | 1.7 | 0.2 | 1.9 | 13 |
| Example 3 | 10 ppm | 70 h, OA | 0.46 | 0.12 | 4.4 | 1.1 | 5.6 | 20 |

Example 22

Heat Inactivation of Lipase in Lipase-Treated Liquefied Corn Mash to Limit Production of Oleyl Alcohol Esters of Corn Oil Free Fatty Acids Tap water (918.4 g) was added to a jacketed 2-L resin kettle, then 474.6 g wet weight (417.6 g dry weight) of ground whole corn kernels (1.0 mm screen on hammer mill) was added with stirring. The mixture was heated to 55° C. with stirring at 300 rpm, and the pH adjusted to 5.8 with 2 N sulfuric acid. To the mixture was added 14.0 g of an aqueous solution containing 0.672 g of Spezyme®-FRED L (Genencor®, Palo Alto, Calif.), and the temperature of the mixture increased to 85° C. with stirring at 600 rpm and pH 5.8. After 120 minutes at 85° C., the mixture was cooled to 50° C. and 45.0 mL aliquots of the resulting liquefied corn mash were transferred to 50-mL polypropylene centrifuge tubes and stored frozen at −80° C.

In a first reaction, 50 g of liquefied corn mash prepared as described above was mixed with 10 ppm Lipolase® 100 L (Novozymes) for 6 h at 55° C. and with no inactivation of lipase at 85° C. for 1 h, the mixture was cooled to 30° C. In a second reaction, 50 g of liquefied corn mash was mixed with 10 ppm Lipolase® for 6 h at 55° C., then heated to 85° C. for 1 h (lipase inactivation), then cooled to 30° C. In a third reaction, 50 g of liquefied corn mash without added lipase was mixed for 6 h at 55° C., and with no heating at 85° C. for 1 h, the mixture was cooled to 30° C., 38 g of oleyl alcohol was added, and the resulting mixture stirred for 73 h at 30° C. In a fourth reaction, 50 g of liquefied corn mash without added lipase was mixed for 6 h at 55° C., then heated to 85° C. for 1 h, then cooled to 30° C. Each of the four reaction mixtures was sampled at 6 h, then 38 g of oleyl alcohol added, and the resulting mixtures stirred at 30° C. and sampled at 25 h and 73 h. Samples (both liquefied mash and oleyl alcohol (OA)) were analyzed for wt % lipid (derivatized as fatty acid methyl esters, FAME) and for wt % free fatty acid (FFA, derivatized as fatty acid methyl esters, FAME) according to the method described by Reference 1.

The % FFA in the OA phase of the second reaction run with heat inactivation of lipase prior to OA addition was 99% at 25 h and 95% at 73 h, compared to only 40% FFA and 21% FFA at 25 h and 73 h, respectively, when the lipase in lipase-treated liquefied corn mash was not heat inactivated (first reaction). No significant change in % FFA was observed in the two control reactions without added lipase. Results are shown in Table 6.

TABLE 6

Lipid and free fatty acid content of a mixture of liquefied corn mash and oleyl alcohol in the presence or absence of active or heat-inactivated lipase

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm active lipase, | 6 h, liq. mash | 0.08 | 0.71 | 41 | 345 | 386 | 89 |
| no 85° C. heat treatment | 25 h, liq. mash | 0.22 | 0.06 | 105 | 27 | 132 | 20 |
| | 25 h, OA | 0.58 | 0.39 | 212 | 143 | 355 | 40 |
| | 73 h, liq. mash | 0.25 | 0.05 | 121 | 22 | 143 | 18 |
| | 73 h, OA | 0.91 | 0.24 | 333 | 88 | 420 | 21 |
| 10 ppm inactive lipase, | 6 h, lip. mash | 0.06 | 0.45 | 28 | 224 | 252 | 89 |
| 85° C. heat treatment | 25 h, lip. mash | 0.10 | 0.11 | 49 | 54 | 103 | 53 |
| | 25 h, OA | 0.02 | 0.96 | 8 | 366 | 374 | 99 |
| | 73 h, lip. mash | 0.24 | 0.15 | 117 | 72 | 189 | 62 |
| | 73 h, OA | 0.06 | 1.11 | 23 | 424 | 447 | 95 |
| no lipase, | 6 h, lip. mash | 0.80 | 0.40 | 401 | 199 | 599 | 33 |
| no 85° C. heat treatment | 25 h, lip. mash | 0.30 | 0.05 | 147 | 25 | 173 | 15 |
| | 25 h, OA | 0.55 | 0.36 | 212 | 139 | 351 | 40 |
| | 73 h, lip. mash | 0.23 | 0.05 | 117 | 26 | 143 | 23 |
| | 73 h, OA | 0.79 | 0.42 | 305 | 162 | 467 | 34 |
| no lipase, | 6 h, lip. mash | 0.74 | 0.36 | 370 | 183 | 553 | 33 |
| 85° C. heat treatment | 25 h, lip. mash | 0.31 | 0.05 | 156 | 27 | 183 | 15 |
| | 25 h, OA | 0.60 | 0.35 | 233 | 136 | 369 | 37 |
| | 73 h, lip. mash | 0.20 | 0.05 | 99 | 23 | 121 | 23 |
| | 73 h, OA | 0.84 | 0.41 | 326 | 159 | 486 | 33 |

Example 23

Heat Inactivation of Lipase in Lipase-Treated Liquefied Corn Mash for Simultaneous Saccharification and Fermentation with In-Situ Product Removal Using Oleyl Alcohol Three fermentations were run as described above in Examples 4, 5, and 6. No lipase was added to the liquefied corn mash in Examples 4 and 6 prior to fermentation, and the Lipase Treatment of the liquefied corn mash in the fermentation described in Example 5 (using 7.2 ppm of Lipolase® total soluble protein) was followed immediately by Heat Inactivation Treatment (to completely inactivate the lipase), and subsequently followed by Nutrient Addition Prior to Inoculation and fermentation. The % FFA in liquefied corn mash prepared without lipase treatment for fermentations run as described in Examples 4 and 6 was 31% and 34%, respectively, compared to 89% with lipase treatment (Example 5). Over the course of the fermentations listed in Table 10, the concentration of FFA in the OA phase did not decrease in any of the three fermentations, including that containing heat-inactivated lipase. The % FFA in the OA phase of the fermentation run according to Example 5 (with heat inactivation of lipase prior to fermentation) was 95% at 70 h (end of run (EOR)), compared to only 33% FFA for the remaining two fermentations (Examples 4 and 6) where liquefied corn mash was not treated with lipase. Results are shown in Table 7.

TABLE 7

Lipid and free fatty acid content of fermentations containing oleyl alcohol as ISPR solvent and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 4 | none | liquefied mash | 0.65 | 0.30 | 7.2 | 3.3 | 10.4 | 31 |
| Example 4 | none | 0.2 h, broth | 0.56 | 0.28 | 6.6 | 3.3 | 9.9 | 33 |
| Example 4 | none | 4.3 h, broth | 0.28 | 0.09 | 3.3 | 1.0 | 4.4 | 24 |
| Example 4 | none | 4.3 h, OA | 0.45 | 0.27 | 4.0 | 2.4 | 6.4 | 37 |
| Example 4 | none | 30 h, broth | 0.17 | 0.05 | 2.0 | 0.6 | 2.7 | 24 |
| Example 4 | none | 30 h, OA | 0.63 | 0.29 | 5.7 | 2.6 | 8.3 | 32 |
| Example 4 | none | 53 h, broth | 0.13 | 0.04 | 1.5 | 0.5 | 2.0 | 23 |
| Example 4 | none | 53 h, OA | 0.67 | 0.32 | 6.0 | 2.9 | 8.9 | 32 |
| Example 4 | none | 70 h, broth | 0.13 | 0.04 | 1.5 | 0.4 | 1.9 | 23 |
| Example 4 | none | 70 h, OA | 0.64 | 0.31 | 5.8 | 2.8 | 8.5 | 33 |
| Example 5 | 7.2 ppm | liquefied mash | 0.11 | 0.89 | 1.3 | 9.9 | 11.2 | 89 |
| Example 5 | 7.2 ppm | 0.2 h, broth | 0.25 | 0.83 | 2.9 | 9.8 | 12.8 | 77 |
| Example 5 | 7.2 ppm | 4.3 h, broth | 0.14 | 0.17 | 1.6 | 2.1 | 3.7 | 56 |
| Example 5 | 7.2 ppm | 4.3 h, OA | 0.02 | 0.84 | 0.2 | 7.9 | 8.1 | 97 |
| Example 5 | 7.2 ppm | 30 h, broth | 0.08 | 0.18 | 1.0 | 2.1 | 3.1 | 68 |
| Example 5 | 7.2 ppm | 30 h, OA | 0.04 | 0.92 | 0.3 | 8.6 | 8.9 | 96 |
| Example 5 | 7.2 ppm | 53 h, broth | 0.07 | 0.11 | 0.9 | 1.3 | 2.2 | 61 |
| Example 5 | 7.2 ppm | 53 h, OA | 0.08 | 0.95 | 0.7 | 8.9 | 9.6 | 93 |
| Example 5 | 7.2 ppm | 70 h, broth | 0.08 | 0.10 | 0.9 | 1.2 | 2.1 | 55 |
| Example 5 | 7.2 ppm | 70 h, OA | 0.05 | 0.94 | 0.4 | 8.8 | 9.2 | 95 |
| Example 6 | none | liquefied mash | 0.66 | 0.34 | 7.3 | 3.8 | 11.1 | 34 |
| Example 6 | none | 0.2 h, broth | 0.63 | 0.34 | 7.6 | 4.0 | 11.6 | 34 |
| Example 6 | none | 4.3 h, broth | 0.33 | 0.10 | 3.9 | 1.2 | 5.1 | 23 |
| Example 6 | none | 4.3 h, OA | 0.45 | 0.27 | 4.0 | 2.4 | 6.4 | 38 |

TABLE 7-continued

Lipid and free fatty acid content of fermentations containing oleyl alcohol as ISPR solvent and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 6 | none | 30 h, broth | 0.17 | 0.06 | 2.1 | 0.8 | 2.8 | 26 |
| Example 6 | none | 30 h, OA | 0.69 | 0.33 | 6.2 | 3.0 | 9.1 | 32 |
| Example 6 | none | 53 h, broth | 0.14 | 0.05 | 1.6 | 0.5 | 2.2 | 25 |
| Example 6 | none | 53 h, OA | 0.72 | 0.35 | 6.4 | 3.1 | 9.5 | 33 |
| Example 6 | none | 70 h, broth | 0.15 | 0.05 | 1.8 | 0.6 | 2.4 | 25 |
| Example 6 | none | 70 h, OA | 0.70 | 0.34 | 6.2 | 3.0 | 9.2 | 33 |

Example 24

Lipase Treatment of Ground Whole Corn Kernels Prior to Liquefaction

Tap water (1377.6 g) was added into each of two jacketed 2-L resin kettles, then 711.9 g wet weight (625.8 g dry weight) of ground whole corn kernels (1.0 mm screen on hammer mill) was added to each kettle with stirring. Each mixture was heated to 55° C. with stirring at 300 rpm, and the pH adjusted to 5.8 with 2 N sulfuric acid. To each mixture was added 21.0 g of an aqueous solution containing 1.008 g of Spezyme®-FRED L (Genencor®, Palo Alto, Calif.). To one mixture was then added 10.5 mL of aqueous solution of Lipolase® 100L Solution (21 mg total soluble protein, 10 ppm lipase final concentration) and to the second mixture was added 1.05 mL of aqueous solution of Lipolase® 100L Solution (2.1 mg total soluble protein, 1.0 ppm lipase final concentration). Samples were withdrawn from each reaction mixture at 1 h, 2 h, 4 h and 6 h at 55° C., then the temperature of the mixture was increased to 85° C. with stirring at 600 rpm and pH 5.8, and a sample was taken when the mixture first reached 85° C. After 120 minutes at 85° C., a sample was taken and the mixtures were cooled to 50° C. and final samples of the resulting liquefied corn mash were transferred to 50-mL polypropylene centrifuge tubes; all samples were stored frozen at −80° C.

In two separate reactions, a 50 g sample of the 10 ppm lipase-treated liquefied corn mash or a 55 g sample of the 1.0 ppm lipase-treated liquefied corn mash prepared as described above was mixed with oleyl alcohol (OA) (38 g) at 30° C. for 20 h, then the liquefied mash and OA in each reaction mixture were separated by centrifugation and each phase analyzed for wt % lipid (derivatized as fatty acid methyl esters, FAME) and for wt % free fatty acid (FFA, derivatized as fatty acid methyl esters, FAME) according to the method described by Reference 1. The % FFA in the OA phase of the liquefied mash/OA mixture prepared using heat inactivation of 10 ppm lipase during liquefaction was 98% at 20 h, compared to only 62% FFA in the OA phase of the liquefied mash/OA mixture prepared using heat inactivation of 1.0 ppm lipase during liquefaction. Results are shown in Table 8.

TABLE 8

Lipid and free fatty acid content of a mixture of liquefied corn mash and oleyl alcohol, using lipase treatment of ground corn suspension prior to liquefaction (heat inactivation of lipase during liquefaction)

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm lipase | 1 h, pre-liquefaction | 0.226 | 0.627 | 112 | 311 | 424 | 74 |
| at 55° C. prior to | 2 h, pre-liquefaction | 0.199 | 0.650 | 99 | 323 | 422 | 77 |
| liquefaction at | 4 h, pre-liquefaction | 0.151 | 0.673 | 75 | 334 | 410 | 82 |
| 85° C., mix with | 6 h, pre-liquefaction | 0.101 | 0.700 | 50 | 348 | 398 | 87 |
| OA for 20 h | 0 h, 85° C., liq. mash | 0.129 | 0.764 | 64 | 380 | 444 | 86 |
| | 2 h, 85° C., liq. mash | 0.129 | 0.751 | 64 | 373 | 437 | 85 |
| | 20 h, 30° C., liq. mash | 0.074 | 0.068 | 37 | 34 | 71 | 48 |
| | 20 h, 30° C., OA | 0.015 | 1.035 | 5.7 | 394 | 400 | 98 |
| 1.0 ppm lipase | 1 h, pre-liquefaction | 0.408 | 0.480 | 226 | 266 | 492 | 54 |
| at 55° C. prior to | 2 h, pre-liquefaction | 0.401 | 0.424 | 222 | 235 | 457 | 51 |
| liquefaction at | 4 h, pre-liquefaction | 0.299 | 0.433 | 165 | 240 | 405 | 58 |
| 85° C., mix with | 6 h, pre-liquefaction | 0.346 | 0.453 | 192 | 251 | 442 | 57 |
| OA for 20 h | 0 h, 85° C., liq. mash | 0.421 | 0.407 | 233 | 225 | 458 | 49 |
| | 2 h, 85° C., liq. mash | 0.424 | 0.429 | 235 | 237 | 472 | 50 |
| | 20 h, 30° C., liq. mash | 0.219 | 0.054 | 121 | 30 | 151 | 20 |
| | 20 h, 30° C., OA | 0.344 | 0.573 | 140 | 233 | 373 | 62 |

Example 25

Lipase Screening for Treatment of Ground Whole Corn Kernels Prior to Liquefaction Seven reaction mixtures containing tap water (67.9 g) and ground whole corn kernels (35.1 g wet wt., ground with 1.0 mm screen using a hammer mill) at pH 5.8 were stirred at 55° C. in stoppered flasks. A 3-mL sample (t=0 h) was removed from each flask and the sample immediately frozen on dry ice, then ca. 0.5 mL of 10 mM sodium phosphate buffer (pH 7.0) containing 1 mg total soluble protein (10 ppm final concentration in reaction mixture) of one of the following lipases (Novozymes) were added to one of each flask: Lipolase® 100 L, Lipex® 100L, Lipoclean® 2000T, Lipozyme® CALB L, Novozyme® CALA L, and Palatase 20000L; no lipase was added to the seventh flask. The resulting mixtures were stirred at 55° C. in stoppered flasks, and 3-mL samples were withdrawn from each reaction mixture at 1 h, 2 h, 4 h and 6 h and immediately frozen in dry ice until analyzed for wt % lipid (derivatized as fatty acid methyl esters, FAME) and for wt % free fatty acid (FFA, derivatized as fatty acid methyl esters, FAME) according to the method described by Reference 1, and the percent free fatty acid content was calculated relative to the total combined concentrations of lipid and free fatty acid was determined for each sample. Results are shown in Table 9.

TABLE 9

Percent free fatty acid content (% FFA) of a mixture of ground whole corn kernels using lipase treatment at 55° C. prior to liquefaction

| | % FFA time | | | | |
|---|---|---|---|---|---|
| | 0 h | 1 h | 2 h | 4 h | 6 h |
| Lipolase ® 100L | 33 | 56 | 74 | 76 | 79 |
| Lipex ® 100L | 34 | 66 | 81 | 83 | 83 |
| Lipoclean ® 2000T | 38 | 55 | 73 | 69 | 65 |
| Lipozyme ® CALB L | 39 | 38 | 37 | 43 | 41 |
| Novozyme ® CALA L | 37 | 40 | 44 | 44 | 45 |
| Palatase ® 20000L | 37 | 49 | 59 | 62 | 66 |
| no enzyme | 38 | 33 | 37 | 41 | 42 |

Example 26

Lipase Treatment of Ground Whole Corn Kernels Prior to Simultaneous Saccharification and Fermentation with In-Situ Product Removal Using Oleyl Alcohol Three fermentations were run as described above in Examples 7, 8, and 10. For fermentations run as described in Examples 7 and 10, lipase (10 ppm of Lipolase® total soluble protein) was added to the suspension of ground corn and heated at 55° C. for 6 h prior to Liquefaction to produce a liquefied corn mash containing heat-inactivated lipase. No lipase was added to the suspension of ground corn used to prepare liquefied corn mash for the fermentation described in Example 8, but the suspension was subjected to the same heating step at 55° C. prior to liquefaction. The % FFA in lipase-treated liquefied corn mash prepared for fermentations run as described in Examples 7 and 10 was 83% and 86%, respectively, compare to 41% without lipase treatment (Example 8). Over the course of the fermentations, the concentration of FFA did not decrease in any of the fermentations, including that containing heat-inactivated lipase. The % FFA in the OA phase of the fermentation run according to Examples 7 and 10 (with heat inactivation of lipase prior to fermentation) was 97% at 70 h (end of run (EOR)), compared to only 49% FFA for the fermentation run according to Example 8 where ground whole corn kernels had not been treated with lipase prior to liquefaction. Results are shown in Table 10.

TABLE 10

Lipid and free fatty acid content of fermentations containing oleyl alcohol as ISPR solvent and heat-inactivated lipase (lipase treatment of ground corn suspension prior to liquefaction)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 7 | 10 ppm | pre-lipase/pre-liq. | 0.65 | 0.22 | 7.1 | 2.4 | 9.4 | 25 |
| Example 7 | 10 ppm | post-lipase/pre-liq. | 0.22 | 0.65 | 2.4 | 7.0 | 9.5 | 74 |
| Example 7 | 10 ppm | liquefied mash | 0.17 | 0.79 | 1.8 | 8.5 | 10.3 | 83 |
| Example 7 | 10 ppm | 0.3 h, broth | 0.16 | 0.79 | 1.8 | 8.9 | 10.7 | 83 |
| Example 7 | 10 ppm | 4.8 h, broth | 0.14 | 0.31 | 1.6 | 3.5 | 5.1 | 69 |
| Example 7 | 10 ppm | 4.8 h, OA | 0.04 | 0.68 | 0.3 | 5.4 | 5.6 | 95 |
| Example 7 | 10 ppm | 29 h, broth | 0.10 | 0.12 | 1.2 | 1.3 | 2.5 | 53 |
| Example 7 | 10 ppm | 29 h, OA | 0.03 | 1.05 | 0.2 | 8.2 | 8.4 | 98 |
| Example 7 | 10 ppm | 53 h, broth | | | | | | |
| Example 7 | 10 ppm | 53 h, OA | 0.07 | 1.14 | 0.5 | 9.0 | 9.5 | 95 |
| Example 7 | 10 ppm | 70 h, broth | 0.11 | 0.07 | 1.2 | 0.8 | 2.0 | 39 |
| Example 7 | 10 ppm | 70 h, OA | 0.03 | 1.10 | 0.2 | 8.7 | 8.9 | 97 |
| Example 8 | none | pre-lipase/pre-liq. | 0.62 | 0.23 | 6.7 | 2.5 | 9.2 | 27 |
| Example 8 | none | post-lipase/pre-liq. | 0.57 | 0.26 | 6.2 | 2.8 | 9.0 | 31 |
| Example 8 | none | liquefied mash | 0.52 | 0.36 | 5.6 | 4.0 | 9.6 | 41 |
| Example 8 | none | 0.3 h, broth | 0.50 | 0.33 | 5.7 | 3.8 | 9.4 | 40 |
| Example 8 | none | 4.8 h, broth | 0.47 | 0.14 | 5.3 | 1.6 | 6.9 | 24 |
| Example 8 | none | 4.8 h, OA | 0.12 | 0.32 | 1.0 | 2.9 | 3.9 | 73 |
| Example 8 | none | 29 h, broth | 0.30 | 0.05 | 3.4 | 0.6 | 4.0 | 16 |
| Example 8 | none | 29 h, OA | 0.31 | 0.46 | 2.7 | 4.1 | 6.9 | 60 |
| Example 8 | none | 53 h, broth | | | | | | |
| Example 8 | none | 53 h, OA | 0.47 | 0.50 | 4.2 | 4.4 | 8.6 | 51 |
| Example 8 | none | 70 h, broth | 0.22 | 0.04 | 2.5 | 0.5 | 3.0 | 17 |
| Example 8 | none | 70 h, OA | 0.40 | 0.39 | 3.6 | 3.5 | 7.0 | 49 |
| Example 10 | 10 ppm | pre-lipase/pre-liq. | 0.67 | 0.23 | 7.4 | 2.5 | 9.9 | 25 |
| Example 10 | 10 ppm | post-lipase/pre-liq. | 0.19 | 0.69 | 2.1 | 7.6 | 9.7 | 78 |
| Example 10 | 10 ppm | liquefied mash | 0.14 | 0.85 | 1.6 | 9.4 | 11.0 | 86 |
| Example 10 | 10 ppm | 0.3 h, broth | 0.13 | 0.82 | 1.5 | 9.4 | 10.9 | 86 |
| Example 10 | 10 ppm | 4.8 h, broth | 0.11 | 0.29 | 1.3 | 3.3 | 4.6 | 72 |
| Example 10 | 10 ppm | 4.8 h, OA | 0.04 | 0.60 | 0.3 | 5.2 | 5.6 | 94 |
| Example 10 | 10 ppm | 29 h, broth | 0.09 | 0.14 | 1.0 | 1.6 | 2.6 | 61 |
| Example 10 | 10 ppm | 29 h, OA | 0.01 | 0.96 | 0.1 | 8.4 | 8.5 | 99 |
| Example 10 | 10 ppm | 53 h, broth | | | | | | |
| Example 10 | 10 ppm | 53 h, OA | 0.02 | 0.95 | 0.2 | 8.3 | 8.4 | 98 |
| Example 10 | 10 ppm | 70 h, broth | 0.09 | 0.08 | 1.1 | 0.9 | 1.9 | 45 |
| Example 10 | 10 ppm | 70 h, OA | 0.03 | 0.99 | 0.3 | 8.7 | 9.0 | 97 |

Example 27

Lipase Treatment of Ground Whole Corn Kernels or Liquefied Corn Mash for Simultaneous Saccharification and Fermentation with In-Situ Product Removal Using Corn Oil Fatty Acids (COFA)

Five fermentations were run as described above in Examples 9, 11, 12, 13, and 14. For the fermentations run as described in Examples 9, 13, and 14, lipase (10 ppm of Lipolase® total soluble protein) was added after Liquefaction and there was no heat-inactivation of lipase. Fermentations run as described in Examples 9 and 14 had 5 g/L of ethanol added prior to inoculation, whereas the fermentation run as described in Example 13 had no added ethanol. The fermentations run as described in Examples 11 and 12 employed the addition of 10 ppm Lipolase® total soluble protein to the suspension of ground corn prior to liquefaction, resulting in heat inactivation of lipase during liquefaction. The fermentation run as described in Example 11 had 5 g/L of ethanol added prior to inoculation, whereas the fermentation run as described in Example 12 had no added ethanol. The final total grams of isobutanol (i-BuOH) present in the COFA phase of the fermentations containing active lipase was significantly greater than the final total grams of i-BuOH present in the COFA phase of the fermentations containing inactive lipase. The final total grams of isobutanol (i-BuOH) present in the fermentation broths containing active lipase were only slightly less than the final total grams of i-BuOH present in the fermentation broths containing inactive lipase, such that the overall production of i-BuOH (as a combination of free i-BuOH and isobutyl esters of COFA (FABE)) was significantly greater in the presence of active lipase when compared to that obtained in the presence of heat-inactivated lipase. Results are shown in Tables 11 and 12.

TABLE 11

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (COFA phase analysis)

| fermentation | fermentation time (h) | g i-BuOH/ kg COFA | g FABE/ kg COFA | g i-BuOH from FABE/ kg COFA | total g i-BuOH/ kg COFA |
|---|---|---|---|---|---|
| Example 9 | 4.5 | 2.4 | 0.0 | 0 | 2.4 |
| Example 9 | 28.8 | 5.4 | 70.9 | 16.5 | 22.0 |
| Example 9 | 52.4 | 8.9 | 199.0 | 46.4 | 55.3 |
| Example 9 | 69.3 | 4.9 | 230.9 | 53.9 | 69.3 |
| Example 11 | 6.6 | 2.3 | 0.0 | 0.0 | 2.3 |
| Example 11 | 53.5 | 25.1 | 2.9 | 0.6 | 25.7 |
| Example 11 | 71.1 | 24.4 | 6.3 | 1.4 | 25.8 |
| Example 12 | 6.6 | 2.3 | 0.0 | 0.0 | 2.3 |
| Example 12 | 53.5 | 12.8 | 1.6 | 0.4 | 13.2 |
| Example 12 | 71.1 | 12.8 | 3.0 | 0.7 | 13.5 |
| Example 13 | 6.6 | 2.3 | 0.0 | 0.0 | 2.3 |
| Example 13 | 53.5 | 4.9 | 72.1 | 16.0 | 20.9 |
| Example 13 | 71.1 | 4.6 | 91.4 | 20.3 | 24.9 |
| Example 14 | 6.6 | 2.1 | 0.0 | 0.0 | 2.1 |
| Example 14 | 53.5 | 9.8 | 197.2 | 43.8 | 53.6 |
| Example 14 | 71.1 | 4.9 | 244.5 | 54.3 | 59.2 |

TABLE 12

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (fermentation broth analysis)

| sample | fermentation time (h) | g i-BuOH/ kg broth | g FABE/ kg broth | g i-BuOH from FABE/ kg broth | total g i-BuOH/ kg broth |
|---|---|---|---|---|---|
| Example 9 | 4.5 | 0.0 | 0.0 | 0 | 0 |
| Example 9 | 28.8 | 0.0 | 12.6 | 2.9 | 2.9 |
| Example 9 | 52.4 | 0.0 | 30.3 | 7.1 | 7.1 |
| Example 9 | 69.3 | 0.0 | 24.7 | 5.8 | 5.8 |
| Example 11 | 6.6 | 0.0 | 0.0 | 0 | 0.0 |
| Example 11 | 53.5 | 9.8 | 0.0 | 0 | 9.8 |
| Example 11 | 71.1 | 9.5 | 0.0 | 0 | 9.5 |
| Example 12 | 6.6 | 0.0 | 0.0 | 0 | 0 |
| Example 12 | 53.5 | 3.8 | 0.0 | 0.0 | 3.8 |
| Example 12 | 71.1 | 5.1 | 0.0 | 0.0 | 5.1 |
| Example 13 | 6.6 | 0.0 | 0.0 | 0 | 0 |
| Example 13 | 53.5 | 2.1 | 3.0 | 0.7 | 2.8 |
| Example 13 | 71.1 | 2.1 | 7.4 | 1.6 | 3.7 |
| Example 14 | 6.6 | 0.0 | 0.0 | 0 | 0.0 |
| Example 14 | 53.5 | 2.9 | 22.4 | 5.0 | 7.9 |
| Example 14 | 71.1 | 3.3 | 19.3 | 4.3 | 7.6 |

Example 28

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol), lipase (Lipolase® 100 L; Novozymes) and corn oil fatty acids prepared from corn oil (Table 13) were stirred at 30° C., and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 14).

TABLE 13

Reaction conditions for conversion of isobutanol (i-BuOH) to isobutyl esters of corn oil fatty acids (i-BuO-COFA)

| reaction | MES (0.2M) (g) | i-BuOH (g) | COFA (g) | lipase (ppm) |
|---|---|---|---|---|
| 1 | 45.96 | 3.6 | 43.4 | 10 |
| 2 | 45.96 | 3.6 | 21.7 | 10 |
| 3 | 45.96 | 3.6 | 10.85 | 10 |
| 4 | 45.96 | 3.6 | 43.4 | 4 |
| 5 | 45.96 | 3.6 | 43.4 | 0 |

TABLE 14

Weights of isobutanol (i-BuOH) and isobutyl esters of corn oil fatty acids (i-BuO-COFA) present in the aqueous fraction (AQ) and organic fraction (ORG) for reactions described in Table 13

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 0.77 | 2.83 | 2.77 | 0.05 | 0.24 |
| 1 | 1 | 0.76 | 2.84 | 2.58 | 0.25 | 1.13 |

TABLE 14-continued

Weights of isobutanol (i-BuOH) and isobutyl esters of corn oil fatty acids (i-BuO-COFA) present in the aqueous fraction (AQ) and organic fraction (ORG) for reactions described in Table 13

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 2 | 0.74 | 2.86 | 2.41 | 0.44 | 2.00 |
| 1 | 4 | 0.66 | 2.94 | 2.05 | 0.89 | 4.03 |
| 1 | 6 | 0.63 | 2.97 | 1.43 | 1.54 | 6.93 |
| 1 | 21.5 | 0.28 | 3.32 | 0.34 | 2.98 | 13.4 |
| 1 | 25.5 | 0.23 | 3.37 | 0.29 | 3.08 | 13.8 |
| 2 | 0.1 | 1.17 | 2.43 | 2.36 | 0.07 | 0.30 |
| 2 | 1 | 1.09 | 2.51 | 2.26 | 0.24 | 1.10 |
| 2 | 2 | 1.07 | 2.53 | 2.19 | 0.34 | 1.52 |
| 2 | 4 | 1.03 | 2.57 | 1.99 | 0.59 | 2.64 |
| 2 | 6 | 1.00 | 2.60 | 1.70 | 0.90 | 4.04 |
| 2 | 21.5 | 0.75 | 2.85 | 0.58 | 2.27 | 10.2 |
| 2 | 25.5 | 0.59 | 3.01 | 0.49 | 2.52 | 11.4 |
| 3 | 0.1 | 1.56 | 2.04 | 1.98 | 0.06 | 0.27 |
| 3 | 1 | 1.55 | 2.05 | 1.77 | 0.28 | 1.24 |
| 3 | 2 | 1.49 | 2.11 | 1.65 | 0.46 | 2.08 |
| 3 | 4 | 1.45 | 2.15 | 1.28 | 0.87 | 3.92 |
| 3 | 6 | 1.33 | 2.27 | 0.96 | 1.31 | 5.92 |
| 3 | 21.5 | 1.12 | 2.48 | 0.26 | 2.22 | 10.0 |
| 3 | 25.5 | 0.88 | 2.72 | 0.26 | 2.46 | 11.1 |
| 4 | 0.1 | 0.84 | 2.76 | 2.75 | 0.02 | 0.07 |
| 4 | 1 | 0.78 | 2.82 | 2.73 | 0.09 | 0.40 |
| 4 | 2 | 0.83 | 2.77 | 2.59 | 0.17 | 0.79 |
| 4 | 4 | 0.78 | 2.82 | 2.44 | 0.38 | 1.71 |
| 4 | 6 | 0.78 | 2.82 | 2.10 | 0.72 | 3.25 |
| 4 | 21.5 | 0.58 | 3.02 | 1.12 | 1.90 | 8.57 |
| 4 | 25.5 | 0.51 | 3.09 | 0.97 | 2.11 | 9.51 |
| 5 | 0.1 | 0.90 | 2.70 | 2.70 | 0.00 | 0.00 |
| 5 | 1 | 0.90 | 2.70 | 2.70 | 0.00 | 0.00 |
| 5 | 2 | 0.92 | 2.68 | 2.68 | 0.00 | 0.00 |
| 5 | 4 | 0.89 | 2.71 | 2.70 | 0.00 | 0.02 |
| 5 | 6 | 0.92 | 2.68 | 2.62 | 0.06 | 0.29 |
| 5 | 21.5 | 0.90 | 2.70 | 2.62 | 0.08 | 0.37 |
| 5 | 25.5 | 0.89 | 2.71 | 2.62 | 0.09 | 0.41 |

Example 29

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol) or n-butanol, lipase (Lipolase® 100 L; Novozymes) and corn oil fatty acids prepared from corn oil (Table 15) were stirred at 30° C., and samples were withdrawn from each reaction mixture at predetermined times, immediately centrifuged, and the aqueous and organic layers separated and analyzed for isobutanol (i-BuOH) or n-butanol (n-BuOH) and isobutyl- or butyl esters of corn oil fatty acids (BuO-COFA) (Table 16).

TABLE 15

Reaction conditions for conversion of isobutanol (i-BuOH) or n-butanol (n-BuOH) to butyl esters of corn oil fatty acids (BuO-COFA)

| reaction | butanol | MES (0.2M) (g) | butanol (g) | COFA (g) | lipase (ppm) |
|---|---|---|---|---|---|
| 6 | iso-butanol | 45.96 | 3.6 | 13.5 | 10 |
| 7 | n-butanol | 45.96 | 3.6 | 13.5 | 10 |
| 8 | iso-butanol | 45.96 | 3.6 | 13.5 | 0 |
| 9 | isobutanol | 45.96 | 3.6 | 13.5 | 4 |

TABLE 16

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 15

| reaction | time (h) | total i-BuOH (g) (AQ) | total i-BuOH (g) (ORG) | total i-BuOH (g) (ORG) | i-BuOH (g) (ORG) | i-BuOH from i-BuO-COFA (g) (ORG) |
|---|---|---|---|---|---|---|
| 6 | 0 | 1.46 | 2.14 | 2.11 | 0.04 | 0.16 |
| 6 | 2 | 1.41 | 2.19 | 1.63 | 0.56 | 2.51 |
| 6 | 4 | 1.27 | 2.33 | 1.31 | 1.02 | 4.58 |
| 6 | 21 | 0.66 | 2.94 | 0.29 | 2.65 | 12.0 |
| 6 | 25 | 0.60 | 3.00 | 0.26 | 2.73 | 12.3 |
| 6 | 46 | 0.54 | 3.06 | 0.22 | 2.83 | 12.8 |
| | | total n-BuOH (g) (AQ) | total n-BuOH (g) (ORG) | n-BuOH (g) (ORG) | n-BuOH from n-BuO-COFA (g) (ORG) | n-BuO-COFA (g) (ORG) |
| 7 | 0 | 1.31 | 2.29 | 2.26 | 0.03 | 0.11 |
| 7 | 2 | 1.26 | 2.34 | 1.89 | 0.45 | 2.03 |
| 7 | 4 | 1.20 | 2.40 | 1.66 | 0.74 | 3.35 |
| 7 | 21 | 0.81 | 2.79 | 0.50 | 2.29 | 10.3 |
| 7 | 25 | 0.77 | 2.83 | 0.40 | 2.43 | 11.0 |
| 7 | 46 | 0.50 | 3.10 | 0.23 | 2.87 | 12.9 |

TABLE 16-continued

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 15

| | | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
|---|---|---|---|---|---|---|
| 8 | 0 | 1.62 | 1.98 | 1.98 | 0.00 | 0.01 |
| 8 | 2 | 1.56 | 2.04 | 2.04 | 0.00 | 0.00 |
| 8 | 4 | 1.59 | 2.01 | 2.01 | 0.00 | 0.00 |
| 8 | 21 | 1.59 | 2.01 | 2.00 | 0.01 | 0.04 |
| 8 | 25 | 1.55 | 2.05 | 2.04 | 0.01 | 0.04 |
| 8 | 46 | 1.45 | 2.15 | 2.12 | 0.02 | 0.11 |
| | | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
| 9 | 0 | 1.57 | 2.03 | 2.02 | 0.01 | 0.04 |
| 9 | 2 | 1.54 | 2.06 | 1.86 | 0.19 | 0.86 |
| 9 | 4 | 1.44 | 2.16 | 1.79 | 0.36 | 1.64 |
| 9 | 21 | 1.14 | 2.46 | 0.95 | 1.51 | 6.82 |
| 9 | 25 | 1.10 | 2.50 | 0.83 | 1.67 | 7.50 |
| 9 | 46 | 0.78 | 2.82 | 0.44 | 2.37 | 10.7 |

Example 30

Production of Iso-Butyl Oleate by Lipase-Catalyzed Reaction of Iso-Butanol and Oleic Acid Reaction mixtures containing aqueous 2-(N-morpholino) ethanesulfonic acid buffer (0.20 M, pH 5.2), isobutanol (2-methyl-1-propanol), lipase (0 ppm or 10 ppm Lipolase® 100 L; Novozymes) and oleic acid (Alfa Aesar) (Table 17) were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 18).

TABLE 17

Reaction conditions for conversion of isobutanol (i-BuOH) to iso-butyl oleate (i-BuO-oleate)

| reaction | MES (0.2M) (g) | i-BuOH (g) | oleic acid (g) | lipase (ppm) |
|---|---|---|---|---|
| 10 | 46.11 | 3.64 | 14.62 | 10 |
| 11 | 46.10 | 3.59 | 14.40 | 0 |

TABLE 18

Weights of isobutanol (i-BuOH) and iso-butyl oleate (i-BuO-COFA) present in the aqueous fraction (AQ) and organic fraction (ORG) for reactions described in Table 17.

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 0 | 1.37 | 2.28 | 2.24 | 0.04 | 0.18 |
| 10 | 2 | 1.30 | 2.34 | 1.95 | 0.40 | 1.81 |
| 10 | 4 | 1.28 | 2.37 | 1.82 | 0.55 | 2.53 |
| 10 | 6 | 1.22 | 2.42 | 1.71 | 0.72 | 3.27 |
| 10 | 23 | 0.92 | 2.72 | 0.71 | 2.01 | 9.20 |
| 10 | 27 | 0.89 | 2.75 | 0.65 | 2.11 | 9.62 |
| 10 | 47 | 0.81 | 2.84 | 0.55 | 2.29 | 10.5 |

TABLE 18-continued

Weights of isobutanol (i-BuOH) and iso-butyl oleate (i-BuO-COFA) present in the aqueous fraction (AQ) and organic fraction (ORG) for reactions described in Table 17.

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 51 | 0.82 | 2.83 | 0.54 | 2.29 | 10.5 |
| 11 | 0 | 1.44 | 2.16 | 2.16 | 0.00 | 0.00 |
| 11 | 2 | 1.45 | 2.15 | 2.15 | 0.00 | 0.00 |
| 11 | 4 | 1.44 | 2.16 | 2.16 | 0.00 | 0.00 |
| 11 | 6 | 1.43 | 2.16 | 2.16 | 0.00 | 0.00 |
| 11 | 23 | 1.49 | 2.10 | 2.10 | 0.01 | 0.02 |
| 11 | 27 | 1.46 | 2.14 | 2.13 | 0.01 | 0.04 |
| 11 | 47 | 1.48 | 2.12 | 2.09 | 0.02 | 0.10 |
| 11 | 51 | 1.52 | 2.07 | 2.05 | 0.02 | 0.11 |

Example 31

Production of Iso-Butyl Oleate by Lipase-Catalyzed Reaction of Iso-Butanol and Oleic Acid Reaction mixtures containing aqueous 2-(N-morpholino) ethanesulfonic acid buffer (MES, 0.20 M, pH 5.2), isobutanol (2-methyl-1-propanol), oleic acid (Alfa Aesar), and lipase (10 ppm) from Lipolase® 100L, Lipex® 100L, Lipozyme® CALB L, Novozyme® CALA L, Palatase® from Novozymes, or lipase (10 ppm) from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* from SigmaAldrich (Table 19), were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 20).

TABLE 19

Reaction conditions for conversion of isobutanol (i-BuOH) to iso-butyl oleate (i-BuO-oleate)

| MES (0.2M) (g) | i-BuOH (g) | oleic acid (g) | lipase (ppm) |
|---|---|---|---|
| 46.105 | 3.601 | 13.72 | 10 |

TABLE 20

Weights of isobutanol (i-BuOH) and iso-butyl oleate (i-BuO-oleate) present in the aqueous fraction (AQ) and organic fraction (ORG) for reactions described in Table 19

| lipase | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| Lipolase ® 100L | 23 | 1.55 | 2.05 | 1.47 | 0.59 | 2.68 |
| Lipex ® 100L | 23 | 0.65 | 2.95 | 0.30 | 2.65 | 12.09 |
| Lipozyme ® CALB L | 23 | 1.01 | 2.59 | 0.82 | 1.77 | 8.08 |
| Novozyme ® CALA L | 23 | 1.39 | 2.22 | 2.16 | 0.06 | 0.27 |
| Palatase ® | 23 | 1.27 | 2.33 | 1.43 | 0.91 | 4.14 |
| *Pseudomonas fluorescens* | 23 | 1.38 | 2.22 | 1.97 | 0.25 | 1.14 |
| *Pseudomonas cepacia* | 23 | 1.39 | 2.21 | 1.95 | 0.26 | 1.20 |
| *Mucor miehei* | 23 | 1.29 | 2.31 | 1.57 | 0.75 | 3.42 |
| hog pancreas | 23 | 1.40 | 2.20 | 2.19 | 0.01 | 0.04 |
| *Candida cylindracea* | 23 | 1.15 | 2.45 | 1.08 | 1.37 | 6.25 |
| *Rhizopus niveus* | 23 | 1.39 | 2.21 | 2.19 | 0.02 | 0.11 |
| *Candida antarctica* | 23 | 1.37 | 2.24 | 2.08 | 0.15 | 0.69 |
| *Rhizopus arrhizus* | 23 | 1.01 | 2.59 | 0.81 | 1.78 | 8.12 |
| *Aspergillus* | 23 | 1.36 | 2.24 | 2.06 | 0.18 | 0.82 |

Example 32

Production of Iso-Butyl COFA Esters by Phospholipase-Catalyzed Reaction of Iso-Butanol and Corn Oil Fatty Acids (COFA)

Reaction mixtures containing aqueous 2-(N-morpholino) ethanesulfonic acid buffer (0.20 M, pH 5.3), isobutanol (2-methyl-1-propanol), phospholipase (Phospholipase A; SigmaAldrich, L3295-250) and corn oil fatty acids prepared from corn oil were stirred at 30° C. (Table 21), and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 22).

TABLE 21

Reaction conditions for conversion of isobutanol (i-BuOH) to isobutyl esters of corn oil fatty acids (i-BuO-COFA)

| reaction # | MES buffer (0.2M) (g) | i-BuOH (g) | COFA (g) | lipase (ppm) |
|---|---|---|---|---|
| 1 | 46.1 | 3.6 | 14.7 | 10 |
| 2 | 46.1 | 3.6 | 14.7 | 3 |
| 3 | 46.1 | 3.6 | 14.7 | 0 |

TABLE 22

Weights of isobutanol (i-BuOH) and isobutyl esters of corn oil fatty acids (i-BuO-COFA) present in the aqueous fraction (AQ) and organic fraction (ORG) for reactions described in Table 21

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 1.29 | 2.39 | 2.39 | 0.00 | 0.00 |
| 1 | 2 | 1.24 | 2.44 | 2.38 | 0.06 | 0.26 |

TABLE 22-continued

Weights of isobutanol (i-BuOH) and isobutyl esters of corn oil fatty acids (i-BuO-COFA) present in the aqueous fraction (AQ) and organic fraction (ORG) for reactions described in Table 21

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 20 | 1.25 | 2.43 | 2.22 | 0.21 | 0.96 |
| 1 | 24 | 1.26 | 2.42 | 2.19 | 0.23 | 1.03 |
| 1 | 44 | 1.27 | 2.41 | 2.13 | 0.28 | 1.28 |
| 1 | 48 | 1.22 | 2.46 | 2.15 | 0.31 | 1.41 |
| 2 | 0.1 | 1.27 | 2.34 | 2.34 | 0.00 | 0.00 |
| 2 | 2 | 1.25 | 2.35 | 2.33 | 0.02 | 0.08 |
| 2 | 20 | 1.24 | 2.37 | 2.30 | 0.07 | 0.30 |
| 2 | 24 | 1.22 | 2.38 | 2.31 | 0.07 | 0.32 |
| 2 | 44 | 1.33 | 2.28 | 2.18 | 0.10 | 0.44 |
| 2 | 48 | 1.23 | 2.38 | 2.27 | 0.11 | 0.48 |
| 3 | 0.1 | 1.27 | 2.33 | 2.33 | 0.00 | 0.00 |
| 3 | 2 | 1.26 | 2.34 | 2.34 | 0.00 | 0.00 |
| 3 | 20 | 1.22 | 2.38 | 2.37 | 0.01 | 0.07 |
| 3 | 24 | 1.25 | 2.35 | 2.33 | 0.02 | 0.08 |
| 3 | 44 | 1.24 | 2.36 | 2.32 | 0.04 | 0.18 |
| 3 | 48 | 1.24 | 2.36 | 2.32 | 0.04 | 0.18 |

Example 33

Comparison of Partition Coefficients for Isobutanol Between Water and Extractant Aqueous solutions of isobutanol (30 g/L) were mixed with corn oil fatty acids (COFA), oleic acid, or corn oil triglycerides, and their measured partition coefficients reported in the table relative to the measured partition coefficient for oleyl alcohol. Results are shown in Table 23.

TABLE 23

Relative partition coefficients for isobutanol (30 g/L) between water and extractant

| extractant | isobutanol partition coefficient, relative to oleyl alcohol |
|---|---|
| oleyl alcohol | 100% |
| corn oil fatty acids | 91% |
| corn oil fatty acid isobutyl esters | 43% |
| corn oil triglycerides | 10% |

Example 34

Hydroxylated Triglycerides from Corn Oil

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1H$ NMR analysis of the crude reaction product showed that 63% of double bonds were epoxidized.

A. Corn Oil Hydroxylation (63% Hydroxylation)

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1H$ NMR analysis of the crude reaction product showed that 63% of double bonds were epoxidized.

To a 500 mL round bottom flask was added epoxidized corn oil (20.0 g), tetrahydrofuran (THF) (100.0 mL), and sulfuric acid (50 mL of 1.7 M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.9 g of dark yellow oil (63% hydroxylation corn oil).

B. Corn Oil Hydroxylation (47% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for one hour, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 49.8 g of yellow oil. The $^1H$ NMR analysis of the crude reaction product showed that 47% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.2 g of dark yellow oil (47% hydroxylation corn oil).

C. Corn Oil Hydroxylation (28% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 47.2 g of yellow oil. The $^1H$ NMR analysis of the crude reaction product showed that 28% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 20.3 g of dark yellow oil (28% hydroxylation corn oil).

Partition Coefficient Measurement

To a 5 mL vial was added 0.910 g of the 67% hydroxylated corn oil, and 0.910 mL of 3 wt % i-BuOH water solution. The biphasic mixture was vigorously stirred using Vortex Genie® for 10 minutes. Upon mixing, the separation of layers was aided by centrifuging the mixture using Fisher Scientific Centrific 228 centrifuge (3300 rpm) for 10 minutes. 0.100 g of both layers were taken. The organic, upper layer was diluted to 1.00 mL with toluene solution of ethylene glycol diethylether (10.1 mg/mL), and the water layer was diluted to 1.00 mL with methanol solution of ethylene glycol diethylether (10.2 mg/mL). The concentrations of i-BuOH in both phases were measured using a calibrated gas chromatograph (GC). The same procedure was repeated for 47% and 28% hydroxylated corn oil. The partition coefficient thus measured was 3.2 for the 67% hydroxylated corn oil, 2.3 for the 47% hydroxylated corn oil, and 2.1 for the 28% hydroxylated corn oil.

The above outlined procedure was repeated with 6% i-BuOH water solution. The partition coefficients for 67%-, 47%-, and 28%-hydroxylated corn oils were 2.9, 2.9, and 2.0, respectively.

Example 34

Fatty Amides Plus Fatty Acids, and Pure Fatty Amides from Corn Oil

Corn oil was reacted with aqueous ammonium hydroxide in a manner similar to that described by Roe, et al., J. Am. Oil Chem. Soc. 29:18-22, 1952. Mazola® corn oil (0.818 L, 755 g) was placed in a 1 gallon stainless steel reactor to which was added 1.71 L (1540 g) of aqueous ammonium hydroxide (28% as $NH_3$). The reactor was heated with stirring to 160° C. and was maintained at that temperature with stirring for 7 h during which time the pressure reached 400 psi. The reactor was cooled and the product, a creamy white solid, was removed and the reactor rinsed with ethyl acetate. The product was dissolved in 5 L ethyl acetate and washed 5 times with 500 mL each of water which was neutralized with $H_2SO_4$. The ethyl acetate was then dried over anhydrous $Na_2SO_4$ and the solvent removed on a rotary evaporator leaving a light brown soft solid.

$^{13}C$ NMR in $CDCl_3$ indicated that the product contained an approximate 2:1 ratio of fatty amide to fatty acid and that the conversion of the corn oil to product was quantitative. The product had a melting point of 57-58° C., but dropped about 11° C. when saturated with water.

Pure corn oil fatty amide was synthesized from corn oil according to Kohlhase, et al., J. Am. Oil Chem. Soc. 48:265-270, 1971 using anhydrous ammonia with ammonium acetate as a catalyst.

Three grams of ammonium acetate were placed in a 400 mL stainless steel shaker tube to which was added 51.8 g of corn oil. Anhydrous ammonia (89.7 g) was then added and the reactor sealed and heated for 7 h at 125° C. during which time the pressure reached 1300 psi. The reactor was cooled, the light colored solid removed and the reactor rinsed with ethyl acetate. The product dissolved in ethyl acetate was then worked up as in the case of the fatty amide/fatty acid mixture above.

Fatty acids were synthesized from corn oil by base hydrolysis using NaOH. Round bottom flask (5 L) was equipped with a mechanical stirrer, thermocouple, heating mantle, condenser, and nitrogen tee. Charged with 500 g of food grade corn oil, 1 L of water and 75 g of sodium hydroxide. Mixture was heated to 90° C. and held for three hours, during which time it became a single thick, emulsion-like single phase. At the end of this time, TLC shows no remaining corn oil in the mixture. The mixture was then cooled to 72° C. and 500 mL of 25% sulfuric acid was added to acidify the mixture. It was then cooled to room temperature and 2 L of diethyl ether was added. The ether layer was washed 3×1 L with 1% sulfuric acid, 1×1 L with saturated brine, dried over $MgSO_4$, and filtered. The ether was removed by rotovap and then the oil was purged with nitrogen overnight, obtaining 470 g of a yellow oil that partially crystallized overnight. Titration for free fatty acids via AOCS method Ca 5a-40 shows a fatty acid content of 95% expressed as oleic acid. A sample was silanized by reacting 104 mg with 100 uL of N-methyl-N-(trimethylsilyl)trifluoroacetamide in 1 mL of dry pyridine. Gas chromatography-mass spectrometry (GCMS) analysis of the silanized product shows the presence of the TMS derivatives of the 16:0, 18:2, 18:1, 18:0, and 20:0 acids Three preparations: (1) the 2:1 mixture of corn oil fatty amide and corn oil fatty acid from aqueous ammonia, (2) a 2:1 mixture of pure corn oil fatty amide:pure corn oil fatty acid, and (3) a 1:2 mixture of pure corn oil fatty amide:corn oil fatty acid, were all tested for their ability to extract isobutanol from a 3% solution in water. Seven hundred milligrams of each was added to 2.1 mL of water containing 3% isobutanol in a 20 mL scintillation vial and placed on a rotary shaker overnight at 30° C. In all three cases, the organic phase became liquid at this temperature, indicating a further lowering of the melting point with the uptake of isobutanol. Fifty microliters of the upper phase were diluted with either 200 μL of toluene containing ethylene glycol diethylether (10.068 mg/mL) as a GC standard or 200 μL of isopropanol containing the same concentration of ethylene glycol diethylether. Fifty microliters of the lower phase was diluted with 150 μL of methanol and 50 μL of isopropanol containing the same concentration of ethylene glycol diethylether. The concentrations of isobutanol in both phases were determined using a calibrated GC. The partition coefficients measured were as follows: 3.81 for (1), 4.31 for (2), and 3.58 for (3).

Fatty amide/fatty acid aqueous ammonia preparation (1), and a preparation (1a) constituted by preparation (1) mixed 1:1 with pure corn oil fatty acid (equivalent to 1:2 fatty amide: fatty acid) were incubated in shake flasks with fermentation broth containing the *Saccharomyces* butanologen NGCI-070 at a ratio of 3 parts broth to 1 part amide/acid mixture. Preparation (1) was a soft solid, while preparation (1a) was a liquid at 30° C. Starting at a glucose concentration of 8.35 g/L, the shake flasks were then incubated for 25 h on an incubator shaker and the consumption of glucose followed as a function of time. Table 24 indicates that the fatty amide/fatty acid mixtures at both ratios were not toxic to the butanologen and even showed higher rates of glucose uptake than with oleyl alcohol.

TABLE 24

| | Glucose conc. (g/L) | | |
|---|---|---|---|
| Flask | Time = 0 | 18 hrs | 25 hrs |
| Oleyl Alcohol | 8.35 | 4.26 | 0 |
| Oleyl Alcohol | 8.35 | 4.46 | 0 |
| 2:1 Synthesized Fatty Amide:Fatty Acid Mix (Preparation (1)) | 8.35 | 3.06 | 0 |
| 2:1 Synthesized Fatty Amide:Fatty Acid Mix (Preparation (1)) | 8.35 | 3.22 | 0 |
| 1:1 Synthesized Fatty Amide Fatty Acid Mix:Pure Fatty Acids (Preparation (1a)) | 8.35 | 2.73 | 0 |
| 1:1 Synthesized Fatty Amide Fatty Acid Mix:Pure Fatty Acids (Preparation (1a)) | 8.35 | 2.73 | 0 |

Example 35

Fatty Alcohols from Corn Oil

With reference to the reaction of Equation IV above for producing fatty alcohols from corn oil, a 22L, round-bottom flask equipped with a mechanical stirrer, reflux condenser with $N_2$ source, addition funnel, internal thermocouple, and rubber septum was flame-dried under nitrogen. The flask was charged with 132 g (3.30 moles) of 95% lithium aluminum hydride powder that is weighed out in a dry box and loaded into a solids addition funnel. The 22L flask was cooled with an ice bath, and 9.0 liters of anhydrous THF were added into the reactor via a cannula. The resulting slurry was cooled to 0-5° C. and a solution of 956 g (1.10 moles) of Wesson® corn oil in 1.00 liter of anhydrous THF was added dropwise over 2-3 hours while holding the reaction temperature at 5-20° C. After adding the corn oil, the slurry was stirred overnight at ambient temperature. When the reaction was done, as verified by TLC chromatography, it was quenched by the dropwise addition of a solution of 130 g of water dissolved in 370 mL of THF. Then 130 g of 15% aqueous NaOH solution was added followed by the addition of 400 g of water. The mixture was vigorously stirred while warming to room temperature and produced a white granular solid. The solids were filtered off using a fritted-glass filter funnel and washed with additional THF. The THF was removed on a rotary evaporator and the residue was taken up in 3.00 liters of ethyl acetate. The product solution was washed with 2×1.00 L of water, 1×1.00 L of brine, dried over $Na_2SO_4$, filtered, and concentrated in vacuo to give 836 g (97%) of fatty alcohols as yellow oil. The crude fatty alcohol mixture was then distilled (140° C./1 mmHg), and used in the following partition coefficients experiments.

Partition Coefficient Experiments

To each of the five 5-mL vials were added 1 mL of fatty alcohol mixture, and 1 mL of 3 wt % i-BuOH water solution. The biphasic mixture was vigorously stirred using Vortex Genie® for 10, 20, 30, 40, and 60 minutes, respectively. Upon mixing, the separation of layers was aided by centrifuging the mixture using Fisher Scientific Centrific 228 centrifuge (3300 rpm) for 10 minutes. 0.100 mL of both layers were taken. The organic, upper layer was diluted to 1.00 mL with toluene solution of ethylene glycol diethylether, and the water layer was diluted to 1.00 mL with methanol solution of ethylene glycol diethylether. The concentrations of i-BuOH in both phases were measured using a calibrated GC. The partition coefficient thus measured was 2.70.

The same partition coefficient measurement, as described above was run for 6 wt % i-BuOH concentration. The partition coefficient thus measured was 3.06.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing an alcohol comprising:

(a) providing biomass comprising water, fermentable sugars, and oil;

(b) liquefying the biomass to produce a liquefied biomass;

(c) contacting the liquefied biomass with one or more catalysts whereby at least a portion of the oil is hydrolyzed to form an extractant, wherein a partition coefficient of the extractant for the product alcohol is greater than a partition coefficient of the oil of the biomass for the product alcohol;

(d) contacting the liquefied biomass with a saccharification enzyme capable of converting oligosaccharides into fermentable sugar; contacting the liquefied biomass with a fermentation broth in a fermentation vessel;

(e) fermenting the carbon source of the liquefied biomass to produce a product alcohol;

(f) removing in situ the product alcohol from the fermentation broth by contacting the broth with the extractant;

and optionally steps (c) and (d) occur concurrently.

2. The method of claim 1, wherein the biomass comprises corn grain, wheat, rye, barley, soy, and mixtures thereof.

3. The method of claim 1, wherein the extractant comprises fatty acids, fatty amides, fatty alcohols, fatty esters, or mixtures thereof.

4. The method of claim 1, wherein the one or more catalysts is selected from esterase, lipase, phospholipase, and lysophospholipase.

5. The method of claim 1, further comprising:

inactivating the catalyst after at least a portion of the oil is hydrolyzed to form the extractant.

6. The method of claim 1, wherein the product alcohol is butanol.

7. The method of claim 1, wherein the biomass comprises hay, sorghum, switchgrass, and mixtures thereof.

8. The method of claim 1, wherein the biomass comprises cellulosic material, lignocellulosic material, and mixtures thereof.

9. The method of claim 1, wherein the biomass comprises sugar cane bagasse.

10. The method of claim 1, wherein the biomass comprises wheat straw, barley straw, rice straw, and mixtures thereof.

11. The method of claim 1, wherein the biomass comprises corn cobs, corn husks, corn stover, and mixtures thereof.

12. The method of claim 1, wherein the biomass comprises crop residues.

* * * * *

SEQUENCE LISTING

```
<160> NUMBER OF SEQ ID NOS: 145

<210> SEQ ID NO 1
<211> LENGTH: 11844
<212> TYPE: DNA
<213> ORGANISM: Artificial Sequence
<220> FEATURE:
<223> OTHER INFORMATION: Plasmid

<400> SEQUENCE: 1

tcccattacc gacatttggg cgctatacgt gcatatgttc atgtatgtat ctgtatttaa     60

aacacttttg tattattttt cctcatatat gtgtataggt ttatacggat gatttaatta    120

ttacttcacc accctttatt tcaggctgat atcttagcct tgttactagt tagaaaaaga    180

catttttgct gtcagtcact gtcaagagat tcttttgctg gcatttcttc tagaagcaaa    240

aagagcgatg cgtcttttcc gctgaaccgt tccagcaaaa aagactacca acgcaatatg    300

gattgtcaga atcatataaa agagaagcaa ataactcctt gtcttgtatc aattgcatta    360

taatatcttc ttgttagtgc aatatcatat agaagtcatc gaaatagata ttaagaaaaa    420

caaactgtac aatcaatcaa tcaatcatcg ctgaggatgt tgacaaaagc aacaaaagaa    480

caaaaatccc ttgtgaaaaa cagaggggcg gagcttgttg ttgattgctt agtggagcaa    540

ggtgtcacac atgtatttgg cattccaggt gcaaaaattg atgcggtatt tgacgcttta    600

caagataaag gacctgaaat tatcgttgcc cggcacgaac aaaacgcagc attcatggcc    660

caagcagtcg gccgtttaac tggaaaaccg ggagtcgtgt tagtcacatc aggaccgggt    720

gcctctaact tggcaacagg cctgctgaca gcgaacactg aaggagaccc tgtcgttgcg    780

cttgctggaa acgtgatccg tgcagatcgt ttaaaacgga cacatcaatc tttggataat    840

gcggcgctat tccagccgat tacaaaatac agtgtagaag ttcaagatgt aaaaaatata    900

ccggaagctg ttacaaatgc atttaggata gcgtcagcag ggcaggctgg ggccgctttt    960

gtgagctttc cgcaagatgt tgtgaatgaa gtcacaaata cgaaaaacgt gcgtgctgtt   1020
```

-continued

```
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat ttgttgaaac atatcaagct   1200
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga aagtggaatt tgcagagcgt   1500
gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgcac ctggtaaaac ctctagtgga   2460
gtagtagatg taatcaatga agcggaagcc aaaagaccag agtagaggcc tatagaagaa   2520
actgcgatac cttttgtgat ggctaaacaa acagacatct tttatatgt ttttacttct   2580
gtatatcgtg aagtagtaag tgataagcga atttggctaa gaacgttgta agtgaacaag   2640
ggacctcttt tgcctttcaa aaaaggatta aatggagtta atcattgaga tttagttttc   2700
gttagattct gtatccctaa ataactccct tacccgacgg gaaggcacaa aagacttgaa   2760
taatagcaaa cggccagtag ccaagaccaa ataatactag agttaactga tggtcttaaa   2820
caggcattac gtggtgaact ccaagaccaa tatacaaaat atcgataagt tattcttgcc   2880
caccaattta aggagcctac atcaggacag tagtaccatt cctcagagaa gaggtataca   2940
taacaagaaa atcgcgtgaa caccttatat aacttagccc gttattgagc taaaaaacct   3000
tgcaaaattt cctatgaata agaatacttc agacgtgata aaaatttact ttctaactct   3060
tctcacgctg cccctatctg ttcttccgct ctaccgtgag aaataaagca tcgagtacgg   3120
cagttcgctg tcactgaact aaaacaataa ggctagttcg aatgatgaac ttgcttgctg   3180
tcaaacttct gagttgccgc tgatgtgaca ctgtgacaat aaattcaaac cggttatagc   3240
ggtctcctcc ggtaccggtt ctgccacctc caatagagct cagtaggagt cagaacctct   3300
gcggtggctg tcagtgactc atccgcgttt cgtaagttgt gcgcgtgcac atttcgcccg   3360
ttcccgctca tcttgcagca ggcggaaatt ttcatcacgc tgtaggacgc aaaaaaaaaa   3420
```

-continued

```
taattaatcg tacaagaatc ttggaaaaaa aattgaaaaa ttttgtataa aagggatgac   3480
ctaacttgac tcaatggctt ttacacccag tattttccct ttccttgttt gttacaatta   3540
tagaagcaag acaaaaacat atagacaacc tattcctagg agttatattt ttttacccta   3600
ccagcaatat aagtaaaaaa ctgtttaaac agtatggcag ttacaatgta ttatgaagat   3660
gatgtagaag tatcagcact tgctggaaag caaattgcag taatcggtta tggttcacaa   3720
ggacatgctc acgcacagaa tttgcgtgat tctggtcaca acgttatcat tggtgtgcgc   3780
cacggaaaat cttttgataa agcaaaagaa gatggctttg aaacatttga agtaggagaa   3840
gcagtagcta aagctgatgt tattatggtt ttggcaccag atgaacttca acaatccatt   3900
tatgaagagg acatcaaacc aaacttgaaa gcaggttcag cacttggttt tgctcacgga   3960
tttaatatcc attttggcta tattaaagta ccagaagacg ttgacgtctt tatggttgcg   4020
cctaaggctc caggtcacct tgtccgtcgg acttatactg aaggttttgg tacaccagct   4080
ttgtttgttt cacaccaaaa tgcaagtggt catgcgcgtg aaatcgcaat ggattgggcc   4140
aaaggaattg gttgtgctcg agtgggaatt attgaaacaa cttttaaaga agaaacagaa   4200
gaagatttgt ttggagaaca agctgttcta tgtggaggtt tgacagcact tgttgaagcc   4260
ggttttgaaa cactgacaga agctggatac gctggcgaat tggcttactt tgaagttttg   4320
cacgaaatga aattgattgt tgacctcatg tatgaaggtg gttttactaa aatgcgtcaa   4380
tccatctcaa atactgctga gtttggcgat tatgtgactg gtccacggat tattactgac   4440
gaagttaaaa agaatatgaa gcttgttttg gctgatattc aatctggaaa atttgctcaa   4500
gatttcgttg atgacttcaa agcggggcgt ccaaaattaa tagcctatcg cgaagctgca   4560
aaaaatcttg aaattgaaaa aattggggca gagctacgtc aagcaatgcc attcacacaa   4620
tctggtgatg acgatgcctt taaaatctat cagtaaggcc ctgcaggcct atcaagtgct   4680
ggaaactttt tctcttggaa tttttgcaac atcaagtcat agtcaattga attgacccaa   4740
tttcacattt aagatttttt ttttttcatc cgacatacat ctgtacacta ggaagccctg   4800
tttttctgaa gcagcttcaa atatatatat tttttacata tttattatga ttcaatgaac   4860
aatctaatta aatcgaaaac aagaaccgaa acgcgaataa ataatttatt tagatggtga   4920
caagtgtata agtcctcatc gggacagcta cgatttctct ttcggttttg gctgagctac   4980
tggttgctgt gacgcagcgg cattagcgcg gcgttatgag ctaccctcgt ggcctgaaag   5040
atggcgggaa taaagcggaa ctaaaaatta ctgactgagc catattgagg tcaatttgtc   5100
aactcgtcaa gtcacgtttg gtggacggcc cctttccaac gaatcgtata tactaacatg   5160
cgcgcgcttc ctatatacac atatacatat atatatatat atatatgtgt gcgtgtatgt   5220
gtacacctgt atttaatttc cttactcgcg ggtttttctt ttttctcaat tcttggcttc   5280
ctctttctcg agcggaccgg atcctccgcg gtgccggcag atctatttaa atggcgcgcc   5340
gacgtcaggt ggcacttttc ggggaaatgt gcgcggaacc cctatttgtt tatttttcta   5400
aatacattca aatatgtatc cgctcatgag acaataaccc tgataaatgc ttcaataata   5460
ttgaaaaagg aagagtatga gtattcaaca tttccgtgtc gcccttattc ccttttttgc   5520
ggcattttgc cttcctgttt ttgctcaccc agaaacgctg gtgaaagtaa aagatgctga   5580
agatcagttg ggtgcacgag tgggttacat cgaactggat ctcaacagcg gtaagatcct   5640
tgagagtttt cgccccgaag aacgttttcc aatgatgagc acttttaaag ttctgctatg   5700
tggcgcggta ttatcccgta ttgacgccgg gcaagagcaa ctcggtcgcc gcatacacta   5760
ttctcagaat gacttggttg agtactcacc agtcacagaa aagcatctta cggatggcat   5820
```

-continued

```
gacagtaaga gaattatgca gtgctgccat aaccatgagt gataacactg cggccaactt   5880
acttctgaca acgatcggag gaccgaagga gctaaccgct tttttgcaca acatggggga   5940
tcatgtaact cgccttgatc gttgggaacc ggagctgaat gaagccatac caaacgacga   6000
gcgtgacacc acgatgcctg tagcaatggc aacaacgttg cgcaaactat taactggcga   6060
actacttact ctagcttccc ggcaacaatt aatagactgg atggaggcgg ataaagttgc   6120
aggaccactt ctgcgctcgg cccttccggc tggctggttt attgctgata aatctggagc   6180
cggtgagcgt gggtctcgcg gtatcattgc agcactgggg ccagatggta agccctcccg   6240
tatcgtagtt atctacacga cggggagtca ggcaactatg gatgaacgaa atagacagat   6300
cgctgagata ggtgcctcac tgattaagca ttggtaactg tcagaccaag tttactcata   6360
tatactttag attgatttaa aacttcattt ttaatttaaa aggatctagg tgaagatcct   6420
ttttgataat ctcatgacca aaatccctta acgtgagttt tcgttccact gagcgtcaga   6480
ccccgtagaa aagatcaaag gatcttcttg agatcctttt tttctgcgcg taatctgctg   6540
cttgcaaaca aaaaaaccac cgctaccagc ggtggtttgt ttgccggatc aagagctacc   6600
aactcttttt ccgaaggtaa ctggcttcag cagagcgcag ataccaaata ctgttcttct   6660
agtgtagccg tagttaggcc accacttcaa gaactctgta gcaccgccta catacctcgc   6720
tctgctaatc ctgttaccag tggctgctgc cagtggcgat aagtcgtgtc ttaccgggtt   6780
ggactcaaga cgatagttac cggataaggc gcagcggtcg ggctgaacgg ggggttcgtg   6840
cacacagccc agcttggagc gaacgaccta caccgaactg agatacctac agcgtgagct   6900
atgagaaagc gccacgcttc ccgaagggag aaaggcggac aggtatccgg taagcggcag   6960
ggtcggaaca ggagagcgca cgagggagct tccaggggga aacgcctggt atctttatag   7020
tcctgtcggg tttcgccacc tctgacttga gcgtcgattt ttgtgatgct cgtcaggggg   7080
gcggagccta tggaaaaacg ccagcaacgc ggccttttta cggttcctgg ccttttgctg   7140
gccttttgct cacatgttct ttcctgcgtt atcccctgat tctgtggata accgtattac   7200
cgcctttgag tgagctgata ccgctcgccg cagccgaacg accgagcgca gcgagtcagt   7260
gagcgaggaa gcggaagagc gcccaatacg caaaccgcct ctccccgcgc gttggccgat   7320
tcattaatgc agctggcacg acaggtttcc cgactggaaa gcgggcagtg agcgcaacgc   7380
aattaatgtg agttagctca ctcattaggc accccaggct ttacacttta tgcttccggc   7440
tcgtatgttg tgtggaattg tgagcggata acaatttcac acaggaaaca gctatgacca   7500
tgattacgcc aagctttttc tttccaattt ttttttttc gtcattataa aaatcattac   7560
gaccgagatt cccgggtaat aactgatata attaaattga agctctaatt tgtgagttta   7620
gtatacatgc atttacttat aatacagttt tttagttttg ctggccgcat cttctcaaat   7680
atgcttccca gcctgctttt ctgtaacgtt caccctctac cttagcatcc cttccctttg   7740
caaatagtcc tcttccaaca ataataatgt cagatcctgt agagaccaca tcatccacgg   7800
ttctatactg ttgacccaat gcgtctccct tgtcatctaa acccacaccg ggtgtcataa   7860
tcaaccaatc gtaaccttca tctcttccac ccatgtctct ttgagcaata aagccgataa   7920
caaaatcttt gtcgctcttc gcaatgtcaa cagtaccctt agtatattct ccagtagata   7980
gggagccctt gcatgacaat tctgctaaca tcaaaaggcc tctaggttcc tttgttactt   8040
cttctgccgc ctgcttcaaa ccgctaacaa tacctgggcc caccacaccg tgtgcattcg   8100
taatgtctgc ccattctgct attctgtata cacccgcaga gtactgcaat ttgactgtat   8160
taccaatgtc agcaaatttt ctgtcttcga agagtaaaaa attgtacttg gcggataatg   8220
```

-continued

```
cctttagcgg cttaactgtg ccctccatgg aaaaatcagt caagatatcc acatgtgttt   8280
ttagtaaaca aattttggga cctaatgctt caactaactc cagtaattcc ttggtggtac   8340
gaacatccaa tgaagcacac aagtttgttt gcttttcgtg catgatatta aatagcttgg   8400
cagcaacagg actaggatga gtagcagcac gttccttata tgtagctttc gacatgattt   8460
atcttcgttt cctgcaggtt tttgttctgt gcagttgggt taagaatact gggcaatttc   8520
atgtttcttc aacactacat atgcgtatat ataccaatct aagtctgtgc tccttccttc   8580
gttcttcctt ctgttcggag attaccgaat caaaaaaatt tcaaggaaac cgaaatcaaa   8640
aaaaagaata aaaaaaaaat gatgaattga aaagcttgca tgcctgcagg tcgactctag   8700
tatactccgt ctactgtacg atacacttcc gctcaggtcc ttgtccttta acgaggcctt   8760
accactcttt tgttactcta ttgatccagc tcagcaaagg cagtgtgatc taagattcta   8820
tcttcgcgat gtagtaaaac tagctagacc gagaaagaga ctagaaatgc aaaaggcact   8880
tctacaatgg ctgccatcat tattatccga tgtgacgctg catttttttt tttttttttt   8940
tttttttttt tttttttttt tttttttttt ttttgtacaa atatcataaa aaaagagaat   9000
ctttttaagc aaggatttc ttaacttctt cggcgacagc atcaccgact tcggtggtac    9060
tgttggaacc acctaaatca ccagttctga tacctgcatc caaaaccttt ttaactgcat   9120
cttcaatggc tttaccttct tcaggcaagt tcaatgacaa tttcaacatc attgcagcag   9180
acaagatagt ggcgataggg ttgaccttat tctttggcaa atctggagcg gaaccatggc   9240
atggttcgta caaaccaaat gcggtgttct tgtctggcaa agaggccaag gacgcagatg   9300
gcaacaaacc caaggagcct gggataacgg aggcttcatc ggagatgata tcaccaaaca   9360
tgttgctggt gattataata ccatttaggt gggttgggtt cttaactagg atcatggcgg   9420
cagaatcaat caattgatgt tgaactttca atgtagggaa ttcgttcttg atggtttcct   9480
ccacagtttt tctccataat cttgaagagg ccaaaacatt agctttatcc aaggaccaaa   9540
taggcaatgg tggctcatgt tgtagggcca tgaaagcggc cattcttgtg attctttgca   9600
cttctggaac ggtgtattgt tcactatccc aagcgacacc atcaccatcg tcttcctttc   9660
tcttaccaaa gtaaatacct cccactaatt ctctaacaac aacgaagtca gtacctttag   9720
caaattgtgg cttgattgga gataagtcta aaagagagtc ggatgcaaag ttacatggtc   9780
ttaagttggc gtacaattga agttctttac ggatttttag taaaccttgt tcaggtctaa   9840
cactaccggt accccattta ggaccaccca cagcacctaa caaaacggca tcagccttct   9900
tggaggcttc cagcgcctca tctggaagtg gaacacctgt agcatcgata gcagcaccac   9960
caattaaatg attttcgaaa tcgaacttga cattggaacg aacatcagaa atagctttaa  10020
gaaccttaat ggcttcggct gtgatttctt gaccaacgtg gtcacctggc aaaacgacga  10080
tcttcttagg ggcagacatt acaatggtat atccttgaaa tatatataaa aaaaaaaaaa  10140
aaaaaaaaaa aaaaaaatgc agcttctcaa tgatattcga atacgctttg aggagataca  10200
gcctaatatc cgacaaactg ttttacagat ttacgatcgt acttgttacc catcattgaa  10260
ttttgaacat ccgaacctgg gagttttccc tgaaacagat agtatatttg aacctgtata  10320
ataatatata gtctagcgct ttacggaaga caatgtatgt atttcggttc ctggagaaac  10380
tattgcatct attgcatagg taatcttgca cgtcgcatcc ccggttcatt ttctgcgttt  10440
ccatcttgca cttcaatagc atatctttgt taacgaagca tctgtgcttc attttgtaga  10500
acaaaaatgc aacgcgagag cgctaatttt tcaaacaaag aatctgagct gcatttttac  10560
agaacagaaa tgcaacgcga aagcgctatt ttaccaacga agaatctgtg cttcattttt  10620
```

-continued gtaaaacaaa aatgcaacgc gagagcgcta atttttcaaa caaagaatct gagctgcatt 10680
tttacagaac agaaatgcaa cgcgagagcg ctattttacc aacaaagaat ctatacttct 10740
tttttgttct acaaaaatgc atcccgagag cgctattttt ctaacaaagc atcttagatt 10800
actttttttc tcctttgtgc gctctataat gcagtctctt gataactttt tgcactgtag 10860
gtccgttaag gttagaagaa ggctactttg gtgtctattt tctcttccat aaaaaaagcc 10920
tgactccact tcccgcgttt actgattact agcgaagctg cgggtgcatt ttttcaagat 10980
aaaggcatcc ccgattatat tctataccga tgtggattgc gcatactttg tgaacagaaa 11040
gtgatagcgt tgatgattct tcattggtca gaaaattatg aacggtttct tctattttgt 11100
ctctatatac tacgtatagg aaatgtttac attttcgtat tgttttcgat tcactctatg 11160
aatagttctt actacaattt ttttgtctaa agagtaatac tagagataaa cataaaaaat 11220
gtagaggtcg agtttagatg caagttcaag gagcgaaagg tggatgggta ggttatatag 11280
ggatatagca cagagatata tagcaaagag atacttttga gcaatgtttg tggaagcggt 11340
attcgcaata ttttagtagc tcgttacagt ccggtgcgtt tttggttttt tgaaagtgcg 11400
tcttcagagc gcttttggtt ttcaaaagcg ctctgaagtt cctatacttt ctagagaata 11460
ggaacttcgg aataggaact tcaaagcgtt tccgaaaacg agcgcttccg aaaatgcaac 11520
gcgagctgcg cacatacagc tcactgttca cgtcgcacct atatctgcgt gttgcctgta 11580
tatatatata catgagaaga acggcatagt gcgtgtttat gcttaaatgc gtacttatat 11640
gcgtctattt atgtaggatg aaaggtagtc tagtacctcc tgtgatatta tcccattcca 11700
tgcggggtat cgtatgcttc cttcagcact accctttagc tgttctatat gctgccactc 11760
ctcaattgga ttagtctcat ccttcaatgc tatcatttcc tttgatattg gatcatatgc 11820
atagtaccga gaaactagag gatc 11844

<210> SEQ ID NO 2
<211> LENGTH: 15539
<212> TYPE: DNA
<213> ORGANISM: Artificial Sequence
<220> FEATURE:
<223> OTHER INFORMATION: Plasmid

<400> SEQUENCE: 2
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat attttttttat gcctcggtaa tgattttcat 360
tttttttttt ccacctagcg gatgactctt tttttttctt agcgattggc attatcacat 420
aatgaattat acattatata aagtaatgtg atttcttcga agaatatact aaaaaatgag 480
caggcaagat aaacgaaggc aaagatgaca gagcagaaag ccctagtaaa gcgtattaca 540
aatgaaacca agattcagat tgcgatctct ttaaagggtg gtcccctagc gatagagcac 600
tcgatcttcc cagaaaaaga ggcagaagca gtagcagaac aggccacaca atcgcaagtg 660
attaacgtcc acacaggtat agggtttctg gaccatatga tacatgctct ggccaagcat 720
tccggctggt cgctaatcgt tgagtgcatt ggtgacttac acatagacga ccatcacacc 780
actgaagact gcgggattgc tctcggtcaa gcttttaaag aggccctagg ggccgtgcgt 840

-continued

```
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat tttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aaggtgttct tatgtagtga caccgattat ttaaagctgc agcatacgat   1200
atatatacat gtgtatatat gtatacctat gaatgtcagt aagtatgtat acgaacagta   1260
tgatactgaa gatgacaagg taatgcatca ttctatacgt gtcattctga acgaggcgcg   1320
ctttcctttt ttctttttgc tttttctttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aaagaataga ccgagatagg gttgagtgtt   1560
gttccagttt ggaacaagag tccactatta aagaacgtgg actccaacgt caaagggcga   1620
aaaaccgtct atcagggcga tggcccacta cgtgaaccat caccctaatc aagttttttg   1680
gggtcgaggt gccgtaaagc actaaatcgg aaccctaaag ggagcccccg atttagagct   1740
tgacggggaa agccggcgaa cgtggcgaga aaggaaggga agaaagcgaa aggagcgggc   1800
gctagggcgc tggcaagtgt agcggtcacg ctgcgcgtaa ccaccacacc cgccgcgctt   1860
aatgcgccgc tacagggcgc gtccattcgc cattcaggct gcgcaactgt tgggaagggc   1920
gcggtgcggg cctcttcgct attacgccag ctggcgaaag ggggatgtgc tgcaaggcga   1980
ttaagttggg taacgccagg gttttcccag tcacgacgtt gtaaaacgac ggccagtgag   2040
cgcgcgtaat acgactcact atagggcgaa ttgggtaccg ggccccccct cgaggtcgac   2100
ggcgcgccac tggtagagag cgactttgta tgccccaatt gcgaaacccg cgatatcctt   2160
ctcgattctt tagtacccga ccaggacaag gaaaaggagg tcgaaacgtt tttgaagaaa   2220
caagaggaac tacacggaag ctctaaagat ggcaaccagc cagaaactaa gaaaatgaag   2280
ttgatggatc caactggcac cgctggcttg aacaacaata ccagccttcc aacttctgta   2340
aataacggcg gtacgccagt gccaccagta ccgttacctt tcggtatacc tcctttcccc   2400
atgtttccaa tgcccttcat gcctccaacg gctactatca caaatcctca tcaagctgac   2460
gcaagcccta agaaatgaat aacaatactg acagtactaa ataattgcct acttggcttc   2520
acatacgttg catacgtcga tatagataat aatgataatg acagcaggat tatcgtaata   2580
cgtaatagct gaaaatctca aaaatgtgtg ggtcattacg taaataatga taggaatggg   2640
attcttctat ttttcctttt tccattctag cagccgtcgg gaaaacgtgg catcctctct   2700
ttcgggctca attggagtca cgctgccgtg agcatcctct ctttccatat ctaacaactg   2760
agcacgtaac caatggaaaa gcatgagctt agcgttgctc caaaaaagta ttggatggtt   2820
aataccattt gtctgttctc ttctgacttt gactcctcaa aaaaaaaaat ctacaatcaa   2880
cagatcgctt caattacgcc ctcacaaaaa ctttttttcct tcttcttcgc ccacgttaaa   2940
ttttatccct catgttgtct aacggatttc tgcacttgat ttattataaa aagacaaaga   3000
cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
```

-continued

```
cgtcggtgtc atttcaactt gggctgaaaa cacaccttgt aatatccact tacatgactt   3300
tggtaaacta gccaaagtcg gtgttaagga agctggtgct tggccagttc agttcggaac   3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccatttttg cttacggcgg aacaattgca cctggtaatt tagacggcaa   3600
agatatcgat ttagtctctg tctttgaagg tgtcggccat tggaaccacg gcgatatgac   3660
caaagaagaa gttaaagctt tggaatgtaa tgcttgtccc ggtcctggag gctgcggtgg   3720
tatgtatact gctaacacaa tggcgacagc tattgaagtt ttgggactta gccttccggg   3780
ttcatcttct cacccggctg aatccgcaga aaagaaagca gatattgaag aagctggtcg   3840
cgctgttgtc aaaatgctcg aaatgggctt aaaaccttct gacattttaa cgcgtgaagc   3900
ttttgaagat gctattactg taactatggc tctgggaggt tcaaccaact caacccttca   3960
cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
tgatttaaca cctggtcaaa aggttattat gccgcttgaa aatcctaaac gtgaagatgg   4260
tccgctcatt attctccatg gtaacttggc tccagacggt gccgttgcca aagtttctgg   4320
tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttccctt tcatcaatga ttgttggtaa   4500
agggcaaggt gaaaaagttg cccttctgac agatggccgc ttctcaggtg gtacttatgg   4560
tcttgtcgtg ggtcatatcg ctcctgaagc acaagatggc ggtccaatcg cctacctgca   4620
aacaggagac atagtcacta ttgaccaaga cactaaggaa ttacactttg atatctccga   4680
tgaagagtta aaacatcgtc aagagaccat tgaattgcca ccgctctatt cacgcggtat   4740
ccttggtaaa tatgctcaca tcgtttcgtc tgcttctagg ggagccgtaa cagacttttg   4800
gaagcctgaa gaaactggca aaaaatgttg tcctggttgc tgtggttaag cggccgcgtt   4860
aattcaaatt aattgatata gtttttttaat gagtattgaa tctgtttaga aataatggaa   4920
tattattttt atttatttat ttatattatt ggtcggctct tttcttctga aggtcaatga   4980
caaaatgata tgaaggaaat aatgatttct aaaattttac aacgtaagat atttttacaa   5040
aagcctagct catcttttgt catgcactat tttactcacg cttgaaatta acggccagtc   5100
cactgcggag tcatttcaaa gtcatcctaa tcgatctatc gtttttgata gctcattttg   5160
gagttcgcga ttgtcttctg ttattcacaa ctgttttaat ttttatttca ttctggaact   5220
cttcgagttc tttgtaaagt ctttcatagt agcttacttt atcctccaac atatttaact   5280
tcatgtcaat ttcggctctt aaattttcca catcatcaag ttcaacatca tcttttaact   5340
tgaatttatt ctctagctct tccaaccaag cctcattgct ccttgattta ctggtgaaaa   5400
gtgatacact ttgcgcgcaa tccaggtcaa aactttcctg caaagaattc accaatttct   5460
cgacatcata gtacaatttg ttttgttctc ccatcacaat ttaatatacc tgatggattc   5520
ttatgaagcg ctgggtaatg gacgtgtcac tctacttcgc ctttttccct actcctttta   5580
gtacggaaga caatgctaat aaataagagg gtaataataa tattattaat cggcaaaaaa   5640
```

-continued

```
gattaaacgc caagcgttta attatcagaa agcaaacgtc gtaccaatcc ttgaatgctt   5700
cccaattgta tattaagagt catcacagca acatattctt gttattaaat taattattat   5760
tgatttttga tattgtataa aaaaaccaaa tatgtataaa aaaagtgaat aaaaaatacc   5820
aagtatggag aaatatatta gaagtctata cgttaaacca cccgggcccc ccctcgaggt   5880
cgacggtatc gataagcttg atatcgaatt cctgcagccc gggggatcca ctagttctag   5940
agcggccgct ctagaactag taccacaggt gttgtcctct gaggacataa aatacacacc   6000
gagattcatc aactcattgc tggagttagc atatctacaa ttgggtgaaa tggggagcga   6060
tttgcaggca tttgctcggc atgccggtag aggtgtggtc aataagagcg acctcatgct   6120
atacctgaga aagcaacctg acctacagga aagagttact caagaataag aattttcgtt   6180
ttaaaaccta agagtcactt taaaatttgt atacacttat ttttttata acttatttaa   6240
taataaaaat cataaatcat aagaaattcg cttactctta attaatcaaa aagttaaaat   6300
tgtacgaata gattcaccac ttcttaacaa atcaaaccct tcattgattt tctcgaatgg   6360
caatacatgt gtaattaaag gatcaagagc aaacttcttc gccataaagt cggcaacaag   6420
ttttggaaca ctatccttgc tcttaaaacc gccaaatata gctcccttcc atgtacgacc   6480
gcttagcaac agcataggat tcatcgacaa attttgtgaa tcaggaggaa cacctacgat   6540
cacactgact ccatatgcct cttgacagca ggacaacgca gttaccatag tatcaagacg   6600
gcctataact tcaaaagaga aatcaactcc accgtttgac atttcagtaa ggacttcttg   6660
tattggtttc ttataatctt gagggttaac acattcagta gccccgacct ccttagcttt   6720
tgcaaatttg tccttattga tgtctacacc tataatcctc gctgcgcctg cagctttaca   6780
ccccataata acgcttagtc ctactcctcc taaaccgaat actgcacaag tcgaaccctg   6840
tgtaaccttt gcaactttaa ctgcggaacc gtaaccggtg gaaaatccgc accctatcaa   6900
gcaaactttt tccagtggtg aagctgcatc gattttagcg acagatatct cgtccaccac   6960
tgtgtattgg gaaaatgtag aagtaccaag gaaatggtgt ataggtttcc ctctgcatgt   7020
aaatctgctt gtaccatcct gcatagtacc tctaggcata gacaaatcat ttttaaggca   7080
gaaattaccc tcaggatgtt tgcagactct acacttacca cattgaggag tgaacagtgg   7140
gatcacttta tcaccaggac gaacagtggt aacaccttca cctatggatt caacgattcc   7200
ggcagcctcg tgtcccgcga ttactggcaa aggagtaact agagtgccac tcaccacatg   7260
gtcgtcggat ctacagattc cggtggcaac catcttgatt ctaacctcgt gtgcttttgg   7320
tggcgctact tctacttctt ctatgctaaa cggcttttc tcttcccaca aaactgccgc   7380
tttacactta ataactttac cggctgttga catcctcagc tagctattgt aatatgtgtg   7440
tttgtttgga ttattaagaa gaataattac aaaaaaaatt acaaaggaag gtaattacaa   7500
cagaattaag aaaggacaag aaggaggaag agaatcagtt cattatttct tctttgttat   7560
ataacaaacc caagtagcga tttggccata cattaaaagt tgagaaccac cctccctggc   7620
aacagccaca actcgttacc attgttcatc acgatcatga aactcgctgt cagctgaaat   7680
ttcacctcag tggatctctc tttttattct tcatcgttcc actaaccttt ttccatcagc   7740
tggcagggaa cggaaagtgg aatcccattt agcgagcttc ctcttttctt caagaaaaga   7800
cgaagcttgt gtgtgggtgc gcgcgctagt atctttccac attaagaaat ataccataaa   7860
ggttacttag acatcactat ggctatatat atatatatat atatatgtaa cttagcacca   7920
tcgcgcgtgc atcactgcat gtgttaaccg aaaagtttgg cgaacacttc accgacacgg   7980
tcatttagat ctgtcgtctg cattgcacgt cccttagcct taaatcctag gcgggagcat   8040
```

-continued

```
tctcgtgtaa ttgtgcagcc tgcgtagcaa ctcaacatag cgtagtctac ccagtttttc   8100
aagggtttat cgttagaaga ttctcccttt tcttcctgct cacaaatctt aaagtcatac   8160
attgcacgac taaatgcaag catgcggatc cccgggctg caggaattcg atatcaagct   8220
tatcgatacc gtcgactggc cattaatctt tcccatatta gatttcgcca agccatgaaa   8280
gttcaagaaa ggtctttaga cgaattaccc ttcatttctc aaactggcgt caagggatcc   8340
tggtatggtt ttatcgtttt atttctggtt cttatagcat cgttttggac ttctctgttc   8400
ccattaggcg gttcaggagc cagcgcagaa tcattctttg aaggatactt atcctttcca   8460
attttgattg tctgttacgt tggacataaa ctgtatacta gaaattggac tttgatggtg   8520
aaactagaag atatggatct tgataccggc agaaaacaag tagatttgac tcttcgtagg   8580
gaagaaatga ggattgagcg agaaacatta gcaaaaagat ccttcgtaac aagattttta   8640
catttctggt gttgaaggga aagatatgag ctatacagcg gaatttccat atcactcaga   8700
ttttgttatc taatttttc cttcccacgt ccgcgggaat ctgtgtatat tactgcatct   8760
agatatatgt tatcttatct tggcgcgtac atttaatttt caacgtattc tataagaaat   8820
tgcgggagtt tttttcatgt agatgatact gactgcacgc aaatataggc atgatttata   8880
ggcatgattt gatggctgta ccgataggaa cgctaagagt aacttcagaa tcgttatcct   8940
ggcggaaaaa attcatttgt aaactttaaa aaaaaaagcc aatatcccca aaattattaa   9000
gagcgcctcc attattaact aaaatttcac tcagcatcca caatgtatca ggtatctact   9060
acagatatta catgtggcga aaaagacaag aacaatgcaa tagcgcatca agaaaaaaca   9120
caaagctttc aatcaatgaa tcgaaaatgt cattaaaata gtatataaat tgaaactaag   9180
tcataaagct ataaaaagaa aatttattta aatgcaagat ttaaagtaaa ttcacggccc   9240
tgcaggcctc agctcttgtt ttgttctgca aataacttac ccatcttttt caaaacttta   9300
ggtgcaccct cctttgctag aataagttct atccaataca tcctatttgg atctgcttga   9360
gcttctttca tcacggatac gaattcattt tctgttctca caattttgga cacaactctg   9420
tcttccgttg ccccgaaact ttctggcagt tttgagtaat tccacatagg aatgtcatta   9480
taactctggt tcggaccatg aatttccctc tcaaccgtgt aaccatcgtt attaatgata   9540
aagcagattg ggtttatctt ctctctaatg gctagtccta attcttggac agtcagttgc   9600
aatgatccat ctccgataaa caataaatgt ctagattctt tatctgcaat ttggctgcct   9660
agagctgcgg ggaaagtgta tcctatagat ccccacaagg gttgaccaat aaaatgtgat   9720
ttcgatttca gaaatataga tgaggcaccg aagaaagaag tgccttgttc agccacgatc   9780
gtctcattac tttgggtcaa attttcgaca gcttgccaca gtctatcttg tgacaacagc   9840
gcgttagaag gtacaaaatc ttcttgcttt ttatctatgt acttgccttt atattcaatt   9900
tcggacaagt caagaagaga tgatatcagg gattcgaagt cgaaattttg gattctttcg   9960
ttgaaaattt taccttcatc gatattcaag gaaatcattt tattttcatt aagatggtga  10020
gtaaatgcac ccgtactaga atcggtaagc tttacaccca acataagaat aaaatcagca  10080
gattccacaa attccttcaa gtttggctct gacagagtac cgttgtaaat ccccaaaaat  10140
gagggcaatg cttcatcaac agatgattta ccaaagttca aagtagtaat aggtaactta  10200
gtctttgaaa taaactgagt aacagtcttc tctaggccga acgatataat ttcatggcct  10260
gtgattacaa ttggtttctt ggcattcttc agactttcct gtattttgtt cagaatctct  10320
tgatcagatg tattcgacgt ggaattttcc ttcttaagag gcaaggatgg tttttcagcc  10380
ttagcggcag ctacatctac aggtaaattg atgtaaaccg gctttctttc ctttagtaag  10440
```

-continued

```
gcagacaaca ctctatcaat ttcaacagtt gcattctcgg ctgtcaataa agtcctggca  10500
gcagtaaccg gttcgtgcat cttcataaag tgcttgaaat caccatcagc caacgtatgg  10560
tgaacaaact taccttcgtt ctgcactttc gaggtaggag atcccacgat ctcaacaaca  10620
ggcaggttct cagcatagga gcccgctaag ccattaactg cggataattc gccaacacca  10680
aatgtagtca agaatgccgc agcctttttc gttcttgcgt acccgtcggc catataggag  10740
gcatttaact cattagcatt tcccacccat ttcatatctt tgtgtgaaat aatttgatct  10800
agaaattgca aattgtagtc acctggtact ccgaatattt cttctatacc taattcgtgt  10860
aatctgtcca acagatagtc acctactgta tacattttgt ttactagttt atgtgtgttt  10920
attcgaaact aagttcttgg tgttttaaaa ctaaaaaaaa gactaactat aaaagtagaa  10980
tttaagaagt ttaagaaata gatttacaga attacaatca atacctaccg tctttatata  11040
cttattagtc aagtagggga ataatttcag ggaactggtt tcaacctttt ttttcagctt  11100
tttccaaatc agagagagca gaaggtaata gaaggtgtaa gaaaatgaga tagatacatg  11160
cgtgggtcaa ttgccttgtg tcatcattta ctccaggcag gttgcatcac tccattgagg  11220
ttgtgcccgt tttttgcctg tttgtgcccc tgttctctgt agttgcgcta agagaatgga  11280
cctatgaact gatggttggt gaagaaaaca atattttggt gctgggattc tttttttttc  11340
tggatgccag cttaaaaagc gggctccatt atatttagtg gatgccagga ataaactgtt  11400
cacccagaca cctacgatgt tatatattct gtgtaacccg cccccctattt tgggcatgta  11460
cgggttacag cagaattaaa aggctaattt tttgactaaa taaagttagg aaaatcacta  11520
ctattaatta tttacgtatt ctttgaaatg gcagtattga taatgataaa ctcgaactga  11580
aaaagcgtgt tttttattca aaatgattct aactccctta cgtaatcaag gaatcttttt  11640
gccttggcct ccgcgtcatt aaacttcttg ttgttgacgc taacattcaa cgctagtata  11700
tattcgtttt tttcaggtaa gttcttttca acgggtctta ctgatgaggc agtcgcgtct  11760
gaacctgtta agaggtcaaa tatgtcttct tgaccgtacg tgtcttgcat gttattagct  11820
ttgggaattt gcatcaagtc ataggaaaat ttaaatcttg gctctcttgg gctcaaggtg  11880
acaaggtcct cgaaaatagg gcgcgcccca ccgcggtgga gctccagctt ttgttccctt  11940
tagtgagggt taattgcgcg cttggcgtaa tcatggtcat agctgtttcc tgtgtgaaat  12000
tgttatccgc tcacaattcc acacaacata cgagccggaa gcataaagtg taaagcctgg  12060
ggtgcctaat gagtgagcta actcacatta attgcgttgc gctcactgcc cgctttccag  12120
tcgggaaacc tgtcgtgcca gctgcattaa tgaatcggcc aacgcgcggg gagaggcggt  12180
ttgcgtattg ggcgctcttc cgcttcctcg ctcactgact cgctgcgctc ggtcgttcgg  12240
ctgcggcgag cggtatcagc tcactcaaag gcggtaatac ggttatccac agaatcaggg  12300
gataacgcag gaaagaacat gtgagcaaaa ggccagcaaa aggccaggaa ccgtaaaaag  12360
gccgcgttgc tggcgttttt ccataggctc cgcccccctg acgagcatca caaaaatcga  12420
cgctcaagtc agaggtggcg aaacccgaca ggactataaa gataccaggc gtttccccct  12480
ggaagctccc tcgtgcgctc tcctgttccg accctgccgc ttaccggata cctgtccgcc  12540
tttctccctt cgggaagcgt ggcgctttct catagctcac gctgtaggta tctcagttcg  12600
gtgtaggtcg ttcgctccaa gctgggctgt gtgcacgaac cccccgttca gcccgaccgc  12660
tgcgccttat ccggtaacta tcgtcttgag tccaacccgg taagacacga cttatcgcca  12720
ctggcagcag ccactggtaa caggattagc agagcgaggt atgtaggcgg tgctacagag  12780
ttcttgaagt ggtggcctaa ctacggctac actagaagaa cagtatttgg tatctgcgct  12840
```

-continued ctgctgaagc cagttacctt cggaaaaaga gttggtagct cttgatccgg caaacaaacc 12900
accgctggta gcggtggttt ttttgtttgc aagcagcaga ttacgcgcag aaaaaaagga 12960
tctcaagaag atcctttgat cttttctacg gggtctgacg ctcagtggaa cgaaaactca 13020
cgttaaggga ttttggtcat gagattatca aaaaggatct tcacctagat ccttttaaat 13080
taaaaatgaa gttttaaatc aatctaaagt atatatgagt aaacttggtc tgacagttac 13140
caatgcttaa tcagtgaggc acctatctca gcgatctgtc tatttcgttc atccatagtt 13200
gcctgactcc ccgtcgtgta gataactacg atacgggagg gcttaccatc tggccccagt 13260
gctgcaatga taccgcgaga cccacgctca ccggctccag atttatcagc aataaaccag 13320
ccagccggaa gggccgagcg cagaagtggt cctgcaactt tatccgcctc catccagtct 13380
attaattgtt gccgggaagc tagagtaagt agttcgccag ttaatagttt gcgcaacgtt 13440
gttgccattg ctacaggcat cgtggtgtca cgctcgtcgt ttggtatggc ttcattcagc 13500
tccggttccc aacgatcaag gcgagttaca tgatccccca tgttgtgcaa aaaagcggtt 13560
agctccttcg gtcctccgat cgttgtcaga agtaagttgg ccgcagtgtt atcactcatg 13620
gttatggcag cactgcataa ttctcttact gtcatgccat ccgtaagatg cttttctgtg 13680
actggtgagt actcaaccaa gtcattctga gaatagtgta tgcggcgacc gagttgctct 13740
tgcccggcgt caatacggga taataccgcg ccacatagca gaactttaaa agtgctcatc 13800
attggaaaac gttcttcggg gcgaaaactc tcaaggatct taccgctgtt gagatccagt 13860
tcgatgtaac ccactcgtgc acccaactga tcttcagcat cttttacttt caccagcgtt 13920
tctgggtgag caaaaacagg aaggcaaaat gccgcaaaaa agggaataag ggcgacacgg 13980
aaatgttgaa tactcatact cttccttttt caatattatt gaagcattta tcagggttat 14040
tgtctcatga gcggatacat atttgaatgt atttagaaaa ataaacaaat aggggttccg 14100
cgcacatttc cccgaaaagt gccacctgaa cgaagcatct gtgcttcatt ttgtagaaca 14160
aaaatgcaac gcgagagcgc taatttttca aacaaagaat ctgagctgca tttttacaga 14220
acagaaatgc aacgcgaaag cgctatttta ccaacgaaga atctgtgctt catttttgta 14280
aaacaaaaat gcaacgcgag agcgctaatt tttcaaacaa agaatctgag ctgcattttt 14340
acagaacaga aatgcaacgc gagagcgcta ttttaccaac aaagaatcta tacttctttt 14400
ttgttctaca aaaatgcatc ccgagagcgc tatttttcta acaaagcatc ttagattact 14460 tttttctcc tttgtgcgct ctataatgca gtctcttgat aactttttgc actgtaggtc 14520
cgttaaggtt agaagaaggc tactttggtg tctattttct cttccataaa aaaagcctga 14580
ctccacttcc cgcgtttact gattactagc gaagctgcgg gtgcattttt tcaagataaa 14640
ggcatccccg attatattct ataccgatgt ggattgcgca tactttgtga acagaaagtg 14700
atagcgttga tgattcttca ttggtcagaa aattatgaac ggtttcttct attttgtctc 14760
tatatactac gtataggaaa tgtttacatt ttcgtattgt tttcgattca ctctatgaat 14820
agttcttact acaatttttt tgtctaaaga gtaatactag agataaacat aaaaaatgta 14880
gaggtcgagt ttagatgcaa gttcaaggag cgaaaggtgg atgggtaggt tatataggga 14940
tatagcacag agatatatag caaagagata cttttgagca atgtttgtgg aagcggtatt 15000
cgcaatattt tagtagctcg ttacagtccg gtgcgttttt ggttttttga aagtgcgtct 15060
tcagagcgct tttggttttc aaaagcgctc tgaagttcct atactttcta gagaatagga 15120
acttcggaat aggaacttca aagcgtttcc gaaaacgagc gcttccgaaa atgcaacgcg 15180
agctgcgcac atacagctca ctgttcacgt cgcacctata tctgcgtgtt gcctgtatat 15240
atatatacat gagaagaacg gcatagtgcg tgtttatgct taaatgcgta cttatatgcg 15300
tctatttatg taggatgaaa ggtagtctag tacctcctgt gatattatcc cattccatgc 15360
ggggtatcgt atgcttcctt cagcactacc ctttagctgt tctatatgct gccactcctc 15420
aattggatta gtctcatcct tcaatgctat catttccttt gatattggat catactaaga 15480
aaccattatt atcatgacat taacctataa aaataggcgt atcacgaggc cctttcgtc 15539

<210> SEQ ID NO 3
<211> LENGTH: 4586
<212> TYPE: DNA
<213> ORGANISM: Artificial Sequence
<220> FEATURE:
<223> OTHER INFORMATION: pLA54 plasmid

<400> SEQUENCE: 3
gggtaccgag ctcgaattca ctggccgtcg ttttacaacg tcgtgactgg gaaaaccctg 60
gcgttaccca acttaatcgc cttgcagcac atcccccttt cgccagctgg cgtaatagcg 120
aagaggcccg caccgatcgc ccttcccaac agttgcgcag cctgaatggc gaatggcgcc 180
tgatgcggta ttttctcctt acgcatctgt gcggtatttc acaccgcata tggtgcactc 240
tcagtacaat ctgctctgat gccgcatagt taagccagcc ccgacacccg ccaacacccg 300
ctgacgcgcc ctgacgggct tgtctgctcc cggcatccgc ttacagacaa gctgtgaccg 360
tctccgggag ctgcatgtgt cagaggtttt caccgtcatc accgaaacgc gcgagacgaa 420
agggcctcgt gatacgccta tttttatagg ttaatgtcat gataataatg gtttcttaga 480
cgtcaggtgg cacttttcgg ggaaatgtgc gcggaacccc tatttgttta tttttctaaa 540
tacattcaaa tatgtatccg ctcatgagac aataaccctg ataaatgctt caataatatt 600
gaaaaaggaa gagtatgagt attcaacatt tccgtgtcgc ccttattccc ttttttgcgg 660
cattttgcct tcctgttttt gctcacccag aaacgctggt gaaagtaaaa gatgctgaag 720
atcagttggg tgcacgagtg ggttacatcg aactggatct caacagcggt aagatccttg 780
agagttttcg ccccgaagaa cgttttccaa tgatgagcac ttttaaagtt ctgctatgtg 840
gcgcggtatt atcccgtatt gacgccgggc aagagcaact cggtcgccgc atacactatt 900
ctcagaatga cttggttgag tactcaccag tcacagaaaa gcatcttacg gatggcatga 960
cagtaagaga attatgcagt gctgccataa ccatgagtga taacactgcg gccaacttac 1020
ttctgacaac gatcggagga ccgaaggagc taaccgcttt tttgcacaac atgggggatc 1080
atgtaactcg ccttgatcgt tgggaaccgg agctgaatga agccatacca aacgacgagc 1140
gtgacaccac gatgcctgta gcaatggcaa caacgttgcg caaactatta actggcgaac 1200
tacttactct agcttcccgg caacaattaa tagactggat ggaggcggat aaagttgcag 1260
gaccacttct gcgctcggcc cttccggctg gctggtttat tgctgataaa tctggagccg 1320
gtgagcgtgg gtctcgcggt atcattgcag cactggggcc agatggtaag ccctcccgta 1380
tcgtagttat ctacacgacg gggagtcagg caactatgga tgaacgaaat agacagatcg 1440
ctgagatagg tgcctcactg attaagcatt ggtaactgtc agaccaagtt tactcatata 1500
tactttagat tgatttaaaa cttcattttt aatttaaaag gatctaggtg aagatccttt 1560
ttgataatct catgaccaaa atcccttaac gtgagttttc gttccactga gcgtcagacc 1620
ccgtagaaaa gatcaaagga tcttcttgag atcctttttt tctgcgcgta atctgctgct 1680
tgcaaacaaa aaaaccaccg ctaccagcgg tggtttgttt gccggatcaa gagctaccaa 1740
ctctttttcc gaaggtaact ggcttcagca gagcgcagat accaaatact gtccttctag 1800

-continued

```
tgtagccgta gttaggccac cacttcaaga actctgtagc accgcctaca tacctcgctc   1860
tgctaatcct gttaccagtg gctgctgcca gtggcgataa gtcgtgtctt accgggttgg   1920
actcaagacg atagttaccg gataaggcgc agcggtcggg ctgaacgggg ggttcgtgca   1980
cacagcccag cttggagcga acgacctaca ccgaactgag atacctacag cgtgagctat   2040
gagaaagcgc cacgcttccc gaagggagaa aggcggacag gtatccggta agcggcaggg   2100
tcggaacagg agagcgcacg agggagcttc caggggggaaa cgcctggtat ctttatagtc   2160
ctgtcgggtt tcgccacctc tgacttgagc gtcgattttt gtgatgctcg tcaggggggc   2220
ggagcctatg gaaaaacgcc agcaacgcgg cctttttacg gttcctggcc ttttgctggc   2280
cttttgctca catgttcttt cctgcgttat cccctgattc tgtggataac cgtattaccg   2340
cctttgagtg agctgatacc gctcgccgca gccgaacgac cgagcgcagc gagtcagtga   2400
gcgaggaagc ggaagagcgc ccaatacgca aaccgcctct ccccgcgcgt tggccgattc   2460
attaatgcag ctggcacgac aggtttcccg actggaaagc gggcagtgag cgcaacgcaa   2520
ttaatgtgag ttagctcact cattaggcac cccaggcttt acactttatg cttccggctc   2580
gtatgttgtg tggaattgtg agcggataac aatttcacac aggaaacagc tatgaccatg   2640
attacgccaa gcttgcatgc ctgcaggtcg actctagagg atccccgcat tgcggattac   2700
gtattctaat gttcagataa cttcgtatag catacattat acgaagttat ctagggattc   2760
ataaccattt tctcaatcga attacacaga acacaccgta caaacctctc tatcataact   2820
acttaatagt cacacacgta ctcgtctaaa tacacatcat cgtcctacaa gttcatcaaa   2880
gtgttggaca gacaactata ccagcatgga tctcttgtat cggttctttt ctcccgctct   2940
ctcgcaataa caatgaacac tgggtcaatc atagcctaca caggtgaaca gagtagcgtt   3000
tatacagggt ttatacggtg attcctacgg caaaaatttt tcatttctaa aaaaaaaaag   3060
aaaaattttt ctttccaacg ctagaaggaa aagaaaaatc taattaaatt gatttggtga   3120
ttttctgaga gttccctttt tcatatatcg aattttgaat ataaaaggag atcgaaaaaa   3180
tttttctatt caatctgttt tctggtttta tttgatagtt tttttgtgta ttattattat   3240
ggattagtac tggtttatat gggtttttct gtataacttc tttttatttt agtttgttta   3300
atcttatttt gagttacatt atagttccct aactgcaaga gaagtaacat taaaactcga   3360
gatgggtaag gaaaagactc acgtttcgag gccgcgatta aattccaaca tggatgctga   3420
tttatatggg tataaatggg ctcgcgataa tgtcgggcaa tcaggtgcga caatctatcg   3480
attgtatggg aagcccgatg cgccagagtt gtttctgaaa catggcaaag gtagcgttgc   3540
caatgatgtt acagatgaga tggtcagact aaactggctg acggaattta tgcctcttcc   3600
gaccatcaag cattttatcc gtactcctga tgatgcatgg ttactcacca ctgcgatccc   3660
cggcaaaaca gcattccagg tattagaaga atatcctgat tcaggtgaaa atattgttga   3720
tgcgctggca gtgttcctgc gccggttgca ttcgattcct gtttgtaatt gtccttttaa   3780
cagcgatcgc gtatttcgtc tcgctcaggc gcaatcacga atgaataacg gtttggttga   3840
tgcgagtgat tttgatgacg agcgtaatgg ctggcctgtt gaacaagtct ggaaagaaat   3900
gcataagctt ttgccattct caccggattc agtcgtcact catggtgatt tctcacttga   3960
taaccttatt tttgacgagg ggaaattaat aggttgtatt gatgttggac gagtcggaat   4020
cgcagaccga taccaggatc ttgccatcct atggaactgc ctcggtgagt tttctccttc   4080
attacagaaa cggctttttc aaaaatatgg tattgataat cctgatatga ataaattgca   4140
gtttcatttg atgctcgatg agtttttcta agtttaactt gatactacta gatttttttct   4200
```

cttcatttat aaaatttttg gttataattg aagctttaga agtatgaaaa aatccttttt 4260
tttcattctt tgcaaccaaa ataagaagct tcttttattc attgaaatga tgaatataaa 4320
cctaacaaaa gaaaaagact cgaatatcaa acattaaaaa aaaataaaag aggttatctg 4380
ttttcccatt tagttggagt ttgcattttc taatagatag aactctcaat taatgtggat 4440
ttagtttctc tgttcgtttt tttttgtttt gttctcactg tatttacatt tctatttagt 4500
atttagttat tcatataatc tataacttcg tatagcatac attatacgaa gttatccagt 4560
gatgatacaa cgagttagcc aaggtg 4586

<210> SEQ ID NO 4
<211> LENGTH: 80
<212> TYPE: DNA
<213> ORGANISM: Artificial Sequence
<220> FEATURE:
<223> OTHER INFORMATION: Primer

<400> SEQUENCE: 4
ttccggtttc tttgaaattt ttttgattcg gtaatctccg agcagaagga gcattgcgga 60
ttacgtattc taatgttcag 80

<210> SEQ ID NO 5
<211> LENGTH: 81
<212> TYPE: DNA
<213> ORGANISM: Artificial Sequence
<220> FEATURE:
<223> OTHER INFORMATION: Primer

<400> SEQUENCE: 5
gggtaataac tgatataatt aaattgaagc tctaatttgt gagtttagta caccttggct 60
aactcgttgt atcatcactg g 81

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gcctcgagtt ttaatgttac ttctcttgca gttaggga 38

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
gctaaattcg agtgaaacac aggaagacca g 31

<210> SEQ ID NO 8
<211> LENGTH: 90
<212> TYPE: DNA
<213> ORGANISM: Artificial Sequence
<220> FEATURE:
<223> OTHER INFORMATION: Primer

<400> SEQUENCE: 8
gtattttggt agattcaatt ctctttccct ttccttttcc ttcgctcccc ttccttatca 60
gcattgcgga ttacgtattc taatgttcag 90

<210> SEQ ID NO 9
<211> LENGTH: 90
<212> TYPE: DNA
<213> ORGANISM: Artificial Sequence
<220> FEATURE:
<223> OTHER INFORMATION: Primer

<400> SEQUENCE: 9
ttggttgggg gaaaaagagg caacaggaaa gatcagaggg ggagggggg ggagagtgtc 60 accttggcta actcgttgta tcatcactgg 90

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tcggtgcggg cctcttcgct a 21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
aatgtgagtt agctcactca t 21

<210> SEQ ID NO 12
<211> LENGTH: 57
<212> TYPE: DNA
<213> ORGANISM: Artificial Sequence
<220> FEATURE:
<223> OTHER INFORMATION: Primer

<400> SEQUENCE: 12
aattggatcc ggcgcgccgt ttaaacggcc ggccaatgtg gctgtggttt cagggtc 57

<210> SEQ ID NO 13
<211> LENGTH: 49
<212> TYPE: DNA
<213> ORGANISM: Artificial Sequence
<220> FEATURE:
<223> OTHER INFORMATION: Primer

<400> SEQUENCE: 13
aatttctaga ttaattaagc ggccgcaagg ccatgaagct ttttctttc 49

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ttctcgacgt gggccttttt cttg 24

<210> SEQ ID NO 15
<211> LENGTH: 49
<212> TYPE: DNA
<213> ORGANISM: Artificial Sequence
<220> FEATURE:

<223> OTHER INFORMATION: Primer

<400> SEQUENCE: 15
tgcagcttta aataatcggt gtcactactt tgccttcgtt tatcttgcc 49

<210> SEQ ID NO 16
<211> LENGTH: 49
<212> TYPE: DNA
<213> ORGANISM: Artificial Sequence
<220> FEATURE:
<223> OTHER INFORMATION: Primer

<400> SEQUENCE: 16
gagcaggcaa gataaacgaa ggcaaagtag tgacaccgat tatttaaag 49

<210> SEQ ID NO 17
<211> LENGTH: 49
<212> TYPE: DNA
<213> ORGANISM: Artificial Sequence
<220> FEATURE:
<223> OTHER INFORMATION: Primer

<400> SEQUENCE: 17
tatggaccct gaaaccacag ccacattgta accaccacga cggttgttg 49

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18
tttagcaaca accgtcgtgg tggttacaat gtggctgtgg tttcagggt 49

<210> SEQ ID NO 19
<211> LENGTH: 49
<212> TYPE: DNA
<213> ORGANISM: Artificial Sequence
<220> FEATURE:
<223> OTHER INFORMATION: Primer

<400> SEQUENCE: 19
ccagaaaccc tatacctgtg tggacgtaag gccatgaagc tttttcttt 49

<210> SEQ ID NO 20
<211> LENGTH: 49
<212> TYPE: DNA
<213> ORGANISM: Artificial Sequence
<220> FEATURE:
<223> OTHER INFORMATION: Primer

<400> SEQUENCE: 20
attggaaaga aaaagcttca tggccttacg tccacacagg tatagggtt 49

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
cataagaaca cctttggtgg ag 22

<210> SEQ ID NO 22

<211> LENGTH: 22
<212> TYPE: DNA
<213> ORGANISM: Artificial Sequence
<220> FEATURE:
<223> OTHER INFORMATION: Primer

<400> SEQUENCE: 22
aggattatca ttcataagtt tc 22

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ttcttggagc tgggacatgt ttg 23

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tgatgatatt tcataaataa tg 22

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
atgcgtccat ctttacagtc ctg 23

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tacgtacgga ccaatcgaag tg 22

<210> SEQ ID NO 27
<211> LENGTH: 49
<212> TYPE: DNA
<213> ORGANISM: Artificial Sequence
<220> FEATURE:
<223> OTHER INFORMATION: Primer

<400> SEQUENCE: 27
aattcgtttg agtacactac taatggcttt gttggcaata tgtttttgc 49

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
atatagcaaa aacatattgc caacaaagcc attagtagtg tactcaaac 49

<210> SEQ ID NO 29
<211> LENGTH: 49
<212> TYPE: DNA
<213> ORGANISM: Artificial Sequence
<220> FEATURE:
<223> OTHER INFORMATION: Primer

<400> SEQUENCE: 29
tatggaccct gaaaccacag ccacattctt gttatttata aaaagacac 49

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
ctcccgtgtc tttttataaa taacaagaat gtggctgtgg tttcagggt 49

<210> SEQ ID NO 31
<211> LENGTH: 49
<212> TYPE: DNA
<213> ORGANISM: Artificial Sequence
<220> FEATURE:
<223> OTHER INFORMATION: Primer

<400> SEQUENCE: 31
taccgtaggc gtccttagga aagatagaag gccatgaagc tttttcttt 49

<210> SEQ ID NO 32
<211> LENGTH: 49
<212> TYPE: DNA
<213> ORGANISM: Artificial Sequence
<220> FEATURE:
<223> OTHER INFORMATION: Primer

<400> SEQUENCE: 32
attggaaaga aaaagcttca tggccttcta tctttcctaa ggacgccta 49

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ttattgtttg gcatttgtag c 21

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
ccaagcatct cataaaccta tg 22

<210> SEQ ID NO 35
<211> LENGTH: 22
<212> TYPE: DNA
<213> ORGANISM: Artificial Sequence
<220> FEATURE:

-continued

<223> OTHER INFORMATION: Primer

<400> SEQUENCE: 35
tgtgcagatg cagatgtgag ac 22

<210> SEQ ID NO 36
<211> LENGTH: 17
<212> TYPE: DNA
<213> ORGANISM: Artificial Sequence
<220> FEATURE:
<223> OTHER INFORMATION: Primer

<400> SEQUENCE: 36
agttattgat accgtac 17

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
cgagataccg taggcgtcc 19

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ttatgtatgc tcttctgact tttc 24

<210> SEQ ID NO 39
<211> LENGTH: 49
<212> TYPE: DNA
<213> ORGANISM: Artificial Sequence
<220> FEATURE:
<223> OTHER INFORMATION: Primer

<400> SEQUENCE: 39
aataattaga gattaaatcg ctcatttttt gccagtttct tcaggcttc 49

<210> SEQ ID NO 40
<211> LENGTH: 49
<212> TYPE: DNA
<213> ORGANISM: Artificial Sequence
<220> FEATURE:
<223> OTHER INFORMATION: Primer

<400> SEQUENCE: 40
agcctgaaga aactggcaaa aaatgagcga tttaatctct aattattag 49

<210> SEQ ID NO 41
<211> LENGTH: 49
<212> TYPE: DNA
<213> ORGANISM: Artificial Sequence
<220> FEATURE:
<223> OTHER INFORMATION: Primer

<400> SEQUENCE: 41
tatggaccct gaaaccacag ccacattttt caatcattgg agcaatcat 49

<210> SEQ ID NO 42

-continued

<211> LENGTH: 49
<212> TYPE: DNA
<213> ORGANISM: Artificial Sequence
<220> FEATURE:
<223> OTHER INFORMATION: Primer

<400> SEQUENCE: 42
taaaatgatt gctccaatga ttgaaaaatg tggctgtggt ttcagggtc 49

<210> SEQ ID NO 43
<211> LENGTH: 49
<212> TYPE: DNA
<213> ORGANISM: Artificial Sequence
<220> FEATURE:
<223> OTHER INFORMATION: Primer

<400> SEQUENCE: 43
accgtaggtg ttgtttggga aagtggaagg ccatgaagct ttttctttc 49

<210> SEQ ID NO 44
<211> LENGTH: 49
<212> TYPE: DNA
<213> ORGANISM: Artificial Sequence
<220> FEATURE:
<223> OTHER INFORMATION: Primer

<400> SEQUENCE: 44
ttggaaagaa aaagcttcat ggccttccac tttcccaaac aacacctac 49

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ttattgctta gcgttggtag cag 23

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
tttttggtgg ttccggcttc c 21

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
aaagttggca tagcggaaac tt 22

<210> SEQ ID NO 48
<211> LENGTH: 16
<212> TYPE: DNA
<213> ORGANISM: Artificial Sequence
<220> FEATURE:
<223> OTHER INFORMATION: Primer

<400> SEQUENCE: 48
gtcattgaca ccatct 16

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
agagataccg taggtgttg 19

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
aattggcgcg ccatgaaagc tctggtttat cac 33

<210> SEQ ID NO 51
<211> LENGTH: 49
<212> TYPE: DNA
<213> ORGANISM: Artificial Sequence
<220> FEATURE:
<223> OTHER INFORMATION: Primer

<400> SEQUENCE: 51
tgaatcatga gttttatgtt aattagctca ggcagcgcct gcgttcgag 49

<210> SEQ ID NO 52
<211> LENGTH: 49
<212> TYPE: DNA
<213> ORGANISM: Artificial Sequence
<220> FEATURE:
<223> OTHER INFORMATION: Primer

<400> SEQUENCE: 52
atcctctcga acgcaggcgc tgcctgagct aattaacata aaactcatg 49

<210> SEQ ID NO 53
<211> LENGTH: 34
<212> TYPE: DNA
<213> ORGANISM: Artificial Sequence
<220> FEATURE:
<223> OTHER INFORMATION: Primer

<400> SEQUENCE: 53
aattgtttaa acaagtaaat aaattaatca gcat 34

<210> SEQ ID NO 54
<211> LENGTH: 49
<212> TYPE: DNA
<213> ORGANISM: Artificial Sequence
<220> FEATURE:
<223> OTHER INFORMATION: Primer

<400> SEQUENCE: 54
acacaataca ataacaagaa gaacaaaatg aaagctctgg tttatcacg 49

<210> SEQ ID NO 55
<211> LENGTH: 49
<212> TYPE: DNA
<213> ORGANISM: Artificial Sequence
<220> FEATURE:

<223> OTHER INFORMATION: Primer

<400> SEQUENCE: 55
agcgtataca tctgttggga aagtagaagg ccatgaagct ttttctttc 49

<210> SEQ ID NO 56
<211> LENGTH: 49
<212> TYPE: DNA
<213> ORGANISM: Artificial Sequence
<220> FEATURE:
<223> OTHER INFORMATION: Primer

<400> SEQUENCE: 56
ttggaaagaa aaagcttcat ggccttctac tttcccaaca gatgtatac 49

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
ttattgttta gcgttagtag cg 22

<210> SEQ ID NO 58
<211> LENGTH: 72
<212> TYPE: DNA
<213> ORGANISM: Artificial Sequence
<220> FEATURE:
<223> OTHER INFORMATION: Primer

<400> SEQUENCE: 58
cataatcaat ctcaaagaga acaacacaat acaataacaa gaagaacaaa atgaaagctc 60
tggtttatca cg 72

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
taggcataat caccgaagaa g 21

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
aaaatggtaa gcagctgaaa g 21

<210> SEQ ID NO 61
<211> LENGTH: 17
<212> TYPE: DNA
<213> ORGANISM: Artificial Sequence
<220> FEATURE:
<223> OTHER INFORMATION: Primer

<400> SEQUENCE: 61
agttgttaga actgttg 17

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gacgatagcg tatacatct 19

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
cttagcctct agccatagcc at 22

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ttagttttgc tggccgcatc ttc 23

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cccattaata tactattgag a 21

<210> SEQ ID NO 66
<211> LENGTH: 7523
<212> TYPE: DNA
<213> ORGANISM: Artificial Sequence
<220> FEATURE:
<223> OTHER INFORMATION: Plasmid

<400> SEQUENCE: 66
ccagcttttg ttccctttag tgagggttaa ttgcgcgctt ggcgtaatca tggtcatagc 60
tgtttcctgt gtgaaattgt tatccgctca caattccaca caacatagga gccggaagca 120
taaagtgtaa agcctggggt gcctaatgag tgaggtaact cacattaatt gcgttgcgct 180
cactgcccgc tttccagtcg ggaaacctgt cgtgccagct gcattaatga atcggccaac 240
gcgcggggag aggcggtttg cgtattgggc gctcttccgc ttcctcgctc actgactcgc 300
tgcgctcggt cgttcggctg cggcgagcgg tatcagctca ctcaaaggcg gtaatacggt 360
tatccacaga atcaggggat aacgcaggaa agaacatgtg agcaaaaggc cagcaaaagg 420
ccaggaaccg taaaaaggcc gcgttgctgg cgtttttcca taggctccgc ccccctgacg 480
agcatcacaa aaatcgacgc tcaagtcaga ggtggcgaaa cccgacagga ctataaagat 540
accaggcgtt tccccctgga agctccctcg tgcgctctcc tgttccgacc ctgccgctta 600
ccggatacct gtccgccttt ctcccttcgg gaagcgtggc gctttctcat agctcacgct 660

-continued

```
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa tttttcaaac aaagaatctg   2280
agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca attttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060
```

-continued

```
tttgtggaag cggtattcgc aatattttag tagctcgtta cagtccggtg cgtttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac ctcctgtgat   3420
attatcccat tccatgcggg gtatcgtatg cttccttcag cactaccctt tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tctttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt tttctttttg ctttttcttt ttttttctct tgaactcgac   4980
ggatctatgc ggtgtgaaat accgcacaga tgcgtaagga gaaaataccg catcaggaaa   5040
ttgtaaacgt taatattttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
caagtttttt ggggtcgagg tgccgtaaag cactaaatcg gaaccctaaa gggagccccc   5340
gatttagagc ttgacgggga aagccggcga acgtggcgag aaaggaaggg aagaaagcga   5400
aaggagcggg cgctagggcg ctggcaagtg tagcggtcac gctgcgcgta accaccacac   5460
```

```
ccgccgcgct taatgcgccg ctacagggcg cgtcgcgcca ttcgccattc aggctgcgca   5520

actgttggga agggcgatcg gtgcgggcct cttcgctatt acgccagctg gcgaaagggg   5580

gatgtgctgc aaggcgatta agttgggtaa cgccagggtt ttcccagtca cgacgttgta   5640

aaacgacggc cagtgagcgc gcgtaatacg actcactata gggcgaattg ggtaccgggc   5700

ccccctcga ggtattagaa gccgccgagc gggcgacagc cctccgacgg aagactctcc   5760

tccgtgcgtc ctcgtcttca ccggtcgcgt tcctgaaacg cagatgtgcc tcgcgccgca   5820

ctgctccgaa caataaagat tctacaatac tagcttttat ggttatgaag aggaaaaatt   5880

ggcagtaacc tggccccaca aaccttcaaa ttaacgaatc aaattaacaa ccataggatg   5940

ataatgcgat tagtttttta gccttatttc tggggtaatt aatcagcgaa gcgatgattt   6000

ttgatctatt aacagatata taaatggaaa agctgcataa ccactttaac taatactttc   6060

aacattttca gtttgtatta cttcttattc aaatgtcata aaagtatcaa caaaaaattg   6120

ttaatatacc tctatacttt aacgtcaagg agaaaaatgt ccaatttact gcccgtacac   6180

caaaatttgc ctgcattacc ggtcgatgca acgagtgatg aggttcgcaa gaacctgatg   6240

gacatgttca gggatcgcca ggcgttttct gagcatacct ggaaaatgct tctgtccgtt   6300

tgccggtcgt gggcggcatg gtgcaagttg aataaccgga aatggtttcc cgcagaacct   6360

gaagatgttc gcgattatct tctatatctt caggcgcgcg gtctggcagt aaaaactatc   6420

cagcaacatt tgggccagct aaacatgctt catcgtcggt ccgggctgcc acgaccaagt   6480

gacagcaatg ctgtttcact ggttatgcgg cggatccgaa aagaaaacgt tgatgccggt   6540

gaacgtgcaa aacaggctct agcgttcgaa cgcactgatt tcgaccaggt tcgttcactc   6600

atggaaaata gcgatcgctg ccaggatata cgtaatctgg catttctggg gattgcttat   6660

aacaccctgt tacgtatagc cgaaattgcc aggatcaggg ttaaagatat ctcacgtact   6720

gacggtggga gaatgttaat ccatattggc agaacgaaaa cgctggttag caccgcaggt   6780

gtagagaagg cacttagcct gggggtaact aaactggtcg agcgatggat ttccgtctct   6840

ggtgtagctg atgatccgaa taactacctg ttttgccggg tcagaaaaaa tggtgttgcc   6900

gcgccatctg ccaccagcca gctatcaact cgcgccctgg aagggatttt tgaagcaact   6960

catcgattga tttacggcgc taaggatgac tctggtcaga gatacctggc ctggtctgga   7020

cacagtgccc gtgtcggagc cgcgcgagat atggcccgcg ctggagtttc aataccggag   7080

atcatgcaag ctggtggctg gaccaatgta aatattgtca tgaactatat ccgtaacctg   7140

gatagtgaaa caggggcaat ggtgcgcctg ctggaagatg gcgattagga gtaagcgaat   7200

ttcttatgat ttatgatttt tattattaaa taagttataa aaaaaataag tgtatacaaa   7260

ttttaaagtg actcttaggt tttaaaacga aaattcttat tcttgagtaa ctctttcctg   7320

taggtcaggt tgctttctca ggtatagcat gaggtcgctc ttattgacca cacctctacc   7380

ggcatgccga gcaaatgcct gcaaatcgct ccccatttca cccaattgta gatatgctaa   7440

ctccagcaat gagttgatga atctcggtgt gtattttatg tcctcagagg acaacacctg   7500

tggtccgcca ccgcggtgga gct                                           7523
```

<210> SEQ ID NO 67
<211> LENGTH: 15456
<212> TYPE: DNA
<213> ORGANISM: Artificial Sequence
<220> FEATURE:
<223> OTHER INFORMATION: Template

<400> SEQUENCE: 67

-continued

```
aaagagtaat actagagata aacataaaaa atgtagaggt cgagtttaga tgcaagttca     60
aggagcgaaa ggtggatggg taggttatat agggatatag cacagagata tatagcaaag    120
agatactttt gagcaatgtt tgtggaagcg gtattcgcaa tattttagta gctcgttaca    180
gtccggtgcg tttttggttt tttgaaagtg cgtcttcaga gcgcttttgg ttttcaaaag    240
cgctctgaag ttcctatact ttctagagaa taggaacttc ggaataggaa cttcaaagcg    300
tttccgaaaa cgagcgcttc cgaaaatgca acgcgagctg cgcacataca gctcactgtt    360
cacgtcgcac ctatatctgc gtgttgcctg tatatatata tacatgagaa gaacggcata    420
gtgcgtgttt atgcttaaat gcgtacttat atgcgtctat ttatgtagga tgaaaggtag    480
tctagtacct cctgtgatat tatcccattc catgcggggt atcgtatgct tccttcagca    540
ctacccttta gctgttctat atgctgccac tcctcaattg gattagtctc atccttcaat    600
gctatcattt cctttgatat tggatcatac taagaaacca ttattatcat gacattaacc    660
tataaaaata ggcgtatcac gaggcccttt cgtctcgcgc gtttcggtga tgacggtgaa    720
aacctctgac acatgcagct cccggagacg gtcacagctt gtctgtaagc ggatgccggg    780
agcagacaag cccgtcaggg cgcgtcagcg ggtgttggcg ggtgtcgggg ctggcttaac    840
tatgcggcat cagagcagat tgtactgaga gtgcaccata aattcccgtt ttaagagctt    900
ggtgagcgct aggagtcact gccaggtatc gtttgaacac ggcattagtc agggaagtca    960
taacacagtc ctttcccgca atttctttt tctattactc ttggcctcct ctagtacact   1020
ctatattttt ttatgcctcg gtaatgattt tcattttttt ttttccacct agcggatgac   1080
tctttttttt tcttagcgat tggcattatc acataatgaa ttatacatta tataaagtaa   1140
tgtgatttct tcgaagaata tactaaaaaa tgagcaggca agataaacga aggcaaagat   1200
gacagagcag aaagccctag taaagcgtat tacaaatgaa accaagattc agattgcgat   1260
ctctttaaag ggtggtcccc tagcgataga gcactcgatc ttcccagaaa aagaggcaga   1320
agcagtagca gaacaggcca cacaatcgca agtgattaac gtccacacag gtatagggtt   1380
tctggaccat atgatacatg ctctggccaa gcattccggc tggtcgctaa tcgttgagtg   1440
cattggtgac ttacacatag acgaccatca caccactgaa gactgcggga ttgctctcgg   1500
tcaagctttt aaagaggccc taggggccgt gcgtggagta aaaaggtttg gatcaggatt   1560
tgcgcctttg gatgaggcac tttccagagc ggtggtagat ctttcgaaca ggccgtacgc   1620
agttgtcgaa cttggtttgc aaagggagaa agtaggagat ctctcttgcg agatgatccc   1680
gcattttctt gaaagctttg cagaggctag cagaattacc ctccacgttg attgtctgcg   1740
aggcaagaat gatcatcacc gtagtgagag tgcgttcaag gctcttgcgg ttgccataag   1800
agaagccacc tcgcccaatg gtaccaacga tgttccctcc accaaaggtg ttcttatgta   1860
gtgacaccga ttatttaaag ctgcagcata cgatatatat acatgtgtat atatgtatac   1920
ctatgaatgt cagtaagtat gtatacgaac agtatgatac tgaagatgac aaggtaatgc   1980
atcattctat acgtgtcatt ctgaacgagg cgcgctttcc tttttctttt ttgctttttc   2040
tttttttttc tcttgaactc gacggatcta tgcggtgtga aataccgcac agatgcgtaa   2100
ggagaaaata ccgcatcagg aaattgtaag cgttaatatt ttgttaaaat tcgcgttaaa   2160
tttttgttaa atcagctcat tttttaacca ataggccgaa atcggcaaaa tcccttataa   2220
atcaaaagaa tagaccgaga tagggttgag tgttgttcca gtttggaaca agagtccact   2280
attaaagaac gtggactcca acgtcaaagg gcgaaaaacc gtctatcagg gcgatggccc   2340
actacgtgaa ccatcaccct aatcaagttt tttggggtcg aggtgccgta aagcactaaa   2400
```

-continued

```
tcggaaccct aaagggagcc cccgatttag agcttgacgg ggaaagccgg cgaacgtggc   2460
gagaaaggaa gggaagaaag cgaaaggagc gggcgctagg gcgctggcaa gtgtagcggt   2520
cacgctgcgc gtaaccacca cacccgccgc gcttaatgcg ccgctacagg gcgcgtccat   2580
tcgccattca ggctgcgcaa ctgttgggaa gggcgcggtg cgggcctctt cgctattacg   2640
ccagctggcg aaagggggat gtgctgcaag gcgattaagt tgggtaacgc cagggttttc   2700
ccagtcacga cgttgtaaaa cgacggccag tgagcgcgcg taatacgact cactataggg   2760
cgaattgggt accgggcccc ccctcgaggt cgacggcgcg ccactggtag agagcgactt   2820
tgtatgcccc aattgcgaaa cccgcgatat ccttctcgat tctttagtac ccgaccagga   2880
caaggaaaag gaggtcgaaa cgtttttgaa gaaacaagag gaactacacg gaagctctaa   2940
agatggcaac cagccagaaa ctaagaaaat gaagttgatg gatccaactg gcaccgctgg   3000
cttgaacaac aataccagcc ttccaacttc tgtaaataac ggcggtacgc cagtgccacc   3060
agtaccgtta cctttcggta tacctccttt ccccatgttt ccaatgccct tcatgcctcc   3120
aacggctact atcacaaatc ctcatcaagc tgacgcaagc cctaagaaat gaataacaat   3180
actgacagta ctaaataatt gcctacttgg cttcacatac gttgcatacg tcgatataga   3240
taataatgat aatgacagca ggattatcgt aatacgtaat agctgaaaat ctcaaaaatg   3300
tgtgggtcat tacgtaaata atgataggaa tgggattctt ctatttttcc tttttccatt   3360
ctagcagccg tcgggaaaac gtggcatcct ctctttcggg ctcaattgga gtcacgctgc   3420
cgtgagcatc ctctctttcc atatctaaca actgagcacg taaccaatgg aaaagcatga   3480
gcttagcgtt gctccaaaaa agtattggat ggttaatacc atttgtctgt tctcttctga   3540
ctttgactcc tcaaaaaaaa aaatctacaa tcaacagatc gcttcaatta cgccctcaca   3600
aaaacttttt tccttcttct tcgcccacgt taaattttat ccctcatgtt gtctaacgga   3660
tttctgcact tgatttatta taaaaagaca aagacataat acttctctat caatttcagt   3720
tattgttctt ccttgcgtta ttcttctgtt cttctttttc ttttgtcata tataaccata   3780
accaagtaat acatattcaa actagtatga ctgacaaaaa aactcttaaa gacttaagaa   3840
atcgtagttc tgtttacgat tcaatggtta aatcacctaa tcgtgctatg ttgcgtgcaa   3900
ctggtatgca agatgaagac tttgaaaaac ctatcgtcgg tgtcatttca acttgggctg   3960
aaaacacacc ttgtaatatc cacttacatg actttggtaa actagccaaa gtcggtgtta   4020
aggaagctgg tgcttggcca gttcagttcg gaacaatcac ggtttctgat ggaatcgcca   4080
tgggaaccca aggaatgcgt ttctccttga catctcgtga tattattgca gattctattg   4140
aagcagccat gggaggtcat aatgcggatg cttttgtagc cattggcggt tgtgataaaa   4200
acatgcccgg ttctgttatc gctatggcta acatggatat cccagccatt tttgcttacg   4260
gcggaacaat tgcacctggt aatttagacg gcaaagatat cgatttagtc tctgtctttg   4320
aaggtgtcgg ccattggaac cacggcgata tgaccaaaga agaagttaaa gctttggaat   4380
gtaatgcttg tcccggtcct ggaggctgcg gtggtatgta tactgctaac acaatggcga   4440
cagctattga agttttggga cttagccttc cgggttcatc ttctcacccg gctgaatccg   4500
cagaaaagaa agcagatatt gaagaagctg gtcgcgctgt tgtcaaaatg ctcgaaatgg   4560
gcttaaaacc ttctgacatt ttaacgcgtg aagcttttga agatgctatt actgtaacta   4620
tggctctggg aggttcaacc aactcaaccc ttcacctctt agctattgcc catgctgcta   4680
atgtggaatt gacacttgat gatttcaata ctttccaaga aaaagttcct catttggctg   4740
atttgaaacc ttctggtcaa tatgtattcc aagaccttta caaggtcgga ggggtaccag   4800
```

-continued

```
cagttatgaa atatctcctt aaaaatggct tccttcatgg tgaccgtatc acttgtactg   4860
gcaaaacagt cgctgaaaat ttgaaggctt ttgatgattt aacacctggt caaaaggtta   4920
ttatgccgct tgaaaatcct aaacgtgaag atggtccgct cattattctc catggtaact   4980
tggctccaga cggtgccgtt gccaaagttt ctggtgtaaa agtgcgtcgt catgtcggtc   5040
ctgctaaggt ctttaattct gaagaagaag ccattgaagc tgtcttgaat gatgatattg   5100
ttgatggtga tgttgttgtc gtacgttttg taggaccaaa gggcggtcct ggtatgcctg   5160
aaatgctttc cctttcatca atgattgttg gtaaagggca aggtgaaaaa gttgcccttc   5220
tgacagatgg ccgcttctca ggtggtactt atggtcttgt cgtgggtcat atcgctcctg   5280
aagcacaaga tggcggtcca atcgcctacc tgcaaacagg agacatagtc actattgacc   5340
aagacactaa ggaattacac tttgatatct ccgatgaaga gttaaaacat cgtcaagaga   5400
ccattgaatt gccaccgctc tattcacgcg gtatccttgg taaatatgct cacatcgttt   5460
cgtctgcttc taggggagcc gtaacagact tttggaagcc tgaagaaact ggcaaaaaat   5520
gttgtcctgg ttgctgtggt taagcggccg cgttaattca aattaattga tatagttttt   5580
taatgagtat tgaatctgtt tagaaataat ggaatattat ttttatttat ttatttatat   5640
tattggtcgg ctcttttctt ctgaaggtca atgacaaaat gatatgaagg aaataatgat   5700
ttctaaaatt ttacaacgta agatattttt acaaaagcct agctcatctt ttgtcatgca   5760
ctattttact cacgcttgaa attaacggcc agtccactgc ggagtcattt caaagtcatc   5820
ctaatcgatc tatcgttttt gatagctcat tttggagttc gcgattgtct tctgttattc   5880
acaactgttt taatttttat ttcattctgg aactcttcga gttctttgta aagtctttca   5940
tagtagctta ctttatcctc caacatattt aacttcatgt caatttcggc tcttaaattt   6000
tccacatcat caagttcaac atcatctttt aacttgaatt tattctctag ctcttccaac   6060
caagcctcat tgctccttga tttactggtg aaaagtgata cactttgcgc gcaatccagg   6120
tcaaaacttt cctgcaaaga attcaccaat ttctcgacat catagtacaa tttgttttgt   6180
tctcccatca caatttaata tacctgatgg attcttatga agcgctgggt aatggacgtg   6240
tcactctact tcgccttttt ccctactcct tttagtacgg aagacaatgc taataaataa   6300
gagggtaata ataatattat taatcggcaa aaaagattaa acgccaagcg tttaattatc   6360
agaaagcaaa cgtcgtacca atccttgaat gcttcccaat tgtatattaa gagtcatcac   6420
agcaacatat tcttgttatt aaattaatta ttattgattt ttgatattgt ataaaaaaac   6480
caaatatgta taaaaaaagt gaataaaaaa taccaagtat ggagaaatat attagaagtc   6540
tatacgttaa accacccggg ccccccctcg aggtcgacgg tatcgataag cttgatatcg   6600
aattcctgca gcccggggga tccactagtt ctagagcggc cgctctagaa ctagtaccac   6660
aggtgttgtc ctctgaggac ataaaataca caccgagatt catcaactca ttgctggagt   6720
tagcatatct acaattgggt gaaatgggga gcgatttgca ggcatttgct cggcatgccg   6780
gtagaggtgt ggtcaataag agcgacctca tgctatacct gagaaagcaa cctgacctac   6840
aggaaagagt tactcaagaa taagaatttt cgttttaaaa cctaagagtc actttaaaat   6900
ttgtatacac ttattttttt tataacttat ttaataataa aaatcataaa tcataagaaa   6960
ttcgcttact cttaattaat caggcagcgc ctgcgttcga gaggatgatc ttcatcgcct   7020
tctccttggc gccattgagg aatacctgat aggcgtgctc gatctcggcc agctcgaagc   7080
gatgggtaat catcttcttc aacggaagct tgtcggtcga ggcgaccttc atcagcatgg   7140
gcgtcgtgtt cgtgttcacc agtcccgtgg tgatcgtcag gttcttgatc cagagcttct   7200
```

-continued gaatctcgaa gtcaaccttg acgccatgca cgccgacgtt ggcgatgtgc gcgccgggct 7260
tgacgatctc ctggcagatg tcccaagtcg ccggtatgcc caccgcctcg atcgcaacat 7320
cgactccctc tgccgcaatc ctatgcacgg cttcgacaac gttctccgtg ccggagttga 7380
tggtgtgcgt tgccccgagc tccttggcga gctggaggcg attctcgtcc atgtcgatca 7440
cgatgatggt cgagggggag tagaactggg cggtcaacag tacggacatg ccgacggggc 7500
ccgcgccgac aatagccacc gcatcgcccg gctggacatt cccatactgg acgccgattt 7560
cgtggccggt gggcaggatg tcgctcagca ggacggcgat ttcgtcgtca attgtctggg 7620
ggatcttgta gaggctgttg tcggcatgcg ggatgcggac gtattcggcc tgcacgccat 7680
cgatcatgta acccaggatc cacccgccgt cgcggcaatg ggagtaaagc tgcttcttgc 7740
agtagtcgca cgagccgcaa gaagtgacgc aggaaatcag gaccttgtcg cctttcttga 7800
actgcgtgac actctcgccc acttcctcga tgacgcctac cccttcatgg cccaggatgc 7860
gcccgtcggc gacctctgga ttcttgcctt tgtagatgcc gagatccgtg ccgcagatcg 7920
tggtcttcaa aacccgtact actacatccg tgggcttttg aagggtgggc ttgggcttgt 7980
cttcaagcga gatcttgtgg tcaccgtgat aaaccagagc tttcatcctc agctattgta 8040
atatgtgtgt ttgtttggat tattaagaag aataattaca aaaaaaatta caaaggaagg 8100
taattacaac agaattaaga aaggacaaga aggaggaaga gaatcagttc attatttctt 8160
ctttgttata taacaaaccc aagtagcgat ttggccatac attaaaagtt gagaaccacc 8220
ctccctggca acagccacaa ctcgttacca ttgttcatca cgatcatgaa actcgctgtc 8280
agctgaaatt tcacctcagt ggatctctct ttttattctt catcgttcca ctaacctttt 8340
tccatcagct ggcagggaac ggaaagtgga atcccattta gcgagcttcc tcttttcttc 8400
aagaaaagac gaagcttgtg tgtgggtgcg cgcgctagta tctttccaca ttaagaaata 8460
taccataaag gttacttaga catcactatg gctatatata tatatatata tatatatgta 8520
acttagcacc atcgcgcgtg catcactgca tgtgttaacc gaaaagtttg gcgaacactt 8580
caccgacacg gtcatttaga tctgtcgtct gcattgcacg tcccttagcc ttaaatccta 8640
ggcgggagca ttctcgtgta attgtgcagc ctgcgtagca actcaacata gcgtagtcta 8700
cccagttttt caagggttta tcgttagaag attctccctt ttcttcctgc tcacaaatct 8760
taaagtcata cattgcacga ctaaatgcaa gcatgcggat cccccgggct gcaggaattc 8820
gatatcaagc ttatcgatac cgtcgactgg ccattaatct ttcccatatt agatttcgcc 8880
aagccatgaa agttcaagaa aggtctttag acgaattacc cttcatttct caaactggcg 8940
tcaagggatc ctggtatggt tttatcgttt tatttctggt tcttatagca tcgttttgga 9000
cttctctgtt cccattaggc ggttcaggag ccagcgcaga atcattcttt gaaggatact 9060
tatcctttcc aattttgatt gtctgttacg ttggacataa actgtatact agaaattgga 9120
ctttgatggt gaaactagaa gatatggatc ttgataccgg cagaaaacaa gtagatttga 9180
ctcttcgtag ggaagaaatg aggattgagc gagaaacatt agcaaaaaga tccttcgtaa 9240
caagattttt acatttctgg tgttgaaggg aaagatatga gctatacagc ggaatttcca 9300
tatcactcag attttgttat ctaatttttt ccttcccacg tccgcgggaa tctgtgtata 9360
ttactgcatc tagatatatg ttatcttatc ttggcgcgta catttaattt tcaacgtatt 9420
ctataagaaa ttgcgggagt ttttttcatg tagatgatac tgactgcacg caaatatagg 9480
catgatttat aggcatgatt tgatggctgt accgatagga acgctaagag taacttcaga 9540
atcgttatcc tggcggaaaa aattcatttg taaactttaa aaaaaaaagc caatatcccc 9600

```
aaaattatta agagcgcctc cattattaac taaaatttca ctcagcatcc acaatgtatc   9660
aggtatctac tacagatatt acatgtggcg aaaaagacaa gaacaatgca atagcgcatc   9720
aagaaaaaac acaaagcttt caatcaatga atcgaaaatg tcattaaaat agtatataaa   9780
ttgaaactaa gtcataaagc tataaaaaga aaatttattt aaatgcaaga tttaaagtaa   9840
attcacggcc ctgcaggcct cagctcttgt tttgttctgc aaataactta cccatctttt   9900
tcaaaacttt aggtgcaccc tcctttgcta gaataagttc tatccaatac atcctatttg   9960
gatctgcttg agcttctttc atcacggata cgaattcatt ttctgttctc acaattttgg  10020
acacaactct gtcttccgtt gccccgaaac tttctggcag ttttgagtaa ttccacatag  10080
gaatgtcatt ataactctgg ttcggaccat gaatttccct ctcaaccgtg taaccatcgt  10140
tattaatgat aaagcagatt gggtttatct tctctctaat ggctagtcct aattcttgga  10200
cagtcagttg caatgatcca tctccgataa acaataaatg tctagattct ttatctgcaa  10260
tttggctgcc tagagctgcg gggaaagtgt atcctataga tccccacaag ggttgaccaa  10320
taaaatgtga tttcgatttc agaaatatag atgaggcacc gaagaaagaa gtgccttgtt  10380
cagccacgat cgtctcatta ctttgggtca aattttcgac agcttgccac agtctatctt  10440
gtgacaacag cgcgttagaa ggtacaaaat cttcttgctt tttatctatg tacttgcctt  10500
tatattcaat ttcggacaag tcaagaagag atgatatcag ggattcgaag tcgaaatttt  10560
ggattctttc gttgaaaatt ttaccttcat cgatattcaa ggaaatcatt ttattttcat  10620
taagatggtg agtaaatgca cccgtactag aatcggtaag ctttacaccc aacataagaa  10680
taaaatcagc agattccaca aattccttca agtttggctc tgacagagta ccgttgtaaa  10740
tccccaaaaa tgagggcaat gcttcatcaa cagatgattt accaaagttc aaagtagtaa  10800
taggtaactt agtctttgaa ataaactgag taacagtctt ctctaggccg aacgatataa  10860
tttcatggcc tgtgattaca attggtttct tggcattctt cagactttcc tgtattttgt  10920
tcagaatctc ttgatcagat gtattcgacg tggaattttc cttcttaaga ggcaaggatg  10980
gtttttcagc cttagcggca gctacatcta caggtaaatt gatgtaaacc ggctttcttt  11040
cctttagtaa ggcagacaac actctatcaa tttcaacagt tgcattctcg gctgtcaata  11100
aagtcctggc agcagtaacc ggttcgtgca tcttcataaa gtgcttgaaa tcaccatcag  11160
ccaacgtatg gtgaacaaac ttaccttcgt tctgcacttt cgaggtagga gatcccacga  11220
tctcaacaac aggcaggttc tcagcatagg agcccgctaa gccattaact gcggataatt  11280
cgccaacacc aaatgtagtc aagaatgccg cagccttttt cgttcttgcg tacccgtcgg  11340
ccatatagga ggcatttaac tcattagcat ttcccaccca tttcatatct ttgtgtgaaa  11400
taatttgatc tagaaattgc aaattgtagt cacctggtac tccgaatatt tcttctatac  11460
ctaattcgtg taatctgtcc aacagatagt cacctactgt atacattttg tttactagtt  11520
tatgtgtgtt tattcgaaac taagttcttg gtgttttaaa actaaaaaaa agactaacta  11580
taaaagtaga atttaagaag tttaagaaat agatttacag aattacaatc aatacctacc  11640
gtctttatat acttattagt caagtagggg aataatttca gggaactggt ttcaaccttt  11700
tttttcagct ttttccaaat cagagagagc agaaggtaat agaaggtgta agaaaatgag  11760
atagatacat gcgtgggtca attgccttgt gtcatcattt actccaggca ggttgcatca  11820
ctccattgag gttgtgcccg ttttttgcct gtttgtgccc ctgttctctg tagttgcgct  11880
aagagaatgg acctatgaac tgatggttgg tgaagaaaac aatattttgg tgctgggatt  11940
cttttttttt ctggatgcca gcttaaaaag cgggctccat tatatttagt ggatgccagg  12000
```

-continued aataaactgt tcacccagac acctacgatg ttatatattc tgtgtaaccc gcccccctatt 12060
ttgggcatgt acgggttaca gcagaattaa aaggctaatt ttttgactaa ataaagttag 12120
gaaaatcact actattaatt atttacgtat tctttgaaat ggcagtattg ataatgataa 12180
actcgaactg aaaaagcgtg ttttttattc aaaatgattc taactccctt acgtaatcaa 12240
ggaatctttt tgccttggcc tccgcgtcat taaacttctt gttgttgacg ctaacattca 12300
acgctagtat atattcgttt ttttcaggta agttcttttc aacgggtctt actgatgagg 12360
cagtcgcgtc tgaacctgtt aagaggtcaa atatgtcttc ttgaccgtac gtgtcttgca 12420
tgttattagc tttgggaatt tgcatcaagt cataggaaaa tttaaatctt ggctctcttg 12480
ggctcaaggt gacaaggtcc tcgaaaatag ggcgcgcccc accgcggtgg agctccagct 12540
tttgttccct ttagtgaggg ttaattgcgc gcttggcgta atcatggtca tagctgtttc 12600
ctgtgtgaaa ttgttatccg ctcacaattc cacacaacat acgagccgga agcataaagt 12660
gtaaagcctg gggtgcctaa tgagtgagct aactcacatt aattgcgttg cgctcactgc 12720
ccgctttcca gtcgggaaac ctgtcgtgcc agctgcatta atgaatcggc caacgcgcgg 12780
ggagaggcgg tttgcgtatt gggcgctctt ccgcttcctc gctcactgac tcgctgcgct 12840
cggtcgttcg gctgcggcga gcggtatcag ctcactcaaa ggcggtaata cggttatcca 12900
cagaatcagg ggataacgca ggaaagaaca tgtgagcaaa aggccagcaa aaggccagga 12960
accgtaaaaa ggccgcgttg ctggcgtttt tccataggct ccgcccccct gacgagcatc 13020
acaaaaatcg acgctcaagt cagaggtggc gaaacccgac aggactataa agataccagg 13080
cgtttccccc tggaagctcc ctcgtgcgct ctcctgttcc gaccctgccg cttaccggat 13140
acctgtccgc ctttctccct tcgggaagcg tggcgctttc tcatagctca cgctgtaggt 13200
atctcagttc ggtgtaggtc gttcgctcca agctgggctg tgtgcacgaa ccccccgttc 13260
agcccgaccg ctgcgcctta tccggtaact atcgtcttga gtccaacccg gtaagacacg 13320
acttatcgcc actggcagca gccactggta acaggattag cagagcgagg tatgtaggcg 13380
gtgctacaga gttcttgaag tggtggccta actacggcta cactagaaga acagtatttg 13440
gtatctgcgc tctgctgaag ccagttacct tcggaaaaag agttggtagc tcttgatccg 13500
gcaaacaaac caccgctggt agcggtggtt tttttgtttg caagcagcag attacgcgca 13560
gaaaaaaagg atctcaagaa gatcctttga tcttttctac ggggtctgac gctcagtgga 13620
acgaaaactc acgttaaggg attttggtca tgagattatc aaaaaggatc ttcacctaga 13680
tccttttaaa ttaaaaatga agttttaaat caatctaaag tatatatgag taaacttggt 13740
ctgacagtta ccaatgctta atcagtgagg cacctatctc agcgatctgt ctatttcgtt 13800
catccatagt tgcctgactc cccgtcgtgt agataactac gatacgggag ggcttaccat 13860
ctggccccag tgctgcaatg ataccgcgag acccacgctc accggctcca gatttatcag 13920
caataaacca gccagccgga agggccgagc gcagaagtgg tcctgcaact ttatccgcct 13980
ccatccagtc tattaattgt tgccgggaag ctagagtaag tagttcgcca gttaatagtt 14040
tgcgcaacgt tgttgccatt gctacaggca tcgtggtgtc acgctcgtcg tttggtatgg 14100
cttcattcag ctccggttcc caacgatcaa ggcgagttac atgatccccc atgttgtgca 14160
aaaaagcggt tagctccttc ggtcctccga tcgttgtcag aagtaagttg gccgcagtgt 14220
tatcactcat ggttatggca gcactgcata attctcttac tgtcatgcca tccgtaagat 14280
gcttttctgt gactggtgag tactcaacca agtcattctg agaatagtgt atgcggcgac 14340
cgagttgctc ttgcccggcg tcaatacggg ataataccgc gccacatagc agaactttaa 14400
aagtgctcat cattggaaaa cgttcttcgg ggcgaaaact ctcaaggatc ttaccgctgt 14460
tgagatccag ttcgatgtaa cccactcgtg cacccaactg atcttcagca tcttttactt 14520
tcaccagcgt ttctgggtga gcaaaaacag gaaggcaaaa tgccgcaaaa aagggaataa 14580
gggcgacacg gaaatgttga atactcatac tcttcctttt tcaatattat tgaagcattt 14640
atcagggtta ttgtctcatg agcggataca tatttgaatg tatttagaaa aataaacaaa 14700
taggggttcc gcgcacattt ccccgaaaag tgccacctga acgaagcatc tgtgcttcat 14760
tttgtagaac aaaaatgcaa cgcgagagcg ctaatttttc aaacaaagaa tctgagctgc 14820
atttttacag aacagaaatg caacgcgaaa gcgctatttt accaacgaag aatctgtgct 14880
tcatttttgt aaaacaaaaa tgcaacgcga gagcgctaat tttcaaaca aagaatctga 14940 gctgcatttt tacagaacag aaatgcaacg cgagagcgct attttaccaa caaagaatct 15000
atacttcttt tttgttctac aaaaatgcat cccgagagcg ctatttttct aacaaagcat 15060
cttagattac ttttttctc ctttgtgcgc tctataatgc agtctcttga taactttttg 15120
cactgtaggt ccgttaaggt tagaagaagg ctactttggt gtctattttc tcttccataa 15180
aaaaagcctg actccacttc ccgcgtttac tgattactag cgaagctgcg ggtgcatttt 15240
ttcaagataa aggcatcccc gattatattc tataccgatg tggattgcgc atactttgtg 15300
aacagaaagt gatagcgttg atgattcttc attggtcaga aaattatgaa cggtttcttc 15360
tattttgtct ctatatacta cgtataggaa atgtttacat tttcgtattg ttttcgattc 15420
actctatgaa tagttcttac tacaattttt ttgtct 15456

<210> SEQ ID NO 68
<211> LENGTH: 1559
<212> TYPE: DNA
<213> ORGANISM: Artificial Sequence
<220> FEATURE:
<223> OTHER INFORMATION: Template

<400> SEQUENCE: 68
gcattgcgga ttacgtattc taatgttcag taccgttcgt ataatgtatg ctatacgaag 60
ttatgcagat tgtactgaga gtgcaccata ccaccttttc aattcatcat ttttttttta 120
ttcttttttt tgatttcggt ttccttgaaa ttttttgat tcggtaatct ccgaacagaa 180
ggaagaacga aggaaggagc acagacttag attggtatat atacgcatat gtagtgttga 240
agaaacatga aattgcccag tattcttaac ccaactgcac agaacaaaaa cctgcaggaa 300
acgaagataa atcatgtcga aagctacata taaggaacgt gctgctactc atcctagtcc 360
tgttgctgcc aagctattta atatcatgca cgaaaagcaa acaaacttgt gtgcttcatt 420
ggatgttcgt accaccaagg aattactgga gttagttgaa gcattaggtc ccaaaatttg 480
tttactaaaa acacatgtgg atatcttgac tgatttttcc atggagggca cagttaagcc 540
gctaaaggca ttatccgcca agtacaattt tttactcttc gaagacagaa aatttgctga 600
cattggtaat acagtcaaat tgcagtactc tgcgggtgta tacagaatag cagaatgggc 660
agacattacg aatgcacacg gtgtggtggg cccaggtatt gttagcggtt tgaagcaggc 720
ggcagaagaa gtaacaaagg aacctagagg ccttttgatg ttagcagaat tgtcatgcaa 780
gggctcccta tctactggag aatatactaa gggtactgtt gacattgcga agagcgacaa 840
agattttgtt atcggcttta ttgctcaaag agacatgggt ggaagagatg aaggttacga 900
ttggttgatt atgacacccg gtgtgggttt agatgacaag ggagacgcat tgggtcaaca 960
gtatagaacc gtggatgatg tggtctctac aggatctgac attattattg ttggaagagg 1020

-continued actatttgca aagggaaggg atgctaaggt agagggtgaa cgttacagaa aagcaggctg 1080
ggaagcatat ttgagaagat gcggccagca aaactaaaaa actgtattat aagtaaatgc 1140
atgtatacta aactcacaaa ttagagcttc aatttaatta tatcagttat taccctatgc 1200
ggtgtgaaat accgcacaga tgcgtaagga gaaaataccg catcaggaaa ttgtaaacgt 1260
taatattttg ttaaaattcg cgttaaattt ttgttaaatc agctcatttt ttaaccaata 1320
ggccgaaatc ggcaaaatcc cttataaatc aaaagaatag accgagatag ggttgagtgt 1380
tgttccagtt tggaacaaga gtccactatt aaagaacgtg gactccaacg tcaaagggcg 1440
aaaaaccgtc tatcagggcg atggcccact acgtgaacca tcaccctaat caagataact 1500
tcgtataatg tatgctatac gaacggtacc agtgatgata caacgagtta gccaaggtg 1559

<210> SEQ ID NO 69
<211> LENGTH: 1047
<212> TYPE: DNA
<213> ORGANISM: Alcaligenes xylosoxydans

<400> SEQUENCE: 69
atgaaagctc tggtttatca cggtgaccac aagatctcgc ttgaagacaa gcccaagccc 60
acccttcaaa agcccacgga tgtagtagta cgggttttga agaccacgat ctgcggcacg 120
gatctcggca tctacaaagg caagaatcca gaggtcgccg acgggcgcat cctgggccat 180
gaaggggtag gcgtcatcga ggaagtgggc gagagtgtca cgcagttcaa gaaaggcgac 240
aaggtcctga tttcctgcgt cacttcttgc ggctcgtgcg actactgcaa gaagcagctt 300
tactcccatt gccgcgacgg cgggtggatc ctgggttaca tgatcgatgg cgtgcaggcc 360
gaatacgtcc gcatcccgca tgccgacaac agcctctaca agatcccccca gacaattgac 420 gacgaaatcg ccgtcctgct gagcgacatc ctgcccaccg gccacgaaat cggcgtccag 480
tatgggaatg tccagccggg cgatgcggtg gctattgtcg gcgcgggccc cgtcggcatg 540
tccgtactgt tgaccgccca gttctactcc ccctcgacca tcatcgtgat cgacatggac 600
gagaatcgcc tccagctcgc caaggagctc ggggcaacgc acaccatcaa ctccggcacg 660
gagaacgttg tcgaagccgt gcataggatt gcggcagagg gagtcgatgt tgcgatcgag 720
gcggtgggca taccggcgac ttgggacatc tgccaggaga tcgtcaagcc cggcgcgcac 780
atcgccaacg tcggcgtgca tggcgtcaag gttgacttcg agattcagaa gctctggatc 840
aagaacctga cgatcaccac gggactggtg aacacgaaca cgacgcccat gctgatgaag 900
gtcgcctcga ccgacaagct tccgttgaag aagatgatta cccatcgctt cgagctggcc 960
gagatcgagc acgcctatca ggtattcctc aatggcgcca aggagaaggc gatgaagatc 1020
atcctctcga acgcaggcgc tgcctga 1047

<210> SEQ ID NO 70
<211> LENGTH: 348
<212> TYPE: PRT
<213> ORGANISM: Alcaligenes xylosoxydans

<400> SEQUENCE: 70

Met Lys Ala Leu Val Tyr His Gly Asp His Lys Ile Ser Leu Glu Asp
1 5 10 15

Lys Pro Lys Pro Thr Leu Gln Lys Pro Thr Asp Val Val Val Arg Val
20 25 30

Leu Lys Thr Thr Ile Cys Gly Thr Asp Leu Gly Ile Tyr Lys Gly Lys
35 40 45

Asn Pro Glu Val Ala Asp Gly Arg Ile Leu Gly His Glu Gly Val Gly

```
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345


<210> SEQ ID NO 71
<211> LENGTH: 1644
<212> TYPE: DNA
<213> ORGANISM: Artificial Sequence
<220> FEATURE:
<223> OTHER INFORMATION: codon optimized L. lactis kivD coding region
      for S. cerevisiae expression

<400> SEQUENCE: 71

atgtatacag taggtgacta tctgttggac agattacacg aattaggtat agaagaaata      60

ttcggagtac caggtgacta caatttgcaa tttctagatc aaattatttc acacaaagat     120

atgaaatggg tgggaaatgc taatgagtta aatgcctcct atatggccga cgggtacgca     180

agaacgaaaa aggctgcggc attcttgact acatttggtg ttggcgaatt atccgcagtt     240

aatggcttag cgggctccta tgctgagaac ctgcctgttg ttgagatcgt gggatctcct     300

acctcgaaag tgcagaacga aggtaagttt gttcaccata cgttggctga tggtgatttc     360

aagcacttta tgaagatgca cgaaccggtt actgctgcca ggactttatt gacagccgag     420
```

aatgcaactg ttgaaattga tagagtgttg tctgccttac taaaggaaag aaagccggtt 480
tacatcaatt tacctgtaga tgtagctgcc gctaaggctg aaaaaccatc cttgcctctt 540
aagaaggaaa attccacgtc gaatacatct gatcaagaga ttctgaacaa aatacaggaa 600
agtctgaaga atgccaagaa accaattgta atcacaggcc atgaaattat atcgttcggc 660
ctagagaaga ctgttactca gtttatttca aagactaagt tacctattac tactttgaac 720
tttggtaaat catctgttga tgaagcattg ccctcatttt tggggattta caacggtact 780
ctgtcagagc caaacttgaa ggaatttgtg gaatctgctg attttattct tatgttgggt 840
gtaaagctta ccgattctag tacgggtgca tttactcacc atcttaatga aaataaaatg 900
atttccttga atatcgatga aggtaaaatt ttcaacgaaa gaatccaaaa tttcgacttc 960
gaatccctga tatcatctct tcttgacttg tccgaaattg aatataaagg caagtacata 1020
gataaaaagc aagaagattt tgtaccttct aacgcgctgt tgtcacaaga tagactgtgg 1080
caagctgtcg aaaatttgac ccaaagtaat gagacgatcg tggctgaaca aggcacttct 1140
ttcttcggtg cctcatctat atttctgaaa tcgaaatcac attttattgg tcaacccttg 1200
tggggatcta taggatacac tttccccgca gctctaggca gccaaattgc agataaagaa 1260
tctagacatt tattgtttat cggagatgga tcattgcaac tgactgtcca agaattagga 1320
ctagccatta gagagaagat aaacccaatc tgctttatca ttaataacga tggttacacg 1380
gttgagaggg aaattcatgg tccgaaccag agttataatg acattcctat gtggaattac 1440
tcaaaactgc cagaaagttt cggggcaacg gaagacagag ttgtgtccaa aattgtgaga 1500
acagaaaatg aattcgtatc cgtgatgaaa gaagctcaag cagatccaaa taggatgtat 1560
tggatagaac ttattctagc aaaggagggt gcacctaaag ttttgaaaaa gatgggtaag 1620
ttatttgcag aacaaaacaa gagc 1644

<210> SEQ ID NO 72
<211> LENGTH: 753
<212> TYPE: DNA
<213> ORGANISM: Saccharomyces cerevisiae

<400> SEQUENCE: 72
gcatgcttgc atttagtcgt gcaatgtatg actttaagat ttgtgagcag gaagaaaagg 60
gagaatcttc taacgataaa cccttgaaaa actgggtaga ctacgctatg ttgagttgct 120
acgcaggctg cacaattaca cgagaatgct cccgcctagg atttaaggct aagggacgtg 180
caatgcagac gacagatcta aatgaccgtg tcggtgaagt gttcgccaaa cttttcggtt 240
aacacatgca gtgatgcacg cgcgatggtg ctaagttaca tatatatata tatagccata 300
gtgatgtcta agtaaccttt atggtatatt tcttaatgtg gaaagatact agcgcgcgca 360
cccacacaca agcttcgtct tttcttgaag aaaagaggaa gctcgctaaa tgggattcca 420
ctttccgttc cctgccagct gatggaaaaa ggttagtgga acgatgaaga ataaaaagag 480
agatccactg aggtgaaatt tcagctgaca gcgagtttca tgatcgtgat gaacaatggt 540
aacgagttgt ggctgttgcc agggagggtg gttctcaact tttaatgtat ggccaaatcg 600
ctacttgggt ttgttatata acaaagaaga aataatgaac tgattctctt cctccttctt 660
gtcctttctt aattctgttg taattacctt cctttgtaat tttttttgta attattcttc 720
ttaataatcc aaacaaacac acatattaca ata 753

<210> SEQ ID NO 73
<211> LENGTH: 316

<212> TYPE: DNA
<213> ORGANISM: Saccharomyces cerevisiae

<400> SEQUENCE: 73
gagtaagcga atttcttatg atttatgatt tttattatta aataagttat aaaaaaaata 60
agtgtataca aattttaaag tgactcttag gttttaaaac gaaaattctt attcttgagt 120
aactctttcc tgtaggtcag gttgctttct caggtatagc atgaggtcgc tcttattgac 180
cacacctcta ccggcatgcc gagcaaatgc ctgcaaatcg ctccccattt cacccaattg 240
tagatatgct aactccagca atgagttgat gaatctcggt gtgtatttta tgtcctcaga 300
ggacaacacc tgtggt 316

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
ggaattcaca catgaaagct ctggtttatc 30

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75
gcgtccaggg cgtcaaagat caggcagc 28

<210> SEQ ID NO 76
<211> LENGTH: 55
<212> TYPE: DNA
<213> ORGANISM: Artificial Sequence
<220> FEATURE:
<223> OTHER INFORMATION: Primer

<400> SEQUENCE: 76
aaacaaacac acatattaca atagctgagg atgaaagctc tggtttatca cggtg 55

<210> SEQ ID NO 77
<211> LENGTH: 55
<212> TYPE: DNA
<213> ORGANISM: Artificial Sequence
<220> FEATURE:
<223> OTHER INFORMATION: primer

<400> SEQUENCE: 77
atcataagaa attcgcttac tcttaattaa tcaggcagcg cctgcgttcg agagg 55

<210> SEQ ID NO 78
<211> LENGTH: 8994
<212> TYPE: DNA
<213> ORGANISM: Artificial Sequence
<220> FEATURE:
<223> OTHER INFORMATION: constructed plasmid

<400> SEQUENCE: 78
ctagttctag agcggccgcc accgcggtgg agctccagct tttgttccct ttagtgaggg 60
ttaattgcgc gcttggcgta atcatggtca tagctgtttc ctgtgtgaaa ttgttatccg 120
ctcacaattc cacacaacat aggagccgga agcataaagt gtaaagcctg gggtgcctaa 180

```
tgagtgaggt aactcacatt aattgcgttg cgctcactgc ccgctttcca gtcgggaaac    240
ctgtcgtgcc agctgcatta atgaatcggc caacgcgcgg ggagaggcgg tttgcgtatt    300
gggcgctctt ccgcttcctc gctcactgac tcgctgcgct cggtcgttcg gctgcggcga    360
gcggtatcag ctcactcaaa ggcggtaata cggttatcca cagaatcagg ggataacgca    420
ggaaagaaca tgtgagcaaa aggccagcaa aaggccagga accgtaaaaa ggccgcgttg    480
ctggcgtttt tccataggct ccgcccccct gacgagcatc acaaaaatcg acgctcaagt    540
cagaggtggc gaaacccgac aggactataa agataccagg cgtttccccc tggaagctcc    600
ctcgtgcgct ctcctgttcc gaccctgccg cttaccggat acctgtccgc ctttctccct    660
tcgggaagcg tggcgctttc tcatagctca cgctgtaggt atctcagttc ggtgtaggtc    720
gttcgctcca agctgggctg tgtgcacgaa ccccccgttc agcccgaccg ctgcgcctta    780
tccggtaact atcgtcttga gtccaacccg gtaagacacg acttatcgcc actggcagca    840
gccactggta acaggattag cagagcgagg tatgtaggcg gtgctacaga gttcttgaag    900
tggtggccta actacggcta cactagaagg acagtatttg gtatctgcgc tctgctgaag    960
ccagttacct tcggaaaaag agttggtagc tcttgatccg gcaaacaaac caccgctggt   1020
agcggtggtt tttttgtttg caagcagcag attacgcgca gaaaaaaagg atctcaagaa   1080
gatcctttga tcttttctac ggggtctgac gctcagtgga acgaaaactc acgttaaggg   1140
attttggtca tgagattatc aaaaaggatc ttcacctaga tccttttaaa ttaaaaatga   1200
agttttaaat caatctaaag tatatatgag taaacttggt ctgacagtta ccaatgctta   1260
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga acgaagcatc tgtgcttcat tttgtagaac aaaaatgcaa   2280
cgcgagagcg ctaatttttc aaacaaagaa tctgagctgc atttttacag aacagaaatg   2340
caacgcgaaa gcgctatttt accaacgaag aatctgtgct tcatttttgt aaaacaaaaa   2400
tgcaacgcga gagcgctaat ttttcaaaca aagaatctga gctgcatttt tacagaacag   2460
aaatgcaacg cgagagcgct attttaccaa caaagaatct atacttcttt tttgttctac   2520
aaaaatgcat cccgagagcg ctatttttct aacaaagcat cttagattac tttttttctc   2580
```

-continued

```
ctttgtgcgc tctataatgc agtctcttga taactttttg cactgtaggt ccgttaaggt   2640
tagaagaagg ctactttggt gtctattttc tcttccataa aaaaagcctg actccacttc   2700
ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggtttcttc tattttgtct ctatatacta   2880
cgtataggaa atgtttacat tttcgtattg ttttcgattc actctatgaa tagttcttac   2940
tacaattttt ttgtctaaag agtaatacta gagataaaca taaaaaatgt agaggtcgag   3000
tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatactttct agagaatagg aacttcggaa   3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac cctttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg ccctttcgtc tcgcgcgttt   3660
cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt tttttagag aaaatcctcc aatatcaaat taggaatcgt   4020
agtttcatga ttttctgtta cacctaactt tttgtgtggt gccctcctcc ttgtcaatat   4080
taatgttaaa gtgcaattct ttttccttat cacgttgagc cattagtatc aatttgctta   4140
cctgtattcc tttactatcc tcctttttct ccttcttgat aaatgtatgt agattgcgta   4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
```

```
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttctttacgg atttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
cttcggctgt gatttcttga ccaacgtggt cacctggcaa aacgacgatc ttcttagggg   5400
cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct cacctttcct ttttctccca   5640
atttttcagt tgaaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgg ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
atgaacaagg aagtacagga caattgattt tgaagagaat gtggattttg atgtaattgt   6000
tgggattcca tttttaataa ggcaataata ttaggtatgt ggatatacta gaagttctcc   6060
tcgaccgtcg atatgcggtg tgaaataccg cacagatgcg taaggagaaa ataccgcatc   6120
aggaaattgt aaacgttaat attttgttaa aattcgcgtt aaatttttgt taaatcagct   6180
cattttttaa ccaataggcc gaaatcggca aaatccctta taaatcaaaa gaatagaccg   6240
agatagggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
gcccccgatt tagagcttga cggggaaagc cggcgaacgt ggcgagaaag gaagggaaga   6480
aagcgaaagg agcgggcgct agggcgctgg caagtgtagc ggtcacgctg cgcgtaacca   6540
ccacacccgc cgcgcttaat gcgccgctac agggcgcgtc gcgccattcg ccattcaggc   6600
tgcgcaactg ttgggaaggg cgatcggtgc gggcctcttc gctattacgc cagctggcga   6660
aagggggatg tgctgcaagg cgattaagtt gggtaacgcc agggttttcc cagtcacgac   6720
gttgtaaaac gacggccagt gagcgcgcgt aatacgactc actatagggc gaattgggta   6780
ccgggccccc cctcgaggtc gacggtatcg ataagcttga tatcgaattc ctgcagcccg   6840
ggggatccgc atgcttgcat ttagtcgtgc aatgtatgac tttaagattt gtgagcagga   6900
agaaaaggga gaatcttcta acgataaacc cttgaaaaac tggtagact acgctatgtt    6960
gagttgctac gcaggctgca caattacacg agaatgctcc cgcctaggat ttaaggctaa   7020
gggacgtgca atgcagacga cagatctaaa tgaccgtgtc ggtgaagtgt tcgccaaact   7080
tttcggttaa cacatgcagt gatgcacgcg cgatggtgct aagttacata tatatatata   7140
tatatatata tagccatagt gatgtctaag taacctttat ggtatatttc ttaatgtgga   7200
aagatactag cgcgcgcacc cacacacaag cttcgtcttt tcttgaagaa aagaggaagc   7260
tcgctaaatg ggattccact ttccgttccc tgccagctga tggaaaaagg ttagtggaac   7320
gatgaagaat aaaaagagag atccactgag gtgaaatttc agctgacagc gagtttcatg   7380
```

```
atcgtgatga acaatggtaa cgagttgtgg ctgttgccag ggagggtggt tctcaacttt   7440

taatgtatgg ccaaatcgct acttgggttt gttatataac aaagaagaaa taatgaactg   7500

attctcttcc tccttcttgt cctttcttaa ttctgttgta attaccttcc tttgtaattt   7560

tttttgtaat tattcttctt aataatccaa acaaacacac atattacaat agctagctga   7620

ggatgaaggc attagtttat catggggatc acaaaatttc gttagaagac aaaccaaaac   7680

ccactctgca gaaaccaaca gacgttgtgg ttagggtgtt gaaaacaaca atttgcggta   7740

ctgacttggg aatatacaaa ggtaagaatc ctgaagtggc agatggcaga atcctgggtc   7800

atgagggcgt tggcgtcatt gaagaagtgg gcgaatccgt gacacaattc aaaaaggggg   7860

ataaagtttt aatctcctgc gttactagct gtggatcgtg tgattattgc aagaagcaac   7920

tgtattcaca ctgtagagac ggtggctgga ttttaggtta catgatcgac ggtgtccaag   7980

ccgaatacgt cagaatacca catgctgaca attcattgta taagatcccg caaactatcg   8040

atgatgaaat tgcagtacta ctgtccgata ttttacctac tggacatgaa attggtgttc   8100

aatatggtaa cgttcaacca ggcgatgctg tagcaattgt aggagcaggt cctgttggaa   8160

tgtcagtttt gttaactgct caattttact cgcctagtac cattattgtt atcgacatgg   8220

acgaaaaccg tttacaatta gcgaaggagc ttggggccac acacactatt aactccggta   8280

ctgaaaatgt tgtcgaagct gtgcatcgta tagcagccga aggagtggat gtagcaatag   8340

aagctgttgg tatacccgca acctgggaca tctgtcagga aattgtaaaa cccggcgctc   8400

atattgccaa cgtgggagtt catggtgtta aggtggactt tgaaattcaa aagttgtgga   8460

ttaagaatct aaccatcacc actggtttgg ttaacactaa tactacccca atgttgatga   8520

aggtagcctc tactgataaa ttgcctttaa agaaaatgat tactcacagg tttgagttag   8580

ctgaaatcga acacgcatat caggttttct tgaatggcgc taaagaaaaa gctatgaaga   8640

ttattctatc taatgcaggt gccgcctaat taattaagag taagcgaatt tcttatgatt   8700

tatgattttt attattaaat aagttataaa aaaaataagt gtatacaaat tttaaagtga   8760

ctcttaggtt ttaaaacgaa aattcttatt cttgagtaac tctttcctgt aggtcaggtt   8820

gctttctcag gtatagcatg aggtcgctct tattgaccac acctctaccg gcatgccgag   8880

caaatgcctg caaatcgctc cccatttcac ccaattgtag atatgctaac tccagcaatg   8940

agttgatgaa tctcggtgtg tattttatgt cctcagagga caacacctgt ggta         8994
```

<210> SEQ ID NO 79
<211> LENGTH: 2145
<212> TYPE: DNA
<213> ORGANISM: Artificial Sequence
<220> FEATURE:
<223> OTHER INFORMATION: constructed chimeric gene

<400> SEQUENCE: 79

```
gcatgcttgc atttagtcgt gcaatgtatg actttaagat ttgtgagcag gaagaaaagg     60

gagaatcttc taacgataaa cccttgaaaa actgggtaga ctacgctatg ttgagttgct    120

acgcaggctg cacaattaca cgagaatgct cccgcctagg atttaaggct aagggacgtg    180

caatgcagac gacagatcta aatgaccgtg tcggtgaagt gttcgccaaa cttttcggtt    240

aacacatgca gtgatgcacg cgcgatggtg ctaagttaca tatatatata tatatatata    300

tatagccata gtgatgtcta agtaaccttt atggtatatt tcttaatgtg gaaagatact    360

agcgcgcgca cccacacaca agcttcgtct tttcttgaag aaaagaggaa gctcgctaaa    420

tgggattcca ctttccgttc cctgccagct gatggaaaaa ggttagtgga acgatgaaga    480
```

ataaaaagag agatccactg aggtgaaatt tcagctgaca gcgagtttca tgatcgtgat 540
gaacaatggt aacgagttgt ggctgttgcc agggagggtg gttctcaact tttaatgtat 600
ggccaaatcg ctacttgggt ttgttatata acaaagaaga aataatgaac tgattctctt 660
cctccttctt gtcctttctt aattctgttg taattacctt cctttgtaat ttttttgta 720 attattcttc ttaataatcc aaacaaacac acatattaca atagctagct gaggatgaag 780
gcattagttt atcatgggga tcacaaaatt tcgttagaag acaaaccaaa acccactctg 840
cagaaaccaa cagacgttgt ggttagggtg ttgaaaacaa caatttgcgg tactgacttg 900
ggaatataca aaggtaagaa tcctgaagtg gcagatggca gaatcctggg tcatgagggc 960
gttggcgtca ttgaagaagt gggcgaatcc gtgacacaat tcaaaaaggg ggataaagtt 1020
ttaatctcct gcgttactag ctgtggatcg tgtgattatt gcaagaagca actgtattca 1080
cactgtagag acggtggctg gattttaggt tacatgatcg acggtgtcca agccgaatac 1140
gtcagaatac cacatgctga caattcattg tataagatcc cgcaaactat cgatgatgaa 1200
attgcagtac tactgtccga tattttacct actggacatg aaattggtgt tcaatatggt 1260
aacgttcaac caggcgatgc tgtagcaatt gtaggagcag gtcctgttgg aatgtcagtt 1320
ttgttaactg ctcaatttta ctcgcctagt accattattg ttatcgacat ggacgaaaac 1380
cgtttacaat tagcgaagga gcttggggcc acacacacta ttaactccgg tactgaaaat 1440
gttgtcgaag ctgtgcatcg tatagcagcc gaaggagtgg atgtagcaat agaagctgtt 1500
ggtatacccg caacctggga catctgtcag gaaattgtaa aacccggcgc tcatattgcc 1560
aacgtgggag ttcatggtgt taaggtggac tttgaaattc aaaagttgtg gattaagaat 1620
ctaaccatca ccactggttt ggttaacact aatactaccc caatgttgat gaaggtagcc 1680
tctactgata aattgccttt aaagaaaatg attactcaca ggtttgagtt agctgaaatc 1740
gaacacgcat atcaggtttt cttgaatggc gctaaagaaa aagctatgaa gattattcta 1800
tctaatgcag gtgccgccta attaattaag agtaagcgaa tttcttatga tttatgattt 1860
ttattattaa ataagttata aaaaaaataa gtgtatacaa attttaaagt gactcttagg 1920
ttttaaaacg aaaattctta ttcttgagta actctttcct gtaggtcagg ttgctttctc 1980
aggtatagca tgaggtcgct cttattgacc acacctctac cggcatgccg agcaaatgcc 2040
tgcaaatcgc tccccatttc acccaattgt agatatgcta actccagcaa tgagttgatg 2100
aatctcggtg tgtattttat gtcctcagag gacaacacct gtggt 2145

<210> SEQ ID NO 80
<211> LENGTH: 4280
<212> TYPE: DNA
<213> ORGANISM: Artificial Sequence
<220> FEATURE:
<223> OTHER INFORMATION: vector

<400> SEQUENCE: 80
ggggatcctc tagagtcgac ctgcaggcat gcaagcttgg cgtaatcatg gtcatagctg 60
tttcctgtgt gaaattgtta tccgctcaca attccacaca acatacgagc cggaagcata 120
aagtgtaaag cctggggtgc ctaatgagtg agctaactca cattaattgc gttgcgctca 180
ctgcccgctt tccagtcggg aaacctgtcg tgccagctgc attaatgaat cggccaacgc 240
gcggggagag gcggtttgcg tattgggcgc tcttccgctt cctcgctcac tgactcgctg 300
cgctcggtcg ttcggctgcg gcgagcggta tcagctcact caaaggcggt aatacggtta 360
tccacagaat caggggataa cgcaggaaag aacatgtgag caaaaggcca gcaaaaggcc 420

-continued

```
aggaaccgta aaaaggccgc gttgctggcg tttttccata ggctccgccc ccctgacgag    480
catcacaaaa atcgacgctc aagtcagagg tggcgaaacc cgacaggact ataaagatac    540
caggcgtttc cccctggaag ctccctcgtg cgctctcctg ttccgaccct gccgcttacc    600
ggatacctgt ccgcctttct cccttcggga agcgtggcgc tttctcatag ctcacgctgt    660
aggtatctca gttcggtgta ggtcgttcgc tccaagctgg gctgtgtgca cgaacccccc    720
gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggtttttttg tttgcaagca gcagattacg   1020
cgcagaaaaa aaggatctca agaagatcct ttgatctttt ctacggggtc tgacgctcag   1080
tggaacgaaa actcacgtta agggattttg gtcatgagat tatcaaaaag gatcttcacc   1140
tagatccttt taaattaaaa atgaagtttt aaatcaatct aaagtatata tgagtaaact   1200
tggtctgaca gttaccaatg cttaatcagt gaggcaccta tctcagcgat ctgtctattt   1260
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
tgcaaaaaag cggttagctc cttcggtcct ccgatcgttg tcagaagtaa gttggccgca   1680
gtgttatcac tcatggttat ggcagcactg cataattctc ttactgtcat gccatccgta   1740
agatgctttt ctgtgactgg tgagtactca accaagtcat tctgagaata gtgtatgcgg   1800
cgaccgagtt gctcttgccc ggcgtcaata cgggataata ccgcgccaca tagcagaact   1860
ttaaaagtgc tcatcattgg aaaacgttct tcggggcgaa aactctcaag gatcttaccg   1920
ctgttgagat ccagttcgat gtaacccact cgtgcaccca actgatcttc agcatctttt   1980
actttcacca gcgtttctgg gtgagcaaaa acaggaaggc aaaatgccgc aaaaaaggga   2040
ataagggcga cacggaaatg ttgaatactc atactcttcc tttttcaata ttattgaagc   2100
atttatcagg gttattgtct catgagcgga tacatatttg aatgtattta gaaaaataaa   2160
caaatagggg ttccgcgcac atttccccga aaagtgccac ctgacgtcta agaaaccatt   2220
attatcatga cattaaccta taaaaatagg cgtatcacga ggccctttcg tctcgcgcgt   2280
ttcggtgatg acggtgaaaa cctctgacac atgcagctcc cggagacggt cacagcttgt   2340
ctgtaagcgg atgccgggag cagacaagcc cgtcagggcg cgtcagcggg tgttggcggg   2400
tgtcggggct ggcttaacta tgcggcatca gagcagattg tactgagagt gcaccatatg   2460
cggtgtgaaa taccgcacag atgcgtaagg agaaaatacc gcatcaggcg ccattcgcca   2520
ttcaggctgc gcaactgttg ggaagggcga tcggtgcggg cctcttcgct attacgccag   2580
ctggcgaaag ggggatgtgc tgcaaggcga ttaagttggg taacgccagg gttttcccag   2640
tcacgacgtt gtaaaacgac ggccagtgaa ttcgagctcg gtacccccgg ctctgagaca   2700
gtagtaggtt agtcatcgct ctaccgacgc gcaggaaaag aaagaagcat tgcggattac   2760
gtattctaat gttcagcccg cggaacgcca gcaaatcacc acccatgcgc atgatactga   2820
```

gtcttgtaca cgctgggctt ccagtgtact gagagtgcac cataccacag cttttcaatt 2880
caattcatca ttttttttt attctttttt ttgatttcgg tttctttgaa attttttga 2940 ttcggtaatc tccgaacaga aggaagaacg aaggaaggag cacagactta gattggtata 3000
tatacgcata tgtagtgttg aagaaacatg aaattgccca gtattcttaa cccaactgca 3060
cagaacaaaa acctgcagga aacgaagata aatcatgtcg aaagctacat ataaggaacg 3120
tgctgctact catcctagtc ctgttgctgc caagctattt aatatcatgc acgaaaagca 3180
aacaaacttg tgtgcttcat tggatgttcg taccaccaag gaattactgg agttagttga 3240
agcattaggt cccaaaattt gtttactaaa aacacatgtg gatatcttga ctgatttttc 3300
catggagggc acagttaagc cgctaaaggc attatccgcc aagtacaatt ttttactctt 3360
cgaagacaga aaatttgctg acattggtaa tacagtcaaa ttgcagtact ctgcgggtgt 3420
atacagaata gcagaatggg cagacattac gaatgcacac ggtgtggtgg gcccaggtat 3480
tgttagcggt ttgaagcagg cggcagaaga agtaacaaag gaacctagag gccttttgat 3540
gttagcagaa ttgtcatgca agggctccct atctactgga gaatatacta agggtactgt 3600
tgacattgcg aagagcgaca aagattttgt tatcggcttt attgctcaaa gagacatggg 3660
tggaagagat gaaggttacg attggttgat tatgacaccc ggtgtgggtt tagatgacaa 3720
gggagacgca ttgggtcaac agtatagaac cgtggatgat gtggtctcta caggatctga 3780
cattattatt gttggaagag gactatttgc aaagggaagg gatgctaagg tagagggtga 3840
acgttacaga aaagcaggct gggaagcata tttgagaaga tgcggccagc aaaactaaaa 3900
aactgtatta taagtaaatg catgtatact aaactcacaa attagagctt caatttaatt 3960
atatcagtta ttaccctatg cggtgtgaaa taccgcacag atgcgtaagg agaaaatacc 4020
gcatcaggaa attgtaaacg ttaatatttt gttaaaattc gcgttaaatt tttgttaaat 4080
cagctcattt tttaaccaat aggccgaaat cggcaaaatc ttcagcccgc ggaacgccag 4140
caaatcacca cccatgcgca tgatactgag tcttgtacac gctgggcttc cagtgatgat 4200
acaacgagtt agccaaggtg agcacggatg tctaaattag aattacgttt taatatcttt 4260
ttttccatat ctagggctag 4280

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
gcatgcttgc atttagtcgt gcaatgtatg 30

<210> SEQ ID NO 82
<211> LENGTH: 54
<212> TYPE: DNA
<213> ORGANISM: Artificial Sequence
<220> FEATURE:
<223> OTHER INFORMATION: primer

<400> SEQUENCE: 82
gaacattaga atacgtaatc cgcaatgcac tagtaccaca ggtgttgtcc tctg 54

<210> SEQ ID NO 83
<211> LENGTH: 54
<212> TYPE: DNA
<213> ORGANISM: Artificial Sequence
<220> FEATURE:
<223> OTHER INFORMATION: primer

<400> SEQUENCE: 83
cagaggacaa cacctgtggt actagtgcat tgcggattac gtattctaat gttc 54

<210> SEQ ID NO 84
<211> LENGTH: 28
<212> TYPE: DNA
<213> ORGANISM: Artificial Sequence
<220> FEATURE:
<223> OTHER INFORMATION: primer

<400> SEQUENCE: 84
caccttggct aactcgttgt atcatcac 28

<210> SEQ ID NO 85
<211> LENGTH: 100
<212> TYPE: DNA
<213> ORGANISM: Artificial Sequence
<220> FEATURE:
<223> OTHER INFORMATION: primer

<400> SEQUENCE: 85
ttttaagccg aatgagtgac agaaaaagcc cacaacttat caagtgatat tgaacaaagg 60
gcgaaacttc gcatgcttgc atttagtcgt gcaatgtatg 100

<210> SEQ ID NO 86
<211> LENGTH: 98
<212> TYPE: DNA
<213> ORGANISM: Artificial Sequence
<220> FEATURE:
<223> OTHER INFORMATION: primer

<400> SEQUENCE: 86
cccaattggt aaatattcaa caagagacgc gcagtacgta acatgcgaat tgcgtaattc 60
acggcgataa caccttggct aactcgttgt atcatcac 98

<210> SEQ ID NO 87
<211> LENGTH: 29
<212> TYPE: DNA
<213> ORGANISM: Artificial Sequence
<220> FEATURE:
<223> OTHER INFORMATION: primer

<400> SEQUENCE: 87
caaaagccca tgtcccacac caaaggatg 29

<210> SEQ ID NO 88
<211> LENGTH: 26
<212> TYPE: DNA
<213> ORGANISM: Artificial Sequence
<220> FEATURE:
<223> OTHER INFORMATION: primer

<400> SEQUENCE: 88
caccatcgcg cgtgcatcac tgcatg 26

<210> SEQ ID NO 89
<211> LENGTH: 28
<212> TYPE: DNA
<213> ORGANISM: Artificial Sequence
<220> FEATURE:
<223> OTHER INFORMATION: primer

<400> SEQUENCE: 89
tcggtttttg caatatgacc tgtgggcc 28

<210> SEQ ID NO 90
<211> LENGTH: 22
<212> TYPE: DNA
<213> ORGANISM: Artificial Sequence
<220> FEATURE:
<223> OTHER INFORMATION: primer

<400> SEQUENCE: 90
gagaagatgc ggccagcaaa ac 22

<210> SEQ ID NO 91
<211> LENGTH: 2745
<212> TYPE: DNA
<213> ORGANISM: Artificial Sequence
<220> FEATURE:
<223> OTHER INFORMATION: constructed coding region-terminator segment

<400> SEQUENCE: 91
atgactgaca aaaaaactct taaagactta agaaatcgta gttctgttta cgattcaatg 60
gttaaatcac ctaatcgtgc tatgttgcgt gcaactggta tgcaagatga agactttgaa 120
aaacctatcg tcggtgtcat ttcaacttgg gctgaaaaca caccttgtaa tatccactta 180
catgactttg gtaaactagc caaagtcggt gttaaggaag ctggtgcttg gccagttcag 240
ttcggaacaa tcacggtttc tgatggaatc gccatgggaa cccaaggaat gcgtttctcc 300
ttgacatctc gtgatattat tgcagattct attgaagcag ccatgggagg tcataatgcg 360
gatgcttttg tagccattgg cggttgtgat aaaaacatgc ccggttctgt tatcgctatg 420
gctaacatgg atatcccagc catttttgct tacggcggaa caattgcacc tggtaattta 480
gacggcaaag atatcgattt agtctctgtc tttgaaggtg tcggccattg gaaccacggc 540
gatatgacca aagaagaagt taaagctttg gaatgtaatg cttgtcccgg tcctggaggc 600
tgcggtggta tgtatactgc taacacaatg gcgacagcta ttgaagtttt gggacttagc 660
cttccgggtt catcttctca cccggctgaa tccgcagaaa agaaagcaga tattgaagaa 720
gctggtcgcg ctgttgtcaa aatgctcgaa atgggcttaa aaccttctga cattttaacg 780
cgtgaagctt ttgaagatgc tattactgta actatggctc tgggaggttc aaccaactca 840
acccttcacc tcttagctat tgcccatgct gctaatgtgg aattgacact tgatgatttc 900
aatactttcc aagaaaaagt tcctcatttg gctgatttga aaccttctgg tcaatatgta 960
ttccaagacc tttacaaggt cggaggggta ccagcagtta tgaaatatct ccttaaaaat 1020
ggcttccttc atggtgaccg tatcacttgt actggcaaaa cagtcgctga aaatttgaag 1080
gcttttgatg atttaacacc tggtcaaaag gttattatgc cgcttgaaaa tcctaaacgt 1140
gaagatggtc cgctcattat tctccatggt aacttggctc cagacggtgc cgttgccaaa 1200
gtttctggtg taaaagtgcg tcgtcatgtc ggtcctgcta aggtctttaa ttctgaagaa 1260
gaagccattg aagctgtctt gaatgatgat attgttgatg gtgatgttgt tgtcgtacgt 1320
tttgtaggac caaagggcgg tcctggtatg cctgaaatgc tttccctttc atcaatgatt 1380
gttggtaaag ggcaaggtga aaaagttgcc cttctgacag atggccgctt ctcaggtggt 1440
acttatggtc ttgtcgtggg tcatatcgct cctgaagcac aagatggcgg tccaatcgcc 1500
tacctgcaaa caggagacat agtcactatt gaccaagaca ctaaggaatt acactttgat 1560
atctccgatg aagagttaaa acatcgtcaa gagaccattg aattgccacc gctctattca 1620
cgcggtatcc ttggtaaata tgctcacatc gtttcgtctg cttctagggg agccgtaaca 1680

```
gacttttgga agcctgaaga aactggcaaa aaatgttgtc ctggttgctg tggttaagcg    1740

gccgcgttaa ttcaaattaa ttgatatagt tttttaatga gtattgaatc tgtttagaaa    1800

taatggaata ttatttttat ttatttattt atattattgg tcggctcttt tcttctgaag    1860

gtcaatgaca aaatgatatg aaggaaataa tgatttctaa aattttacaa cgtaagatat    1920

ttttacaaaa gcctagctca tcttttgtca tgcactattt tactcacgct tgaaattaac    1980

ggccagtcca ctgcggagtc atttcaaagt catcctaatc gatctatcgt ttttgatagc    2040

tcattttgga gttcgcgatt gtcttctgtt attcacaact gttttaattt ttatttcatt    2100

ctggaactct tcgagttctt tgtaaagtct ttcatagtag cttactttat cctccaacat    2160

atttaacttc atgtcaattt cggctcttaa attttccaca tcatcaagtt caacatcatc    2220

ttttaacttg aatttattct ctagctcttc caaccaagcc tcattgctcc ttgatttact    2280

ggtgaaaagt gatacacttt gcgcgcaatc caggtcaaaa ctttcctgca aagaattcac    2340

caatttctcg acatcatagt acaatttgtt ttgttctccc atcacaattt aatatacctg    2400

atggattctt atgaagcgct gggtaatgga cgtgtcactc tacttcgcct ttttccctac    2460

tccttttagt acgaagacaa atgctaataa ataagagggt aataataata ttattaatcg    2520

gcaaaaaaga ttaaacgcca agcgtttaat tatcagaaag caaacgtcgt accaatcctt    2580

gaatgcttcc caattgtata ttaagagtca tcacagcaac atattcttgt tattaaatta    2640

attattattg attttgata ttgtataaaa aaaccaaata tgtataaaaa aagtgaataa    2700

aaaataccaa gtatggagaa atatattaga agtctatacg ttaaa                   2745

<210> SEQ ID NO 92
<211> LENGTH: 27
<212> TYPE: DNA
<213> ORGANISM: Artificial Sequence
<220> FEATURE:
<223> OTHER INFORMATION: primer

<400> SEQUENCE: 92

gacttttgga agcctgaaga aactggc                                         27

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93

cttggcagca acaggactag                                                 20

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94

ccaggccaat tcaacagact gtcggc                                          26

<210> SEQ ID NO 95
<211> LENGTH: 2347
<212> TYPE: DNA
<213> ORGANISM: Artificial Sequence
<220> FEATURE:
<223> OTHER INFORMATION: constructed URA3 marker with flanking
```

-continued homologous repeat sequences for HIS gene replacement and marker excision

<400> SEQUENCE: 95

```
gcattgcgga ttacgtattc taatgttcag gtgctggaag aagagctgct taaccgccgc     60
gcccagggtg aagatccacg ctactttacc ctgcgtcgtc tggatttcgg cggctgtcgt    120
ctttcgctgg caacgccggt tgatgaagcc tgggacggtc cgctctcctt aaacggtaaa    180
cgtatcgcca cctcttatcc tcacctgctc aagcgttatc tcgaccagaa aggcatctct    240
tttaaatcct gcttactgaa cggttctgtt gaagtcgccc cgcgtgccgg actggcggat    300
gcgatttgcg atctggtttc caccggtgcc acgctggaag ctaacggcct gcgcgaagtc    360
gaagttatct atcgctcgaa agcctgcctg attcaacgcg atggcgaaat ggaagaatcc    420
aaacagcaac tgatcgacaa actgctgacc cgtattcagg gtgtgatcca ggcgcgcgaa    480
tcaaaataca tcatgatgca cgcaccgacc gaacgtctgg atgaagtcat ggtacctact    540
gagagtgcac cataccacag cttttcaatt caattcatca tttttttttt attctttttt    600
ttgatttcgg tttctttgaa atttttttga ttcggtaatc tccgaacaga aggaagaacg    660
aaggaaggag cacagactta gattggtata tatacgcata tgtagtgttg aagaaacatg    720
aaattgccca gtattcttaa cccaactgca cagaacaaaa acctgcagga aacgaagata    780
aatcatgtcg aaagctacat ataaggaacg tgctgctact catcctagtc ctgttgctgc    840
caagctattt aatatcatgc acgaaaagca aacaaacttg tgtgcttcat tggatgttcg    900
taccaccaag gaattactgg agttagttga agcattaggt cccaaaattt gtttactaaa    960
aacacatgtg gatatcttga ctgatttttc catggagggc acagttaagc cgctaaaggc   1020
attatccgcc aagtacaatt ttttactctt cgaagacaga aaatttgctg acattggtaa   1080
tacagtcaaa ttgcagtact ctgcgggtgt atacagaata gcagaatggg cagacattac   1140
gaatgcacac ggtgtggtgg gcccaggtat tgttagcggt ttgaagcagg cggcagaaga   1200
agtaacaaag gaacctagag gccttttgat gttagcagaa ttgtcatgca agggctccct   1260
atctactgga gaatatacta agggtactgt tgacattgcg aagagcgaca aagattttgt   1320
tatcggcttt attgctcaaa gagacatggg tggaagagat gaaggttacg attggttgat   1380
tatgacaccc ggtgtgggtt tagatgacaa gggagacgca ttgggtcaac agtatagaac   1440
cgtggatgat gtggtctcta caggatctga cattattatt gttggaagag gactatttgc   1500
aaagggaagg gatgctaagg tagagggtga acgttacaga aaagcaggct gggaagcata   1560
tttgagaaga tgcggccagc aaaactaaaa aactgtatta taagtaaatg catgtatact   1620
aaactcacaa attagagctt caatttaatt atatcagtta ttaccctatg cggtgtgaaa   1680
taccgcacag atgcgtaagg agaaaatacc gcatcaggaa attgtaaacg ttaatatttt   1740
gttaaaattc gcgttaaatt tttgttaaat cagctcattt tttaaccaat aggccgaaat   1800
cggcaaaatc tctagagtgc tggaagaaga gctgcttaac cgccgcgccc agggtgaaga   1860
tccacgctac tttaccctgc gtcgtctgga tttcggcggc tgtcgtcttt cgctggcaac   1920
gccggttgat gaagcctggg acggtccgct ctccttaaac ggtaaacgta tcgccacctc   1980
ttatcctcac ctgctcaagc gttatctcga ccagaaaggc atctctttta aatcctgctt   2040
actgaacggt tctgttgaag tcgccccgcg tgccggactg gcggatgcga tttgcgatct   2100
ggtttccacc ggtgccacgc tggaagctaa cggcctgcgc gaagtcgaag ttatctatcg   2160
ctcgaaagcc tgcctgattc aacgcgatgg cgaaatggaa gaatccaaac agcaactgat   2220
cgacaaactg ctgacccgta ttcagggtgt gatccaggcg cgcgaatcaa aatacatcat   2280
```

gatgcacgca ccgaccgaac gtctggatga agtcatccag tgatgataca acgagttagc 2340
caaggtg 2347

<210> SEQ ID NO 96
<211> LENGTH: 80
<212> TYPE: DNA
<213> ORGANISM: Artificial Sequence
<220> FEATURE:
<223> OTHER INFORMATION: primer

<400> SEQUENCE: 96
cttcgaagaa tatactaaaa aatgagcagg caagataaac gaaggcaaag gcattgcgga 60
ttacgtattc taatgttcag 80

<210> SEQ ID NO 97
<211> LENGTH: 81
<212> TYPE: DNA
<213> ORGANISM: Artificial Sequence
<220> FEATURE:
<223> OTHER INFORMATION: primer

<400> SEQUENCE: 97
tatacacatg tatatatatc gtatgctgca gctttaaata atcggtgtca caccttggct 60
aactcgttgt atcatcactg g 81

<210> SEQ ID NO 98
<211> LENGTH: 26
<212> TYPE: DNA
<213> ORGANISM: Artificial Sequence
<220> FEATURE:
<223> OTHER INFORMATION: primer

<400> SEQUENCE: 98
gacttgaata atgcagcggc gcttgc 26

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
ccaccctctt caattagcta agatcatagc 30

<210> SEQ ID NO 100
<211> LENGTH: 25
<212> TYPE: DNA
<213> ORGANISM: Artificial Sequence
<220> FEATURE:
<223> OTHER INFORMATION: primer

<400> SEQUENCE: 100
aaaaattgat tctcatcgta aatgc 25

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
ctgcagcgag gagccgtaat 20

-continued

<210> SEQ ID NO 102
<211> LENGTH: 90
<212> TYPE: DNA
<213> ORGANISM: Artificial Sequence
<220> FEATURE:
<223> OTHER INFORMATION: primer

<400> SEQUENCE: 102
atggttcatt taggtccaaa aaaaccacaa gccagaaagg gttccatggc cgatgtgcca    60
gcattgcgga ttacgtattc taatgttcag                                    90

<210> SEQ ID NO 103
<211> LENGTH: 91
<212> TYPE: DNA
<213> ORGANISM: Artificial Sequence
<220> FEATURE:
<223> OTHER INFORMATION: primer

<400> SEQUENCE: 103
ttaagcaccg atgataccaa cggacttacc ttcagcaatt cttttttggg ccaaagcagc    60
caccttggct aactcgttgt atcatcactg g                                  91

<210> SEQ ID NO 104
<211> LENGTH: 24
<212> TYPE: DNA
<213> ORGANISM: Artificial Sequence
<220> FEATURE:
<223> OTHER INFORMATION: primer

<400> SEQUENCE: 104
ctaggatgag tagcagcacg ttcc                                          24

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
ccaattccgt gatgtctctt tgttgc                                        26

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
gtgaacgagt tcacaaccgc                                               20

<210> SEQ ID NO 107
<211> LENGTH: 22
<212> TYPE: DNA
<213> ORGANISM: Artificial Sequence
<220> FEATURE:
<223> OTHER INFORMATION: primer

<400> SEQUENCE: 107
gttcgttcca gaattatcac gc                                            22

<210> SEQ ID NO 108
<211> LENGTH: 28

<212> TYPE: DNA
<213> ORGANISM: Artificial Sequence
<220> FEATURE:
<223> OTHER INFORMATION: primer

<400> SEQUENCE: 108
ggatccgcat gcttgcattt agtcgtgc 28

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
gggatgcgga cgtattcggc 20

<210> SEQ ID NO 110
<211> LENGTH: 4506
<212> TYPE: DNA
<213> ORGANISM: Saccharomyces cerevisiae

<400> SEQUENCE: 110
atgtcgaata cccccttataa ttcatctgtg ccttccattg catccatgac ccagtcttcg 60
gtctcaagaa gtcctaacat gcatacagca actacgcccg gtgccaacac cagctctaac 120
tctccaccct tgcacatgtc ttcagattcg tccaagatca agaggaagcg taacagaatt 180
ccgctcagtt gcaccatttg tcggaaaagg aaagtcaaat gtgacaaact cagaccacac 240
tgccagcagt gcactaaaac tggggtagcc catctctgcc actacatgga acagacctgg 300
gcagaagagg cagagaaaga attgctgaag gacaacgaat taaagaagct tagggagcgc 360
gtaaaatctt tagaaaagac tctttctaag gtgcactctt ctccttcgtc taactccttg 420
aaaagttaca acactcccga gagcagcaac ctgtttatgg gtagcgatga acacaccacc 480
cttgttaatg caaatacagg ctctgcttcc tctgcctcgc atatgcatca gcaacaacag 540
caacagcagc aacaggaaca acaacaagac ttttccagaa gtgcgaacgc caacgcgaat 600
tcctcgtccc tttctatctc aaataaatat gacaacgatg agctggactt aactaaggac 660
tttgatcttt tgcatatcaa aagtaacgga accatccact taggtgccac ccactggttg 720
tctatcatga aaggtgaccc gtacctaaaa cttttgtggg gtcatatctt cgctatgagg 780
gaaaagttaa atgaatggta ctaccaaaaa aattcgtact ctaagctgaa gtcaagcaaa 840
tgtcccatca atcacgcgca agcgccgcct tctgccgctg ccgccgctac cagaaaatgt 900
cctgttgatc actccgcgtt ttcgtctggc atggtggccc caaaggagga gactcctctt 960
cctaggaaat gtccagttga ccacaccatg ttctcttcgg gaatgattcc tcccagagag 1020
gacacttcgt cccagaagag gtgtcccgtt gaccacacca tgtattccgc aggaatgatg 1080
ccgcccaagg acgagacacc ttccccattt tccactaaag ctatgataga ccataacaag 1140
catacaatga atccgcctca gtcaaaatgt cctgtggacc atagaaacta tatgaaggat 1200
tatccctctg acatggcaaa ttcttcttcg aacccggcaa gtcgttgccc cattgaccat 1260
tcaagcatga aaaatacagc ggccttacca gcttcaacgc acaataccat cccacaccac 1320
caaccacagt ccggatctca tgctcgttcg catcccgcac aaagcaggaa acatgattcc 1380
tacatgacag aatctgaagt cctcgcaaca ctttgtgaga tgttgccacc aaagcgcgtc 1440
atcgcattat tcatcgagaa attcttcaaa catttatacc ctgccattcc aatcttagat 1500
gaacagaatt tcaaaaatca cgtgaatcaa atgctttcgt tgtcttcgat gaatcccaca 1560

```
gttaacaact ttggtatgag catgccatct tcatctacac tagagaacca acccataaca   1620
caaatcaatc ttccaaaact ttccgattct tgtaacttag gtattctgat aataatcttg   1680
agattgacat ggctatccat accttctaat tcctgcgaag tcgacctggg agaagaaagt   1740
ggctcatttt tagtgcccaa cgaatctagc aatatgtctg catctgcatt gacctcgatg   1800
gctaaagaag aatcacttct gctaaagcat gagacaccgg tcgaggcact ggagctatgt   1860
caaaaatact tgattaaatt cgatgaactt tctagtattt ccaataacaa cgttaattta   1920
accacggtgc agtttgccat tttttacaac ttctatatga aaagtgcctc taatgatttg   1980
actaccttga caaataccaa caacactggc atggccaatc ctggtcacga ttccgagtct   2040
caccagatcc tattgtccaa tattactcaa atggccttta gttgtgggtt acacagagac   2100
cctgataatt ttcctcaatt aaacgctacc attccagcaa ccagccagga cgtgtctaac   2160
aacgggagca aaaaggcaaa ccctagcacc aatccaactt tgaataacaa catgtctgct   2220
gccactacca acagcagtag cagatctggc agtgctgatt caagaagtgg ttctaaccct   2280
gtgaacaaga aggaaaatca ggttagtatc gaaagattta aacacacttg gaggaaaatt   2340
tggtattaca ttgttagcat ggatgttaac caatctcttt ccctggggag ccctcgacta   2400
ctaagaaatc tgagggattt cagcgataca aagctaccaa gtgcgtcaag gattgattat   2460
gttcgcgata tcaaagagtt aatcattgtg aagaatttta ctcttttttt ccaaattgat   2520
ttgtgtatta ttgctgtatt aaatcacatt ttgaatgttt ctttagcaag aagcgtgaga   2580
aaatttgaac tggattcatt gattaattta ttgaaaaatc tgacctatgg tactgagaat   2640
gtcaatgatg tagtgagctc cttgatcaac aaagggttat taccaacttc ggaaggtggt   2700
tctgtagatt caaataatga tgaaatttac ggtctaccga aactacccga tattctaaac   2760
catggtcaac ataaccaaaa cttgtatgct gatggaagaa atacttctag tagtgatata   2820
gataagaaat tggaccttcc tcacgaatct acaacgagag ctctattctt ttccaagcat   2880
atgacaatta gaatgttgct gtacttattg aactacattt tgtttactca ttatgaacca   2940
atgggcagtg aagatcctgg tactaatatc ctagctaagg agtacgctca agaggcatta   3000
aattttgcca tggatggcta cagaaactgc atgattttct tcaacaatat cagaaacacc   3060
aattcactat tcgattacat gaatgttatc ttgtcttacc cttgtttgga cattggacat   3120
cgttctttac aatttatcgt ttgtttgatc ctgagagcta aatgtggccc attgactggt   3180
atgcgtgaat catcgatcat tactaatggt acatcaagtg gatttaatag ttcggtagaa   3240
gatgaggacg tcaaagttaa acaagaatct tctgatgaat tgaaaaaaga cgatttcatg   3300
aaagatgtaa atttggattc aggcgattca ttagcagaga ttctaatgtc aagaatgctg   3360
ctatttcaaa aactaacaaa acaactatca aagaagtaca actacgctat tcgtatgaac   3420
aaatccactg gattctttgt ctctttacta gatacacctt caaagaaatc agactcgaaa   3480
tcgggtggta gttcattcat gttgggtaat tggaaacatc caaaggtttc aaacatgagc   3540
ggatttcttg ctggtgacaa agaccaatta cagaaatgcc ccgtgtacca agatgcgctg   3600
gggtttgtta gtccaaccgg tgctaatgaa ggttctgctc cgatgcaagg catgtcctta   3660
cagggctcta ctgctaggat gggagggacc cagttgccac caattagatc atacaaacct   3720
atcacgtaca caagtagtaa tctacgtcgt atgaatgaaa cgggtgaggc agaagctaag   3780
agaagaagat ttaatgatgg ctatattgat aataatagta acaacgatat acctagagga   3840
atcagcccaa aaccttcaaa tggctatca tcggtgcagc cactattatc gtcattttcc   3900
atgaaccagc taaacggggg taccattcca acggttccat cgttaaccaa cattacttca   3960
```

caaatgggag ctttaccatc tttagatagg atcaccacta atcaaataaa tttgccagac 4020
ccatctagag atgaagcatt tgacaactcc atcaagcaaa tgacgcctat gacaagtgca 4080
ttcatgaatg ctaatactac aattccaagt tcaactttaa acgggaatat gaacatgaat 4140
ggagctggaa ctgcgaatac agatacaagt gccaacggca gtgctttatc gacactgaca 4200
agcccacaag gctcagactt agcatccaat tctgctacac agtataaacc tgacttagaa 4260
gactttttga tgcaaaattc taactttaat gggctaatga taaatccttc cagtctggta 4320
gaagttgttg gtggatacaa cgatcctaat aaccttggaa gaaatgacgc ggttgatttt 4380
ctacccgttg ataatgttga aattgatggt gttggaataa aaatcaacta tcatctacta 4440
actagtattt acgttactag tatattatca tatacggtgt tagaagatga cgcaaatgat 4500
gagaaa 4506

<210> SEQ ID NO 111
<211> LENGTH: 99
<212> TYPE: DNA
<213> ORGANISM: Artificial Sequence
<220> FEATURE:
<223> OTHER INFORMATION: primer

<400> SEQUENCE: 111
tcctttctca attattattt tctactcata acctcacgca aaataacaca gtcaaatcaa 60
tcaaagtatg actgacaaaa aaactcttaa agacttaag 99

<210> SEQ ID NO 112
<211> LENGTH: 77
<212> TYPE: DNA
<213> ORGANISM: Artificial Sequence
<220> FEATURE:
<223> OTHER INFORMATION: primer

<400> SEQUENCE: 112
gaacattaga atacgtaatc cgcaatgctt ctttcttttc cgtttaacgt atagacttct 60
aatatatttc tccatac 77

<210> SEQ ID NO 113
<211> LENGTH: 45
<212> TYPE: DNA
<213> ORGANISM: Artificial Sequence
<220> FEATURE:
<223> OTHER INFORMATION: primer

<400> SEQUENCE: 113
aaacggaaaa gaaagaagca ttgcggatta cgtattctaa tgttc 45

<210> SEQ ID NO 114
<211> LENGTH: 88
<212> TYPE: DNA
<213> ORGANISM: Artificial Sequence
<220> FEATURE:
<223> OTHER INFORMATION: primer

<400> SEQUENCE: 114
tatttttcgt tacataaaaa tgcttataaa actttaacta ataattagag attaaatcgc 60
caccttggct aactcgttgt atcatcac 88

<210> SEQ ID NO 115
<211> LENGTH: 1713
<212> TYPE: DNA
<213> ORGANISM: Streptococcus mutans

<400> SEQUENCE: 115
atgactgaca aaaaaactct taaagactta agaaatcgta gttctgttta cgattcaatg 60
gttaaatcac ctaatcgtgc tatgttgcgt gcaactggta tgcaagatga agactttgaa 120
aaacctatcg tcggtgtcat ttcaacttgg gctgaaaaca caccttgtaa tatccactta 180
catgactttg gtaaactagc caaagtcggt gttaaggaag ctggtgcttg gccagttcag 240
ttcggaacaa tcacggtttc tgatggaatc gccatgggaa cccaaggaat gcgtttctcc 300
ttgacatctc gtgatattat tgcagattct attgaagcag ccatgggagg tcataatgcg 360
gatgcttttg tagccattgg cggttgtgat aaaaacatgc ccggttctgt tatcgctatg 420
gctaacatgg atatcccagc catttttgct tacggcggaa caattgcacc tggtaattta 480
gacggcaaag atatcgattt agtctctgtc tttgaaggtg tcggccattg gaaccacggc 540
gatatgacca aagaagaagt taaagctttg gaatgtaatg cttgtcccgg tcctggaggc 600
tgcggtggta tgtatactgc taacacaatg gcgacagcta ttgaagtttt gggacttagc 660
cttccgggtt catcttctca cccggctgaa tccgcagaaa agaaagcaga tattgaagaa 720
gctggtcgcg ctgttgtcaa aatgctcgaa atgggcttaa aaccttctga catttttaacg 780 cgtgaagctt ttgaagatgc tattactgta actatggctc tgggaggttc aaccaactca 840
acccttcacc tcttagctat tgcccatgct gctaatgtgg aattgacact tgatgatttc 900
aatactttcc aagaaaaagt tcctcatttg gctgatttga aaccttctgg tcaatatgta 960
ttccaagacc tttacaaggt cggaggggta ccagcagtta tgaaatatct ccttaaaaat 1020
ggcttccttc atggtgaccg tatcacttgt actggcaaaa cagtcgctga aaatttgaag 1080
gcttttgatg atttaacacc tggtcaaaag gttattatgc cgcttgaaaa tcctaaacgt 1140
gaagatggtc cgctcattat tctccatggt aacttggctc cagacggtgc cgttgccaaa 1200
gtttctggtg taaaagtgcg tcgtcatgtc ggtcctgcta aggtctttaa ttctgaagaa 1260
gaagccattg aagctgtctt gaatgatgat attgttgatg gtgatgttgt tgtcgtacgt 1320
tttgtaggac caaagggcgg tcctggtatg cctgaaatgc tttccctttc atcaatgatt 1380
gttggtaaag ggcaaggtga aaaagttgcc cttctgacag atggccgctt ctcaggtggt 1440
acttatggtc ttgtcgtggg tcatatcgct cctgaagcac aagatggcgg tccaatcgcc 1500
tacctgcaaa caggagacat agtcactatt gaccaagaca ctaaggaatt acactttgat 1560
atctccgatg aagagttaaa acatcgtcaa gagaccattg aattgccacc gctctattca 1620
cgcggtatcc ttggtaaata tgctcacatc gtttcgtctg cttctagggg agccgtaaca 1680
gacttttgga agcctgaaga aactggcaaa aaa 1713

<210> SEQ ID NO 116
<211> LENGTH: 571
<212> TYPE: PRT
<213> ORGANISM: Streptococcus mutans

<400> SEQUENCE: 116

Met Thr Asp Lys Lys Thr Leu Lys Asp Leu Arg Asn Arg Ser Ser Val
1 5 10 15

Tyr Asp Ser Met Val Lys Ser Pro Asn Arg Ala Met Leu Arg Ala Thr
20 25 30

Gly Met Gln Asp Glu Asp Phe Glu Lys Pro Ile Val Gly Val Ile Ser
35 40 45

Thr Trp Ala Glu Asn Thr Pro Cys Asn Ile His Leu His Asp Phe Gly
50 55 60

```
Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
```

```
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570


<210> SEQ ID NO 117
<211> LENGTH: 548
<212> TYPE: PRT
<213> ORGANISM: Lactococcus lactis

<400> SEQUENCE: 117

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
```

-continued

```
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545


<210> SEQ ID NO 118
<211> LENGTH: 1125
<212> TYPE: DNA
<213> ORGANISM: Artificial Sequence
<220> FEATURE:
<223> OTHER INFORMATION: horse ADH coding region codon optimized for S.
      cerevisiae expression

<400> SEQUENCE: 118

atgtcaacag ccggtaaagt tattaagtgt aaagcggcag ttttgtggga agagaaaaag      60

ccgtttagca tagaagaagt agaagtagcg ccaccaaaag cacacgaggt tagaatcaag     120

atggttgcca ccggaatctg tagatccgac gaccatgtgg tgagtggcac tctagttact     180

cctttgccag taatcgcggg acacgaggct gccggaatcg ttgaatccat aggtgaaggt     240

gttaccactg ttcgtcctgg tgataaagtg atcccactgt tcactcctca atgtggtaag     300

tgtagagtct gcaaacatcc tgagggtaat ttctgcctta aaaatgattt gtctatgcct     360

agaggtacta tgcaggatgg tacaagcaga tttacatgca gagggaaacc tatacaccat     420

ttccttggta cttctacatt ttcccaatac acagtggtgg acgagatatc tgtcgctaaa     480

atcgatgcag cttcaccact ggaaaaagtt tgcttgatag ggtgcggatt ttccaccggt     540

tacggttccg cagttaaagt tgcaaaggtt acacagggtt cgacttgtgc agtattcggt     600
```

ttaggaggag taggactaag cgttattatg gggtgtaaag ctgcaggcgc agcgaggatt 660
ataggtgtag acatcaataa ggacaaattt gcaaaagcta aggaggtcgg ggctactgaa 720
tgtgttaacc ctcaagatta taagaaacca atacaagaag tccttactga aatgtcaaac 780
ggtggagttg atttctcttt tgaagttata ggccgtcttg atactatggt aactgcgttg 840
tcctgctgtc aagaggcata tggagtcagt gtgatcgtag gtgttcctcc tgattcacaa 900
aatttgtcga tgaatcctat gctgttgcta agcggtcgta catggaaggg agctatattt 960
ggcggtttta agagcaagga tagtgttcca aaacttgttg ccgactttat ggcgaagaag 1020
tttgctcttg atcctttaat tacacatgta ttgccattcg agaaaatcaa tgaagggttt 1080
gatttgttaa gaagtggtga atctattcgt acaattttaa ctttt 1125

<210> SEQ ID NO 119
<211> LENGTH: 375
<212> TYPE: PRT
<213> ORGANISM: Equus caballus

<400> SEQUENCE: 119

Met Ser Thr Ala Gly Lys Val Ile Lys Cys Lys Ala Ala Val Leu Trp
1 5 10 15

Glu Glu Lys Lys Pro Phe Ser Ile Glu Glu Val Glu Val Ala Pro Pro
20 25 30

Lys Ala His Glu Val Arg Ile Lys Met Val Ala Thr Gly Ile Cys Arg
35 40 45

Ser Asp Asp His Val Val Ser Gly Thr Leu Val Thr Pro Leu Pro Val
50 55 60

Ile Ala Gly His Glu Ala Ala Gly Ile Val Glu Ser Ile Gly Glu Gly
65 70 75 80

Val Thr Thr Val Arg Pro Gly Asp Lys Val Ile Pro Leu Phe Thr Pro
85 90 95

Gln Cys Gly Lys Cys Arg Val Cys Lys His Pro Glu Gly Asn Phe Cys
100 105 110

Leu Lys Asn Asp Leu Ser Met Pro Arg Gly Thr Met Gln Asp Gly Thr
115 120 125

Ser Arg Phe Thr Cys Arg Gly Lys Pro Ile His His Phe Leu Gly Thr
130 135 140

Ser Thr Phe Ser Gln Tyr Thr Val Val Asp Glu Ile Ser Val Ala Lys
145 150 155 160

Ile Asp Ala Ala Ser Pro Leu Glu Lys Val Cys Leu Ile Gly Cys Gly
165 170 175

Phe Ser Thr Gly Tyr Gly Ser Ala Val Lys Val Ala Lys Val Thr Gln
180 185 190

Gly Ser Thr Cys Ala Val Phe Gly Leu Gly Gly Val Gly Leu Ser Val
195 200 205

Ile Met Gly Cys Lys Ala Ala Gly Ala Ala Arg Ile Ile Gly Val Asp
210 215 220

Ile Asn Lys Asp Lys Phe Ala Lys Ala Lys Glu Val Gly Ala Thr Glu
225 230 235 240

Cys Val Asn Pro Gln Asp Tyr Lys Lys Pro Ile Gln Glu Val Leu Thr
245 250 255

Glu Met Ser Asn Gly Gly Val Asp Phe Ser Phe Glu Val Ile Gly Arg
260 265 270

Leu Asp Thr Met Val Thr Ala Leu Ser Cys Cys Gln Glu Ala Tyr Gly
275 280 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375

<210> SEQ ID NO 120
<211> LENGTH: 643
<212> TYPE: DNA
<213> ORGANISM: Saccharomyces cerevisiae

<400> SEQUENCE: 120
gaaatgaata acaatactga cagtactaaa taattgccta cttggcttca catacgttgc 60
atacgtcgat atagataata atgataatga cagcaggatt atcgtaatac gtaatagttg 120
aaaatctcaa aaatgtgtgg gtcattacgt aaataatgat aggaatggga ttcttctatt 180
tttccttttt ccattctagc agccgtcggg aaaacgtggc atcctctctt tcgggctcaa 240
ttggagtcac gctgccgtga gcatcctctc tttccatatc taacaactga gcacgtaacc 300
aatggaaaag catgagctta gcgttgctcc aaaaaagtat tggatggtta ataccatttg 360
tctgttctct tctgactttg actcctcaaa aaaaaaaaat ctacaatcaa cagatcgctt 420
caattacgcc ctcacaaaaa ctttttttcct tcttcttcgc ccacgttaaa ttttatccct 480
catgttgtct aacggatttc tgcacttgat ttattataaa aagacaaaga cataatactt 540
ctctatcaat ttcagttatt gttcttcctt gcgttattct tctgttcttc tttttctttt 600
gtcatatata accataacca agtaatacat attcaaatct aga 643

<210> SEQ ID NO 121
<211> LENGTH: 9089
<212> TYPE: DNA
<213> ORGANISM: Artificial Sequence
<220> FEATURE:
<223> OTHER INFORMATION: constructed plasmid

<400> SEQUENCE: 121
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataccac agcttttcaa ttcaattcat cattttttt ttattctttt ttttgatttc 240
ggtttctttg aaattttttt gattcggtaa tctccgaaca gaaggaagaa cgaaggaagg 300
agcacagact tagattggta tatatacgca tatgtagtgt tgaagaaaca tgaaattgcc 360
cagtattctt aacccaactg cacagaacaa aaacctgcag gaaacgaaga taaatcatgt 420
cgaaagctac atataaggaa cgtgctgcta ctcatcctag tcctgttgct gccaagctat 480
ttaatatcat gcacgaaaag caaacaaact tgtgtgcttc attggatgtt cgtaccacca 540
aggaattact ggagttagtt gaagcattag gtcccaaaat ttgtttacta aaaacacatg 600
tggatatctt gactgatttt tccatggagg gcacagttaa gccgctaaag gcattatccg 660

-continued

```
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggcctttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggcccccct cgaggtcgac tggccattaa    2040
tctttcccat attagatttc gccaagccat gaaagttcaa gaaaggtctt tagacgaatt   2100
acccttcatt tctcaaactg gcgtcaaggg atcctggtat ggttttatcg ttttatttct   2160
ggttcttata gcatcgtttt ggacttctct gttcccatta ggcggttcag gagccagcgc   2220
agaatcattc tttgaaggat acttatcctt tccaattttg attgtctgtt acgttggaca   2280
taaactgtat actagaaatt ggactttgat ggtgaaacta gaagatatgg atcttgatac   2340
cggcagaaaa caagtagatt tgactcttcg tagggaagaa atgaggattg agcgagaaac   2400
attagcaaaa agatccttcg taacaagatt tttacatttc tggtgttgaa gggaaagata   2460
tgagctatac agcggaattt ccatatcact cagattttgt tatctaattt tttccttccc   2520
acgtccgcgg gaatctgtgt atattactgc atctagatat atgttatctt atcttggcgc   2580
gtacatttaa ttttcaacgt attctataag aaattgcggg agttttttc atgtagatga    2640
tactgactgc acgcaaatat aggcatgatt tataggcatg atttgatggc tgtaccgata   2700
ggaacgctaa gagtaacttc agaatcgtta tcctggcgga aaaaattcat ttgtaaactt   2760
taaaaaaaaa agccaatatc cccaaaatta ttaagagcgc ctccattatt aactaaaatt   2820
tcactcagca tccacaatgt atcaggtatc tactacagat attacatgtg gcgaaaaaga   2880
caagaacaat gcaatagcgc atcaagaaaa aacacaaagc tttcaatcaa tgaatcgaaa   2940
atgtcattaa aatagtatat aaattgaaac taagtcataa agctataaaa agaaaattta   3000
tttaaatgca agatttaaag taaattcacg gccctgcagg ccctaacctg ctaggacaca   3060
```

acgtctttgc ctggtaaagt ttctagctga cgtgattcct tcacctgtgg atccggcaat 3120
tgtaaaggtt gtgaaaccct cagcttcata accgacacct gcaaatgact ttgcattctt 3180
aacaaagata gttgtatcaa tttcacgttc gaatctatta aggttatcga tgttcttaga 3240
ataaatgtag gcggaatgtt ttctattctg ctcagctatc ttggcgtatt taatggcttc 3300
atcaatgtcc ttcactctaa ctataggcaa aattggcatc atcaactccg tcataacgaa 3360
cggatggttt gcgttgactt cacaaataat acactttaca ttacttggtg actctacatc 3420
tatttcatcc aaaaacagtt tagcgtcctt accaacccac ttcttattaa tgaaatattc 3480
ttgagtttca ttgttctttt gaagaacaag gtctatcagc ttggatactt ggtcttcatt 3540
gataatgacg gcgttgtttt tcaacatgtt agagatcaga tcatctgcaa cgttttcaaa 3600
cacgaacact tctttttccg cgatacaagg aagattgttg tcaaacgaac aaccttcaat 3660
aatgcttctg ccggccttct cgatatctgc tgtatcgtct acaataaccg gaggattacc 3720
cgcgccagct ccgatggcct tttaccaga attaagaagg gtttttacca tacccgggcc 3780
acccgtaccg cacaacaatt ttatggatgg atgtttgata atagcgtcta aactttccat 3840
agttgggttc tttatagtag tgacaaggtt ttcaggtcca ccacagctaa ttatggcttt 3900
gtttatcatt tctactgcga aagcgacaca ctttttggcg catgggtgac cattaaatac 3960
aactgcattc cccgcagcta tcatacctat agaattgcag ataacggttt ctgttggatt 4020
cgtgcttgga gttatagcgc cgataactcc gtatggactc atttcaacca ctgttagtcc 4080
attatcgccg gaccatgctg ttgttgtcag atcttcagtg cctggggtat acttggccac 4140
taattcatgt ttcaagattt tatcctcata ccttcccatg tgggtttcct ccaggatcat 4200
tgtggctaag acctctttat tctgtaatgc ggcttttctt atttcggtga ttattttctc 4260
tctttgttcc tttgtgtagt gtagggaaag aatcttttgt gcatgtactg cagaagaaat 4320
ggcattctca acattttcaa atactccaaa acatgaagag ttatctttgt aattctttaa 4380
gttgatgttt tcaccattag tcttcacttt caagtctttg gtggttggga ttaaggtatc 4440
tttatccatg gtgtttgttt atgtgtgttt attcgaaact aagttcttgg tgttttaaaa 4500
ctaaaaaaaa gactaactat aaaagtagaa tttaagaagt ttaagaaata gatttacaga 4560
attacaatca atacctaccg tctttatata cttattagtc aagtagggga ataatttcag 4620
ggaactggtt tcaacctttt ttttcagctt tttccaaatc agagagagca gaaggtaata 4680
gaaggtgtaa gaaaatgaga tagatacatg cgtgggtcaa ttgccttgtg tcatcattta 4740
ctccaggcag gttgcatcac tccattgagg ttgtgcccgt tttttgcctg tttgtgcccc 4800
tgttctctgt agttgcgcta agagaatgga cctatgaact gatggttggt gaagaaaaca 4860
atattttggt gctgggattc ttttttttttc tggatgccag cttaaaaagc gggctccatt 4920
atatttagtg gatgccagga ataaactgtt cacccagaca cctacgatgt tatatattct 4980
gtgtaacccg ccccctattt tgggcatgta cgggttacag cagaattaaa aggctaattt 5040
tttgactaaa taaagttagg aaaatcacta ctattaatta tttacgtatt ctttgaaatg 5100
gcagtattga taatgataaa ctcgaactga aaaagcgtgt tttttattca aaatgattct 5160
aactccctta cgtaatcaag gaatcttttt gccttggcct ccgcgtcatt aaacttcttg 5220
ttgttgacgc taacattcaa cgctagtata tattcgtttt tttcaggtaa gttcttttca 5280
acgggtctta ctgatgaggc agtcgcgtct gaacctgtta agaggtcaaa tatgtcttct 5340
tgaccgtacg tgtcttgcat gttattagct ttgggaattt gcatcaagtc ataggaaaat 5400
ttaaatcttg gctctcttgg gctcaaggtg acaaggtcct cgaaaatagg gcgcgcccca 5460
ccgcggtgga gctccagctt ttgttccctt tagtgagggt taattgcgcg cttggcgtaa 5520
tcatggtcat agctgtttcc tgtgtgaaat tgttatccgc tcacaattcc acacaacata 5580
ggagccggaa gcataaagtg taaagcctgg ggtgcctaat gagtgaggta actcacatta 5640
attgcgttgc gctcactgcc cgctttccag tcgggaaacc tgtcgtgcca gctgcattaa 5700
tgaatcggcc aacgcgcggg gagaggcggt ttgcgtattg ggcgctcttc cgcttcctcg 5760
ctcactgact cgctgcgctc ggtcgttcgg ctgcggcgag cggtatcagc tcactcaaag 5820
gcggtaatac ggttatccac agaatcaggg gataacgcag gaaagaacat gtgagcaaaa 5880
ggccagcaaa aggccaggaa ccgtaaaaag gccgcgttgc tggcgttttt ccataggctc 5940
cgcccccctg acgagcatca caaaaatcga cgctcaagtc agaggtggcg aaacccgaca 6000
ggactataaa gataccaggc gtttccccct ggaagctccc tcgtgcgctc tcctgttccg 6060
accctgccgc ttaccggata cctgtccgcc tttctccctt cgggaagcgt ggcgctttct 6120
catagctcac gctgtaggta tctcagttcg gtgtaggtcg ttcgctccaa gctgggctgt 6180
gtgcacgaac cccccgttca gcccgaccgc tgcgccttat ccggtaacta tcgtcttgag 6240
tccaacccgg taagacacga cttatcgcca ctggcagcag ccactggtaa caggattagc 6300
agagcgaggt atgtaggcgg tgctacagag ttcttgaagt ggtggcctaa ctacggctac 6360
actagaagga cagtatttgg tatctgcgct ctgctgaagc cagttacctt cggaaaaaga 6420
gttggtagct cttgatccgg caaacaaacc accgctggta gcggtggttt ttttgtttgc 6480
aagcagcaga ttacgcgcag aaaaaaagga tctcaagaag atcctttgat cttttctacg 6540
gggtctgacg ctcagtggaa cgaaaactca cgttaaggga ttttggtcat gagattatca 6600
aaaaggatct tcacctagat ccttttaaat taaaaatgaa gttttaaatc aatctaaagt 6660
atatatgagt aaacttggtc tgacagttac caatgcttaa tcagtgaggc acctatctca 6720
gcgatctgtc tatttcgttc atccatagtt gcctgactcc ccgtcgtgta gataactacg 6780
atacgggagg gcttaccatc tggccccagt gctgcaatga taccgcgaga cccacgctca 6840
ccggctccag atttatcagc aataaaccag ccagccggaa gggccgagcg cagaagtggt 6900
cctgcaactt tatccgcctc catccagtct attaattgtt gccgggaagc tagagtaagt 6960
agttcgccag ttaatagttt gcgcaacgtt gttgccattg ctacaggcat cgtggtgtca 7020
cgctcgtcgt ttggtatggc ttcattcagc tccggttccc aacgatcaag gcgagttaca 7080
tgatccccca tgttgtgcaa aaaagcggtt agctccttcg gtcctccgat cgttgtcaga 7140
agtaagttgg ccgcagtgtt atcactcatg gttatggcag cactgcataa ttctcttact 7200
gtcatgccat ccgtaagatg cttttctgtg actggtgagt actcaaccaa gtcattctga 7260
gaatagtgta tgcggcgacc gagttgctct tgcccggcgt caatacggga taataccgcg 7320
ccacatagca gaactttaaa agtgctcatc attggaaaac gttcttcggg gcgaaaactc 7380
tcaaggatct taccgctgtt gagatccagt tcgatgtaac ccactcgtgc acccaactga 7440
tcttcagcat cttttacttt caccagcgtt tctgggtgag caaaaacagg aaggcaaaat 7500
gccgcaaaaa agggaataag ggcgacacgg aaatgttgaa tactcatact cttccttttt 7560
caatattatt gaagcattta tcagggttat tgtctcatga gcggatacat atttgaatgt 7620
atttagaaaa ataaacaaat aggggttccg cgcacatttc cccgaaaagt gccacctgaa 7680
cgaagcatct gtgcttcatt ttgtagaaca aaaatgcaac gcgagagcgc taatttttca 7740
aacaaagaat ctgagctgca tttttacaga acagaaatgc aacgcgaaag cgctatttta 7800
ccaacgaaga atctgtgctt catttttgta aaacaaaaat gcaacgcgag agcgctaatt 7860

```
tttcaaacaa agaatctgag ctgcattttt acagaacaga aatgcaacgc gagagcgcta   7920

ttttaccaac aaagaatcta tacttctttt ttgttctaca aaaatgcatc ccgagagcgc   7980

tatttttcta acaaagcatc ttagattact tttttctcc tttgtgcgct ctataatgca   8040

gtctcttgat aactttttgc actgtaggtc cgttaaggtt agaagaaggc tactttggtg   8100

tctattttct cttccataaa aaaagcctga ctccacttcc cgcgtttact gattactagc   8160

gaagctgcgg gtgcattttt tcaagataaa ggcatccccg attatattct ataccgatgt   8220

ggattgcgca tactttgtga acagaaagtg atagcgttga tgattcttca ttggtcagaa   8280

aattatgaac ggtttcttct attttgtctc tatatactac gtataggaaa tgtttacatt   8340

ttcgtattgt tttcgattca ctctatgaat agttcttact acaatttttt tgtctaaaga   8400

gtaatactag agataaacat aaaaaatgta gaggtcgagt ttagatgcaa gttcaaggag   8460

cgaaaggtgg atgggtaggt tatataggga tatagcacag agatatatag caaagagata   8520

cttttgagca atgtttgtgg aagcggtatt cgcaatattt tagtagctcg ttacagtccg   8580

gtgcgttttt ggtttttga aagtgcgtct tcagagcgct tttggttttc aaaagcgctc   8640

tgaagttcct atactttcta gagaatagga acttcggaat aggaacttca aagcgtttcc   8700

gaaaacgagc gcttccgaaa atgcaacgcg agctgcgcac atacagctca ctgttcacgt   8760

cgcacctata tctgcgtgtt gcctgtatat atatatacat gagaagaacg gcatagtgcg   8820

tgtttatgct taaatgcgta cttatatgcg tctatttatg taggatgaaa ggtagtctag   8880

tacctcctgt gatattatcc cattccatgc ggggtatcgt atgcttcctt cagcactacc   8940

ctttagctgt tctatatgct gccactcctc aattggatta gtctcatcct tcaatgctat   9000

catttccttt gatattggat catactaaga aaccattatt atcatgacat taacctataa   9060

aaataggcgt atcacgaggc cctttcgtc                                     9089
```

<210> SEQ ID NO 122
<211> LENGTH: 1023
<212> TYPE: DNA
<213> ORGANISM: Saccharomyces cerevisiae

<400> SEQUENCE: 122

```
caccgcggtg gggcgcgccc tattttcgag gaccttgtca ccttgagccc aagagagcca     60

agatttaaat tttcctatga cttgatgcaa attcccaaag ctaataacat gcaagacacg    120

tacggtcaag aagacatatt tgacctctta acaggttcag acgcgactgc ctcatcagta    180

agacccgttg aaaagaactt acctgaaaaa aacgaatata tactagcgtt gaatgttagc    240

gtcaacaaca agaagtttaa tgacgcggag gccaaggcaa aaagattcct tgattacgta    300

agggagttag aatcatttg aataaaaaac acgcttttc agttcgagtt tatcattatc    360

aatactgcca tttcaaagaa tacgtaaata attaatagta gtgattttcc taactttatt    420

tagtcaaaaa attagccttt taattctgct gtaacccgta catgcccaaa atagggggcg    480

ggttacacag aatatataac atcgtaggtg tctgggtgaa cagtttattc ctggcatcca    540

ctaaatataa tggagcccgc tttttaagct ggcatccaga aaaaaaaaga atcccagcac    600

caaaatattg ttttcttcac caaccatcag ttcataggtc cattctctta gcgcaactac    660

agagaacagg ggcacaaaca ggcaaaaaac gggcacaacc tcaatggagt gatgcaacct    720

gcctggagta aatgatgaca caaggcaatt gacccacgca tgtatctatc tcattttctt    780

acaccttcta ttaccttctg ctctctctga tttggaaaaa gctgaaaaaa aaggttgaaa    840

ccagttccct gaaattattc ccctacttga ctaataagta tataaagacg gtaggtattg    900
```

attgtaattc tgtaaatcta tttcttaaac ttcttaaatt ctacttttat agttagtctt 960 tttttagtt ttaaaacacc aagaacttag tttcgaataa acacacataa actagtaaac 1020
aaa 1023

<210> SEQ ID NO 123
<211> LENGTH: 21
<212> TYPE: DNA
<213> ORGANISM: Artificial Sequence
<220> FEATURE:
<223> OTHER INFORMATION: primer

<400> SEQUENCE: 123
caaaagctga gctccaccgc g 21

<210> SEQ ID NO 124
<211> LENGTH: 44
<212> TYPE: DNA
<213> ORGANISM: Artificial Sequence
<220> FEATURE:
<223> OTHER INFORMATION: primer

<400> SEQUENCE: 124
gtttactagt ttatgtgtgt ttattcgaaa ctaagttctt ggtg 44

<210> SEQ ID NO 125

<400> SEQUENCE: 125

000

<210> SEQ ID NO 126
<211> LENGTH: 39
<212> TYPE: DNA
<213> ORGANISM: Artificial Sequence
<220> FEATURE:
<223> OTHER INFORMATION: primer

<400> SEQUENCE: 126
cacacatatt acaatagcta gctgaggatg aaagctctg 39

<210> SEQ ID NO 127
<211> LENGTH: 39
<212> TYPE: DNA
<213> ORGANISM: Artificial Sequence
<220> FEATURE:
<223> OTHER INFORMATION: primer

<400> SEQUENCE: 127
cagagctttc atcctcagct agctattgta atatgtgtg 39

<210> SEQ ID NO 128
<211> LENGTH: 9491
<212> TYPE: DNA
<213> ORGANISM: Artificial Sequence
<220> FEATURE:
<223> OTHER INFORMATION: constructed plasmid

<400> SEQUENCE: 128
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240

-continued

```
gaacacggca ttagtcaggg aagtcataac acagtccttt cccgcaattt tctttttcta    300
ttactcttgg cctcctctag tacactctat atttttttat gcctcggtaa tgattttcat    360
tttttttttt ccccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
cctttttttct ttttgctttt tcttttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa agggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggcccccc ctcgaggtcg   2100
acggcgcgcc actggtagag agcgactttg tatgccccaa ttgcgaaacc cgcgatatcc   2160
ttctcgattc tttagtaccc gaccaggaca aggaaaagga ggtcgaaacg tttttgaaga   2220
aacaagagga actacacgga agctctaaag atggcaacca gccagaaact aagaaaatga   2280
agttgatgga tccaactggc accgctggct tgaacaacaa taccagcctt ccaacttctg   2340
taaataacgg cggtacgcca gtgccaccag taccgttacc tttcggtata cctcctttcc   2400
ccatgtttcc aatgcccttc atgcctccaa cggctactat cacaaatcct catcaagctg   2460
acgcaagccc taagaaatga ataacaatac tgacagtact aaataattgc ctacttggct   2520
tcacatacgt tgcatacgtc gatatagata ataatgataa tgacagcagg attatcgtaa   2580
tacgtaatag ttgaaaatct caaaaatgtg tgggtcatta cgtaaataat gataggaatg   2640
```

-continued

```
ggattcttct atttttcctt tttccattct agcagccgtc gggaaaacgt ggcatcctct   2700
ctttcgggct caattggagt cacgctgccg tgagcatcct ctctttccat atctaacaac   2760
tgagcacgta accaatggaa aagcatgagc ttagcgttgc tccaaaaaag tattggatgg   2820
ttaataccat ttgtctgttc tcttctgact ttgactcctc aaaaaaaaaa aatctacaat   2880
caacagatcg cttcaattac gccctcacaa aaactttttt ccttcttctt cgcccacgtt   2940
aaattttatc cctcatgttg tctaacggat ttctgcactt gatttattat aaaaagacaa   3000
agacataata cttctctatc aatttcagtt attgttcttc cttgcgttat tcttctgttc   3060
ttctttttct tttgtcatat ataaccataa ccaagtaata catattcaaa ctagtatgac   3120
tgacaaaaaa actcttaaag acttaagaaa tcgtagttct gtttacgatt caatggttaa   3180
atcacctaat cgtgctatgt tgcgtgcaac tggtatgcaa gatgaagact ttgaaaaacc   3240
tatcgtcggt gtcatttcaa cttgggctga aaacacacct tgtaatatcc acttacatga   3300
ctttggtaaa ctagccaaag tcggtgttaa ggaagctggt gcttggccag ttcagttcgg   3360
aacaatcacg gtttctgatg gaatcgccat gggaacccaa ggaatgcgtt tctccttgac   3420
atctcgtgat attattgcag attctattga agcagccatg ggaggtcata atgcggatgc   3480
ttttgtagcc attggcggtt gtgataaaaa catgcccggt tctgttatcg ctatggctaa   3540
catggatatc ccagccattt ttgcttacgg cggaacaatt gcacctggta atttagacgg   3600
caaagatatc gatttagtct ctgtctttga aggtgtcggc cattggaacc acggcgatat   3660
gaccaaagaa gaagttaaag ctttggaatg taatgcttgt cccggtcctg gaggctgcgg   3720
tggtatgtat actgctaaca caatggcgac agctattgaa gttttgggac ttagccttcc   3780
gggttcatct tctcacccgg ctgaatccgc agaaaagaaa gcagatattg aagaagctgg   3840
tcgcgctgtt gtcaaaatgc tcgaaatggg cttaaaacct tctgacattt taacgcgtga   3900
agcttttgaa gatgctatta ctgtaactat ggctctggga ggttcaacca actcaaccct   3960
tcacctctta gctattgccc atgctgctaa tgtggaattg acacttgatg atttcaatac   4020
tttccaagaa aaagttcctc atttggctga tttgaaacct tctggtcaat atgtattcca   4080
agacctttac aaggtcggag ggtaccagc agttatgaaa tatctcctta aaaatggctt   4140
ccttcatggt gaccgtatca cttgtactgg caaaacagtc gctgaaaatt tgaaggcttt   4200
tgatgattta acacctggtc aaaaggttat tatgccgctt gaaaatccta aacgtgaaga   4260
tggtccgctc attattctcc atggtaactt ggctccagac ggtgccgttg ccaaagtttc   4320
tggtgtaaaa gtgcgtcgtc atgtcggtcc tgctaaggtc tttaattctg aagaagaagc   4380
cattgaagct gtcttgaatg atgatattgt tgatggtgat gttgttgtcg tacgttttgt   4440
aggaccaaag ggcggtcctg gtatgcctga aatgctttcc ctttcatcaa tgattgttgg   4500
taaagggcaa ggtgaaaaag ttgcccttct gacagatggc cgcttctcag gtggtactta   4560
tggtcttgtc gtgggtcata tcgctcctga agcacaagat ggcggtccaa tcgcctacct   4620
gcaaacagga gacatagtca ctattgacca agacactaag gaattacact ttgatatctc   4680
cgatgaagag ttaaaacatc gtcaagagac cattgaattg ccaccgctct attcacgcgg   4740
tatccttggt aaatatgctc acatcgtttc gtctgcttct aggggagccg taacagactt   4800
ttggaagcct gaagaaactg gcaaaaaatg ttgtcctggt tgctgtggtt aagcggccgc   4860
gttaattcaa attaattgat atagtttttt aatgagtatt gaatctgttt agaaataatg   4920
gaatattatt tttatttatt tatttatatt attggtcggc tcttttcttc tgaaggtcaa   4980
tgacaaaatg atatgaagga aataatgatt tctaaaattt tacaacgtaa gatattttta   5040
```

-continued

```
caaaagccta gctcatcttt tgtcatgcac tattttactc acgcttgaaa ttaacggcca   5100
gtccactgcg gagtcatttc aaagtcatcc taatcgatct atcgtttttg atagctcatt   5160
ttggagttcg cgattgtctt ctgttattca caactgtttt aatttttatt tcattctgga   5220
actcttcgag ttctttgtaa agtctttcat agtagcttac tttatcctcc aacatattta   5280
acttcatgtc aatttcggct cttaaatttt ccacatcatc aagttcaaca tcatctttta   5340
acttgaattt attctctagc tcttccaacc aagcctcatt gctccttgat ttactggtga   5400
aaagtgatac actttgcgcg caatccaggt caaaactttc ctgcaaagaa ttcaccaatt   5460
tctcgacatc atagtacaat ttgttttgtt ctcccatcac aatttaatat acctgatgga   5520
ttcttatgaa gcgctgggta atggacgtgt cactctactt cgcctttttc cctactcctt   5580
ttagtacgga agacaatgct aataaataag agggtaataa taatattatt aatcggcaaa   5640
aaagattaaa cgccaagcgt ttaattatca gaaagcaaac gtcgtaccaa tccttgaatg   5700
cttcccaatt gtatattaag agtcatcaca gcaacatatt cttgttatta aattaattat   5760
tattgatttt tgatattgta taaaaaaacc aaatatgtat aaaaaaagtg aataaaaaat   5820
accaagtatg gagaaatata ttagaagtct atacgttaaa ccaccgcggt ggagctccag   5880
cttttgttcc ctttagtgag ggttaattgc gcgcttggcg taatcatggt catagctgtt   5940
tcctgtgtga aattgttatc cgctcacaat tccacacaac ataggagccg gaagcataaa   6000
gtgtaaagcc tggggtgcct aatgagtgag gtaactcaca ttaattgcgt tgcgctcact   6060
gcccgctttc cagtcgggaa acctgtcgtg ccagctgcat taatgaatcg gccaacgcgc   6120
ggggagaggc ggtttgcgta ttgggcgctc ttccgcttcc tcgctcactg actcgctgcg   6180
ctcggtcgtt cggctgcggc gagcggtatc agctcactca aaggcggtaa tacggttatc   6240
cacagaatca ggggataacg caggaaagaa catgtgagca aaaggccagc aaaaggccag   6300
gaaccgtaaa aaggccgcgt tgctggcgtt tttccatagg ctccgccccc ctgacgagca   6360
tcacaaaaat cgacgctcaa gtcagaggtg gcgaaacccg acaggactat aaagatacca   6420
ggcgtttccc cctggaagct ccctcgtgcg ctctcctgtt ccgaccctgc cgcttaccgg   6480
atacctgtcc gcctttctcc cttcgggaag cgtggcgctt tctcatagct cacgctgtag   6540
gtatctcagt tcggtgtagg tcgttcgctc caagctgggc tgtgtgcacg aaccccccgt   6600
tcagcccgac cgctgcgcct tatccggtaa ctatcgtctt gagtccaacc cggtaagaca   6660
cgacttatcg ccactggcag cagccactgg taacaggatt agcagagcga ggtatgtagg   6720
cggtgctaca gagttcttga agtggtggcc taactacggc tacactagaa ggacagtatt   6780
tggtatctgc gctctgctga agccagttac cttcggaaaa agagttggta gctcttgatc   6840
cggcaaacaa accaccgctg gtagcggtgg tttttttgtt tgcaagcagc agattacgcg   6900
cagaaaaaaa ggatctcaag aagatccttt gatcttttct acggggtctg acgctcagtg   6960
gaacgaaaac tcacgttaag ggattttggt catgagatta tcaaaaagga tcttcaccta   7020
gatcctttta aattaaaaat gaagttttaa atcaatctaa agtatatatg agtaaacttg   7080
gtctgacagt taccaatgct taatcagtga ggcacctatc tcagcgatct gtctatttcg   7140
ttcatccata gttgcctgac tccccgtcgt gtagataact acgatacggg agggcttacc   7200
atctggcccc agtgctgcaa tgataccgcg agacccacgc tcaccggctc cagatttatc   7260
agcaataaac cagccagccg gaagggccga gcgcagaagt ggtcctgcaa ctttatccgc   7320
ctccatccag tctattaatt gttgccggga agctagagta agtagttcgc cagttaatag   7380
tttgcgcaac gttgttgcca ttgctacagg catcgtggtg tcacgctcgt cgtttggtat   7440
```

ggcttcattc agctccggtt cccaacgatc aaggcgagtt acatgatccc ccatgttgtg 7500
caaaaaagcg gttagctcct tcggtcctcc gatcgttgtc agaagtaagt tggccgcagt 7560
gttatcactc atggttatgg cagcactgca taattctctt actgtcatgc catccgtaag 7620
atgcttttct gtgactggtg agtactcaac caagtcattc tgagaatagt gtatgcggcg 7680
accgagttgc tcttgcccgg cgtcaatacg ggataatacc gcgccacata gcagaacttt 7740
aaaagtgctc atcattggaa aacgttcttc ggggcgaaaa ctctcaagga tcttaccgct 7800
gttgagatcc agttcgatgt aacccactcg tgcacccaac tgatcttcag catcttttac 7860
tttcaccagc gtttctgggt gagcaaaaac aggaaggcaa aatgccgcaa aaaagggaat 7920
aagggcgaca cggaaatgtt gaatactcat actcttcctt tttcaatatt attgaagcat 7980
ttatcagggt tattgtctca tgagcggata catatttgaa tgtatttaga aaaataaaca 8040
aataggggtt ccgcgcacat ttccccgaaa agtgccacct gaacgaagca tctgtgcttc 8100
attttgtaga acaaaaatgc aacgcgagag cgctaatttt tcaaacaaag aatctgagct 8160
gcatttttac agaacagaaa tgcaacgcga aagcgctatt ttaccaacga agaatctgtg 8220
cttcattttt gtaaaacaaa aatgcaacgc gagagcgcta atttttcaaa caaagaatct 8280
gagctgcatt tttacagaac agaaatgcaa cgcgagagcg ctattttacc aacaaagaat 8340
ctatacttct tttttgttct acaaaaatgc atcccgagag cgctattttt ctaacaaagc 8400
atcttagatt acttttttc tcctttgtgc gctctataat gcagtctctt gataactttt 8460
tgcactgtag gtccgttaag gttagaagaa ggctactttg gtgtctattt tctcttccat 8520
aaaaaaagcc tgactccact tcccgcgttt actgattact agcgaagctg cgggtgcatt 8580
ttttcaagat aaaggcatcc ccgattatat tctataccga tgtggattgc gcatactttg 8640
tgaacagaaa gtgatagcgt tgatgattct tcattggtca gaaaattatg aacggtttct 8700
tctattttgt ctctatatac tacgtatagg aaatgtttac attttcgtat tgttttcgat 8760
tcactctatg aatagttctt actacaattt ttttgtctaa agagtaatac tagagataaa 8820
cataaaaaat gtagaggtcg agtttagatg caagttcaag gagcgaaagg tggatgggta 8880
ggttatatag ggatatagca cagagatata tagcaaagag atacttttga gcaatgtttg 8940
tggaagcggt attcgcaata ttttagtagc tcgttacagt ccggtgcgtt tttggttttt 9000
tgaaagtgcg tcttcagagc gcttttggtt ttcaaaagcg ctctgaagtt cctatacttt 9060
ctagagaata ggaacttcgg aataggaact tcaaagcgtt tccgaaaacg agcgcttccg 9120
aaaatgcaac gcgagctgcg cacatacagc tcactgttca cgtcgcacct atatctgcgt 9180
gttgcctgta tatatatata catgagaaga acggcatagt gcgtgtttat gcttaaatgc 9240
gtacttatat gcgtctattt atgtaggatg aaaggtagtc tagtacctcc tgtgatatta 9300
tcccattcca tgcggggtat cgtatgcttc cttcagcact accctttagc tgttctatat 9360
gctgccactc ctcaattgga ttagtctcat ccttcaatgc tatcatttcc tttgatattg 9420
gatcatctaa gaaaccatta ttatcatgac attaacctat aaaaataggc gtatcacgag 9480
gccctttcgt c 9491

<210> SEQ ID NO 129
<211> LENGTH: 1000
<212> TYPE: DNA
<213> ORGANISM: Saccharomyces cerevisiae

<400> SEQUENCE: 129
gttaattcaa attaattgat atagtttttt aatgagtatt gaatctgttt agaaataatg 60
gaatattatt tttatttatt tatttatatt attggtcggc tcttttcttc tgaaggtcaa 120
tgacaaaatg atatgaagga aataatgatt tctaaaattt tacaacgtaa gatattttta 180
caaaagccta gctcatcttt tgtcatgcac tattttactc acgcttgaaa ttaacggcca 240
gtccactgcg gagtcatttc aaagtcatcc taatcgatct atcgtttttg atagctcatt 300
ttggagttcg cgattgtctt ctgttattca caactgtttt aatttttatt tcattctgga 360
actcttcgag ttctttgtaa agtctttcat agtagcttac tttatcctcc aacatattta 420
acttcatgtc aatttcggct cttaaatttt ccacatcatc aagttcaaca tcatctttta 480
acttgaattt attctctagc tcttccaacc aagcctcatt gctccttgat ttactggtga 540
aaagtgatac actttgcgcg caatccaggt caaaactttc ctgcaaagaa ttcaccaatt 600
tctcgacatc atagtacaat ttgttttgtt ctcccatcac aatttaatat acctgatgga 660
ttcttatgaa gcgctgggta atggacgtgt cactctactt cgcctttttc cctactcctt 720
ttagtacgga agacaatgct aataaataag agggtaataa taatattatt aatcggcaaa 780
aaagattaaa cgccaagcgt ttaattatca gaaagcaaac gtcgtaccaa tccttgaatg 840
cttcccaatt gtatattaag agtcatcaca gcaacatatt cttgttatta aattaattat 900
tattgatttt tgatattgta taaaaaaacc aaatatgtat aaaaaaagtg aataaaaaat 960
accaagtatg gagaaatata ttagaagtct atacgttaaa 1000

<210> SEQ ID NO 130
<211> LENGTH: 16387
<212> TYPE: DNA
<213> ORGANISM: Artificial Sequence
<220> FEATURE:
<223> OTHER INFORMATION: Plasmid

<400> SEQUENCE: 130
gatcctctag tttctcggta ctatgcatat gatccaatat caaaggaaat gatagcattg 60
aaggatgaga ctaatccaat tgaggagtgg cagcatatag aacagctaaa gggtagtgct 120
gaaggaagca tacgataccc cgcatggaat gggataaatat cacaggaggt actagactac 180
ctttcatcct acataaatag acgcatataa gtacgcattt aagcataaac acgcactatg 240
ccgttcttct catgtatata tatatacagg caacacgcag atataggtgc gacgtgaaca 300
gtgagctgta tgtgcgcagc tcgcgttgca ttttcggaag cgctcgtttt cggaaacgct 360
ttgaagttcc tattccgaag ttcctattct ctagaaagta taggaacttc agagcgcttt 420
tgaaaaccaa aagcgctctg aagacgcact ttcaaaaaac caaaaacgca ccggactgta 480
acgagctact aaaatattgc gaataccgct tccacaaaca ttgctcaaaa gtatctcttt 540
gctatatatc tctgtgctat atccctatat aacctaccca tccacctttc gctccttgaa 600
cttgcatcta aactcgacct ctacattttt tatgtttatc tctagtatta ctctttagac 660
aaaaaaattg tagtaagaac tattcataga gtgaatcgaa aacaatacga aaatgtaaac 720
atttcctata cgtagtatat agagacaaaa tagaagaaac cgttcataat tttctgacca 780
atgaagaatc atcaacgcta tcactttctg ttcacaaagt atgcgcaatc cacatcggta 840
tagaatataa tcggggatgc ctttatcttg aaaaaatgca cccgcagctt cgctagtaat 900
cagtaaacgc gggaagtgga gtcaggcttt ttttatggaa gagaaaatag acaccaaagt 960
agccttcttc taaccttaac ggacctacag tgcaaaaagt tatcaagaga ctgcattata 1020
gagcgcacaa aggagaaaaa aagtaatcta agatgctttg ttagaaaaat agcgctctcg 1080
ggatgcattt ttgtagaaca aaaaagaagt atagattctt tgttggtaaa atagcgctct 1140

-continued

```
cgcgttgcat ttctgttctg taaaaatgca gctcagattc tttgtttgaa aaattagcgc   1200
tctcgcgttg catttttgtt ttacaaaaat gaagcacaga ttcttcgttg gtaaaatagc   1260
gctttcgcgt tgcatttctg ttctgtaaaa atgcagctca gattctttgt ttgaaaaatt   1320
agcgctctcg cgttgcattt ttgttctaca aaatgaagca cagatgcttc gttaacaaag   1380
atatgctatt gaagtgcaag atggaaacgc agaaaatgaa ccggggatgc gacgtgcaag   1440
attacctatg caatagatgc aatagtttct ccaggaaccg aaatacatac attgtcttcc   1500
gtaaagcgct agactatata ttattataca ggttcaaata tactatctgt ttcagggaaa   1560
actcccaggt tcggatgttc aaaattcaat gatgggtaac aagtacgatc gtaaatctgt   1620
aaaacagttt gtcggatatt aggctgtatc tcctcaaagc gtattcgaat atcattgaga   1680
agctgcattt tttttttttt tttttttttt tttttttata tatatttcaa ggatatacca   1740
ttgtaatgtc tgcccctaag aagatcgtcg ttttgccagg tgaccacgtt ggtcaagaaa   1800
tcacagccga agccattaag gttcttaaag ctatttctga tgttcgttcc aatgtcaagt   1860
tcgatttcga aaatcattta attggtggtg ctgctatcga tgctacaggt gttccacttc   1920
cagatgaggc gctggaagcc tccaagaagg ctgatgccgt tttgttaggt gctgtgggtg   1980
gtcctaaatg gggtaccggt agtgttagac ctgaacaagg tttactaaaa atccgtaaag   2040
aacttcaatt gtacgccaac ttaagaccat gtaactttgc atccgactct cttttagact   2100
tatctccaat caagccacaa tttgctaaag gtactgactt cgttgttgtt agagaattag   2160
tgggaggtat ttactttggt aagagaaagg aagacgatgg tgatggtgtc gcttgggata   2220
gtgaacaata caccgttcca gaagtgcaaa gaatcacaag aatggccgct ttcatggccc   2280
tacaacatga gccaccattg cctatttggt ccttggataa agctaatgtt ttggcctctt   2340
caagattatg gagaaaaact gtggaggaaa ccatcaagaa cgaattccct acattgaaag   2400
ttcaacatca attgattgat tctgccgcca tgatcctagt taagaaccca acccacctaa   2460
atggtattat aatcaccagc aacatgtttg gtgatatcat ctccgatgaa gcctccgtta   2520
tcccaggctc cttgggtttg ttgccatctg cgtccttggc ctctttgcca gacaagaaca   2580
ccgcatttgg tttgtacgaa ccatgccatg gttccgctcc agatttgcca aagaataagg   2640
tcaaccctat cgccactatc ttgtctgctg caatgatgtt gaaattgtca ttgaacttgc   2700
ctgaagaagg taaagccatt gaagatgcag ttaaaaaggt tttggatgca ggtatcagaa   2760
ctggtgattt aggtggttcc aacagtacca ccgaagtcgg tgatgctgtc gccgaagaag   2820
ttaagaaaat ccttgcttaa aaagattctc tttttttatg atatttgtac aaaaaaaaaa   2880
aaaaaaaaaa aaaaaaaaaa aaaaaaaaaa aaaaaaaaaa aatgcagcgt cacatcggat   2940
aataatgatg gcagccattg tagaagtgcc ttttgcattt ctagtctctt tctcggtcta   3000
gctagtttta ctacatcgcg aagatagaat cttagatcac actgcctttg ctgagctgga   3060
tcaatagagt aacaaaagag tggtaaggcc tcgttaaagg acaaggacct gagcggaagt   3120
gtatcgtaca gtagacggag tatactagag tcgacctgca ggcatgcaag cttttcaatt   3180
catcattttt tttttattct ttttttttgat ttcggtttcc ttgaaatttt tttgattcgg   3240
taatctccga acagaaggaa gaacgaagga aggagcacag acttagattg gtatatatac   3300
gcatatgtag tgttgaagaa acatgaaatt gcccagtatt cttaacccaa ctgcacagaa   3360
caaaaacctg caggaaacga agataaatca tgtcgaaagc tacatataag gaacgtgctg   3420
ctactcatcc tagtcctgtt gctgccaagc tatttaatat catgcacgaa aagcaaacaa   3480
acttgtgtgc ttcattggat gttcgtacca ccaaggaatt actggagtta gttgaagcat   3540
```

-continued

```
taggtcccaa aatttgttta ctaaaaacac atgtggatat cttgactgat ttttccatgg   3600
agggcacagt taagccgcta aaggcattat ccgccaagta caattttttta ctcttcgaag   3660
acagaaaatt tgctgacatt ggtaatacag tcaaattgca gtactctgcg ggtgtataca   3720
gaatagcaga atgggcagac attacgaatg cacacggtgt ggtgggccca ggtattgtta   3780
gcggtttgaa gcaggcggca gaagaagtaa caaaggaacc tagaggcctt ttgatgttag   3840
cagaattgtc atgcaagggc tccctatcta ctggagaata tactaagggt actgttgaca   3900
ttgcgaagag cgacaaagat tttgttatcg gctttattgc tcaaagagac atgggtggaa   3960
gagatgaagg ttacgattgg ttgattatga cacccggtgt gggtttagat gacaagggag   4020
acgcattggg tcaacagtat agaaccgtgg atgatgtggt ctctacagga tctgacatta   4080
ttattgttgg aagaggacta tttgcaaagg gaagggatgc taaggtagag ggtgaacgtt   4140
acagaaaagc aggctgggaa gcatatttga gaagatgcgg ccagcaaaac taaaaaactg   4200
tattataagt aaatgcatgt atactaaact cacaaattag agcttcaatt taattatatc   4260
agttattacc cgggaatctc ggtcgtaatg atttttataa tgacgaaaaa aaaaaaattg   4320
gaaagaaaaa gcttggcgta atcatggtca tagctgtttc ctgtgtgaaa ttgttatccg   4380
ctcacaattc cacacaacat acgagccgga agcataaagt gtaaagcctg gggtgcctaa   4440
tgagtgagct aactcacatt aattgcgttg cgctcactgc ccgctttcca gtcgggaaac   4500
ctgtcgtgcc agctgcatta atgaatcggc caacgcgcgg ggagaggcgg tttgcgtatt   4560
gggcgctctt ccgcttcctc gctcactgac tcgctgcgct cggtcgttcg gctgcggcga   4620
gcggtatcag ctcactcaaa ggcggtaata cggttatcca cagaatcagg ggataacgca   4680
ggaaagaaca tgtgagcaaa aggccagcaa aaggccagga accgtaaaaa ggccgcgttg   4740
ctggcgtttt tccataggct ccgcccccct gacgagcatc acaaaaatcg acgctcaagt   4800
cagaggtggc gaaacccgac aggactataa agataccagg cgtttccccc tggaagctcc   4860
ctcgtgcgct ctcctgttcc gaccctgccg cttaccggat acctgtccgc ctttctccct   4920
tcgggaagcg tggcgctttc tcatagctca cgctgtaggt atctcagttc ggtgtaggtc   4980
gttcgctcca agctgggctg tgtgcacgaa ccccccgttc agcccgaccg ctgcgcctta   5040
tccggtaact atcgtcttga gtccaacccg gtaagacacg acttatcgcc actggcagca   5100
gccactggta acaggattag cagagcgagg tatgtaggcg gtgctacaga gttcttgaag   5160
tggtggccta actacggcta cactagaaga acagtatttg gtatctgcgc tctgctgaag   5220
ccagttacct tcggaaaaag agttggtagc tcttgatccg gcaaacaaac caccgctggt   5280
agcggtggtt tttttgtttg caagcagcag attacgcgca gaaaaaaagg atctcaagaa   5340
gatcctttga tcttttctac ggggtctgac gctcagtgga acgaaaactc acgttaaggg   5400
attttggtca tgagattatc aaaaaggatc ttcacctaga tccttttaaa ttaaaaatga   5460
agttttaaat caatctaaag tatatatgag taaacttggt ctgacagtta ccaatgctta   5520
atcagtgagg cacctatctc agcgatctgt ctatttcgtt catccatagt tgcctgactc   5580
cccgtcgtgt agataactac gatacgggag ggcttaccat ctggccccag tgctgcaatg   5640
ataccgcgag acccacgctc accggctcca gatttatcag caataaacca gccagccgga   5700
agggccgagc gcagaagtgg tcctgcaact ttatccgcct ccatccagtc tattaattgt   5760
tgccgggaag ctagagtaag tagttcgcca gttaatagtt tgcgcaacgt tgttgccatt   5820
gctacaggca tcgtggtgtc acgctcgtcg tttggtatgg cttcattcag ctccggttcc   5880
caacgatcaa ggcgagttac atgatccccc atgttgtgca aaaaagcggt tagctccttc   5940
```

-continued

```
ggtcctccga tcgttgtcag aagtaagttg gccgcagtgt tatcactcat ggttatggca   6000
gcactgcata attctcttac tgtcatgcca tccgtaagat gcttttctgt gactggtgag   6060
tactcaacca agtcattctg agaatagtgt atgcggcgac cgagttgctc ttgcccggcg   6120
tcaatacggg ataataccgc gccacatagc agaactttaa aagtgctcat cattggaaaa   6180
cgttcttcgg ggcgaaaact ctcaaggatc ttaccgctgt tgagatccag ttcgatgtaa   6240
cccactcgtg cacccaactg atcttcagca tcttttactt tcaccagcgt ttctgggtga   6300
gcaaaaacag gaaggcaaaa tgccgcaaaa aagggaataa gggcgacacg gaaatgttga   6360
atactcatac tcttcctttt tcaatattat tgaagcattt atcagggtta ttgtctcatg   6420
agcggataca tatttgaatg tatttagaaa aataaacaaa taggggttcc gcgcacattt   6480
ccccgaaaag tgccacctga cgtctaagaa accattatta tcatgacatt aacctataaa   6540
aataggcgta tcacgaggcc ctttcgtctc gcgcgtttcg gtgatgacgg tgaaaacctc   6600
tgacacatgc agctcccgga gacggtcaca gcttgtctgt aagcggatgc cgggagcaga   6660
caagcccgtc agggcgcgtc agcgggtgtt ggcgggtgtc ggggctggct taactatgcg   6720
gcatcagagc agattgtact gagagtgcac cataaaattg taaacgttaa tattttgtta   6780
aaattcgcgt taaatttttg ttaaatcagc tcatttttta accaatagac cgaaatcggc   6840
aaaatccctt ataaatcaaa agaatagccc gagatagagt tgagtgttgt tccagtttgg   6900
aacaagagtc cactattaaa gaacgtggac tccaacgtca aagggcgaaa aaccgtctat   6960
cagggcgatg gcccactacg tgaaccatca cccaaatcaa gttttttggg gtcgaggtgc   7020
cgtaaagcac taaatcggaa ccctaaaggg agcccccgat ttagagcttg acggggaaag   7080
ccggcgaacg tggcgagaaa ggaagggaag aaagcgaaag gagcgggcgc taaggcgctg   7140
gcaagtgtag cggtcacgct gcgcgtaacc accacacccg ccgcgcttaa tgcgccgcta   7200
cagggcgcgt actatggttg ctttgacgta tgcggtgtga aataccgcac agatgcgtaa   7260
ggagaaaata ccgcatcagg cgccattcgc cattcaggct gcgcaactgt tgggaagggc   7320
gatcggtgcg ggcctcttcg ctattacgcc agctggcgaa agggggatgt gctgcaaggc   7380
gattaagttg ggtaacgcca gggttttccc agtcacgacg ttgtaaaacg acggccagtg   7440
aattcgagct ccaccgcgga tagatctgaa atgaataaca atactgacag tactaaataa   7500
ttgcctactt ggcttcacat acgttgcata cgtcgatata gataataatg ataatgacag   7560
caggattatc gtaatacgta atagttgaaa atctcaaaaa tgtgtgggtc attacgtaaa   7620
taatgatagg aatgggattc ttctattttt cctttttcca ttctagcagc cgtcgggaaa   7680
acgtggcatc ctctctttcg ggctcaattg gagtcacgct gccgtgagca tcctctcttt   7740
ccatatctaa caactgagca cgtaaccaat ggaaaagcat gagcttagcg ttgctccaaa   7800
aaagtattgg atggttaata ccatttgtct gttctcttct gactttgact cctcaaaaaa   7860
aaaaaatcta caatcaacag atcgcttcaa ttacgccctc acaaaaactt ttttccttct   7920
tcttcgccca cgttaaattt tatccctcat gttgtctaac ggatttctgc acttgattta   7980
ttataaaaag acaaagacat aatacttctc tatcaatttc agttattgtt cttccttgcg   8040
ttattcttct gttcttcttt ttcttttgtc atatataacc ataaccaagt aatacatatt   8100
caaatctaga gctgaggatg ttgaagcaaa tcaacttcgg tggtactgtt gaaaccgtct   8160
acgaaagagc tgactggcca agagaaaagt tgttggacta cttcaagaac gacacttttg   8220
ctttgatcgg ttacggttcc caaggttacg gtcaaggttt gaacttgaga gacaacggtt   8280
tgaacgttat cattggtgtc cgtaaagatg gtgcttcttg gaaggctgcc atcgaagacg   8340
```

```
gttgggttcc aggcaagaac ttgttcactg ttgaagatgc tatcaagaga ggtagttacg   8400
ttatgaactt gttgtccgat gccgctcaat cagaaacctg gcctgctatc aagccattgt   8460
tgaccaaggg taagactttg tacttctccc acggtttctc cccagtcttc aaggacttga   8520
ctcacgttga accaccaaag gacttagatg ttatcttggt tgctccaaag ggttccggta   8580
gaactgtcag atctttgttc aaggaaggtc gtggtattaa ctcttcttac gccgtctgga   8640
acgatgtcac cggtaaggct cacgaaaagg cccaagcttt ggccgttgcc attggttccg   8700
gttacgttta ccaaaccact ttcgaaagag aagtcaactc tgacttgtac ggtgaaagag   8760
gttgtttaat gggtggtatc cacggtatgt tcttggctca atacgacgtc ttgagagaaa   8820
acggtcactc cccatctgaa gctttcaacg aaaccgtcga agaagctacc caatctctat   8880
acccattgat cggtaagtac ggtatggatt acatgtacga tgcttgttcc accaccgcca   8940
gaagaggtgc tttggactgg tacccaatct tcaagaatgc tttgaagcct gttttccaag   9000
acttgtacga atctaccaag aacggtaccg aaaccaagag atctttggaa ttcaactctc   9060
aacctgacta cagagaaaag ctagaaaagg aattagacac catcagaaac atggaaatct   9120
ggaaggttgg taaggaagtc agaaagttga gaccagaaaa ccaataatta attaatcatg   9180
taattagtta tgtcacgctt acattcacgc cctcccccca catccgctct aaccgaaaag   9240
gaaggagtta gacaacctga agtctaggtc cctatttatt tttttatagt tatgttagta   9300
ttaagaacgt tatttatatt tcaaattttt cttttttttc tgtacagacg cgtgtacgca   9360
tgtaacatta tactgaaaac cttgcttgag aaggttttgg gacgctcgaa ggctttaatt   9420
tgcgggcggc cgctctagag agttgttagc aacctttgt ttcttttgag ctggttcaga   9480
cattatgtac acgtatatgt gacgagttcg agaagtattt tactatcgta ctaaatttta   9540
cctgaaaaat tatatactcg agaaagagga agccaagaat tgagaaaaaa gaaaaacccg   9600
cgagtaagga aattaaatac aggtgtacac atacacgcac acatatatat atatatatat   9660
atgtatatgt gtatatagga agcgcgcgca tgttagtata tacgattcgt tggaaagggg   9720
ccgtccacca aacgtgactt gacgagttga caaattgacc tcaatatggc tcagtcagta   9780
atttttagtt ccgctttatt cccgccatct ttcaggccac gagggtagct cataacgccg   9840
cgctaatgcc gctgcgtcac agcaaccagt agctcagcca aaaccgaaag agaaatcgta   9900
gctgtcccga tgaggactta tacacttgtc accatctaaa taaattattt attcgcgttt   9960
cggttcttgt tttcgattta attagattgt tcattgaatc ataataaata tgtaaaaaat  10020
atatatattt gaagctgctt cagaaaaaca gggcttccta gtgtacagat gtatgtcgga  10080
tgaaaaaaaa aaaatcttaa atgtgaaatt gggtcaattc aattgactat gacttgatgt  10140
tgcaaaaatt ccaagagaaa aagtttccag cacttgatat tattttcctc tttaattttt  10200
cgccttgtct acgatcttat tagcaccgat ccagggcatc atagacctta actgttcacc  10260
aataatttcg ataccatgtg ctgcattgtt tcttctttta gcagtcatac tcgggtaacc  10320
cgtagcgcct tcacttatga acatcttagc gtattcaccg tcctggatac gtttcaaggc  10380
atttctcatg gcttgtcttg attctgcgtt aatgacttca ggtccggtga catactcacc  10440
atattctgca ttatttgaaa tggaatagtt catattagct ataccacctt catacattaa  10500
gtctactatc aacttcaatt catgtagaca ttcgaagtat gccatttcgg gagcgtaccc  10560
tgcttcgaca agcgtctcaa agcctgcttt aaccaattca acagttcctc cgcacagaac  10620
cgcttgttct ccaaataaat ctgtctcagt ctcgtcttta aaagtggttt ctattatacc  10680
cgttctcccg ccaccaactc ctgctgcgta gcttaaagct acattcttag cgtttccgct  10740
```

-continued

```
tgcgtcttgg tatatagcga tcaaatctgg aataccacca cccttaacaa attcgctcct  10800
aacagtatgc cccggagcct taggtgcaat cataataacg tccaaatctg ccctggggac  10860
tacttgattg taatgaatgg caaatccatg actgaaggcc aaggtagcgc ccttcttaat  10920
gtttggttct atttcatttt tgtacaattg cgattgaaat tcatctggcg ttaaaatcat  10980
gactaaatca gcgccggcaa cagccgctgc aacatctgtg actttcaagc catgtgcttc  11040
agcctttgca acggtagcac taccttttct cagacctact gtcacgtcga ccccagaatc  11100
tttcaagtta caggcttgtg cgtgtccttg ggaaccatat cctataatag caaccttctt  11160
tccctggatg atgctcagat cgcagtcttt atcgtaaaac accttcatgt tttatttttt  11220
acttatattg ctggtagggt aaaaaaatat aactcctagg aataggttgt ctatatgttt  11280
ttgtcttgct tctataattg taacaaacaa ggaaagggaa aatactgggt gtaaaagcca  11340
ttgagtcaag ttaggtcatc ccttttatac aaaatttttc aatttttttt ccaagattct  11400
tgtacgatta attatttttt ttttgcgtcc tacagcgtga tgaaaatttc cgcctgctgc  11460
aagatgagcg ggaacgggcg aaatgtgcac gcgcacaact tacgaaacgc ggatgagtca  11520
ctgacagcca ccgcagaggt tctgactcct actgagctct attggaggtg gcagaaccgg  11580
taccggagga gaccgctata accggtttga atttattgtc acagtgtcac atcagcggca  11640
actcagaagt ttgacagcaa gcaagttcat cattcgaact agccttattg ttttagttca  11700
gtgacagcga actgccgtac tcgatgcttt atttctcacg gtagagcgga agaacagata  11760
ggggcagcgt gagaagagtt agaaagtaaa tttttatcac gtctgaagta ttcttattca  11820
taggaaattt tgcaaggttt tttagctcaa taacgggcta agttatataa ggtgttcacg  11880
cgattttctt gttatgtata cctcttctct gaggaatggt actactgtcc tgatgtaggc  11940
tccttaaatt ggtgggcaag aataacttat cgatattttg tatattggtc ttggagttca  12000
ccacgtaatg cctgtttaag accatcagtt aactctagta ttatttggtc ttggctactg  12060
gccgtttgct attattcaag tcttttgtgc cttcccgtcg ggtaagggag ttatttaggg  12120
atacagaatc taacgaaaac taaatctcaa tgattaactc catttaatcc ttttttgaaa  12180
ggcaaaagag gtcccttgtt cacttacaac gttcttagcc aaattcgctt atcacttact  12240
acttcacgat atacagaagt aaaaacatat aaaaagatgt ctgtttgttt agccatcaca  12300
aaaggtatcg cagtttcttc tataggcctc tactctggtc ttttggcttc cgcttcattg  12360
attacatcta ctactccact agaggtttta acaggatctc taaaaacatc gatatcgtct  12420
ctgcgttcca atcctacggt gaatatattt ccaagcaatt cactgaagaa gaaagagaag  12480
atgttgtgga acatgcatgc ccaggtcctg gttcttgtgg tggtatgtat actgccaaca  12540
caatggcttc tgccgctgaa gtgctaggtt tgaccattcc aaactcctct tccttcccag  12600
ccgtttccaa ggagaagtta gctgagtgtg acaacattgg tgaatacatc aagaagacaa  12660
tggaattggg tattttacct cgtgatatcc tcacaaaaga ggcttttgaa aacgccatta  12720
cttatgtcgt tgcaaccggt gggtccacta atgctgtttt gcatttggtg gctgttgctc  12780
actctgcggg tgtcaagttg tcaccagatg atttccaaag aatcagtgat actacaccat  12840
tgatcggtga cttcaaacct tctggtaaat acgtcatggc cgatttgatt aacgttggtg  12900
gtacccaatc tgtgattaag tatctatatg aaaacaacat gttgcacggt aacacaatga  12960
ctgttaccgg tgacactttg gcagaacgtg caaagaaagc accaagccta cctgaaggac  13020
aagagattat taagccactc tcccacccaa tcaaggccaa cggtcacttg caaattctgt  13080
acggttcatt ggcaccaggt ggagctgtgg gtaaaattac cggtaaggaa ggtacttact  13140
```

-continued

```
tcaagggtag agcacgtgtg ttcgaagagg aaggtgcctt tattgaagcc ttggaaagag  13200
gtgaaatcaa gaagggtgaa aaaaccgttg ttgttatcag atatgaaggt ccaagaggtg  13260
caccaggtat gcctgaaatg ctaaagcctt cctctgctct gatgggttac ggtttgggta  13320
aagatgttgc attgttgact gatggtagat tctctggtgg ttctcacggg ttcttaatcg  13380
gccacattgt tcccgaagcc gctgaaggtg gtcctatcgg gttggtcaga gacggcgatg  13440
agattatcat tgatgctgat aataacaaga ttgacctatt agtctctgat aaggaaatgg  13500
ctcaacgtaa acaaagttgg gttgcacctc cacctcgtta cacaagaggt actctatcca  13560
agtatgctaa gttggtttcc aacgcttcca acggttgtgt tttagatgct tgattaatta  13620
agagtaagcg aatttcttat gatttatgat ttttattatt aaataagtta taaaaaaaat  13680
aagtgtatac aaattttaaa gtgactctta ggttttaaaa cgaaaattct tattcttgag  13740
taactctttc ctgtaggtca ggttgctttc tcaggtatag catgaggtcg ctcttattga  13800
ccacacctct accggcatgc cgagcaaatg cctgcaaatc gctccccatt tcacccaatt  13860
gtagatatgc taactccagc aatgagttga tgaatctcgg tgtgtatttt atgtcctcag  13920
aggacaacac ctgtggtact agttctagag cggccgcccg caaattaaag ccttcgagcg  13980
tcccaaaacc ttctcaagca aggttttcag tataatgtta catgcgtaca cgcgtctgta  14040
cagaaaaaaa agaaaaattt gaaatataaa taacgttctt aatactaaca taactataaa  14100
aaaataaata gggacctaga cttcaggttg tctaactcct tcctttcgg ttagagcgga  14160
tgtgggggga gggcgtgaat gtaagcgtga cataactaat tacatgatta attaactaga  14220
gagctttcgt tttcatgagt tccccgaatt ctttcggaag cttgtcactt gctaaattaa  14280
tgttatcact gtagtcaacc gggacatcga tgatgacagg accttcagcg ttcatgcctt  14340
gacgcagaac atctgccagc tggtctggtg attctacgcg caagccagtt gctccgaagc  14400
tttccgcata tttcacgata tcgatatttc cgaaatcgac cgcagatgta cggttatatt  14460
ttttcaattg ctggaatgca accatgtcat atgtgctgtc gttccataca atgtgtacaa  14520
ttggtgcttt tagtcgaact gctgtctcta attccattgc tgagaataag aaaccgccgt  14580
caccagagac agaaaccact ttttctcccg gtttcaccaa tgaagcgccg attgcccaag  14640
gaagcgcaac gccgagtgtt tgcataccgt tactgatcat taatgttaac ggctcgtagc  14700
tgcggaaata acgtgacatc caaatggcgt gcgaaccgat atcgcaagtt actgtaacat  14760
gatcatcgac tgcattacgc aactctttaa cgatttcaag agggtgcgct ctgtctgatt  14820
tccaatctgc aggcacctgc tcaccttcat gcatatattg ttttaaatca gaaaggattt  14880
tctgctcacg ctctgcaaat tccactttca cagcatcgtg ttcgatatga ttgatcgtgg  14940
acggaatgtc accgatcaat tcaagatcag gctggtaagc atgatcaatg tcagcgataa  15000
tctcgtctaa atggataatt gtccggtctc cattgatatt ccagaatttc ggatcatatt  15060
caatcgggtc atagccgatc gtcagaacaa catctgcctg ctctagcagt aaatcgccag  15120
gctggttgcg gaacaaaccg atacggccaa aatattgatc ctctaaatct ctagaaaggg  15180
taccggcagc ttgatatgtt tcaacaaatg gaagctgaac ctttttcaaa agcttgcgaa  15240
ccgctttaat tgcttccggt cttccgcctt tcatgccgac caaaacgaca ggaagttttg  15300
ctgtttggat ttttgctatg gccgcactga ttgcatcatc tgctgcagga ccgagttttg  15360
gcgctgcaac agcacgcacg tttttcgtat ttgtgacttc attcacaaca tcttgcggaa  15420
agctcacaaa agcggcccca gcctgccctg ctgacgctat cctaaatgca tttgtaacag  15480
cttccggtat atttttttaca tcttgaactt ctacactgta ttttgtaatc ggctggaata  15540
```

-continued

```
gcgccgcatt atccaaagat tgatgtgtcc gttttaaacg atctgcacgg atcacgtttc  15600

cagcaagcgc aacgacaggg tctccttcag tgttcgctgt cagcaggcct gttgccaagt  15660

tagaggcacc cggtcctgat gtgactaaca cgactcccgg ttttccagtt aaacggccga  15720

ctgcttgggc catgaatgct gcgttttgtt cgtgccgggc aacgataatt tcaggtcctt  15780

tatcttgtaa agcgtcaaat accgcatcaa tttttgcacc tggaatgcca aatacatgtg  15840

tgacaccttg ctccactaag caatcaacaa caagctccgc ccctctgttt ttcacaaggg  15900

atttttgttc ttttgttgct tttgtcaaca tcctcagcga tgattgattg attgattgta  15960

cagtttgttt ttcttaatat ctatttcgat gacttctata tgatattgca ctaacaagaa  16020

gatattataa tgcaattgat acaagacaag gagttatttg cttctctttt atatgattct  16080

gacaatccat attgcgttgg tagtcttttt tgctggaacg gttcagcgga aaagacgcat  16140

cgctcttttt gcttctagaa gaaatgccag caaaagaatc tcttgacagt gactgacagc  16200

aaaaatgtct ttttctaact agtaacaagg ctaagatatc agcctgaaat aaagggtggt  16260

gaagtaataa ttaaatcatc cgtataaacc tatacacata tatgaggaaa aataatacaa  16320

aagtgtttta aatacagata catacatgaa catatgcacg tatagcgccc aaatgtcggt  16380

aatggga                                                            16387
```

<210> SEQ ID NO 131
<211> LENGTH: 1188
<212> TYPE: DNA
<213> ORGANISM: Saccharomyces cerevisiae

<400> SEQUENCE: 131

```
atgttgagaa ctcaagccgc cagattgatc tgcaactccc gtgtcatcac tgctaagaga     60

acctttgctt tggccacccg tgctgctgct tacagcagac cagctgcccg tttcgttaag    120

ccaatgatca ctacccgtgg tttgaagcaa atcaacttcg gtggtactgt tgaaaccgtc    180

tacgaaagag ctgactggcc aagagaaaag ttgttggact acttcaagaa cgacactttt    240

gctttgatcg gttacggttc ccaaggttac ggtcaaggtt tgaacttgag agacaacggt    300

ttgaacgtta tcattggtgt ccgtaaagat ggtgcttctt ggaaggctgc catcgaagac    360

ggttgggttc caggcaagaa cttgttcact gttgaagatg ctatcaagag aggtagttac    420

gttatgaact tgttgtccga tgccgctcaa tcagaaacct ggcctgctat caagccattg    480

ttgaccaagg gtaagacttt gtacttctcc cacggtttct ccccagtctt caaggacttg    540

actcacgttg aaccaccaaa ggacttagat gttatcttgg ttgctccaaa gggttccggt    600

agaactgtca gatctttgtt caaggaaggt cgtggtatta actcttctta cgccgtctgg    660

aacgatgtca ccggtaaggc tcacgaaaag gcccaagctt tggccgttgc cattggttcc    720

ggttacgttt accaaaccac tttcgaaaga gaagtcaact ctgacttgta cggtgaaaga    780

ggttgtttaa tgggtggtat ccacggtatg ttcttggctc aatacgacgt cttgagagaa    840

aacggtcact ccccatctga agctttcaac gaaaccgtcg aagaagctac ccaatctcta    900

tacccattga tcggtaagta cggtatggat tacatgtacg atgcttgttc caccaccgcc    960

agaagaggtg ctttggactg gtacccaatc ttcaagaatg ctttgaagcc tgttttccaa   1020

gacttgtacg aatctaccaa gaacggtacc gaaaccaaga gatctttgga attcaactct   1080

caacctgact acagagaaaa gctagaaaag gaattagaca ccatcagaaa catggaaatc   1140

tggaaggttg gtaaggaagt cagaaagttg agaccagaaa accaataa                1188
```

<210> SEQ ID NO 132

<211> LENGTH: 1014
<212> TYPE: DNA
<213> ORGANISM: Pseudomonas fluorescens

<400> SEQUENCE: 132
atgaaagttt tctacgataa agactgcgac ctgtcgatca tccaaggtaa gaaagttgcc 60
atcatcggct acggttccca gggccacgct caagcatgca acctgaagga ttccggcgta 120
gacgtgactg ttggcctgcg taaaggctcg gctaccgttg ccaaggctga agcccacggc 180
ttgaaagtga ccgacgttgc tgcagccgtt gccggtgccg acttggtcat gatcctgacc 240
ccggacgagt tccagtccca gctgtacaag aacgaaatcg agccgaacat caagaagggc 300
gccactctgg ccttctccca cggcttcgcg atccactaca accaggttgt gcctcgtgcc 360
gacctcgacg tgatcatgat cgcgccgaag gctccaggcc acaccgtacg ttccgagttc 420
gtcaagggcg gtggtattcc tgacctgatc gcgatctacc aggacgcttc cggcaacgcc 480
aagaacgttg ccctgtccta cgccgcaggc gtgggcggcg gccgtaccgg catcatcgaa 540
accaccttca aggacgagac tgaaaccgac ctgttcggtg agcaggctgt tctgtgtggc 600
ggtaccgtcg agctggtcaa agccggtttc gaaaccctgg ttgaagctgg ctacgctcca 660
gaaatggcct acttcgagtg cctgcacgaa ctgaagctga tcgttgacct catgtacgaa 720
ggcggtatcg ccaacatgaa ctactcgatc tccaacaacg ctgaatacgg cgagtacgtg 780
actggtccag aagtcatcaa cgccgaatcc cgtcaggcca tgcgcaatgc tctgaagcgc 840
atccaggacg gcgaatacgc gaagatgttc atcagcgaag gcgctaccgg ctacccatcg 900
atgaccgcca agcgtcgtaa caacgctgct cacggtatcg aaatcatcgg cgagcaactg 960
cgctcgatga tgccttggat cggtgccaac aaaatcgtcg acaaagccaa gaac 1014

<210> SEQ ID NO 133
<211> LENGTH: 250
<212> TYPE: DNA
<213> ORGANISM: Saccharomyces cerevisiae

<400> SEQUENCE: 133
ccgcaaatta aagccttcga gcgtcccaaa accttctcaa gcaaggtttt cagtataatg 60
ttacatgcgt acacgcgtct gtacagaaaa aaaagaaaaa tttgaaatat aaataacgtt 120
cttaatacta acataactat aaaaaaataa atagggacct agacttcagg ttgtctaact 180
ccttcctttt cggttagagc ggatgtgggg ggagggcgtg aatgtaagcg tgacataact 240
aattacatga 250

<210> SEQ ID NO 134
<211> LENGTH: 1181
<212> TYPE: DNA
<213> ORGANISM: Saccharomyces cerevisiae

<400> SEQUENCE: 134
taaaacctct agtggagtag tagatgtaat caatgaagcg gaagccaaaa gaccagagta 60
gaggcctata gaagaaactg cgataccttt tgtgatggct aaacaaacag acatcttttt 120
atatgttttt acttctgtat atcgtgaagt agtaagtgat aagcgaattt ggctaagaac 180
gttgtaagtg aacaagggac ctcttttgcc tttcaaaaaa ggattaaatg gagttaatca 240
ttgagattta gttttcgtta gattctgtat ccctaaataa ctcccttacc cgacgggaag 300
gcacaaaaga cttgaataat agcaaacggc cagtagccaa gaccaaataa tactagagtt 360
aactgatggt cttaaacagg cattacgtgg tgaactccaa gaccaatata caaaatatcg 420

```
ataagttatt cttgcccacc aatttaagga gcctacatca ggacagtagt accattcctc    480

agagaagagg tatacataac aagaaaatcg cgtgaacacc ttatataact tagcccgtta    540

ttgagctaaa aaaccttgca aaatttccta tgaataagaa tacttcagac gtgataaaaa    600

tttactttct aactcttctc acgctgcccc tatctgttct tccgctctac cgtgagaaat    660

aaagcatcga gtacggcagt tcgctgtcac tgaactaaaa caataaggct agttcgaatg    720

atgaacttgc ttgctgtcaa acttctgagt tgccgctgat gtgacactgt gacaataaat    780

tcaaaccggt tatagcggtc tcctccggta ccggttctgc cacctccaat agagctcagt    840

aggagtcaga acctctgcgg tggctgtcag tgactcatcc gcgtttcgta agttgtgcgc    900

gtgcacattt cgcccgttcc cgctcatctt gcagcaggcg gaaattttca tcacgctgta    960

ggacgcaaaa aaaaaataat taatcgtaca agaatcttgg aaaaaaaatt gaaaaatttt   1020

gtataaaagg gatgacctaa cttgactcaa tggcttttac acccagtatt ttccctttcc   1080

ttgtttgtta caattataga agcaagacaa aaacatatag acaacctatt cctaggagtt   1140

atattttttt accctaccag caatataagt aaaaaactag t                        1181
```

<210> SEQ ID NO 135
<211> LENGTH: 759
<212> TYPE: DNA
<213> ORGANISM: Saccharomyces cerevisiae

<400> SEQUENCE: 135

```
ggccctgcag gcctatcaag tgctggaaac tttttctctt ggaatttttg caacatcaag     60

tcatagtcaa ttgaattgac ccaatttcac atttaagatt tttttttttt catccgacat    120

acatctgtac actaggaagc cctgtttttc tgaagcagct tcaaatatat atattttta    180

catatttatt atgattcaat gaacaatcta attaaatcga aacaagaac cgaaacgcga    240

ataaataatt tatttagatg gtgacaagtg tataagtcct catcgggaca gctacgattt    300

ctctttcggt tttggctgag ctactggttg ctgtgacgca gcggcattag cgcggcgtta    360

tgagctaccc tcgtggcctg aaagatggcg ggaataaagc ggaactaaaa attactgact    420

gagccatatt gaggtcaatt tgtcaactcg tcaagtcacg tttggtggac ggcccctttc    480

caacgaatcg tatatactaa catgcgcgcg cttcctatat acacatatac atatatatat    540

atatatatat gtgtgcgtgt atgtgtacac ctgtatttaa tttccttact cgcgggtttt    600

tctttttttct caattcttgg cttcctcttt ctcgagtata taatttttca ggtaaaattt    660

agtacgatag taaaatactt ctcgaactcg tcacatatac gtgtacataa tgtctgaacc    720

agctcaaaag aaacaaaagg ttgctaacaa ctctctaga                            759
```

<210> SEQ ID NO 136
<211> LENGTH: 643
<212> TYPE: DNA
<213> ORGANISM: Saccharomyces cerevisiae

<400> SEQUENCE: 136

```
gaaatgaata acaatactga cagtactaaa taattgccta cttggcttca catacgttgc     60

atacgtcgat atagataata atgataatga cagcaggatt atcgtaatac gtaatagttg    120

aaaatctcaa aaatgtgtgg gtcattacgt aaataatgat aggaatggga ttcttctatt    180

tttccttttt ccattctagc agccgtcggg aaaacgtggc atcctctctt tcgggctcaa    240

ttggagtcac gctgccgtga gcatcctctc tttccatatc taacaactga gcacgtaacc    300

aatggaaaag catgagctta gcgttgctcc aaaaaagtat tggatggtta ataccatttg    360
```

```
tctgttctct tctgactttg actcctcaaa aaaaaaaaat ctacaatcaa cagatcgctt    420
caattacgcc ctcacaaaaa ctttttttcct tcttcttcgc ccacgttaaa ttttatccct    480
catgttgtct aacggatttc tgcacttgat ttattataaa aagacaaaga cataatactt    540
ctctatcaat ttcagttatt gttcttcctt gcgttattct tctgttcttc tttttctttt    600
gtcatatata accataacca agtaatacat attcaaatct aga                      643
```

<210> SEQ ID NO 137
<211> LENGTH: 1716
<212> TYPE: DNA
<213> ORGANISM: Bacillus subtilis

<400> SEQUENCE: 137

```
atgttgacaa aagcaacaaa agaacaaaaa tcccttgtga aaaacagagg ggcggagctt     60
gttgttgatt gcttagtgga gcaaggtgtc acacatgtat ttggcattcc aggtgcaaaa    120
attgatgcgg tatttgacgc tttacaagat aaaggacctg aaattatcgt tgcccggcac    180
gaacaaaacg cagcattcat ggcccaagca gtcggccgtt taactggaaa accgggagtc    240
gtgttagtca catcaggacc gggtgcctct aacttggcaa caggcctgct gacagcgaac    300
actgaaggag accctgtcgt tgcgcttgct ggaaacgtga tccgtgcaga tcgtttaaaa    360
cggacacatc aatctttgga taatgcggcg ctattccagc cgattacaaa atacagtgta    420
gaagttcaag atgtaaaaaa tataccggaa gctgttacaa atgcatttag gatagcgtca    480
gcagggcagg ctggggccgc ttttgtgagc tttccgcaag atgttgtgaa tgaagtcaca    540
aatacgaaaa acgtgcgtgc tgttgcagcg ccaaaactcg gtcctgcagc agatgatgca    600
atcagtgcgg ccatagcaaa aatccaaaca gcaaaacttc ctgtcgtttt ggtcggcatg    660
aaaggcggaa gaccggaagc aattaaagcg gttcgcaagc ttttgaaaaa ggttcagctt    720
ccatttgttg aaacatatca agctgccggt accctttcta gagatttaga ggatcaatat    780
tttggccgta tcggtttgtt ccgcaaccag cctggcgatt tactgctaga gcaggcagat    840
gttgttctga cgatcggcta tgacccgatt gaatatgatc cgaaattctg gaatatcaat    900
ggagaccgga caattatcca tttagacgag attatcgctg acattgatca tgcttaccag    960
cctgatcttg aattgatcgg tgacattccg tccacgatca atcatatcga acacgatgct   1020
gtgaaagtgg aatttgcaga gcgtgagcag aaaatccttt ctgatttaaa acaatatatg   1080
catgaaggtg agcaggtgcc tgcagattgg aaatcagaca gagcgcaccc tcttgaaatc   1140
gttaaagagt tgcgtaatgc agtcgatgat catgttacag taacttgcga tatcggttcg   1200
cacgccattt ggatgtcacg ttatttccgc agctacgagc cgttaacatt aatgatcagt   1260
aacggtatgc aaacactcgg cgttgcgctt ccttgggcaa tcggcgcttc attggtgaaa   1320
ccgggagaaa aagtggtttc tgtctctggt gacggcggtt tcttattctc agcaatggaa   1380
ttagagacag cagttcgact aaaagcacca attgtacaca ttgtatggaa cgacagcaca   1440
tatgacatgg ttgcattcca gcaattgaaa aaatataacc gtacatctgc ggtcgatttc   1500
ggaaatatcg atatcgtgaa atatgcggaa agcttcggag caactggctt gcgcgtagaa   1560
tcaccagacc agctggcaga tgttctgcgt caaggcatga acgctgaagg tcctgtcatc   1620
atcgatgtcc cggttgacta cagtgataac attaatttag caagtgacaa gcttccgaaa   1680
gaattcgggg aactcatgaa aacgaaagct ctctag                             1716
```

<210> SEQ ID NO 138
<211> LENGTH: 571
<212> TYPE: PRT

<213> ORGANISM: Bacillus subtilis

<400> SEQUENCE: 138

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
```

```
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570


<210> SEQ ID NO 139
<211> LENGTH: 448
<212> TYPE: DNA
<213> ORGANISM: Saccharomyces cerevisiae

<400> SEQUENCE: 139

cccattaccg acatttgggc gctatacgtg catatgttca tgtatgtatc tgtatttaaa      60

acacttttgt attatttttc ctcatatatg tgtataggtt tatacggatg atttaattat     120

tacttcacca ccctttattt caggctgata tcttagcctt gttactagtt agaaaaagac     180

atttttgctg tcagtcactg tcaagagatt cttttgctgg catttcttct agaagcaaaa     240

agagcgatgc gtcttttccg ctgaaccgtt ccagcaaaaa agactaccaa cgcaatatgg     300

attgtcagaa tcatataaaa gagaagcaaa taactccttg tcttgtatca attgcattat     360

aatatcttct tgttagtgca atatcatata gaagtcatcg aaatagatat taagaaaaac     420

aaactgtaca atcaatcaat caatcatc                                        448


<210> SEQ ID NO 140
<211> LENGTH: 16387
<212> TYPE: DNA
<213> ORGANISM: Artificial Sequence
<220> FEATURE:
<223> OTHER INFORMATION: plasmid construct

<400> SEQUENCE: 140

tcccattacc gacatttggg cgctatacgt gcatatgttc atgtatgtat ctgtatttaa      60

aacacttttg tattattttt cctcatatat gtgtataggt ttatacggat gatttaatta     120

ttacttcacc accctttatt tcaggctgat atcttagcct tgttactagt tagaaaaaga     180

catttttgct gtcagtcact gtcaagagat tcttttgctg gcatttcttc tagaagcaaa     240

aagagcgatg cgtcttttcc gctgaaccgt tccagcaaaa aagactacca acgcaatatg     300

gattgtcaga atcatataaa agagaagcaa ataactcctt gtcttgtatc aattgcatta     360

taatatcttc ttgttagtgc aatatcatat agaagtcatc gaaatagata ttaagaaaaa     420
```

-continued

```
caaactgtac aatcaatcaa tcaatcatcg ctgaggatgt tgacaaaagc aacaaaagaa    480
caaaaatccc ttgtgaaaaa cagaggggcg gagcttgttg ttgattgctt agtggagcaa    540
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggaccgggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc cgcaagatgt tgtgaatgaa gtcacaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat ttgttgaaac atatcaagct   1200
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga aagtggaatt tgcagagcgt   1500
gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgctc tagaactagt accacaggtg   2460
ttgtcctctg aggacataaa atacacaccg agattcatca actcattgct ggagttagca   2520
tatctacaat tgggtgaaat ggggagcgat ttgcaggcat ttgctcggca tgccggtaga   2580
ggtgtggtca ataagagcga cctcatgcta tacctgagaa agcaacctga cctacaggaa   2640
agagttactc aagaataaga attttcgttt taaaacctaa gagtcacttt aaaatttgta   2700
tacacttatt ttttttataa cttatttaat aataaaaatc ataaatcata agaaattcgc   2760
ttactcttaa ttaatcaagc atctaaaaca caaccgttgg aagcgttgga aaccaactta   2820
```

-continued

```
gcatacttgg atagagtacc tcttgtgtaa cgaggtggag gtgcaaccca actttgttta   2880
cgttgagcca tttccttatc agagactaat aggtcaatct tgttattatc agcatcaatg   2940
ataatctcat cgccgtctct gaccaacccg ataggaccac cttcagcggc ttcgggaaca   3000
atgtggccga ttaagaaccc gtgagaacca ccagagaatc taccatcagt caacaatgca   3060
acatctttac ccaaaccgta acccatcaga gcagaggaag gctttagcat ttcaggcata   3120
cctggtgcac ctcttggacc ttcatatctg ataacaacaa cggttttttc acccttcttg   3180
atttcacctc tttccaaggc ttcaataaag gcaccttcct cttcgaacac acgtgctcta   3240
cccttgaagt aagtaccttc cttaccggta attttaccca cagctccacc tggtgccaat   3300
gaaccgtaca gaatttgcaa gtgaccgttg gccttgattg ggtgggagag tggcttaata   3360
atctcttgtc cttcaggtag gcttggtgct ttctttgcac gttctgccaa agtgtcaccg   3420
gtaacagtca ttgtgttacc gtgcaacatg ttgttttcat atagatactt aatcacagat   3480
tgggtaccac caacgttaat caaatcggcc atgacgtatt taccagaagg tttgaagtca   3540
ccgatcaatg gtgtagtatc actgattctt tggaaatcat ctggtgacaa cttgacaccc   3600
gcagagtgag caacagccac caaatgcaaa acagcattag tggacccacc ggttgcaacg   3660
acataagtaa tggcgttttc aaaagcctct tttgtgagga tatcacgagg taaaataccc   3720
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gtttttagag atcctgttaa aacctctagt ggagtagtag   4020
atgtaatcaa tgaagcggaa gccaaaagac cagagtagag gcctatagaa gaaactgcga   4080
taccttttgt gatggctaaa caaacagaca tctttttata tgtttttact tctgtatatc   4140
gtgaagtagt aagtgataag cgaatttggc taagaacgtt gtaagtgaac aagggacctc   4200
ttttgccttt caaaaaagga ttaaatggag ttaatcattg agatttagtt ttcgttagat   4260
tctgtatccc taaataactc ccttacccga cgggaaggca caaaagactt gaataatagc   4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacacctta tataacttag cccgttattg agctaaaaaa ccttgcaaaa   4560
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aaataattaa   4980
tcgtacaaga atcttggaaa aaaaattgaa aaattttgta taaaagggat gacctaactt   5040
gactcaatgg cttttacacc cagtattttc cctttccttg tttgttacaa ttatagaagc   5100
aagacaaaaa catatagaca acctattcct aggagttata tttttttacc ctaccagcaa   5160
tataagtaaa aaactagtat gaaggtgttt tacgataaag actgcgatct gagcatcatc   5220
```

```
cagggaaaga aggttgctat tataggatat ggttcccaag gacacgcaca agccttgaac   5280
ttgaaagatt ctggggtcga cgtgacagta ggtctgtata aaggtgctgc tgatgcagca   5340
aaggctgaag cacatggctt taaagtcaca gatgttgcag cggctgttgc tggcgctgat   5400
ttagtcatga ttttaattcc agatgaattt caatcgcaat tgtacaaaaa tgaaatagaa   5460
ccaaacatta agaagggcgc taccttggcc ttcagtcatg gatttgccat tcattacaat   5520
caagtagtcc ccagggcaga tttggacgtt attatgattg cacctaaggc tccggggcat   5580
actgttagga gcgaatttgt taagggtggt ggtattccag atttgatcgc tatataccaa   5640
gacgttagcg gaaacgctaa gaatgtagct ttaagctacg cagcaggagt tggtggcggg   5700
agaacgggta taatagaaac cacttttaaa gacgagactg agacagattt atttggagaa   5760
caagcggttc tgtgcggagg aactgttgaa ttggttaaag caggctttga gacgcttgtc   5820
gaagcagggt acgctcccga aatggcatac ttcgaatgtc tacatgaatt gaagttgata   5880
gtagacttaa tgtatgaagg tggtatagct aatatgaact attccatttc aaataatgca   5940
gaatatggtg agtatgtcac cggacctgaa gtcattaacg cagaatcaag acaagccatg   6000
agaaatgcct tgaaacgtat ccaggacggt gaatacgcta agatgttcat aagtgaaggc   6060
gctacgggtt acccgagtat gactgctaaa agaagaaaca atgcagcaca tggtatcgaa   6120
attattggtg aacagttaag gtctatgatg ccctggatcg gtgctaataa gatcgtagac   6180
aaggcgaaaa attaaggccc tgcaggccta tcaagtgctg gaaacttttt ctcttggaat   6240
ttttgcaaca tcaagtcata gtcaattgaa ttgacccaat ttcacattta agattttttt   6300
tttttcatcc gacatacatc tgtacactag gaagccctgt tttctgaag cagcttcaaa    6360
tatatatatt ttttacatat ttattatgat tcaatgaaca atctaattaa atcgaaaaca   6420
agaaccgaaa cgcgaataaa taatttattt agatggtgac aagtgtataa gtcctcatcg   6480
ggacagctac gatttctctt tcggttttgg ctgagctact ggttgctgtg acgcagcggc   6540
attagcgcgg cgttatgagc taccctcgtg gcctgaaaga tggcgggaat aaagcggaac   6600
taaaaattac tgactgagcc atattgaggt caatttgtca actcgtcaag tcacgtttgg   6660
tggacggccc ctttccaacg aatcgtatat actaacatgc gcgcgcttcc tatatacaca   6720
tatacatata tatatatata tatatgtgtg cgtgtatgtg tacacctgta tttaatttcc   6780
ttactcgcgg gtttttcttt tttctcaatt cttggcttcc tctttctcga gtatataatt   6840
tttcaggtaa aatttagtac gatagtaaaa tacttctcga actcgtcaca tatacgtgta   6900
cataatgtct gaaccagctc aaaagaaaca aaaggttgct aacaactctc tagagcggcc   6960
gcccgcaaat taaagccttc gagcgtccca aaaccttctc aagcaaggtt ttcagtataa   7020
tgttacatgc gtacacgcgt ctgtacagaa aaaaaagaaa aatttgaaat ataaataacg   7080
ttcttaatac taacataact ataaaaaaat aaatagggac ctagacttca ggttgtctaa   7140
ctccttcctt ttcggttaga gcggatgtgg ggggagggcg tgaatgtaag cgtgacataa   7200
ctaattacat gattaattaa ttattggttt tctggtctca actttctgac ttccttacca   7260
accttccaga tttccatgtt tctgatggtg tctaattcct tttctagctt ttctctgtag   7320
tcaggttgag agttgaattc caaagatctc ttggtttcgg taccgttctt ggtagattcg   7380
tacaagtctt ggaaaacagg cttcaaagca ttcttgaaga ttgggtacca gtccaaagca   7440
cctcttctgg cggtggtgga acaagcatcg tacatgtaat ccataccgta cttaccgatc   7500
aatgggtata gagattgggt agcttcttcg acggtttcgt tgaaagcttc agatggggag   7560
tgaccgtttt ctctcaagac gtcgtattga gccaagaaca taccgtggat accacccatt   7620
```

-continued

```
aaacaacctc tttcaccgta caagtcagag ttgacttctc tttcgaaagt ggtttggtaa   7680
acgtaaccgg aaccaatggc aacggccaaa gcttgggcct tttcgtgagc cttaccggtg   7740
acatcgttcc agacggcgta agaagagtta ataccacgac cttccttgaa caaagatctg   7800
acagttctac cggaaccctt tggagcaacc aagataacat ctaagtcctt tggtggttca   7860
acgtgagtca agtccttgaa gactggggag aaaccgtggg agaagtacaa agtcttaccc   7920
ttggtcaaca atggcttgat agcaggccag gtttctgatt gagcggcatc ggacaacaag   7980
ttcataacgt aactacctct cttgatagca tcttcaacag tgaacaagtt cttgcctgga   8040
acccaaccgt cttcgatggc agccttccaa gaagcaccat ctttacggac accaatgata   8100
acgttcaaac cgttgtctct caagttcaaa ccttgaccgt aaccttggga accgtaaccg   8160
atcaaagcaa aagtgtcgtt cttgaagtag tccaacaact tttctcttgg ccagtcagct   8220
ctttcgtaga cggtttcaac agtaccaccg aagttgattt gcttcaacat cctcagctct   8280
agatttgaat atgtattact tggttatggt tatatatgac aaaagaaaaa gaagaacaga   8340
agaataacgc aaggaagaac aataactgaa attgatagag aagtattatg tctttgtctt   8400
tttataataa atcaagtgca gaaatccgtt agacaacatg agggataaaa tttaacgtgg   8460
gcgaagaaga aggaaaaaag tttttgtgag ggcgtaattg aagcgatctg ttgattgtag   8520
attttttttt tttgaggagt caaagtcaga agagaacaga caaatggtat taaccatcca   8580
atactttttt ggagcaacgc taagctcatg cttttccatt ggttacgtgc tcagttgtta   8640
gatatggaaa gagaggatgc tcacggcagc gtgactccaa ttgagcccga aagagaggat   8700
gccacgtttt cccgacggct gctagaatgg aaaaaggaaa aatagaagaa tcccattcct   8760
atcattattt acgtaatgac ccacacattt ttgagatttt caactattac gtattacgat   8820
aatcctgctg tcattatcat tattatctat atcgacgtat gcaacgtatg tgaagccaag   8880
taggcaatta tttagtactg tcagtattgt tattcatttc agatctatcc gcggtggagc   8940
tcgaattcac tggccgtcgt tttacaacgt cgtgactggg aaaaccctgg cgttacccaa   9000
cttaatcgcc ttgcagcaca tccccctttc gccagctggc gtaatagcga agaggcccgc   9060
accgatcgcc cttcccaaca gttgcgcagc ctgaatggcg aatggcgcct gatgcggtat   9120
tttctcctta cgcatctgtg cggtatttca caccgcatac gtcaaagcaa ccatagtacg   9180
cgccctgtag cggcgcatta agcgcggcgg gtgtggtggt tacgcgcagc gtgaccgcta   9240
cacttgccag cgccttagcg cccgctcctt tcgctttctt cccttccttt ctcgccacgt   9300
tcgccggctt tccccgtcaa gctctaaatc gggggctccc tttagggttc cgatttagtg   9360
ctttacggca cctcgacccc aaaaaacttg atttgggtga tggttcacgt agtgggccat   9420
cgccctgata gacggttttt cgccctttga cgttggagtc cacgttcttt aatagtggac   9480
tcttgttcca aactggaaca acactcaact ctatctcggg ctattctttt gatttataag   9540
ggattttgcc gatttcggtc tattggttaa aaaatgagct gatttaacaa aaatttaacg   9600
cgaattttaa caaaatatta acgtttacaa ttttatggtg cactctcagt acaatctgct   9660
ctgatgccgc atagttaagc cagccccgac acccgccaac acccgctgac gcgccctgac   9720
gggcttgtct gctcccggca tccgcttaca gacaagctgt gaccgtctcc gggagctgca   9780
tgtgtcagag gttttcaccg tcatcaccga aacgcgcgag acgaaagggc ctcgtgatac   9840
gcctattttt ataggttaat gtcatgataa taatggtttc ttagacgtca ggtggcactt   9900
ttcggggaaa tgtgcgcgga acccctattt gtttattttt ctaaatacat tcaaatatgt   9960
atccgctcat gagacaataa ccctgataaa tgcttcaata atattgaaaa aggaagagta  10020
```

-continued

```
tgagtattca acatttccgt gtcgccctta ttcccttttt tgcggcattt tgccttcctg  10080
tttttgctca cccagaaacg ctggtgaaag taaaagatgc tgaagatcag ttgggtgcac  10140
gagtgggtta catcgaactg gatctcaaca gcggtaagat ccttgagagt tttcgccccg  10200
aagaacgttt tccaatgatg agcactttta aagttctgct atgtggcgcg gtattatccc  10260
gtattgacgc cgggcaagag caactcggtc gccgcataca ctattctcag aatgacttgg  10320
ttgagtactc accagtcaca gaaaagcatc ttacggatgg catgacagta agagaattat  10380
gcagtgctgc cataaccatg agtgataaca ctgcggccaa cttacttctg acaacgatcg  10440
gaggaccgaa ggagctaacc gcttttttgc acaacatggg ggatcatgta actcgccttg  10500
atcgttggga accggagctg aatgaagcca taccaaacga cgagcgtgac accacgatgc  10560
ctgtagcaat ggcaacaacg ttgcgcaaac tattaactgg cgaactactt actctagctt  10620
cccggcaaca attaatagac tggatggagg cggataaagt tgcaggacca cttctgcgct  10680
cggcccttcc ggctggctgg tttattgctg ataaatctgg agccggtgag cgtgggtctc  10740
gcggtatcat tgcagcactg gggccagatg gtaagccctc ccgtatcgta gttatctaca  10800
cgacggggag tcaggcaact atggatgaac gaaatagaca gatcgctgag ataggtgcct  10860
cactgattaa gcattggtaa ctgtcagacc aagtttactc atatatactt tagattgatt  10920
taaaacttca tttttaattt aaaaggatct aggtgaagat cctttttgat aatctcatga  10980
ccaaaatccc ttaacgtgag ttttcgttcc actgagcgtc agaccccgta gaaaagatca  11040
aaggatcttc ttgagatcct ttttttctgc gcgtaatctg ctgcttgcaa acaaaaaaac  11100
caccgctacc agcggtggtt tgtttgccgg atcaagagct accaactctt tttccgaagg  11160
taactggctt cagcagagcg cagataccaa atactgttct tctagtgtag ccgtagttag  11220
gccaccactt caagaactct gtagcaccgc ctacatacct cgctctgcta atcctgttac  11280
cagtggctgc tgccagtggc gataagtcgt gtcttaccgg gttggactca agacgatagt  11340
taccggataa ggcgcagcgg tcgggctgaa cggggggttc gtgcacacag cccagcttgg  11400
agcgaacgac ctacaccgaa ctgagatacc tacagcgtga gctatgagaa agcgccacgc  11460
ttcccgaagg gagaaaggcg gacaggtatc cggtaagcgg cagggtcgga acaggagagc  11520
gcacgaggga gcttccaggg ggaaacgcct ggtatcttta tagtcctgtc gggtttcgcc  11580
acctctgact tgagcgtcga tttttgtgat gctcgtcagg ggggcggagc ctatggaaaa  11640
acgccagcaa cgcggccttt ttacggttcc tggccttttg ctggcctttt gctcacatgt  11700
tctttcctgc gttatcccct gattctgtgg ataaccgtat taccgccttt gagtgagctg  11760
ataccgctcg ccgcagccga acgaccgagc gcagcgagtc agtgagcgag gaagcggaag  11820
agcgcccaat acgcaaaccg cctctccccg cgcgttggcc gattcattaa tgcagctggc  11880
acgacaggtt tcccgactgg aaagcgggca gtgagcgcaa cgcaattaat gtgagttagc  11940
tcactcatta ggcaccccag gctttacact ttatgcttcc ggctcgtatg ttgtgtggaa  12000
ttgtgagcgg ataacaattt cacacaggaa acagctatga ccatgattac gccaagcttt  12060
ttctttccaa tttttttttt ttcgtcatta taaaaatcat tacgaccgag attcccgggt  12120
aataactgat ataattaaat tgaagctcta atttgtgagt ttagtataca tgcatttact  12180
tataatacag tttttttagtt ttgctggccg catcttctca aatatgcttc ccagcctgct  12240
tttctgtaac gttcaccctc taccttagca tcccttccct ttgcaaatag tcctcttcca  12300
acaataataa tgtcagatcc tgtagagacc acatcatcca cggttctata ctgttgaccc  12360
aatgcgtctc ccttgtcatc taaacccaca ccgggtgtca taatcaacca atcgtaacct  12420
```

-continued tcatctcttc cacccatgtc tctttgagca ataaagccga taacaaaatc tttgtcgctc 12480
ttcgcaatgt caacagtacc cttagtatat tctccagtag atagggagcc cttgcatgac 12540
aattctgcta acatcaaaag gcctctaggt tcctttgtta cttcttctgc cgcctgcttc 12600
aaaccgctaa caatacctgg gcccaccaca ccgtgtgcat tcgtaatgtc tgcccattct 12660
gctattctgt atacacccgc agagtactgc aatttgactg tattaccaat gtcagcaaat 12720
tttctgtctt cgaagagtaa aaaattgtac ttggcggata atgcctttag cggcttaact 12780
gtgccctcca tggaaaaatc agtcaagata tccacatgtg tttttagtaa acaaattttg 12840
ggacctaatg cttcaactaa ctccagtaat tccttggtgg tacgaacatc caatgaagca 12900
cacaagtttg tttgcttttc gtgcatgata ttaaatagct tggcagcaac aggactagga 12960
tgagtagcag cacgttcctt atatgtagct ttcgacatga tttatcttcg tttcctgcag 13020
gtttttgttc tgtgcagttg ggttaagaat actgggcaat ttcatgtttc ttcaacacta 13080
catatgcgta tatataccaa tctaagtctg tgctccttcc ttcgttcttc cttctgttcg 13140
gagattaccg aatcaaaaaa atttcaagga aaccgaaatc aaaaaaaaga ataaaaaaaa 13200
aatgatgaat tgaaaagctt gcatgcctgc aggtcgactc tagtatactc cgtctactgt 13260
acgatacact tccgctcagg tccttgtcct ttaacgaggc cttaccactc ttttgttact 13320
ctattgatcc agctcagcaa aggcagtgtg atctaagatt ctatcttcgc gatgtagtaa 13380
aactagctag accgagaaag agactagaaa tgcaaaaggc acttctacaa tggctgccat 13440
cattattatc cgatgtgacg ctgcattttt tttttttttt tttttttttt tttttttttt 13500
tttttttttt tttttttgta caaatatcat aaaaaaagag aatcttttta agcaaggatt 13560
ttcttaactt cttcggcgac agcatcaccg acttcggtgg tactgttgga accacctaaa 13620
tcaccagttc tgatacctgc atccaaaacc tttttaactg catcttcaat ggctttacct 13680
tcttcaggca agttcaatga caatttcaac atcattgcag cagacaagat agtggcgata 13740
gggttgacct tattctttgg caaatctgga gcggaaccat ggcatggttc gtacaaacca 13800
aatgcggtgt tcttgtctgg caaagaggcc aaggacgcag atggcaacaa acccaaggag 13860
cctgggataa cggaggcttc atcggagatg atatcaccaa acatgttgct ggtgattata 13920
ataccattta ggtgggttgg gttcttaact aggatcatgg cggcagaatc aatcaattga 13980
tgttgaactt tcaatgtagg gaattcgttc ttgatggttt cctccacagt tttctccat 14040 aatcttgaag aggccaaaac attagcttta tccaaggacc aaataggcaa tggtggctca 14100
tgttgtaggg ccatgaaagc ggccattctt gtgattcttt gcacttctgg aacggtgtat 14160
tgttcactat cccaagcgac accatcacca tcgtcttcct ttctcttacc aaagtaaata 14220
cctcccacta attctctaac aacaacgaag tcagtacctt tagcaaattg tggcttgatt 14280
ggagataagt ctaaaagaga gtcggatgca aagttacatg gtcttaagtt ggcgtacaat 14340
tgaagttctt tacggatttt tagtaaacct tgttcaggtc taacactacc ggtaccccat 14400
ttaggaccac ccacagcacc taacaaaacg gcatcagcct tcttggaggc ttccagcgcc 14460
tcatctggaa gtggaacacc tgtagcatcg atagcagcac caccaattaa atgattttcg 14520
aaatcgaact tgacattgga acgaacatca gaaatagctt taagaacctt aatggcttcg 14580
gctgtgattt cttgaccaac gtggtcacct ggcaaaacga cgatcttctt aggggcagac 14640
attacaatgg tatatccttg aaatatatat aaaaaaaaaa aaaaaaaaaa aaaaaaaaaa 14700
tgcagcttct caatgatatt cgaatacgct ttgaggagat acagcctaat atccgacaaa 14760
ctgttttaca gatttacgat cgtacttgtt acccatcatt gaattttgaa catccgaacc 14820
tgggagtttt ccctgaaaca gatagtatat ttgaacctgt ataataatat atagtctagc 14880
gctttacgga agacaatgta tgtatttcgg ttcctggaga aactattgca tctattgcat 14940
aggtaatctt gcacgtcgca tccccggttc attttctgcg tttccatctt gcacttcaat 15000
agcatatctt tgttaacgaa gcatctgtgc ttcattttgt agaacaaaaa tgcaacgcga 15060
gagcgctaat ttttcaaaca aagaatctga gctgcatttt tacagaacag aaatgcaacg 15120
cgaaagcgct attttaccaa cgaagaatct gtgcttcatt tttgtaaaac aaaaatgcaa 15180
cgcgagagcg ctaatttttc aaacaaagaa tctgagctgc atttttacag aacagaaatg 15240
caacgcgaga gcgctatttt accaacaaag aatctatact tctttttttgt tctacaaaaa 15300 tgcatcccga gagcgctatt tttctaacaa agcatcttag attacttttt ttctcctttg 15360
tgcgctctat aatgcagtct cttgataact tttgcactg taggtccgtt aaggttagaa 15420
gaaggctact ttggtgtcta ttttctcttc cataaaaaaa gcctgactcc acttcccgcg 15480
tttactgatt actagcgaag ctgcgggtgc atttttttcaa gataaaggca tccccgatta 15540
tattctatac cgatgtggat tgcgcatact ttgtgaacag aaagtgatag cgttgatgat 15600
tcttcattgg tcagaaaatt atgaacggtt tcttctattt tgtctctata tactacgtat 15660
aggaaatgtt tacattttcg tattgttttc gattcactct atgaatagtt cttactacaa 15720 ttttttgtc taaagagtaa tactagagat aaacataaaa aatgtagagg tcgagtttag 15780
atgcaagttc aaggagcgaa aggtggatgg gtaggttata tagggatata gcacagagat 15840
atatagcaaa gagatacttt tgagcaatgt ttgtggaagc ggtattcgca atattttagt 15900
agctcgttac agtccggtgc gtttttggtt ttttgaaagt gcgtcttcag agcgcttttg 15960
gttttcaaaa gcgctctgaa gttcctatac tttctagaga ataggaactt cggaatagga 16020
acttcaaagc gtttccgaaa acgagcgctt ccgaaaatgc aacgcgagct gcgcacatac 16080
agctcactgt tcacgtcgca cctatatctg cgtgttgcct gtatatatat atacatgaga 16140
agaacggcat agtgcgtgtt tatgcttaaa tgcgtactta tatgcgtcta tttatgtagg 16200
atgaaaggta gtctagtacc tcctgtgata ttatcccatt ccatgcgggg tatcgtatgc 16260
ttccttcagc actacccttt agctgttcta tatgctgcca ctcctcaatt ggattagtct 16320
catccttcaa tgctatcatt tcctttgata ttggatcata tgcatagtac cgagaaacta 16380
gaggatc 16387

<210> SEQ ID NO 141
<211> LENGTH: 2237
<212> TYPE: DNA
<213> ORGANISM: Artificial Sequence
<220> FEATURE:
<223> OTHER INFORMATION: PDC1 Fragment A-ilvDSm

<400> SEQUENCE: 141
ttatgtatgc tcttctgact tttcgtgtga tgaggctcgt ggaaaaaatg aataatttat 60
gaatttgaga acaattttgt gttgttacgg tattttacta tggaataatc aatcaattga 120
ggattttatg caaatatcgt ttgaatattt ttccgaccct ttgagtactt ttcttcataa 180
ttgcataata ttgtccgctg ccccttttttc tgttagacgg tgtcttgatc tacttgctat 240
cgttcaacac caccttattt tctaactatt ttttttttag ctcatttgaa tcagcttatg 300
gtgatggcac atttttgcat aaacctagct gtcctcgttg aacataggaa aaaaaaatat 360
ataaacaagg ctctttcact ctccttgcaa tcagatttgg gtttgttccc tttattttca 420
tatttcttgt catattcctt tctcaattat tattttctac tcataacctc acgcaaaata 480

```
acacagtcaa atcaatcaaa atgactgaca aaaaaactct taaagactta agaaatcgta    540

gttctgttta cgattcaatg gttaaatcac ctaatcgtgc tatgttgcgt gcaactggta    600

tgcaagatga agactttgaa aaacctatcg tcggtgtcat ttcaacttgg gctgaaaaca    660

caccttgtaa tatccactta catgactttg gtaaactagc caaagtcggt gttaaggaag    720

ctggtgcttg gccagttcag ttcggaacaa tcacggtttc tgatggaatc gccatgggaa    780

cccaaggaat gcgtttctcc ttgacatctc gtgatattat tgcagattct attgaagcag    840

ccatgggagg tcataatgcg gatgcttttg tagccattgg cggttgtgat aaaaacatgc    900

ccggttctgt tatcgctatg gctaacatgg atatcccagc catttttgct tacggcggaa    960

caattgcacc tggtaattta gacggcaaag atatcgattt agtctctgtc tttgaaggtg   1020

tcggccattg gaaccacggc gatatgacca aagaagaagt taaagctttg gaatgtaatg   1080

cttgtcccgg tcctggaggc tgcggtggta tgtatactgc taacacaatg gcgacagcta   1140

ttgaagtttt gggacttagc cttccgggtt catcttctca cccggctgaa tccgcagaaa   1200

agaaagcaga tattgaagaa gctggtcgcg ctgttgtcaa aatgctcgaa atgggcttaa   1260

aaccttctga cattttaacg cgtgaagctt ttgaagatgc tattactgta actatggctc   1320

tgggaggttc aaccaactca acccttcacc tcttagctat tgcccatgct gctaatgtgg   1380

aattgacact tgatgatttc aatactttcc aagaaaaagt tcctcatttg gctgatttga   1440

aaccttctgg tcaatatgta ttccaagacc tttacaaggt cggaggggta ccagcagtta   1500

tgaaatatct ccttaaaaat ggcttccttc atggtgaccg tatcacttgt actggcaaaa   1560

cagtcgctga aaatttgaag gcttttgatg atttaacacc tggtcaaaag gttattatgc   1620

cgcttgaaaa tcctaaacgt gaagatggtc cgctcattat tctccatggt aacttggctc   1680

cagacggtgc cgttgccaaa gtttctggtg taaaagtgcg tcgtcatgtc ggtcctgcta   1740

aggtctttaa ttctgaagaa gaagccattg aagctgtctt gaatgatgat attgttgatg   1800

gtgatgttgt tgtcgtacgt tttgtaggac caaagggcgg tcctggtatg cctgaaatgc   1860

tttccctttc atcaatgatt gttggtaaag ggcaaggtga aaaagttgcc cttctgacag   1920

atggccgctt ctcaggtggt acttatggtc ttgtcgtggg tcatatcgct cctgaagcac   1980

aagatggcgg tccaatcgcc tacctgcaaa caggagacat agtcactatt gaccaagaca   2040

ctaaggaatt acactttgat atctccgatg aagagttaaa acatcgtcaa gagaccattg   2100

aattgccacc gctctattca cgcggtatcc ttggtaaata tgctcacatc gtttcgtctg   2160

cttctagggg agccgtaaca gacttttgga agcctgaaga aactggcaaa aaatgagcga   2220

tttaatctct aattatt                                                  2237
```

<210> SEQ ID NO 142
<211> LENGTH: 4420
<212> TYPE: DNA
<213> ORGANISM: Artificial Sequence
<220> FEATURE:
<223> OTHER INFORMATION: PDC1 A-ilvDSm-BUC cassette

<400> SEQUENCE: 142

```
ttatgtatgc tcttctgact tttcgtgtga tgaggctcgt ggaaaaaatg aataatttat     60

gaatttgaga acaattttgt gttgttacgg tattttacta tggaataatc aatcaattga    120

ggattttatg caaatatcgt ttgaatattt ttccgaccct ttgagtactt ttcttcataa    180

ttgcataata ttgtccgctg ccccttttttc tgttagacgg tgtcttgatc tacttgctat    240

cgttcaacac caccttattt tctaactatt tttttttag ctcatttgaa tcagcttatg    300
```

-continued

```
gtgatggcac atttttgcat aaacctagct gtcctcgttg aacataggaa aaaaaaatat    360
ataaacaagg ctctttcact ctccttgcaa tcagatttgg gtttgttccc tttattttca    420
tatttcttgt catattcctt tctcaattat tattttctac tcataacctc acgcaaaata    480
acacagtcaa atcaatcaaa atgactgaca aaaaaactct taaagactta agaaatcgta    540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
ctggtgcttg gccagttcag ttcggaacaa tcacggtttc tgatggaatc gccatgggaa    780
cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta gacggcaaag atatcgattt agtctctgtc tttgaaggtg   1020
tcggccattg gaaccacggc gatatgacca aagaagaagt taaagctttg gaatgtaatg   1080
cttgtcccgg tcctggaggc tgcggtggta tgtatactgc taacacaatg gcgacagcta   1140
ttgaagtttt gggacttagc cttccgggtt catcttctca cccggctgaa tccgcagaaa   1200
agaaagcaga tattgaagaa gctggtcgcg ctgttgtcaa aatgctcgaa atgggcttaa   1260
aaccttctga catttttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860
tttccctttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattattagt taaagtttta taagcatttt tatgtaacga aaaataaatt   2280
ggttcatatt attactgcac tgtcacttac catggaaaga ccagacaaga agttgccgac   2340
agtctgttga attggcctgg ttaggcttaa gtctgggtcc gcttctttac aaatttggag   2400
aatttctctt aaacgatatg tatattcttt tcgttggaaa agatgtcttc caaaaaaaaa   2460
accgatgaat tagtggaacc aaggaaaaaa aaagaggtat ccttgattaa ggaacactgt   2520
ttaaacagtg tggtttccaa aaccctgaaa ctgcattagt gtaatagaag actagacacc   2580
tcgatacaaa taatggttac tcaattcaaa actgccagcg aattcgactc tgcaattgct   2640
caagacaagc tagttgtcgt agatttctac gccacttggt gcggtccatg taaaatgatt   2700
```

```
gctccaatga ttgaaaaatg tggctgtggt ttcagggtcc ataaagcttt tcaattcatc   2760

ttttttttt ttgttctttt ttttgattcc ggtttctttg aaattttttt gattcggtaa   2820

tctccgagca gaaggaagaa cgaaggaagg agcacagact tagattggta tatatacgca   2880

tatgtggtgt tgaagaaaca tgaaattgcc cagtattctt aacccaactg cacagaacaa   2940

aaacctgcag gaaacgaaga taaatcatgt cgaaagctac atataaggaa cgtgctgcta   3000

ctcatcctag tcctgttgct gccaagctat ttaatatcat gcacgaaaag caaacaaact   3060

tgtgtgcttc attggatgtt cgtaccacca aggaattact ggagttagtt gaagcattag   3120

gtcccaaaat ttgtttacta aaaacacatg tggatatctt gactgatttt tccatggagg   3180

gcacagttaa gccgctaaag gcattatccg ccaagtacaa tttttactc ttcgaagaca   3240

gaaaatttgc tgacattggt aatacagtca aattgcagta ctctgcgggt gtatacagaa   3300

tagcagaatg ggcagacatt acgaatgcac acggtgtggt gggcccaggt attgttagcg   3360

gtttgaagca ggcggcggaa gaagtaacaa aggaacctag aggccttttg atgttagcag   3420

aattgtcatg caagggctcc ctagctactg gagaatatac taagggtact gttgacattg   3480

cgaagagcga caaagatttt gttatcggct ttattgctca aagagacatg ggtggaagag   3540

atgaaggtta cgattggttg attatgacac ccggtgtggg tttagatgac aagggagacg   3600

cattgggtca acagtataga accgtggatg atgtggtctc tacaggatct gacattatta   3660

ttgttggaag aggactattt gcaaagggaa gggatgctaa ggtagagggt gaacgttaca   3720

gaaaagcagg ctgggaagca tatttgagaa gatgcggcca gcaaaactaa aaaactgtat   3780

tataagtaaa tgcatgtata ctaaactcac aaattagagc ttcaatttaa ttatatcagt   3840

tattacccgg gaatctcggt cgtaatgatt tctataatga cgaaaaaaaa aaaattggaa   3900

agaaaaagct tcatggcctt ccactttccc aaacaacacc tacggtatct ctcaagtctt   3960

atggggttcc attggtttca ccactggtgc taccttgggt gctgctttcg ctgctgaaga   4020

aattgatcca aagaagagag ttatcttatt cattggtgac ggttctttgc aattgactgt   4080

tcaagaaatc tccaccatga tcagatgggg cttgaagcca tacttgttcg tcttgaacaa   4140

cgatggttac accattgaaa agttgattca cggtccaaag gctcaataca acgaaattca   4200

aggttgggac cacctatcct tgttgccaac tttcggtgct aaggactatg aaacccacag   4260

agtcgctacc accggtgaat gggacaagtt gacccaagac aagtctttca acgacaactc   4320

taagatcaga atgattgaaa tcatgttgcc agtcttcgat gctccacaaa acttggttga   4380

acaagctaag ttgactgctg ctaccaacgc taagcaataa                         4420
```

<210> SEQ ID NO 143
<211> LENGTH: 2686
<212> TYPE: DNA
<213> ORGANISM: Artificial Sequence
<220> FEATURE:
<223> OTHER INFORMATION: pUC19

<400> SEQUENCE: 143

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360
```

```
tttcccagtc acgacgttgt aaaacgacgg ccagtgaatt cgagctcggt acccggggat    420
cctctagagt cgacctgcag gcatgcaagc ttggcgtaat catggtcata gctgtttcct    480
gtgtgaaatt gttatccgct cacaattcca cacaacatac gagccggaag cataaagtgt    540
aaagcctggg gtgcctaatg agtgagctaa ctcacattaa ttgcgttgcg ctcactgccc    600
gctttccagt cgggaaacct gtcgtgccag ctgcattaat gaatcggcca acgcgcgggg    660
agaggcggtt tgcgtattgg gcgctcttcc gcttcctcgc tcactgactc gctgcgctcg    720
gtcgttcggc tgcggcgagc ggtatcagct cactcaaagg cggtaatacg gttatccaca    780
gaatcagggg ataacgcagg aaagaacatg tgagcaaaag gccagcaaaa ggccaggaac    840
cgtaaaaagg ccgcgttgct ggcgtttttc cataggctcc gcccccctga cgagcatcac    900
aaaaatcgac gctcaagtca gaggtggcga aacccgacag gactataaag ataccaggcg    960
tttccccctg gaagctccct cgtgcgctct cctgttccga ccctgccgct taccggatac   1020
ctgtccgcct ttctcccttc gggaagcgtg gcgctttctc atagctcacg ctgtaggtat   1080
ctcagttcgg tgtaggtcgt tcgctccaag ctgggctgtg tgcacgaacc ccccgttcag   1140
cccgaccgct gcgccttatc cggtaactat cgtcttgagt ccaacccggt aagacacgac   1200
ttatcgccac tggcagcagc cactggtaac aggattagca gagcgaggta tgtaggcggt   1260
gctacagagt tcttgaagtg gtggcctaac tacggctaca ctagaaggac agtatttggt   1320
atctgcgctc tgctgaagcc agttaccttc ggaaaaagag ttggtagctc ttgatccggc   1380
aaacaaacca ccgctggtag cggtggtttt tttgtttgca agcagcagat tacgcgcaga   1440
aaaaaaggat ctcaagaaga tcctttgatc ttttctacgg ggtctgacgc tcagtggaac   1500
gaaaactcac gttaagggat tttggtcatg agattatcaa aaaggatctt cacctagatc   1560
cttttaaatt aaaaatgaag ttttaaatca atctaaagta tatatgagta aacttggtct   1620
gacagttacc aatgcttaat cagtgaggca cctatctcag cgatctgtct atttcgttca   1680
tccatagttg cctgactccc cgtcgtgtag ataactacga tacgggaggg cttaccatct   1740
ggccccagtg ctgcaatgat accgcgagac ccacgctcac cggctccaga tttatcagca   1800
ataaaccagc cagccggaag ggccgagcgc agaagtggtc ctgcaacttt atccgcctcc   1860
atccagtcta ttaattgttg ccgggaagct agagtaagta gttcgccagt taatagtttg   1920
cgcaacgttg ttgccattgc tacaggcatc gtggtgtcac gctcgtcgtt tggtatggct   1980
tcattcagct ccggttccca acgatcaagg cgagttacat gatcccccat gttgtgcaaa   2040
aaagcggtta gctccttcgg tcctccgatc gttgtcagaa gtaagttggc cgcagtgtta   2100
tcactcatgg ttatggcagc actgcataat tctcttactg tcatgccatc cgtaagatgc   2160
ttttctgtga ctggtgagta ctcaaccaag tcattctgag aatagtgtat gcggcgaccg   2220
agttgctctt gcccggcgtc aatacgggat aataccgcgc cacatagcag aactttaaaa   2280
gtgctcatca ttggaaaacg ttcttcgggg cgaaaactct caaggatctt accgctgttg   2340
agatccagtt cgatgtaacc cactcgtgca cccaactgat cttcagcatc ttttactttc   2400
accagcgttt ctgggtgagc aaaaacagga aggcaaaatg ccgcaaaaaa gggaataagg   2460
gcgacacgga aatgttgaat actcatactc ttcctttttc aatattattg aagcatttat   2520
cagggttatt gtctcatgag cggatacata tttgaatgta tttagaaaaa taaacaaata   2580
ggggttccgc gcacatttcc ccgaaaagtg ccacctgacg tctaagaaac cattattatc   2640
atgacattaa cctataaaaa taggcgtatc acgaggccct ttcgtc                 2686
```

<210> SEQ ID NO 144

<211> LENGTH: 3521
<212> TYPE: DNA
<213> ORGANISM: Artificial Sequence
<220> FEATURE:
<223> OTHER INFORMATION: PDC5 A-sadB-BUC cassette

<400> SEQUENCE: 144
aaggaaataa agcaaataac aataacacca ttattttaat ttttttttcta ttactgtcgc 60 taacacctgt atggttgcaa ccaggtgaga atccttctga tgcatacttt atgcgtttat 120
gcgttttgcg ccccttggaa aaaaattgat tctcatcgta aatgcatact acatgcgttt 180
atgggaaaag cctccatatc caaaggtcgc gtttctttta gaaaaactaa tacgtaaacc 240
tgcattaagg taagattata tcagaaaatg tgttgcaaga aatgcattat gcaatttttt 300
gattatgaca atctctcgaa agaaatttca tatgatgaga cttgaataat gcagcggcgc 360
ttgctaaaag aacttgtata taagagctgc cattctcgat caatatactg tagtaagtcc 420
tttcctctct ttcttattac acttatttca cataatcaat ctcaaagaga acaacacaat 480
acaataacaa gaagaacaaa atgaaagctc tggtttatca cggtgaccac aagatctcgc 540
ttgaagacaa gcccaagccc acccttcaaa agcccacgga tgtagtagta cgggttttga 600
agaccacgat ctgcggcacg gatctcggca tctacaaagg caagaatcca gaggtcgccg 660
acgggcgcat cctgggccat gaaggggtag gcgtcatcga ggaagtgggc gagagtgtca 720
cgcagttcaa gaaaggcgac aaggtcctga tttcctgcgt cacttcttgc ggctcgtgcg 780
actactgcaa gaagcagctt tactcccatt gccgcgacgg cgggtggatc ctgggttaca 840
tgatcgatgg cgtgcaggcc gaatacgtcc gcatcccgca tgccgacaac agcctctaca 900
agatccccca gacaattgac gacgaaatcg ccgtcctgct gagcgacatc ctgcccaccg 960
gccacgaaat cggcgtccag tatgggaatg tccagccggg cgatgcggtg gctattgtcg 1020
gcgcgggccc cgtcggcatg tccgtactgt tgaccgccca gttctactcc ccctcgacca 1080
tcatcgtgat cgacatggac gagaatcgcc tccagctcgc caaggagctc ggggcaacgc 1140
acaccatcaa ctccggcacg gagaacgttg tcgaagccgt gcataggatt gcggcagagg 1200
gagtcgatgt tgcgatcgag gcggtgggca taccggcgac ttgggacatc tgccaggaga 1260
tcgtcaagcc cggcgcgcac atcgccaacg tcggcgtgca tggcgtcaag gttgacttcg 1320
agattcagaa gctctggatc aagaacctga cgatcaccac gggactggtg aacacgaaca 1380
cgacgcccat gctgatgaag gtcgcctcga ccgacaagct tccgttgaag aagatgatta 1440
cccatcgctt cgagctggcc gagatcgagc acgcctatca ggtattcctc aatggcgcca 1500
aggagaaggc gatgaagatc atcctctcga acgcaggcgc tgcctgagct aattaacata 1560
aaactcatga ttcaacgttt gtgtattttt ttacttttga aggttataga tgtttaggta 1620
aataattggc atagatatag ttttagtata ataaatttct gatttggttt aaaatatcaa 1680
ctattttttt tcacatatgt tcttgtaatt actttctgt cctgtcttcc aggttaaaga 1740
ttagcttcta atattttagg tggtttatta tttaatttta tgctgattaa tttatttact 1800
tgtttaaacg gccggccaat gtggctgtgg tttcagggtc cataaagctt ttcaattcat 1860
cttttttttt tttgttcttt tttttgattc cggtttcttt gaaatttttt tgattcggta 1920
atctccgagc agaaggaaga acgaaggaag gagcacagac ttagattggt atatatacgc 1980
atatgtggtg ttgaagaaac atgaaattgc ccagtattct taacccaact gcacagaaca 2040
aaaacctgca ggaaacgaag ataaatcatg tcgaaagcta catataagga acgtgctgct 2100
actcatccta gtcctgttgc tgccaagcta tttaatatca tgcacgaaaa gcaaacaaac 2160

```
ttgtgtgctt cattggatgt tcgtaccacc aaggaattac tggagttagt tgaagcatta   2220
ggtcccaaaa tttgtttact aaaaacacat gtggatatct tgactgattt ttccatggag   2280
ggcacagtta agccgctaaa ggcattatcc gccaagtaca atttttttact cttcgaagac   2340
agaaaatttg ctgacattgg taatacagtc aaattgcagt actctgcggg tgtatacaga   2400
atagcagaat gggcagacat tacgaatgca cacggtgtgg tgggcccagg tattgttagc   2460
ggtttgaagc aggcggcgga agaagtaaca aaggaaccta gaggcctttt gatgttagca   2520
gaattgtcat gcaagggctc cctagctact ggagaatata ctaagggtac tgttgacatt   2580
gcgaagagcg acaaagattt tgttatcggc tttattgctc aaagagacat gggtggaaga   2640
gatgaaggtt acgattggtt gattatgaca cccggtgtgg gtttagatga caagggagac   2700
gcattgggtc aacagtatag aaccgtggat gatgtggtct ctacaggatc tgacattatt   2760
attgttggaa gaggactatt tgcaaaggga agggatgcta aggtagaggg tgaacgttac   2820
agaaaagcag gctgggaagc atatttgaga agatgcggcc agcaaaacta aaaaactgta   2880
ttataagtaa atgcatgtat actaaactca caaattagag cttcaattta attatatcag   2940
ttattacccg ggaatctcgg tcgtaatgat ttctataatg acgaaaaaaa aaaaattgga   3000
aagaaaaagc ttcatggcct tctactttcc caacagatgt atacgctatc gtccaagtct   3060
tgtggggttc cattggtttc acagtcggcg ctctattggg tgctactatg gccgctgaag   3120
aacttgatcc aaagaagaga gttattttat tcattggtga cggttctcta caattgactg   3180
ttcaagaaat ctctaccatg attagatggg gtttgaagcc atacattttt gtcttgaata   3240
acaacggtta caccattgaa aaattgattc acggtcctca tgccgaatat aatgaaattc   3300
aaggttggga ccacttggcc ttattgccaa cttttggtgc tagaaactac gaaacccaca   3360
gagttgctac cactggtgaa tgggaaaagt tgactcaaga caaggacttc caagacaact   3420
ctaagattag aatgattgaa gttatgttgc cagtctttga tgctccacaa aacttggtta   3480
aacaagctca attgactgcc gctactaacg ctaaacaata a                        3521
```

<210> SEQ ID NO 145
<211> LENGTH: 1685
<212> TYPE: DNA
<213> ORGANISM: Artificial Sequence
<220> FEATURE:
<223> OTHER INFORMATION: gpd2::loxP-URA3-loxP cassette

<400> SEQUENCE: 145

```
gtattttggt agattcaatt ctctttccct ttccttttcc ttcgctcccc ttccttatca     60
gcattgcgga ttacgtattc taatgttcag ataacttcgt atagcataca ttatacgaag    120
ttatgcagat tgtactgaga gtgcaccata ccacagcttt tcaattcaat tcatcatttt    180
tttttattc tttttttga tttcggtttc tttgaaattt ttttgattcg gtaatctccg    240
aacagaagga agaacgaagg aaggagcaca gacttagatt ggtatatata cgcatatgta    300
gtgttgaaga aacatgaaat tgcccagtat tcttaaccca actgcacaga acaaaaacct    360
gcaggaaacg aagataaatc atgtcgaaag ctacatataa ggaacgtgct gctactcatc    420
ctagtcctgt tgctgccaag ctatttaata tcatgcacga aaagcaaaca aacttgtgtg    480
cttcattgga tgttcgtacc accaaggaat tactggagtt agttgaagca ttaggtccca    540
aaatttgttt actaaaaaca catgtggata tcttgactga tttttccatg gagggcacag    600
ttaagccgct aaaggcatta tccgccaagt acaatttttt actcttcgaa gacagaaaat    660
ttgctgacat tggtaataca gtcaaattgc agtactctgc gggtgtatac agaatagcag    720
```

-continued

| | |
|---|---|
| aatgggcaga cattacgaat gcacacggtg tggtgggccc aggtattgtt agcggtttga | 780 |
| agcaggcggc agaagaagta acaaaggaac ctagaggcct tttgatgtta gcagaattgt | 840 |
| catgcaaggg ctccctatct actggagaat atactaaggg tactgttgac attgcgaaga | 900 |
| gcgacaaaga ttttgttatc ggctttattg ctcaaagaga catgggtgga agagatgaag | 960 |
| gttacgattg gttgattatg acacccggtg tgggtttaga tgacaaggga gacgcattgg | 1020 |
| gtcaacagta tagaaccgtg gatgatgtgg tctctacagg atctgacatt attattgttg | 1080 |
| gaagaggact atttgcaaag ggaagggatg ctaaggtaga gggtgaacgt tacagaaaag | 1140 |
| caggctggga agcatatttg agaagatgcg gccagcaaaa ctaaaaaact gtattataag | 1200 |
| taaatgcatg tatactaaac tcacaaatta gagcttcaat ttaattatat cagttattac | 1260 |
| cctatgcggt gtgaaatacc gcacagatgc gtaaggagaa aataccgcat caggaaattg | 1320 |
| taaacgttaa tattttgtta aaattcgcgt taaatttttg ttaaatcagc tcatttttta | 1380 |
| accaataggc cgaaatcggc aaaatccctt ataaatcaaa agaatagacc gagatagggt | 1440 |
| tgagtgttgt tccagtttgg aacaagagtc cactattaaa gaacgtggac tccaacgtca | 1500 |
| aagggcgaaa aaccgtctat cagggcgatg gcccactacg tgaaccatca ccctaatcaa | 1560 |
| gataacttcg tatagcatac attatacgaa gttatccagt gatgatacaa cgagttagcc | 1620 |
| aaggtgacac tctccccccc cctccccctc tgatctttcc tgttgcctct tttcccccca | 1680 |
| accaa | 1685 |